(12) United States Patent
Marban et al.

(10) Patent No.: US 9,763,999 B2
(45) Date of Patent: Sep. 19, 2017

(54) TRANSCRIPTION FACTOR-BASED GENERATION OF PACEMAKER CELLS AND METHODS OF USING SAME

(71) Applicant: Cedars-Sinai Medical Center, Los Angeles, CA (US)

(72) Inventors: Eduardo Marban, Santa Monica, CA (US); Hee Cheol Cho, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 14/357,195

(22) PCT Filed: Nov. 8, 2012

(86) PCT No.: PCT/US2012/064204
§ 371 (c)(1),
(2) Date: May 8, 2014

(87) PCT Pub. No.: WO2013/070952
PCT Pub. Date: May 16, 2013

(65) Prior Publication Data
US 2015/0359845 A1    Dec. 17, 2015

Related U.S. Application Data

(60) Provisional application No. 61/557,812, filed on Nov. 9, 2011.

(51) Int. Cl.
| | |
|---|---|
| *A61P 9/00* | (2006.01) |
| *A61P 9/06* | (2006.01) |
| *A61K 38/17* | (2006.01) |
| *A61K 48/00* | (2006.01) |
| *C12N 15/00* | (2006.01) |
| *C07K 14/47* | (2006.01) |
| *C12N 5/077* | (2010.01) |
| *A61K 35/34* | (2015.01) |

(52) U.S. Cl.
CPC .......... *A61K 38/1709* (2013.01); *A61K 35/34* (2013.01); *C07K 14/4702* (2013.01); *C12N 5/0657* (2013.01); *A61K 48/00* (2013.01); *C12N 2501/60* (2013.01); *C12N 2506/02* (2013.01); *C12N 2799/022* (2013.01)

(58) Field of Classification Search
None
See application file for complete search history.

(56) References Cited

U.S. PATENT DOCUMENTS

| | | | |
|---|---|---|---|
| 9,017,661 B2* | 4/2015 | Nam .................. | C07K 14/4702 424/93.2 |
| 2004/0214182 A1 | 10/2004 | Sharma et al. | |
| 2004/0254134 A1 | 12/2004 | Marban et al. | |
| 2007/0099268 A1 | 5/2007 | Cohen et al. | |
| 2008/0103536 A1 | 5/2008 | Xiao | |
| 2009/0099611 A1 | 4/2009 | Sigg et al. | |
| 2010/0172883 A1* | 7/2010 | Bruneau ............ | C07K 14/4702 424/93.7 |

FOREIGN PATENT DOCUMENTS

| | | | |
|---|---|---|---|
| JP | 2004-534015 A | 11/2004 | |
| WO | 2008088882 A2 | 7/2008 | |
| WO | 2010059806 A2 | 5/2010 | |
| WO | 20100108126 A2 | 9/2010 | |
| WO | WO2011/139688 * | 11/2011 | ........... C12N 5/0735 |
| WO | 2013070952 A1 | 5/2013 | |

OTHER PUBLICATIONS

Ieda et al., Direct Reprogramming of Fibroblasts into Functional Cardiomyocytes by Defined Factors. Cell, vol. 142, Issue 3, Aug. 6, 2010, pp. 375-386.*
Christoffels et al., Development of the Pacemaker Tissues of the Heart. Circulation Research.2010; 106: 240-254.*
Janavel et al., Plasmid-mediated VEGF gene transfer induces cardiomyogenesis and reduces myocardial infarct size in sheep. Gene Therapy (2006) 13, 1133-1142.*
Vale et al., Randomized, Single-Blind, Placebo-Controlled Pilot Study of Catheter-Based Myocardial Gene Transfer for Therapeutic Angiogenesis Using Left Ventricular Electromechanical Mapping in Patients With Chronic Myocardial Ischemia. Circulation. 2001;103:2138-2143.*
M. L. Bakker et al., "T-box transcription factor TBX3 reprogrammes mature cardiac myocytes into pacemaker-like cells", Cardiovascular Research, vol. 94, No. 3, Jun. 1, 2012 (Jun. 1, 2012), pp. 439-449, XP055163087.
Liang Wenbin et al., "Induced Pacemaker Cells Created by In Vivo Somatic Reprogramming: Phenotypic Comparison with Native Sinoatrial Node Cells", Biophysical Journal, vol. 102, No. 3, Jan. 31, 2012 (Jan. 31, 2012), XP028892753, p. 673a.
Kapoor Nidhi et al., "Lineage Reprogramming from Cardiomyocytes to Pacemaker Cells via a Single Transcription Factor", Biophysical Journal, vol. 102, No. 3, Jan. 31, 2012 (Jan. 31, 2012), XP028893265, p. 673a.
Ionta Vittoria et al., "Enhanced Embryonic Stem Cell Differentiation to Cardiac Pacemaker Cells by Transduction with a Single Transcription Factor", Biophysical Journal, vol. 102, No. 3, Jan. 31, 2012 (Jan. 31, 2012), XP028892341, p. 673a.
Kapoor N et al., "Transcriptional suppression of connexin43 by Tbx18 undermines cell-cell electrical coupling in postnatal cardiomyocytes", Journal of Biological Chemistry, vol. 286, No. 16, Apr. 22, 2011 (Apr. 22, 2011), pp. 14073-14079, XP002738799.
Nidhi Kapoor et al., "Direct conversion of 1-23 quiescent cardiomyocytes to pacemaker cells by expression of Tbx18", Nature Biotechnology, vol. 31, No. 1, Dec. 16, 2012 (Dec. 16, 2012), pp. 54-62, XP055184482.

(Continued)

*Primary Examiner* — Christopher M Babic
*Assistant Examiner* — Arthur S Leonard
(74) *Attorney, Agent, or Firm* — Stephen W. Chen; Nixon Peabody LLP

(57) ABSTRACT

Several embodiments disclosed herein relate generally to methods and compositions for the generation of biological pacemakers. In some embodiments, the methods comprise contacting non-pacemaker cells with one or more transcription factors (in vivo or in vitro) and inducing pacemaker functionality in the cells.

36 Claims, 75 Drawing Sheets

(56) References Cited

OTHER PUBLICATIONS

Cho Hee Cheol et al., "Transcription Factor-Driven Conversion of Quiescent Cardiomyocytes to Pacemaker Cells", Database Biosis [Online], Biosciences Information Service, Philadephia, PA, US, XP002738717, p. 1.
Cho et al., Abstract 14678: Transcription Factor-Driven Conversion of Quiescent Cardiomyocytes to Pacemaker Cells, American Heart Association Resuscitation Science Symposium, 2012; 126 (10021): A1 4678, p. 1.
PCT/US2012/064204 International Search Report and Written Opinion dated Feb. 5, 2013; 13 pages.
PCT/US2012/064204 International Preliminary Report on Patentability dated May 13, 2014; 9 pages.
EP Application No. 12847179.4 Extended Search Report dated Jun. 25, 2015; 14 pages.
Espinoza-Lewis et al. Shox2 is essential for the differentiation of cardiac pacemaker cells by repressing Nkx2-5. Developmental Biology (2009). 327:376-385.
Igaku No Ayumi. An attempt to generate a cardiac biopacemaker by transcriptional modulations of the T-type $Ca^{2+}$ channel. Journal of Clinical and Experimental Medicine (2008). 226(13):1151-1152.

\* cited by examiner

FIG. 5A
GFP-NRVMs
FIG. 5B
Tbx18-NRVMs
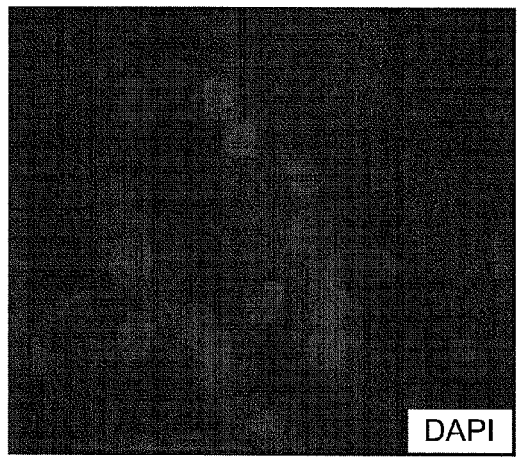
DAPI
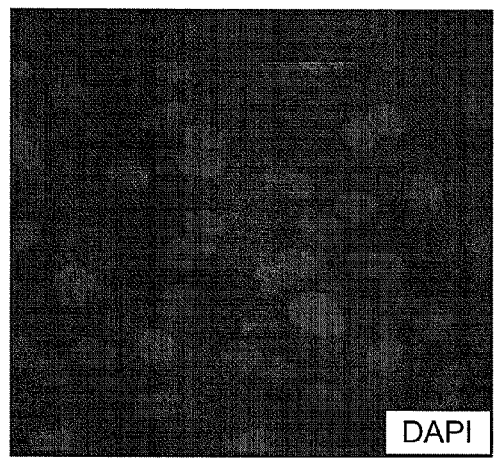
DAPI
GFP
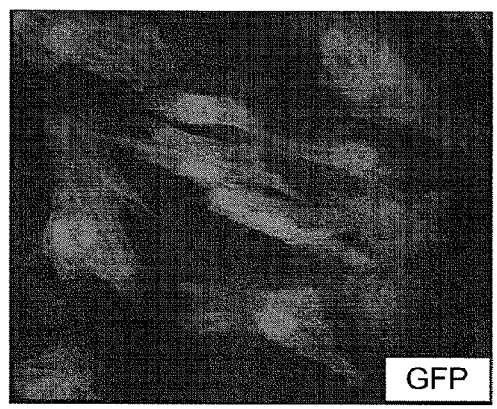
GFP
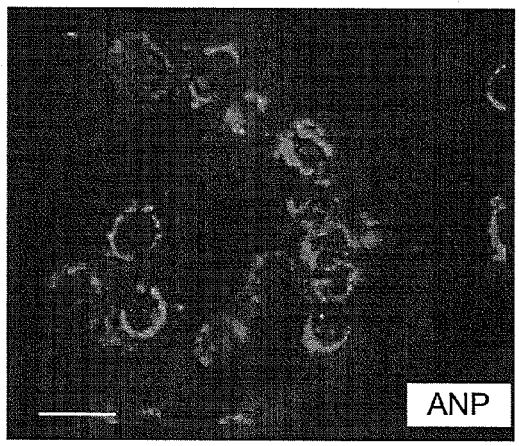
ANP
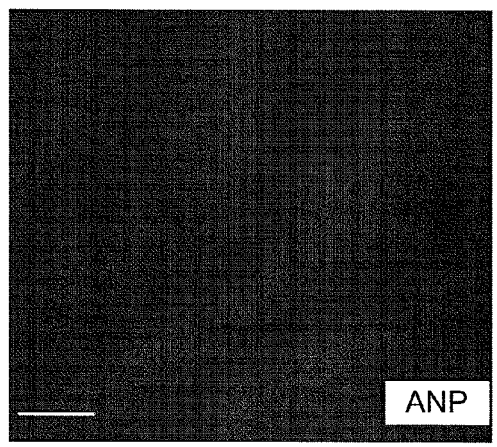
ANP Induced SAN (iSAN) pacemaker cell created by somatic reprogramming by Tbx18

Freshly isolated, living myocytes

SAN myocyte    Tbx18-VM    GFP-VM

Immunostaining of fixed myocytes

SAN myocyte    Tbx18-VM    GFP-VM

SEQUENCE LISTING

<160> NUMBER OF SEQ ID NOS: 10

<210> SEQ ID NO 1
<211> LENGTH: 4754
<212> TYPE: DNA
<213> ORGANISM: Homo sapiens
<220> FEATURE:
<221> NAME/KEY: misc_feature
<223> OTHER INFORMATION: Homo sapiens T-box 3 (TBX3), transcript variant 1
<220> FEATURE:
<221> NAME/KEY: misc_feature
<223> OTHER INFORMATION: NM_005996.3

<400> SEQUENCE: 1

```
gaattctaga ggcggcggag ggtggcgagg agctctcgct ttctctcgct ccctccctct      60
ccgactccgt ctctctctct ctctctctct ctcccctccc tctctttccc tctgttccat     120
tttttccccc tctaaatcct ccctgccctg cgcgcctgga cacagattta ggaagcgaat     180
tcgctcacgt tttaggacaa ggaagagaga gaggcacggg agaagagccc agcaagattt     240
ggattgaaac cgagacaccc tccggaggct cggagcagag gaaggaggag gagggcggcg     300
aacggaagcc agtttgcaat tcaagttttg atagcgctgg tagaaggggg tttaaatcag     360
attttttttt ttttaaagga gagagacttt ttccgctctc tcgctcccct gttaaagccgg    420
gtctagcaca gctgcagacg ccaccagcga gaaagaggga gaggaagaca gatagggggc     480
gggggaagaa gaaaagaaa ggtaaaaagt cttctaggag aacctttcac atttgcaaca     540
aaagacctag gggctggaga gagattcctg ggacgcaggg ctggagtgtc tatttcgagc     600
tcagcggcag ggctcgggcg cgagtcgaga ccctgctcgc tcctctcgct tctgaaaccg     660
acgttcagga gcggcttttt aaaaacgcaa ggcacaagga cggtcacccg cgcgactatg     720
tttgctgatt tttcgccttg ccctctttaa aagcggcctc ccattctcca aaagacactt     780
cccctcctcc ctttgaagtg cattagttgt gatttctgcc tccttttctt ttttcttct     840
tttttgtttt gcttttccc ccttttgaa ttatgtgctg ctgttaaaca acaacaaaaa       900
aacaacaaaa cacagcagct gcggacttgt ccccggctgg agcccagcgc ccgcctgga      960
gtggatgagc ctctccatga gagatccggt cattcctggg acaagcatgg cctaccatcc    1020
gttcctacct caccgggcgc cggacttcgc catgagcgcg gtgctgggtc accagccgcc    1080
gttcttcccc gcgctgacgc tgcctcccaa cggcgcggcg gcgctctcgc tgccgggcgc    1140
cctggccaag ccgatcatgg atcaattggt ggggcggcc gagaccggca tcccgttctc    1200
ctccctgggg ccccaggcgc atctgaggcc tttgaagacc atggagcccg aagaagaggt    1260
ggaggacgac cccaaggtgc acctggaggc taaagaactt gggatcagt ttcacaagcg     1320
gggcaccgag atggtcatta ccaagtcggg aaggcgaatg tttcctccat ttaaagtgag    1380
atgttctggg ctggataaaa aagccaaata cattttattg atggacatta tagctgctga    1440
tgactgtcgt tataaatttc acaattctcg gtggatggtg gctggtaagg ccgaccccga    1500
aatgccaaag aggatgtaca ttcacccgga cagccccgct actggggaac agtggatgtc    1560
caaagtcgtc actttccaca aactgaaact caccaacaac atttcagaca acatggatt    1620
tactatattg aactccatgc acaaatacca gccccggttc acattgtaa gagccaatga    1680
catcttgaaa ctccccttata gtacatttcg gacatacttg ttccccgaaa ctgaattcat    1740
cgctgtgact gcataccaga atgataagat aacccagtta aaaatagaca caaccccttt    1800
tgcaaaaggt ttccgggaca ctggaaatgg ccgaagagaa aaagaaaac agctcaccct    1860
```

```
gcagtccatg agggtgtttg atgaaagaca caaaaaggag aatgggacct ctgatgagtc   1920
ctccagtgaa caagcagctt tcaactgctt cgcccaggct tcttctccag ccgcctccac   1980
tgtagggaca tcgaacctca aagatttatg tcccagcgag ggtgagagcg acgccgaggc   2040
cgagagcaaa gaggagcatg gccccgaggc ctgcgacgcg gccaagatct ccaccaccac   2100
gtcggaggag ccctgccgtg acaagggcag ccccgcggtc aaggctcacc ttttcgctgc   2160
tgagcggccc cgggacagcg ggcggctgga caaagcgtcg cccgactcac gccatagccc   2220
cgccaccatc tcgtccagca ctcgcggcct gggcgcggag gagcgcagga gcccggttcg   2280
cgagggcaca cgcgccggcca aggtggaaga ggcgcgcgcg ctcccgggca aggaggcctt   2340
cgcgccgctc acggtgcaga cggacgcggc cgccgcgcac ctggcccagg gccccctgcc   2400
tggcctcggc ttcgcccgg gcctggcggg ccaacagttc ttcaacgggc acccgctctt   2460
cctgcacccc agccagtttg ccatgggggg cgccttctcc agcatggcgg ccgctggcat   2520
gggtcccctc ctggccacgg tttctggggc ctccaccggt gtctcgggcc tggattccac   2580
ggccatggcc tctgccgctg cggcgcaggg actgtccggg gcgtccgcgg ccaccctgcc   2640
cttccacctc cagcagcacg tcctggcctc tcagggcctg gccatgtccc ctttcggaag   2700
cctgttccct tacccctaca gtacatggc cgcagcggcg gccgcctcct ctgcggcagc   2760
ctccagctcg gtgcaccgcc accccttcct caatctgaac accatgcgcc cgcggctgcg   2820
ctacagcccc tactccatcc ggtgccggt cccggacggc agcagtctgc tcaccaccgc   2880
cctgccctcc atggcggcgg ccgcggggcc cctggacggc aaagtcgccg ccctggccgc   2940
cagcccggcc tcgtggcag tggactcggg ctctgaactc aacagccgct cctccacgct   3000
ctcctccagc tccatgtcct tgtcgcccaa actctgcgcg gagaaagagg cggccaccag   3060
cgaactgcag agcatccagc ggttggttag cggcttggaa gccaagccgg acaggtcccg   3120
cagcgcgtcc ccgtagaccc gtcccagaca cgtctttttca ttccagtcca gttcaggctg   3180
ccgtgcactt tgtcggatat aaaataaacc acgggcccgc catggcgtta gcccttcctt   3240
ttgcagttgc gtctgggaag gggccccgga ctccctcgag agaatgtgct agagacagcc   3300
cctgtcttct tggcgtggtt tatatgtccg ggatctggat cagattctgg gggctcagaa   3360
acgtcggttg cattgagcta ctgggggtag gagttccaac atttatgtcc agagcaactt   3420
ccagcaaggc tggtctgggt ctctgcccac caggcgggga ggtgttcaaa gacatctccc   3480
tcagtgcgga tttatatata tattttcct tcactgtgtc aagtggaaac aaaaacaaaa   3540
tctttcaaaa aaaaaatcgg gacaagtgaa cacattaaca tgattctgtt tgtgcagatt   3600
aaaaacttta tagggacttg cattatcggt tctcaataaa ttactgagca gctttgtttg   3660
gggagggaag tccctaccat ccttgtttag tctatattaa gaaaatctgt gtcttttaa   3720 tattcttgtg atgttttcag agccgctgta ggtctcttct tgcatgtcca cagtaatgta   3780
tttgtggttt ttattttgaa cgcttgcttt tagagagaaa acaatatagc ccctacccct   3840
tttcccaatc ctttgccctc aaatcagtga cccaaggag ggggggattt aagggaagg   3900 agtgggcaaa acacataaaa tgaatttatt atatctaagc tctgtagcag gattcatgtc   3960
gttctttgac agttctttct cttcctgta tatgcaataa caaggttta aaaaataat   4020 aaagaagtga gactattaga caaagtattt atgtaattat ttgataactc ttgtaaatag   4080
gtggaatatg aatgcttgga aaattaaact ttaatttatt gacattgtac atagctctgt   4140
gtaaatagaa ttgcaactgt caggttttgt gttcttgttt tcctttagtt gggttttatt   4200
ccaggtcaca gaattgctgt taacactaga aaacacactt cctgcaccaa caccaatacc   4260
```

-continued

| | |
|---|---|
| ctttcaaaag agttgtctgc aacattttg ttttctttt taatgtccaa aagtgggga | 4320 |
| aagtgctatt tcctatttc accaaaattg gggaaggagt gccactttcc agctccactt | 4380 |
| caaattcctt aaaatataac tgagattgct gtggggaggg aggagggcag aggctgcggt | 4440 |
| ttgacttttt aattttctt ttgttatttg tatttgctag tctctgattt cctcaaaacg | 4500 |
| aagtggaatt tactactgtt gtcagtatcg gtgttttgaa ttggtgcctg cctatagaga | 4560 |
| tatattcaca gttcaaaagt caggtgctga gagatggttt aaagacaaat tcatgaaggt | 4620 |
| atattttgtg ttatagttgt tgatgagttc tttggttttc tgtatttttc ccctctctt | 4680 |
| taaaacatca ctgaaatttc aataaatttt tattgaaatg tctaaaaaaa aaaaaaaaa | 4740 |
| aaaaaaaaaa aaaa | 4754 |

<210> SEQ ID NO 2
<211> LENGTH: 4814
<212> TYPE: DNA
<213> ORGANISM: Homo sapiens
<220> FEATURE:
<221> NAME/KEY: misc_feature
<223> OTHER INFORMATION: Homo sapiens T-box 3 (TBX3), transcript
      variant 2
<220> FEATURE:
<221> NAME/KEY: misc_feature
<223> OTHER INFORMATION: Accession Number - NM_016569.3

<400> SEQUENCE: 2

| | |
|---|---|
| gaattctaga ggcggcggag ggtggcgagg agctctcgct ttctctcgct ccctccctct | 60 |
| ccgactccgt ctctctctct ctctctctct ctccctccc tctcttttccc tctgttccat | 120 |
| ttttttcccc tctaaatcct ccctgccctg cgcgcctgga cacagattta ggaagcgaat | 180 |
| tcgctcacgt tttaggacaa ggaagagaga gaggcacggg agaagagccc agcaagattt | 240 |
| ggattgaaac cgagacaccc tccggaggct cggagcagag gaaggaggag gagggcggcg | 300 |
| aacggaagcc agtttgcaat tcaagtttg atagcgctgg tagaaggggg tttaaatcag | 360 |
| atttttttt ttttaaagga gagagacttt ttccgctctc tcgctccctg ttaaagccgg | 420 |
| gtctagcaca gctgcagacg ccaccagcga gaaagaggga gaggaagaca gatggggc | 480 |
| gggggaagaa gaaaaagaaa ggtaaaaagt cttctaggag aacctttcac atttgcaaca | 540 |
| aaagacctag gggctggaga gagattcctg ggacgcaggg ctggagtgtc tatttcgagc | 600 |
| tcagcggcag ggctcgggcg cgagtcgaga ccctgctcgc tcctctcgct tctgaaaccg | 660 |
| acgttcagga gcggcttttt aaaaacgcaa ggcacaagga cggtcacccg cgcgactatg | 720 |
| tttgctgatt tttcgccttg ccctctttaa aagcggcctc ccattctcca aaagacactt | 780 |
| cccctcctcc ctttgaagtg cattagttgt gatttctgcc tccttttctt ttttctttct | 840 |
| ttttgtttt gctttttccc cccttttgaa ttatgtgctg ctgttaaaca acaacaaaaa | 900 |
| aacaacaaaa cacagcagct gcggacttgt cccggctgg agcccagcgc ccgcctgga | 960 |
| gtggatgagc ctctccatga gagatccggt cattcctggg acaagcatgg cctaccatcc | 1020 |
| gttcctacct caccgggcgc cggacttcgc catgagcgcg gtgctgggtc accagccgcc | 1080 |
| gttcttcccc gcgctgacgc tgcctccaa cggcgcggcg gcgctctcgc tgccgggcgc | 1140 |
| cctggccaag ccgatcatgg atcaattggt gggggcggcc gagaccggca tcccgttctc | 1200 |
| ctcccctgggg cccaggcgc atctgaggcc tttgaagacc atggagcccg aagaagaggt | 1260 |
| ggaggacgac cccaaggtgc acctggaggc taaagaactt tgggatcagt tcacaagcg | 1320 |
| gggcaccgag atggtcatta ccaagtcggg aaggcgaatg tttcctccat ttaaagtgag | 1380 |

```
atgttctggg ctggataaaa aagccaaata cattttattg atggacatta tagctgctga    1440
tgactgtcgt tataaatttc acaattctcg gtggatggtg gctggtaagg ccgaccccga    1500
aatgccaaag aggatgtaca ttcacccgga cagccccgct actggggaac agtggatgtc    1560
caaagtcgtc actttccaca aactgaaact caccaacaac atttcagaca acatggatt     1620
tactttggcc ttcccaagtg atcacgctac gtggcagggg aattatagtt ttggtactca    1680
gactatattg aactccatgc acaaatacca gccccggttc acattgtaa gagccaatga     1740
catcttgaaa ctcccttata gtacatttcg gacatacttg ttccccgaaa ctgaattcat    1800
cgctgtgact gcataccaga atgataagat aacccagtta aaatagaca caacccttt      1860
tgcaaaaggt ttccgggaca ctggaaatgg ccgaagagaa aaagaaaac agctcaccct     1920
gcagtccatg agggtgtttg atgaaagaca caaaaaggag aatgggacct ctgatgagtc    1980
ctccagtgaa caagcagctt tcaactgctt cgcccaggct tcttctccag ccgcctccac    2040
tgtagggaca tcgaacctca agatttatg tcccagcgag ggtgagagcg acgccgaggc     2100
cgagagcaaa gaggagcatg gccccgaggc ctgcgacgcg gccaagatct ccaccaccac    2160
gtcggaggag ccctgccgtg caagggcag ccccgcggtc aaggctcacc ttttcgctgc     2220
tgagcggccc cggacagcg gcggctgga caaagcgtcg cccgactcac gccatagccc      2280
cgccaccatc tcgtccagca ctcgcggcct gggcgcggag gagcgcagga gcccggttcg    2340
cgagggcaca gcgccggcca aggtggaaga ggcgcgcgcg ctcccgggca aggaggcctt    2400
cgcgccgctc acggtgcaga cggacgcggc cgccgcgcac ctggcccagg gcccctgcc    2460
tggcctcggc ttcgccccgg gcctggcggg ccaacagttc ttcaacggc acccgctctt    2520
cctgcaccc agccagtttg ccatgggggg cgccttctcc agcatggcgg ccgctggcat     2580
gggtcccctc ctggccacgg tttctggggc ctccaccggt gtctcgggcc tggattccac    2640
ggccatggcc tctgccgctg cggcgcaggg actgtccggg gcgtccgcgg ccaccctgcc    2700
cttccacctc cagcagcacg tcctggcctc tcagggcctg gccatgtccc ctttcggaag    2760
cctgttccct taccctaca cgtacatggc cgcagcggcg gccgcctcct ctgcggcagc     2820
ctccagctcg gtgcaccgcc acccttcct caatctgaac accatgcgcc cgcggctgcg    2880
ctacagcccc tactccatcc cggtgccggt cccggacggc agcagtctgc tcaccaccgc    2940
cctgccctcc atggcggcgg ccgcggggcc cctggacggc aaagtcgccg ccctggccgc    3000
cagcccggcc tcggtggcag tggactcggg ctctgaactc aacagccgct cctccacgct    3060
ctcctccagc tccatgtcct tgtcgcccaa actctgcgcg gagaaagagg cggccaccag    3120
cgaactgcag agcatccagc ggttggttag cggcttggaa gccaagccgg acaggtcccg    3180
cagcgcgtcc ccgtagaccc gtcccagaca cgtctttca ttccagtcca gttcaggctg     3240
ccgtgcactt tgtcggatat aaaataaacc acgggcccgc catggcgtta gcccttcctt    3300
ttgcagttgc gtctgggaag gggccccgga ctccctcgag agaatgtgct agagacagcc    3360
cctgtcttct tggcgtggtt tatatgtccg ggatctggat cagattctgg gggctcagaa    3420
acgtcggttg cattgagcta ctgggggtag gagttccaac atttatgtcc agagcaactt    3480
ccagcaaggc tggtctgggt ctctgccac caggcgggga ggtgttcaaa gacatctccc     3540
tcagtgcgga tttatatata tattttcct tcactgtgtc aagtggaaac aaaaacaaaa     3600
tctttcaaaa aaaaaatcgg gacaagtgaa cacattaaca tgattctgtt tgtgcagatt    3660
aaaaacttta tagggacttg cattatcggt tctcaataaa ttactgagca gcttttgtttg   3720
gggagggaag tccctaccat ccttgtttag tctatattaa gaaaatctgt gtctttttaa    3780
```

```
tattcttgtg atgttttcag agccgctgta ggtctcttct tgcatgtcca cagtaatgta    3840
tttgtggttt ttattttgaa cgcttgcttt tagagagaaa acaatatagc cccctacccct   3900 tttcccaatc ctttgccctc aaatcagtga cccaagggag gggggatttt aaagggaagg    3960
agtgggcaaa acacataaaa tgaatttatt atatctaagc tctgtagcag gattcatgtc    4020
gttctttgac agttctttct ctttcctgta tatgcaataa caaggtttta aaaaataat    4080 aaagaagtga gactattaga caaagtattt atgtaattat ttgataactc ttgtaaatag    4140
gtggaatatg aatgcttgga aaattaaact ttaatttatt gacattgtac atagctctgt    4200
gtaaatagaa ttgcaactgt caggttttgt gttcttgttt cctttagtt gggtttattt     4260 ccaggtcaca gaattgctgt taacactaga aaacacactt cctgcaccaa caccaatacc    4320 cttcaaaag agttgtctgc aacattttg ttttctttt taatgtccaa aagtgggga       4380 aagtgctatt tcctatttc accaaaattg gggaaggagt gccactttcc agctccactt    4440
caaattcctt aaaatataac tgagattgct gtggggaggg aggagggcag aggctgcggt    4500 ttgactttt aattttctt ttgttatttg tatttgctag tctctgattt cctcaaaacg      4560
aagtggaatt tactactgtt gtcagtatcg gtgttttgaa ttggtgcctg cctatagaga    4620
tatattcaca gttcaaaagt caggtgctga gagatggttt aaagacaaat tcatgaaggt    4680
atattttgtg ttatagttgt tgatgagttc tttggttttc tgtatttttc cccctctctt    4740
taaaacatca ctgaaatttc aataaatttt tattgaaatg tctaaaaaaa aaaaaaaaa    4800 aaaaaaaaaa aaaa                                                      4814

<210> SEQ ID NO 3
<211> LENGTH: 3921
<212> TYPE: DNA
<213> ORGANISM: Homo sapiens
<220> FEATURE:
<221> NAME/KEY: misc_feature
<223> OTHER INFORMATION: Homo sapiens T-box 5 (TBX5), transcript
      variant 1
<220> FEATURE:
<221> NAME/KEY: misc_feature
<223> OTHER INFORMATION: Accession Number - NM_000192.3

<400> SEQUENCE: 3
catgccttat gcaagagacc tcagtccccc ggaacaactc gatttccttc aatagaggt     60 ctgaggtgga ctcccacctc ccttcgtgaa gagttccctc ctctccccct tcctaagaaa    120
gtcgatcttg gctctatttg tgtcttatgt tcatcaccct cattcctccg gagaaagccg    180
ggttggttta tgtctttatt tattcccggg gccaagacgt ccggaacctg tggctgcgca    240
gacccggcac tgataggcga agacggagag aaatttaccct cccgccgctg ccccccagcc   300
aaacgtgaca gcgcgcgggc cggttgcgtg actcgtgacg tctccaagtc ctataggtgc    360
agcggctggt gagatagtcg ctatcgcctg gttgcctctt tattttactg gggtatgcct    420
ggtaataaac agtaatattt aatttgtcgg agaccacaaa ccaaccttga gctgggaggt    480
acgtgctctt cttgacagac gttggaagaa gacctggcct aaagaggtct cttttggtgg    540
tccttttcaa agtcttcacc tgagccctgc tctccagcga ggcgcactcc tggcttttgc    600
gctccaaaga agaggtggga tagttggaga gcagaacctt gcgcgggcac agggccctgg    660
gcgcaccatg gccgacgcag acgagggctt tggcctggcg cacacgcctc tggagcctga    720
cgcaaaagac ctgcccctgcg attcgaaacc cgagagcgcg ctcggggccc ccagcaagtc    780
cccgtcgtcc ccgcaggccg ccttcaccca gcagggcatg gagggaatca agtgtttct    840
```

```
ccatgaaaga gaactgtggc taaaattcca cgaagtgggc acggaaatga tcataaccaa      900
ggctggaagg cggatgtttc ccagttacaa agtgaaggtg acgggcctta atcccaaaac      960
gaagtacatt cttctcatgg acattgtacc tgccgacgat cacagataca aattcgcaga     1020
taataaatgg tctgtgacgg gcaaagctga gcccgccatg cctggccgcc tgtacgtgca     1080
cccagactcc cccgccaccg gggcgcattg gatgaggcag ctcgtctcct tccagaaact     1140
caagctcacc aacaaccacc tggacccatt tgggcatatt attctaaatt ccatgcacaa     1200
ataccagcct agattacaca tcgtgaaagc ggatgaaaat aatggatttg gctcaaaaaa     1260
tacagcgttc tgcactcacg tctttcctga gactgcgttt atagcagtga cttcctacca     1320
gaaccacaag atcacgcaat taagattga gaataatccc tttgccaaag gatttcgggg       1380
cagtgatgac atggagctgc acagaatgtc aagaatgcaa agtaaagaat atcccgtggt     1440
ccccaggagc accgtgaggc aaaaagtggc ctccaaccac agtcctttca gcagcgagtc     1500
tcgagctctc tccacctcat ccaatttggg gtcccaatac cagtgtgaga atggtgtttc     1560
cggcccctcc caggacctcc tgcctccacc caacccatac ccactgcccc aggagcatag     1620
ccaaatttac cattgtacca agaggaaaga ggaagaatgt tccaccacag accatcccta     1680
taagaagccc tacatggaga catcacccag tgaagaagat tccttctacc gctctagcta     1740
tccacagcag cagggcctgg gtgcctccta caggacagag tcggcacagc ggcaagcttg     1800
catgtatgcc agctctgcgc ccccagcga gcctgtgccc agcctagagg acatcagctg      1860
caacacgtgg ccaagcatgc cttcctacag cagctgcacc gtcaccaccg tgcagcccat     1920
ggacaggcta ccctaccagc acttctccgc tcacttcacc tcggggcccc tggtccctcg     1980
gctggctggc atggccaacc atggctcccc acagctggga gagggaatgt tccagcacca     2040
gacctccgtg gccaccagc ctgtggtcag gcagtgtggg cctcagactg gcctgcagtc      2100
ccctggcacc cttcagcccc ctgagttcct ctactctcat ggcgtgccaa ggactctatc     2160
ccctcatcag taccactctg tgcacggagt tggcatggtg ccagagtgga gcgacaatag     2220
ctaaagtgag gcctgcttca caacagacat ttcctagaga agagagaga gagaggagaa      2280
agagagagaa ggagagagac agtagccaag agaaccccac ggacaagatt tttcatttca     2340
cccaatgttc acatctgcac tcaaggtcgc tggatgctga tctaatcagt agcttgaaac     2400
cacaatttta aaaatgtgac tttcttgttt tgtctcaaaa cttaaaaaaa caaacacaaa     2460
aagatgagtc ccaccccca ctaccaccac acccatcaac cagccacatt cacgctactc      2520
cccagatctc ttccccatt ccttcttttg ggctctagaa agtcttgcct cattgagtgt      2580
ttttccctag tgcgtagttg gagtctgtcc ctgtcttggt gttaatgttg acattgttat     2640
ataataaatg ataatatatt ttttctttc aattttctta atgggaccca gtcccttatt      2700
tggggggagg tctgaggcaa gtatatttca aaatatgtac ttgcgggatt cccttcaagt     2760
aaaccatccc tgaaacctaa attcacgttt cccttgact aagaaaagca cctacctctg      2820
ccatgtgatg tttctgaaaa gcctctgtat gtccccatt gctttggttt tgtcctgcct      2880
tctccaatat cacgtgctca gttttgcctc tacttaccca tggagtcagg ataacactga     2940
cgctccctgg catcctatct tattcagccc taccatcttg ccagctctgt ctttccagct     3000
gtctgtcgct aaaacgtggc ctatagcttc ccttccggaa agcttgcttt gaaaaactta     3060
aaaagccccc gtttacatgt aggcaggact gtgataacag tgcaagctct gtgttgacaa     3120
gagttgtgga caaaaagcca aaataaatat tcttcctgat taaaaaaatt ttttttgaaa     3180
```

| | |
|---|---|
| aaaacaaggc cagccccaac cttccaaacc tccatcacca acaacccaaa ctggatgtca | 3240 |
| agcaaaatgc acaattccta cagaagaggc aagacacagt caccaatgat atctcgccaa | 3300 |
| agaaaccacg cccacaccaa tgccaacaca aaactgtgtt tactgaaagc cgaaaacagt | 3360 |
| attaaaaaaa gtgtgtaagt aaagtgttat ggtagggttc ttcagatgta atattttact | 3420 |
| ggtactattt atttataaat aggaattcta attaagtaat aacatgaaat gaaacccagc | 3480 |
| ataggagctg gccaagagct tttaatttta ttgatactca aaaccaagtt tgtgtttttt | 3540 |
| tgtttttttt tgttttttc ctctttcgaa tgtgctttgc ttttttgat taaaagaat | 3600 |
| ttttttttc cttttttata aacagaccct aataaagaga acagggtaag atgtgaggct | 3660 |
| gagtgtgttt aagtacgtga gagagtgtga gtgtgtttgt aagtgagtgt ccctatgcga | 3720 |
| ttatgtctct ttacgttgct aaggggggag ggtgaggatt aagtactcgt gccttatatt | 3780 |
| tgtgtgccaa ttaatgccta ataaatacca tgtgcttaaa caagtaaaaa aaaaaaaaaa | 3840 |
| aaaaaaaaaa aaaaaaaaaa aaaaaaaaaa aaaaaaaaaa aaaaaaaaaa aaaaaaaaaa | 3900 |
| aaaaaaaaaa aaaaaaaaaa a | 3921 |

```
<210> SEQ ID NO 4
<211> LENGTH: 1050
<212> TYPE: DNA
<213> ORGANISM: Homo sapiens
<220> FEATURE:
<221> NAME/KEY: misc_feature
<223> OTHER INFORMATION: Homo sapiens T-box 5 (TBX5), transcript
      variant 2
<220> FEATURE:
<221> NAME/KEY: misc_feature
<223> OTHER INFORMATION: Accession Number - NM_080718.1

<400> SEQUENCE: 4
```

| | |
|---|---|
| atggccgacg cagacgaggg ctttggcctg gcgcacacgc tctggagcc tgacgcaaaa | 60 |
| gacctgccct gcgattcgaa acccgagagc gcgctcgggg ccccagcaa gtccccgtcg | 120 |
| tccccgcagg ccgccttcac ccagcagggc atggagggaa tcaaagtgtt tctccatgaa | 180 |
| agagaactgt ggctaaaatt ccacgaagtg gcacggaaa tgatcataac caaggctgga | 240 |
| aggcggatgt ttcccagtta caaagtgaag gtgacgggcc ttaatcccaa aacgaagtac | 300 |
| attcttctca tggacattgt acctgccgac gatcacagat acaaattcgc agataataaa | 360 |
| tggtctgtga cgggcaaagc tgagcccgcc atgcctggcc gcctgtacgt gcacccagac | 420 |
| tcccccgcca ccggggcgca ttggatgagg cagctcgtct ccttccagaa actcaagctc | 480 |
| accaacaacc acctggaccc atttgggcat attattctaa attccatgca caatccag | 540 |
| cctagattac acatcgtgaa agcggatgaa ataatggat ttggctcaaa aaatacagcg | 600 |
| ttctgcactc acgtctttcc tgagactgcg tttatagcag tgacttccta ccagaaccac | 660 |
| aagatcacgc aattaaagat tgagaataat ccctttgcca aaggatttcg gggcagtgat | 720 |
| gacatggagc tgcacagaat gtcaagaatg caaagtaaag aatatcccgt ggtccccagg | 780 |
| agcaccgtga ggcaaaaagt ggcctccaac cacagtcctt tcagcagcga gtctcgagct | 840 |
| ctctccacct catccaattt ggggtcccaa taccagtgtg agaatggtgt ttccggcccc | 900 |
| tcccaggacc tcctgcctcc acccaaccca tacccactgc cccaggagca tagccaaatt | 960 |
| taccattgta ccaagaggaa aggtgagtgt gatcacccct ggtcaatttg ctttctttct | 1020 |
| taccttttcc tttccttggg ttgggggtga | 1050 |

```
<210> SEQ ID NO 5
<211> LENGTH: 3736
<212> TYPE: DNA
<213> ORGANISM: Homo sapiens
<220> FEATURE:
<221> NAME/KEY: misc_feature
<223> OTHER INFORMATION: Homo sapiens T-box 5 (TBX5), transcript
      variant 3
<220> FEATURE:
<221> NAME/KEY: misc_feature
<223> OTHER INFORMATION: Accession Number - NM_080717.2

<400> SEQUENCE: 5
catgccttat gcaagagacc tcagtccccc ggaacaactc gatttccttc caatagaggt      60
ctgaggtgga ctcccacctc ccttcgtgaa gagttccctc ctctcccct tcctaagaaa      120 gtcgatcttg gctctatttg tgtcttatgt tcatcaccct cattcctccg gagaaagccg     180
ggttggttta tgtctttatt tattcccggg gccaagacgt ccggaacctg tggctgcgca     240
gacccggcac tgataggcga agacggagag aaatttacct cccgccgctg cccccccagcc    300 aaacgtgaca gcgcgcgggc cggttgcgtg actcgtgacg tctccaagtc ctataggtgc     360
agcggctggt gagatagtcg ctatcgcctg gttgcctctt tattttactg gggtatgcct     420
ggtaataaac agtaatattt aatttgtcgg agaccacaaa ccaaccttga gctgggaggt     480
acgtgctctt cttgacagac gttggaagaa gacctggcct aaagaggtct cttttggtgg    540
tccttttcaa agtcttcacc tgagccctgc tctccagcga ggcgcactcc tggcttttgc    600
gctccaaaga gaggtggga tagttggagg gcatggaggg aatcaaagtg tttctccatg      660
aaagagaact gtggctaaaa ttccacgaag tgggcacgga aatgatcata accaaggctg     720
gaaggcggat gtttcccagt tacaaagtga aggtgacggg ccttaatccc aaaacgaagt     780
acattcttct catggacatt gtacctgccg acgatcacag atacaaattc gcagataata     840
aatggtctgt gacgggcaaa gctgagcccg ccatgcctgg ccgcctgtac gtgcacccag     900
actcccccgc caccggggcg cattggatga ggcagctcgt ctccttccag aaactcaagc     960
tcaccaacaa ccacctggac ccatttgggc atattattct aaattccatg cacaaatacc    1020
agcctagatt acacatcgtg aaagcggatg aaaataatgg atttggctca aaaaatacag    1080
cgttctgcac tcacgtcttt cctgagactg cgtttatagc agtgacttcc taccagaacc    1140
acaagatcac gcaattaaag attgagaata atcccttttgc caaaggattt cggggcagtg    1200
atgacatgga gctgcacaga atgtcaagaa tgcaaagtaa agaatatccc gtggtcccca    1260
ggagcaccgt gaggcaaaaa gtggcctcca ccacagtcc tttcagcagc gagtctcgag     1320
ctctctccac tcatccaat tggggtccc ataccagtg tgagaatggt gtttccggcc      1380
cctcccagga cctcctgcct ccacccaacc cataccacct gccccaggag catagccaaa    1440
tttaccattg taccaagagg aaagaggaag aatgttccac cacagaccat ccctataaga    1500
agccctacat ggagacatca cccagtgaag aagattcctt ctaccgctct agctatccac    1560
agcagcaggg cctgggtgcc tcctacagga cagagtcggc acagcggcaa gcttgcatgt    1620
atgccagctc tgcgcccccc agcgagcctg tgcccagcct agaggacatc agctgcaaca    1680
cgtggccaag catgccttcc tacagcagct gcaccgtcac caccgtgcag cccatggaca    1740
ggctacccta ccagcacttc tccgctcact tcacctcggg gccctggtc cctcggctgg     1800 ctggcatggc caaccatggc tccccacagc tgggagaggg aatgttccag caccagacct    1860
ccgtggccca ccagctgtg gtcaggcagt gtgggcctca gactggctg cagtcccctg      1920 gcaccccttca gccccctgag ttcctctact ctcatggcgt gccaaggact ctatcccctc    1980
```

| | |
|---|---|
| atcagtacca ctctgtgcac ggagttggca tggtgccaga gtggagcgac aatagctaaa | 2040 |
| gtgaggcctg cttcacaaca gacatttcct agagaaagag agagagagag gagaaagaga | 2100 |
| gagaaggaga gagacagtag ccaagagaac cccacggaca agatttttca tttcacccaa | 2160 |
| tgttcacatc tgcactcaag gtcgctggat gctgatctaa tcagtagctt gaaaccacaa | 2220 |
| ttttaaaaat gtgactttct tgttttgtct caaaacttaa aaaacaaac acaaaaagat | 2280 |
| gagtcccacc ccccactacc accacaccca tcaaccagcc acattcacgc tactcccag | 2340 |
| atctcttccc ccattccttc ttttgggctc tagaaagtct tgcctcattg agtgtttttc | 2400 |
| cctagtgcgt agttggagtc tgtccctgtc ttggtgttaa tgttgacatt gttatataat | 2460 |
| aaatgataat atatttttt ctttcaattt tcttaatggg acccagtccc ttatttgggg | 2520 |
| ggaggtctga ggcaagtata tttcaaaata tgtacttgcg ggattcccct caagtaaacc | 2580 |
| atccctgaaa cctaaattca cgtttcccct tgactaagaa aagcacctac ctctgccatg | 2640 |
| tgatgtttct gaaaagcctc tgtatgtccc catttgcttt ggttttgtcc tgccttctcc | 2700 |
| aatatcacgt gctcagtttt gcctctactt acccatggag tcaggataac actgacgctc | 2760 |
| cctggcatcc tatcttattc agccctacca tcttgccagc tctgtctttc cagctgtctg | 2820 |
| tcgctaaaac gtggcctata gcttcccttc cggaaagctt gctttgaaaa acttaaaaag | 2880 |
| cccccgttta catgtaggca ggactgtgat aacagtgcaa gctctgtgtt gacaagagtt | 2940 |
| gtggacaaaa agccaaaata aatattcttc ctgattaaaa aaattttttt tgaaaaaac | 3000 |
| aaggccagcc ccaaccttcc aaacctccat caccaacaac ccaaactgga tgtcaagcaa | 3060 |
| aatgcacaat tcctacagaa gaggcaagac acagtcacca atgatatctc gccaaagaaa | 3120 |
| ccacgcccac accaatgcca acacaaaact gtgtttactg aaagccgaaa acagtattaa | 3180 |
| aaaaagtgtg taagtaaagt gttatggtag ggttcttcag atgtaatatt ttactggtac | 3240 |
| tatttattta taaataggaa ttctaattaa gtaataacat gaaatgaaac ccagcatagg | 3300 |
| agctggccaa gagcttttaa ttttattgat actcaaaacc aagtttgtgt ttttttgttt | 3360 |
| tttttgttt ttttcctctt tcgaatgtgc tttgcttttt ttgattaaaa agaatttttt | 3420 |
| ttttcctttt ttataaacag accctaataa agagaacagg gtaagatgtg aggctgagtg | 3480 |
| tgtttaagta cgtgagagag tgtgagtgtg tttgtaagtg agtgtcccta tgcgattatg | 3540 |
| tctctttacg ttgctaaggg gggagggtga ggattaagta ctcgtgcctt atatttgtgt | 3600 |
| gccaattaat gcctaataaa taccatgtgc ttaaacaagt aaaaaaaaaa aaaaaaaaa | 3660 |
| aaaaaaaaaa aaaaaaaaaa aaaaaaaaaa aaaaaaaaaa aaaaaaaaaa aaaaaaaaaa | 3720 |
| aaaaaaaaaa aaaaaa | 3736 |

<210> SEQ ID NO 6
<211> LENGTH: 3749
<212> TYPE: DNA
<213> ORGANISM: Homo sapiens
<220> FEATURE:
<221> NAME/KEY: misc_feature
<223> OTHER INFORMATION: Homo sapiens T-box 5 (TBX5), transcript
      variant 4
<220> FEATURE:
<221> NAME/KEY: misc_feature
<223> OTHER INFORMATION: Accession Number - NM_181486.1

<400> SEQUENCE: 6

| | |
|---|---|
| ttcagagaga gagagagagg gagagagagt gagagagact gactcttacc tcgaatccgg | 60 |
| gaactttaat cctgaaagct gcgctcagaa aggacttcga ccattcactg ggcttccaac | 120 |

| | |
|---|---|
| tttccctccc tgggggtgta aaggaggagc ggggcactga gattatatgg ttgccggtgc | 180 |
| tcttggaggc tattttgtgt tctttggcgc ttgccaactg ggaagtattt agggagagca | 240 |
| agcgcacagc agaggaggtg tgtgttggag gtgggcagtc gccgcggagg ctccagcggt | 300 |
| aggtgcgccc tagtaggcag cagtagccgc tattctgggt aagcagtaaa ccccgcataa | 360 |
| accccggagc caccatgcct gctccccgc ctcaccgccg gcttccctgc taggagcagc | 420 |
| agaggatgtg gtgaatgcac cggcttcacc gaacgagagc agaaccttgc gcgggcacag | 480 |
| ggccctgggc gcaccatggc cgacgcagac gagggctttg gcctggcgca cacgcctctg | 540 |
| gagcctgacg caaaagacct gccctgcgat tcgaaacccg agagcgcgct cggggccccc | 600 |
| agcaagtccc cgtcgtcccc gcaggccgcc ttcacccagc agggcatgga gggaatcaaa | 660 |
| gtgtttctcc atgaaagaga actgtggcta aaattccacg aagtgggcac ggaaatgatc | 720 |
| ataaccaagg ctggaaggcg gatgtttccc agttacaaag tgaaggtgac gggccttaat | 780 |
| cccaaaacga agtacattct tctcatggac attgtacctg ccgacgatca cagatacaaa | 840 |
| ttcgcagata ataaatggtc tgtgacgggc aaagctgagc cgccatgcc tggccgcctg | 900 |
| tacgtgcacc cagactcccc cgccaccggg gcgcattgga tgaggcagct cgtctccttc | 960 |
| cagaaactca agctcaccaa caaccacctg gacccatttg gcatattat tctaaattcc | 1020 |
| atgcacaaat accagcctag attacacatc gtgaaagcgg atgaaaataa tggatttggc | 1080 |
| tcaaaaaata cagcgttctg cactcacgtc tttcctgaga ctgcgtttat agcagtgact | 1140 |
| tcctaccaga accacaagat cacgcaatta agattgaga ataatcccctt tgccaaagga | 1200 |
| tttcggggca gtgatgacat ggagctgcac agaatgtcaa gaatgcaaag taaagaatat | 1260 |
| cccgtggtcc ccaggagcac cgtgaggcaa aaagtggcct ccaaccacag tcctttcagc | 1320 |
| agcgagtctc gagctctctc cacctcatcc aatttggggt cccaataccca gtgtgagaat | 1380 |
| ggtgtttccg gcccctccca ggacctcctg cctccaccca acccataccc actgccccag | 1440 |
| gagcatagcc aaatttacca ttgtaccaag aggaaagagg aagaatgttc caccacagac | 1500 |
| catccctata agaagcccta catggagaca tcacccagtg aagaagattc cttctaccgc | 1560 |
| tctagctatc cacagcagca gggcctgggt gcctcctaca ggacagagtc ggcacagcgg | 1620 |
| caagcttgca tgtatgccag ctctgcgccc cccagcgagc ctgtgcccag cctagaggac | 1680 |
| atcagctgca acacgtggcc aagcatgcct tcctacagca gctgcaccgt caccaccgtg | 1740 |
| cagcccatgg acaggctacc ctaccagcac ttctccgctc acttcacctc ggggcccctg | 1800 |
| gtccctcggc tggctggcat ggccaaccat ggctccccac agctgggaga gggaatgttc | 1860 |
| cagcaccaga cctccgtggc ccaccagcct gtggtcaggc agtgtgggcc tcagactggc | 1920 |
| ctgcagtccc ctggcaccct tcagcccct gagttcctct actctcatgg cgtgccaagg | 1980 |
| actctatccc ctcatcagta ccactctgtg cacggagttg gcatggtgcc agagtggagc | 2040 |
| gacaatagct aaagtgaggc ctgcttcaca acagacattt cctagagaaa gagagagaga | 2100 |
| gaggagaaag agagagaagg agagagacag tagccaagag aaccccacgg acaagatttt | 2160 |
| tcatttcacc caatgttcac atctgcactc aaggtcgctg gatgctgatc taatcagtag | 2220 |
| cttgaaacca caatttttaaa aatgtgactt tcttgttttg tctcaaaact taaaaaaaca | 2280 |
| aacacaaaaa gatgagtccc accccccact accaccacac ccatcaacca gccacattca | 2340 |
| cgctactccc cagatctctt ccccccattcc ttctttgggg ctctagaaag tcttgcctca | 2400 |
| ttgagtgttt ttccctagtg cgtagttgga gtctgtccct gtcttggtgt taatgttgac | 2460 |
| attgttatat aataaatgat aatatatttt tttctttcaa ttttcttaat gggacccagt | 2520 |

| | | |
|---|---|---|
| cccttatttg gggggaggtc tgaggcaagt atatttcaaa atatgtactt gcgggattcc | 2580 |
| cttcaagtaa accatccctg aaacctaaat tcacgtttcc ccttgactaa gaaaagcacc | 2640 |
| tacctctgcc atgtgatgtt tctgaaaagc ctctgtatgt ccccatttgc tttggttttg | 2700 |
| tcctgccttc tccaatatca cgtgctcagt tttgcctcta cttacccatg gagtcaggat | 2760 |
| aacactgacg ctccctggca tcctatctta ttcagcccta ccatcttgcc agctctgtct | 2820 |
| ttccagctgt ctgtcgctaa aacgtggcct atagcttccc ttccggaaag cttgctttga | 2880 |
| aaaacttaaa aagcccccgt ttacatgtag gcaggactgt gataacagtg caagctctgt | 2940 |
| gttgacaaga gttgtggaca aaaagccaaa ataaatattc ttcctgatta aaaaaatttt | 3000 |
| ttttgaaaaa aacaaggcca gccccaacct tccaaacctc catcaccaac acccaaact | 3060 |
| ggatgtcaag caaatgcac aattcctaca aagaggcaa gacacagtca ccaatgatat | 3120 |
| ctcgccaaag aaaccacgcc cacaccaatg ccaacacaaa actgtgttta ctgaaagccg | 3180 |
| aaaacagtat taaaaaaagt gtgtaagtaa agtgttatgg tagggttctt cagatgtaat | 3240 |
| atttactgg tactatttat ttataaatag gaattctaat taagtaataa catgaaatga | 3300 |
| aacccagcat aggagctggc caagagcttt taattttatt gatactcaaa accaagtttg | 3360 |
| tgttttttg ttttttttg ttttttttcct ctttcgaatg tgctttgctt tttttgatta | 3420 |
| aaaagaattt ttttttttcct tttttataaa cagaccctaa taaagagaac agggtaagat | 3480 |
| gtgaggctga gtgtgtttaa gtacgtgaga gagtgtgagt gtgtttgtaa gtgagtgtcc | 3540 |
| ctatgcgatt atgtctcttt acgttgctaa gggggagggg tgaggattaa gtactcgtgc | 3600 |
| cttatatttg tgtgccaatt aatgcctaat aaataccatg tgcttaaaca agtaaaaaaa | 3660 |
| aaaaaaaaaa aaaaaaaaaa aaaaaaaaaa aaaaaaaaaa aaaaaaaaaa aaaaaaaaaa | 3720 |
| aaaaaaaaaa aaaaaaaaaa aaaaaaaaa | 3749 |

```
<210> SEQ ID NO 7
<211> LENGTH: 4070
<212> TYPE: DNA
<213> ORGANISM: Homo sapiens
<220> FEATURE:
<221> NAME/KEY: misc_feature
<223> OTHER INFORMATION: Homo sapiens T-box 18 (TBX18)
<220> FEATURE:
<221> NAME/KEY: misc_feature
<223> OTHER INFORMATION: Accession Number - NM_001080508.1

<400> SEQUENCE: 7
```

| | | |
|---|---|---|
| atggccgaga agcgaagggg ctcgccgtgc agcatgctaa gcctcaaggc gcacgctttc | 60 |
| tcggtggagg cgctgatcgg cgccgagaag cagcaacagc ttcagaagaa gcggcgaaaa | 120 |
| ctgggcgccg aagaggcggc gggggccgtg gacgacggag gctgcagccg cggcggcggc | 180 |
| gcgggcgaaa agggttcttc tgagggagac gaaggcgctg cgctcccgcc gccggctggg | 240 |
| gcgacgtctg ggccggctcg gagtggcgca gacctggagc gcggagccgc gggcggctgt | 300 |
| gaggacggct tccagcaggg agcttcccct ctggcgtcac cggaggctc ccccaagggg | 360 |
| tctccggcgc gctccctggc ccggcccggg acccctctgc cctcgccgca ggccccgcgg | 420 |
| gtggatctgc agggagccga gctctggaag cgctttcatg agataggcac tgagatgatc | 480 |
| atcaccaagg ccggcaggcg catgtttcca gcaatgagag tgaagatctc tggattagat | 540 |
| cctcaccagc aatattacat tgccatggat attgtaccag tggacaacaa aagatacagg | 600 |
| tatgtttacc acagttcgaa atggatggtg gcaggtaatg ctgactcgcc tgtgccaccc | 660 |
| cgtgtgtaca ttcatccaga ctcgcctgcc tcgggggaga cttggatgag acaagttatc | 720 |

```
agcttcgaca agctgaagct caccaacaat gaactggatg accaaggcca tattattctt    780
cattctatgc acaaatacca accgcgagtg cacgtcatcc gtaaagactg tggagacgat    840
ctttctccca tcaagcctgt tccatccggg gagggagtaa aggcattctc ctttccagaa    900
actgtcttca caaccgtcac tgcctatcag aatcagcaga ttactcgcct gaagatagat    960
aggaatccat ttgctaaagg cttccgagac tccgggcgca acagaatggg tttggaagcc   1020
ttggtggaat catatgcatt ctggcgacca tcactacgga ctctgacctt tgaagatatc   1080
cctggaattc ccaagcaagg caatgcaagt tcctccacct tgctccaagg tactgggaat   1140
ggcgttcctg ccactcaccc tcaccttttg tctggctcct cttgctcctc tcctgccttc   1200
catctggggc ccaacaccag ccagctgtgt agtctggccc ctgctgacta ttctgcctgt   1260
gcccgctcag gcctcaccct caaccgatac agcacatctt tggcagagac ctacaacagg   1320
ctcaccaacc aggctggtga gacctttgcc ccgcccagga ctccctccta tgtgggcgtg   1380
agcagcagca cctccgtgaa catgtccatg ggtggcactg atgggacac cttcagctgc   1440
ccacagacca gcttatccat gcagatttcg ggaatgtccc cccagctcca gtatatcatg   1500
ccatcaccct ccagcaatgc cttcgccact aaccagaccc atcagggttc ctataatact   1560
tttagattac acagccctg tgcactatat ggatataact tctccacatc ccccaaactg   1620
gctgccagtc ctgagaaaat tgtttcttcc caaggaagtt tcttggggtc ctcaccgagt   1680
gggaccatga cggatcggca gatgttgccc cctgtggaag gagtgcacct gcttagcagt   1740
gggggtcagc agagtttctt tgactctagg accctaggaa gcttaactct gtcatcatct   1800
caagtatctg cacatatggt ctgatgaagc ctttaagtta aatgacattt ggatctgtct   1860
aacatatttt cttttctt tttaaaagct atgtggaaag aaactctctg tggtttataa   1920
aatgtacata taatagaaaa tgaaggctca ctgggttttt tgactttatc atggtgagat   1980
tgtaattatc tatggtatat atgtatgctg tatatacata gcacatggag tatcacggcc   2040
cctattgttc ccctgtttca tccagttgca cggagtattg gcatgcgtgt agtatgttta   2100
agcaaagttc tcagactctt ttaaaaacaa gatggtaaac ttaaaacttg gcaattatac   2160
tatccagaag aacacttata acttaattta tcagaaaaat gctctaaacg gtttcatact   2220
tgatgtattg ataaccagca gtaaccagca tgtagagtct tgtgatttct gttattcttg   2280
gacacagtgt gagaatctaa aatacaaaag ccagttgaag tcttagtgtt agtcctgagg   2340
tatttgtaat catgaaggat cagctttttc attcctgctt attatttacc acacatacta   2400
tatgaccttg ggtctataaa aaaatcataa cccataataa ttgttatttt cttaaggaag   2460
gtaaaggaga ggcttgtgat ttttttttt acactttcca ttgggcacat aagaggttct   2520
tattcatctg tagagaacaa atttccagta ttttcgattt tttgcttatt ttatatatca   2580
aatagaccat taagaatgt tctataaaca tttttaaatt ccaattttca ccaggggagg   2640
aatatgtgat atgagtggaa tggcaaaagg aaaataaatc cacctcaaat tcattgattc   2700
caatgagaaa tgtctatctt ttaaatcaag agtaatacta ttgttaacta taccttatgt   2760
ttttgtatag tttgttttta aatttagaat attttttcca tcttgctctg agcttcctga   2820
ccgatagtat ataagtaaaa aaaatgcatt tatgctactt atttatatct tgtaattcct   2880
acacattgaa ccccttttccc cttcttaacc ttgtccgtct gcctgagtct ttcccaaaac   2940
agatagttcc taggcctgta tggtgttaaa taacacggtg aggaatttca gtaggttatc   3000
tccagcaatc tgtcttttgg gagctatagt gcaaaggcca aagccccatta ctataaagac   3060
cctcttggag gactaagaag gaagatacta attatgataa aggaactata aaactttaa   3120
```

| | |
|---|---|
| cctcaacaga atttgtaatg tcagaactgg agaaattaaa atcagtatta aatttttaa | 3180 |
| ttcctaaaat aatatatgca tggttgaaga gttaaaaaca agtaactttg agagcacagt | 3240 |
| atgagataaa taaaaaggc taagaataca tgatgaggca cattcccctt ctgaggagaa | 3300 |
| agcgaaataa catgtctgtg cattgaccca ttcattacat ttcatgtatc ttaagcaaaa | 3360 |
| gagcatgatt ttctctcatt gctaaaaaga gttgctttaa ctcatccctg gatttggtgg | 3420 |
| ggaaagggta caactcctga tttgctgttt cactttgaaa caacacaatt tgttagatac | 3480 |
| ttagggagat atactgttga atttgcacag gatgtgactc tgtttataca tattaacaaa | 3540 |
| tttccttttg gattccttag cagttcatca aattagtatt aaattttaa atttaaaact | 3600 |
| agcatgaagg gacatgaaat atttgcagta ggtggatcta tgtaagatgt ttgggtatgg | 3660 |
| cattaatagc ttgacaaaga tttggggaaa ggtgttaaga atgagtccat ctcagccaat | 3720 |
| agtgcttggt gtataattca agaacagaga gttttccatc ttgaaaaaac atggaaagta | 3780 |
| atgctctata cccatatgta ttaataagag cattttcctt cttgccgttg atcatttcag | 3840 |
| atgataccac aatatgagta taatttttta ttaatctttt ttctggtaaa attttagcaa | 3900 |
| tattgtacaa atgcttttt taggttttac tgtaaatatt aatcaccacg tcacttcaga | 3960 |
| gactagcctt ttattgctga attaaatgac atgcatacat tgataattat atatctgtat | 4020 |
| tttattaaaa agtacttaaa attatattaa aatatgttat taaacccttt | 4070 |

<210> SEQ ID NO 8
<211> LENGTH: 3233
<212> TYPE: DNA
<213> ORGANISM: Homo sapiens
<220> FEATURE:
<221> NAME/KEY: misc_feature
<223> OTHER INFORMATION: sapiens short stature homeobox 2 (SHOX2),
    transcript variant 1
<220> FEATURE:
<221> NAME/KEY: misc_feature
<223> OTHER INFORMATION: Accession Number - NM_003030.4

<400> SEQUENCE: 8

| | |
|---|---|
| cctcctccct ctcctccccc acctcctgtc ccattgatgt gttattattg gggggctgg | 60 |
| agcagtaaaa aaagaagaag gaaaaaaaga gcggggctct gctggcagag gttgagcgcc | 120 |
| gggctgacgt gcggcggcga tggaagaact tacggcgttc gtctccaagt cttttgacca | 180 |
| gaaagtgaag gagaagaagg aggcgatcac gtaccgggag gtgctggaga gcggccgct | 240 |
| gcgcggggcc aaggagccga ccggctgcac cgaggcgggc cgcgacgacc gcagcagccc | 300 |
| ggcagtccgg gcggccggcg gaggcggcgg cggaggaggc ggaggcggcg gcggaggagg | 360 |
| cggaggaggt gtaggaggag gaggagcagg cggaggagct ggaggagggc gctctcccgt | 420 |
| ccgggagctg gacatgggcg ccgccgagag aagcagggag ccgggcagcc cgcgactgac | 480 |
| ggagggtaga aggaagccaa cgaaagctga ggtccaggct acgctgcttc tcccgggcga | 540 |
| ggcgtttcgg tttcttgtgt ccccggagct gaaagatcgc aaagaggatg cgaaagggat | 600 |
| ggaggacgaa ggccagacca aaatcaagca gaggcgaagt cggaccaatt tcaccctgga | 660 |
| acaactcaat gagctggaga ggcttttga cgagaccac tatcccgacg ccttcatgcg | 720 |
| agaggaactg agccagcgac tgggcctgtc ggaggcccga gtgcaggttt ggtttcaaaa | 780 |
| tcgaagagct aaatgtagaa aacaagaaaa tcaactccat aaaggtgttc tcatagggc | 840 |
| cgccagccag tttgaagctt gtagagtcgc accttatgtc aacgtaggtg ctttaaggat | 900 |

```
gccatttcag caggatagtc attgcaacgt gacgcccttg tcctttcagg ttcaggcgca    960
gctgcagctg gacagcgctg tggcgcacgc gcaccaccac ctgcatccgc acctggccgc   1020
gcacgcgccc tacatgatgt tcccagcacc gcccttcgga ctgccgctcg ccacgctggc   1080
cgcggattcg gcttccgccg cctcggtagt ggcggccgca gcagccgcca agaccaccag   1140
caagaactcc agcatcgccg atctcagact gaaagccaaa aagcacgccg cagccctggg   1200
tctgtgacgc caacgccagc accaatgtcg cgcctgtccc gcggcactca gcctgcacgc   1260
cctccgcgcc ccgctgcttc tccgttaccc ctttgagacc tcgggagccg gccctcttcc   1320
cgcctcactg accatccctc gtccgctatc gcatcttgga ctcggaaagc cagactccac   1380
gcaggaccag ggatctcacg aggcacgcag gctccgtggc tcctgcccgt tttcctactc   1440
gagggcctag aattgggttt tgtaggagcg ggtttggggg agtctggaga gagactggac   1500
aggggagtgc tggaaccgcg gagtttggct caccgcaaag ctgcaacgat ggactcttgc   1560
atagaaaaaa aaatcttgtt aacaatgaaa aaatgagcaa acaaaaaaat cgaaagacaa   1620
acgggagaga aaaagaggaa gggaacttat ttcttaactg ctatttggca gaagctgaaa   1680
ttggagaacc aaggagcaaa aacaaatttt aaaattaaag tattttatac atttaaaaat   1740
atggaaaaac aacccagacg attctcgaga gactgggggg agttaccaac ttaaatgtgt   1800
gttttttaaaa atgcgctaag aaggcaaagc agaaagaaga ggtatactta tttaaaaaac   1860
taagatgaaa aaagtgcgca gctgggaagt tcacaggttt tgaaactgac cttttctgc    1920
gaagttcacg ttaacacgag aaatttgatg agagaggcgg gcctcctttt acgttgaatc   1980
agatgctttg agtttaaacc caccatgtat ggaagagcaa gaaaagagaa aatattaaaa   2040
cgaggagaga gaaaaataat attaacacaa aaaaatgcca cagacaatga tttctctgag   2100
aaattattat ggcaaaactg tctggactgc tgacagtaaa ttccggtttg catgttactt   2160
gtattccatt gatggtgtgt ctcctcccac ccccttatct cccatgcact cactccattt   2220
tcatcttcac tatgaaaaac aataccaaaa gtatctggaa attgatatat atatatccat   2280
atatatatat catatatttg ccatatatat atatatatat atatatatat atatatatat   2340
atatttgccc tgtctttgat cctggggaac aaaagaaaaa agtcagaaag ggaaaaaatt   2400
acactcattg tcctaagaag acagaggtgg gcagaatatg tggggaaagg aaaaagaaaa   2460
caagaccacc aaatgaaata atgaaggtac agcgcctcgc tgtgccagac acagtaggcg   2520
ctcaatcagt attagttccc accattcccc ttttcttgtg ttccttcttg ttggtttcct   2580
gaagtcctat ttgaagacag tggtttattt cccctctct atcccgtcaa attcaccttta   2640
aataacaccc agctagatac aggcactagg tttgtgtaag atatgttgat acacacgaac   2700
aaagtttatt ttgactataa tgtgtggact gactttcaac atttgcattt tatctcacaa   2760
aggtgtatct attcaagtaa cctttttttt ttgtttgttt gtttcttttt tgttttttt    2820
tttcttttgg ttgtttgttt caattcatgt agctatttaa actgggatac cttggactaa   2880
gccagtctgt atcccaattc gctagcaagc ctaagtttgt ggggttttgt ttttgttttt   2940
gttttacctt ctaatttaca agaaagagga aaagctcttc taactgaact ttggtatgcg   3000
gttgagcttt gtaactattt gttctccatg aaaacaaaat tatttatatt tgacatattt   3060
ttttctagtg tattaagtta ttttaaacaa aagatgttat ctcatgacgt gttgtcagta   3120
caaaatgtgt cgcctccaat tctgttaaac cttttaaata agtgccaagt tattaattga   3180
agacactttg cgatcaattg aatgaaaata tcgtttcatt tgaaaaaaaa aaa          3233
```

```
<210> SEQ ID NO 9
<211> LENGTH: 3161
<212> TYPE: DNA
<213> ORGANISM: Homo sapiens
<220> FEATURE:
<221> NAME/KEY: misc_feature
<223> OTHER INFORMATION: Homo sapiens short stature homeobox 2 (SHOX2),
      transcript variant 2
<220> FEATURE:
<221> NAME/KEY: misc_feature
<223> OTHER INFORMATION: Accession Number - NM_006884.3

<400> SEQUENCE: 9
cctcctccct ctcctccccc acctcctgtc ccattgatgt gttattattg gggggctgg       60 agcagtaaaa aagaagaag gaaaaaaaga gcggggctct gctggcagag gttgagcgcc      120
gggctgacgt gcggcggcga tggaagaact tacggcgttc gtctccaagt cttttgacca     180
gaaagtgaag gagaagaagg aggcgatcac gtaccgggag gtgctggaga gcgggccgct    240
gcgcggggcc aaggagccga ccggctgcac cgaggcgggc cgcgacgacc gcagcagccc    300
ggcagtccgg gcggccggcg gaggcggcgg cggaggagga ggaggcggcg gcggaggagga   360 cggaggaggt gtaggaggag gaggagcagg cggaggagct ggaggagggc gctctcccgt    420
ccgggagctg gacatgggcg ccgccgagag aagcagggag ccgggcagcc cgcgactgac    480
ggaggtgtcc ccggagctga agatcgcaa agaggatgcg aaagggatgg aggacgaagg    540
ccagaccaaa atcaagcaga ggcgaagtcg gaccaatttc accctggaac aactcaatga   600
gctggagagg ctttttgacg agacccacta tcccgacgcc ttcatgcgag aggaactgag   660
ccagcgactg ggcctgtcgg aggcccgagt gcaggtttgg tttcaaaatc gaagagctaa   720
atgtagaaaa caagaaaatc aactccataa aggtgttctc ataggggccg ccagccagtt   780
tgaagcttgt agagtcgcac cttatgtcaa cgtaggtgct ttaaggatgc catttcagca    840
ggatagtcat tgcaacgtga cgcccttgtc ctttcaggtt caggcgcagc tgcagctgga    900
cagcgctgtg gcgcacgcgc accaccacct gcatccgcac ctggccgcgc acgcgcccta    960
catgatgttc ccagcaccgc ccttcggact gccgctcgcc acgctggccg cggattcggc   1020
ttccgccgcc tcggtagtgg cggccgcagc agccgccaag accaccagca agaactccag   1080
catcgccgat ctcagactga agccaaaaa gcacgccgca gccctgggtc tgtgacgcca    1140
acgccagcac caatgtcgcg cctgtcccgc ggcactcagc ctgacgccc tccgcgcccc    1200 gctgcttctc cgttacccct ttgagacctc gggagccggc cctcttcccg cctcactgac    1260
catccctcgt cccctatcgc atcttggact cggaaagcca gactccacgc aggaccaggg   1320
atctcacgag gcacgcaggc tccgtggctc ctgcccgttt tcctactcga gggcctagaa    1380
ttgggttttg taggagcggg tttgggggag tctggagaga gactgcacag gggagtgctg   1440
gaaccgcgga gtttggctca ccgcaaagct gcaacgatgg actcttgcat agaaaaaaaa   1500
atcttgttaa caatgaaaaa atgagcaaac aaaaaaatcg aaagacaaac gggagagaaa   1560
aagaggaagg gaacttattt cttaactgct atttggcaga agctgaaatt ggagaaccaa   1620
ggagcaaaaa caaatttta aattaaagta ttttatacat ttaaaaatat ggaaaaacaa   1680
cccagacgat tctcgagaga ctggggggag ttaccaactt aaatgtgtgt ttttaaaaat   1740
gcgctaagaa ggcaaagcag aaagaagagg tatacttatt taaaaaacta agtgaaaaaa   1800
agtgcgcagc tggaagttc acaggttttg aaactgacct ttttctgcga agttcacgtt    1860
aacacgagaa atttgatgag agaggcgggc ctccttttac gttgaatcag atgctttgag   1920 tttaaacccca ccatgtatgg aagagcaaga aaagagaaaa tattaaaacg aggagagaga   1980
```

| | |
|---|---|
| aaaataatat taacacaaaa aaatgccaca gacaatgatt tctctgagaa attattatgg | 2040 |
| caaaactgtc tggactgctg acagtaaatt ccggtttgca tgttacttgt attccattga | 2100 |
| tggtgtgtct cctcccaccc ccttatctcc catgcactca ctccattttc atcttcacta | 2160 |
| tgaaaaacaa taccaaaagt atctggaaat tgatatatat atatccatat atatatatca | 2220 |
| tatatttgcc atatatatat atatatatat atatatatat atatatatat atttgccctg | 2280 |
| tctttgatcc tggggaacaa agaaaaaaag tcagaaaggg aaaaaattac actcattgtc | 2340 |
| ctaagaagac agaggtgggc agaatatgtg gggaaaggaa aaagaaaaca agaccaccaa | 2400 |
| atgaaataat gaaggtacag cgcctcgctg tgccagacac agtaggcgct caatcagtat | 2460 |
| tagttcccac cattcccctt ttcttgtgtt ccttcttgtt ggtttcctga agtcctattt | 2520 |
| gaagacagtg gtttatttcc ccctctctat cccgtcaaat tcaccttaaa taacacccag | 2580 |
| ctagatacag gcactaggtt tgtgtaagat atgttgatac acacgaacaa agtttatttt | 2640 |
| gactataatg tgtggactga cttttcaacat ttgcatttta tctcacaaag gtgtatctat | 2700 |
| tcaagtaacc tttttttttt gtttgtttgt ttctttttg tttttttttt tcttttggtt | 2760 |
| gtttgtttca attcatgtag ctatttaaac tgggatacct tggactaagc cagtctgtat | 2820 |
| cccaattcgc tagcaagcct aagtttgtgg ggttttgttt ttgttttgt tttaccttct | 2880 |
| aatttacaag aaagaggaaa agctcttcta actgaacttt ggtatgcggt tgagctttgt | 2940 |
| aactatttgt tctccatgaa aacaaaatta tttatatttg acatattttt ttctagtgta | 3000 |
| ttaagttatt ttaaacaaaa gatgttatct catgacgtgt tgtcagtaca aaatgtgtcg | 3060 |
| cctccaattc tgttaaacct tttaaataag tgccaagtta ttaattgaag cactttgcg | 3120 |
| atcaattgaa tgaaaatatc gtttcatttg aaaaaaaaaa a | 3161 |

<210> SEQ ID NO 10
<211> LENGTH: 3125
<212> TYPE: DNA
<213> ORGANISM: Homo sapiens
<220> FEATURE:
<221> NAME/KEY: misc_feature
<223> OTHER INFORMATION: Homo sapiens short stature homeobox 2 (SHOX2),
      transcript variant 3
<220> FEATURE:
<221> NAME/KEY: misc_feature
<223> OTHER INFORMATION: Accession Number - NM_001163678.1

<400> SEQUENCE: 10

| | |
|---|---|
| cctcctccct ctcctccccc acctcctgtc ccattgatgt gttattattg gggggggctgg | 60 |
| agcagtaaaa aaagaagaag gaaaaaaaga gcggggctct gctggcagag gttgagcgcc | 120 |
| gggctgacgt gcggcggcga tgaagaact tacggcgttc gtctccaagt cttttgacca | 180 |
| gaaagtgaag gagaagaagg aggcgatcac gtaccgggag gtgctggaga gcgggccgct | 240 |
| gcgcggggcc aaggagccga ccggctgcac cgaggcgggc cgcgacgacc gcagcagccc | 300 |
| ggcagtccgg gcggccggcg gaggcggcgg cggaggaggc ggaggcggcg gcggaggagg | 360 |
| cggaggaggt gtaggaggag gaggagcagg cggaggagct ggaggagggc gctctcccgt | 420 |
| ccgggagctg gacatgggcg ccgccagag aagcagggag ccgggcagcc cgcgactgac | 480 |
| ggaggtgtcc ccggagctga agatcgcaa agaggatgcg aaagggatgg aggacgaagg | 540 |
| ccagaccaaa atcaagcaga ggcgaagtcg gaccaatttc accctggaac aactcaatga | 600 |
| gctggagagg cttttgacg agacccacta tcccgacgcc ttcatgcgag aggaactgag | 660 |
| ccagcgactg ggcctgtcgg aggcccgagt gcaggttgg tttcaaaatc gaagagctaa | 720 |

```
atgtagaaaa caagaaaatc aactccataa aggtgttctc ataggggccg ccagccagtt    780
tgaagcttgt agagtcgcac cttatgtcaa cgtaggtgct ttaaggatgc catttcagca    840
ggttcaggcg cagctgcagc tggacagcgc tgtggcgcac gcgcaccacc acctgcatcc    900
gcacctggcc gcgcacgcgc cctacatgat gttcccagca ccgcccttcg gactgccgct    960
cgccacgctg gccgcggatt cggcttccgc cgcctcggta gtggcggccg cagcagccgc   1020
caagaccacc agcaagaact ccagcatcgc cgatctcaga ctgaaagcca aaaagcacgc   1080
cgcagccctg ggtctgtgac gccaacgcca gcaccaatgt cgcgcctgtc ccgcggcact   1140
cagcctgcac gccctccgcg ccccgctgct tctccgttac ccctttgaga cctcgggagc   1200
cggccctctt cccgcctcac tgaccatccc tcgtcccctc tcgcatcttg gactcggaaa   1260
gccagactcc acgcaggacc agggatctca cgaggcacgc aggctccgtg gctcctgccc   1320
gttttcctac tcgagggcct agaattgggt tttgtaggag cgggtttggg ggagtctgga   1380
gagagactgg acaggggagt gctgaaccg cggagtttgg ctcaccgcaa agctgcaacg   1440
atggactctt gcatagaaaa aaaaatcttg ttaacaatga aaaatgagc aaacaaaaaa   1500 atcgaaagac aaacgggaga gaaaagagg aagggaactt atttcttaac tgctatttgg   1560
cagaagctga aattggagaa ccaaggagca aaaacaaatt ttaaaattaa agtattttat   1620
acatttaaaa atatggaaaa acaacccaga cgattctcga gagactgggg ggagttacca   1680
acttaaatgt gtgttttttaa aaatgcgcta agaaggcaaa gcagaaagaa gaggtatact   1740
tatttaaaaa actaagatga aaaaagtgcg cagctgggaa gttcacaggt tttgaaactg   1800 accttttttct gcgaagttca cgttaacacg agaaatttga tgagagaggc gggcctcctt   1860
ttacgttgaa tcagatgctt tgagtttaaa cccaccatgt atggaagagc aagaaaagag   1920
aaaatattaa aacgaggaga gagaaaaata atattaacac aaaaaaatgc cacagacaat   1980
gatttctctg agaaattatt atggcaaaac tgtctggact gctgacagta aattccggtt   2040
tgcatgttac ttgtattcca ttgatggtgt gtctcctccc accccttat ctcccatgca    2100 ctcactccat tttcatcttc actatgaaaa acaataccaa agtatctgg aaattgatat    2160 atatatatcc atatatatat atcatatatt tgccatatat atatatatat atatatatat   2220
atatatatat atatatttgc cctgtctttg atcctgggga acaaaagaaa aaagtcagaa   2280
agggaaaaaa ttacactcat tgtcctaaga agacagaggt gggcagaata tgtggggaaa   2340
ggaaaaagaa aacaagacca ccaaatgaaa taatgaaggt acagcgcctc gctgtgccag   2400
acacagtagg cgctcaatca gtattagttc ccaccattcc ccttttcttg tgttccttct   2460
tgttggtttc ctgaagtcct atttgaagac agtggtttat ttccccctct ctatcccgtc   2520
aaattcacct taaataacac ccagctagat acaggcacta ggtttgtgta agatatgttg   2580
atacacacga acaaagttta ttttgactat aatgtgtgga ctgactttca acatttgcat   2640
tttatctcac aaaggtgtat ctattcaagt aaccttttt ttttgtttgt ttgtttcttt    2700
tttgtttttt tttttctttt ggttgtttgt ttcaattcat gtagctattt aaactgggat   2760
accttggact aagccagtct gtatcccaat tcgctagcaa gcctaagttt gtggggtttt   2820
gtttttgttt ttgtttttacc ttctaattta caagaaagag gaaaagctct tctaactgaa   2880
ctttggtatg cggttgagct ttgtaactat ttgttctcca tgaaaacaaa attatttata   2940
tttgacatat ttttttctag tgtattaagt tattttaaac aaaagatgtt atctcatgac   3000
gtgttgtcag tacaaaatgt gtcgcctcca attctgttaa acctttaaa taagtgccaa    3060
```

```
gttattaatt gaagacactt tgcgatcaat tgaatgaaaa tatcgtttca tttgaaaaaa    3120
aaaaa                                                                3125
```

TRANSCRIPTION FACTOR-BASED GENERATION OF PACEMAKER CELLS AND METHODS OF USING SAME

CROSS-REFERENCE TO RELATED APPLICATIONS

This application is a National Phase of International Application No. PCT/US2012/064204, filed Nov. 8, 2012, which designated the U.S. and that International Application was published under PCT Article 21(2) in English. This application also includes a claim of priority under 35 U.S.C. §119(e) to U.S. provisional patent application No. 61/557,812, filed Nov. 9, 2011.

BACKGROUND

Field of the Invention

Several embodiments of the present application relate generally to methods and compositions for the generation of pacemaker cells (e.g., cardiac cells that have regular, rhythmic electrical activity). In particular, some embodiments of the invention relate to gene and cell therapy methods (and associated compositions) to generate pacemaker cells using transcription factors.

Description of the Related Art

During cardiogenesis, cardiomyocytes become specialized to exhibit either ventricular, atrial, or pacemaker properties. The sinoatrial node (SAN), the primary pacemaker region of the heart, is a highly-specialized structure containing fewer than 10,000 pacemaker cells, which function to initiate contractions in the SAN. These SAN contractions then propagate to the rest of the excitable heart tissue and result in a heartbeat. Irregularities of excitable cardiac tissue and/or irregularities of pacemaker cells can lead to abnormalities in heart rhythm. Many cardiac abnormalities typically involve irregular heartbeat, tachycardia (where the heart rate is too high), or bradycardia (where the heart rate is too slow). These abnormalities are collectively known as arrhythmias.

Current therapies for cardiac arrhythmias typically rely on drug therapy, ablation, electronic pacemaker devices or combinations thereof. However, the usefulness of each of these therapies has met with limited and varying success. While antiarrhythmic drugs are widely prescribed and used, they may result in adverse systemic side effects in certain patient populations. Further, many drugs have a propensity to provoke new arrhythmic events, which can lead to an increase in morbidity. Radiofrequency ablation is used in some treatments of arrhythmias. Ablation involves permanent removal of the tissue identified as the source of, or critical to, the maintenance of the arrhythmias. While this method has found some success in the treatment of atrioventricular node reentry tachycardia, accessory pathway tachycardia, and atrial flutter, it has found limited success in the treatment of other arrhythmias. For instance, catheter ablation is less successful in treating more complex cases, such as atrial fibrillation (AF) or ventricular tachycardia (VT). Moreover, catheter ablation is not useful in the treatment of bradycardia. Electronic pacemaker devices can sustain heart rate, or deliver shocks to terminate tachycardias. However, the high cost of devices, and complications such as pulmonary collapse, hemorrhage, bacterial infection, and lead/generator failure or other types of malfunction represent limitations of the technology.

SUMMARY

In light of the limitations associated with traditional therapies for dysfunctions of cardiac pacing and arrhythmias, there is a need for alternative methods and compositions that can be used to modulate cardiac pacing and rhythm to treat cardiac arrhythmias (both simple and complex varieties), to treat heart failure (as in cardiac resynchronization applications of electronic pacemakers), and/or supplement or obviate the need for electrically-powered pacemakers.

Currently, biological pacemakers typically elicit their effects through the gene delivery of nucleotides that transcribe mutant ion-channel proteins. In contrast, several embodiments of the present invention operate through delivery to cells of polynucleotides that encode one or more transcription factors, which allows direct somatic-to-somatic cell reprogramming (e.g., a non-pacemaker cell is reprogrammed to a pacemaker cell or a malfunctioning pacemaker cell is reprogrammed to a functional pacemaker cell). Thus, in several embodiments, pacemaker cells are generated without the induced alteration expression of ion-channel proteins. Additional embodiments involve the conversion of stem cells, or in some embodiments cardiomyocytes or combinations of stem cells and cardiomyocytes, to biological pacemaker cells in vitro (e.g., by administration of one or more transcription factors disclosed herein), followed by subsequent implantation of the converted cells. Thus, delivery of the transcription factors, or cells converted by those transcription factors, treats a variety of cardiac rhythmic abnormalities and/or lessens or obviates the needs for traditional therapies.

Thus, there is provided in several embodiments, methods for generating a biological pacemaker using transcription factors in order to modify the electrical activity of the cardiac tissue of a subject, the method comprising identifying a subject having cardiac tissue exhibiting abnormal electrical activity, wherein the subject has cardiac tissue comprising quiescent cells, wherein the quiescent cells comprise one or more of cardiomyocytes and stem cells, wherein the quiescent cells do not exhibit spontaneous, repetitive electrical activity; and administering one or more transcription factors to the quiescent cells to generate treated cells, wherein the treated cells exhibit spontaneous, repetitive electrical activity, thereby modifying electrical activity of the cardiac tissue the subject.

In several embodiments, the abnormal cardiac electrical activity is due to a cardiac arrhythmia. However, other abnormalities in cardiac electrical activity, signaling or function can be addressed with the methods disclosed herein. For example, in several embodiments, the subject is afflicted with a condition selected from the group consisting of sick sinus syndrome, sinus bradycardia, tachycardia-bradycardia syndrome, atrial fibrillation, atrioventricular block, chronotropic incompetence, prolonged QT syndrome, and heart failure.

In several embodiments, the administration occurs in vitro, and the method further comprises administering the treated cells to the subject. Advantageously, however, the methods disclosed herein allow the administration to occur in vivo.

There are also provided methods of converting a population of stem cells through the use of transcription factors into cells suitable for generation of a biological pacemaker, comprising obtaining a population of stem cells, culturing the stem cells in vitro, wherein the cultured stem cells comprise quiescent cells that do not exhibit spontaneous, repetitive electrical activity, delivering one or more transcription factors to the quiescent cells to generate converted cells, wherein the converted cells exhibit spontaneous, repetitive electrical activity, thereby converting the stem cells into cells capable of generating a biological pacemaker.

There is additionally provided a method of treating a cardiac arrhythmia using transcription factors comprising identifying a subject suffering from cardiac arrhythmia, wherein the subject has cardiac tissue comprising quiescent cells, wherein the quiescent cells comprise one or more of cardiomyocytes and stem cells, wherein the quiescent cells do not exhibit spontaneous, repetitive electrical activity; and administering one or more of Tbx18, Shox-2, Tbx3, Tbx5, functional fragments thereof, or combinations thereof, to the quiescent cells to generate treated cells, wherein the treated cells exhibit spontaneous, repetitive electrical activity; thereby treating the cardiac arrhythmia.

There is also provided a method of treating a cardiac arrhythmia by generating a biological pacemaker using transcription factors, comprising identifying a subject suffering from cardiac arrhythmia, obtaining a population of converted stem cells, wherein, prior to the conversion, the stem cells comprised quiescent cells that did not exhibit spontaneous, repetitive electrical activity, wherein one or more of Tbx18, Shox-2, Tbx3, Tbx5, functional fragments thereof, or combinations thereof were administered to the quiescent cells to generate converted cells that exhibit spontaneous, repetitive electrical activity; and administering the converted cells to the subject, wherein the administered converted cells engraft into the cardiac tissue of the subject and continue to exhibit spontaneous, repetitive electrical activity, thereby generating a biological pacemaker and treating the cardiac arrhythmia.

In several embodiments, the one or more transcription factors are regulators of embryonic sinoatrial node development and/or promote de novo cellular differentiation into sinoatrial nodal cells. In several embodiments, the one or more transcription factors define the sinus venosus during development. In several embodiments, the one or more transcription factors are negative regulators of Nkx2.5 in the sinus venosus.

In several embodiments, the one or more transcription factors is selected from the group consisting of Tbx18, Shox-2, Tbx3, Tbx5, functional fragments thereof, and combinations thereof. In several embodiments, the one or more transcription factors comprises Tbx-18. In several embodiments, Tbx18 (or other Tbox factors) are used to cause myocytes to generate spontaneous electrical activity. In several embodiments, the one or more transcription factors comprises Shox-2. In some embodiments, Shox-2 is used to convert stem cells to cells that generate spontaneous electrical activity. However, in additional embodiments, Shox-2 may optionally be used to convert myocytes to pacemaker cells, and/or Tbx18 is used to convert stem cells to pacemaker cells.

In several embodiments, the administration of the transcription factors is in vivo, and is to a site selected from the group consisting of the apex of the heart, right branch of the Bundle of His, the left branch of the Bundle of His, the Purkinje fibers, the inter-ventricular septum, the right ventricular free wall, the left ventricular free wall, the SA node, the AV node. In several embodiments the administration site is accessed via the right ventricle, via the right atrium, or by accessing the heart directly. In several embodiments, direct access is achieved by a map guided catheter injection system, by fluoroscopy guidance, by X-ray guidance, by echocardiography guidance, by guidance via magnetic resonance imaging, or combinations thereof. Each particular subject may present with symptoms or other relevant medical issues that determine an optimal rout of administration.

In several embodiments, the administration of the transcription factors is achieved by delivering to the target tissue a DNA delivery system comprising a polynucleotide encoding the one or more transcription factors. In several embodiments, the DNA delivery system comprises a viral vector. Various viral vectors are used, depending on the embodiment, such as, for example, adenovirus, adeno-associated virus, lentivirus, retrovirus, HJV, HIV, and/or HSV. In embodiments wherein more that one transcription factor is administered, the transcription factors can optionally be packed in different viral vectors. Alternatively, in some embodiments, multiple transcription factors can be packaged in a single viral vector.

In several embodiments, however, the DNA delivery system comprises a non-viral vector. Various non-viral vectors can be used, depending on the embodiment, such as for example, liposomal vectors, a cationic polymers, and/or DNA binding polymers. In several embodiments, the DNA delivery system comprises naked DNA. In several embodiments, a patient that is immuno-suppressed or otherwise has deficient immune function may benefit from a non-viral delivery system.

In several embodiments, in addition to functioning like pacemaker cells, the treated cells exhibit characteristics that are similar to those of natural pacemaker cells. However, certain of these characteristics need not be present in order to have the treated cells function as pacemaker cells. In several embodiments, the treated cells exhibit a length-to-width morphology substantially similar to a length-to-width morphology of native SAN cells. In several embodiments, this length-to-width ratio is at least about 10. In several embodiments, the treated cells exhibit an increase in spontaneous intracellular $Ca^{++}$ oscillations. In several embodiments, the spontaneous, repetitive electrical activity increases in response to $\beta$-adrenergic stimulation. In several embodiments, the converted cells do not express atrial natriuretic peptide (ANP) or skeletal $\alpha$-actin ($\alpha$SkA).

In several embodiments, the subject has an electronic pacemaker to modify the electrical activity of the cardiac tissue, which in some patients may be implanted in the subject. In several embodiments, the generation of the biological pacemaker supplements the function of the electronic pacemaker (e.g., the workload of the electronic pacemaker is decreased due to the generation of the biological pacemaker). In several embodiments, the generation of the pacemaker cells serves as a temporary bridge until a replacement or alternative electronic pacemaker can be implanted in a subject. In several embodiments, however, the generation of the biological pacemaker functionally replaces the electronic pacemaker. In several embodiments, this functional replacement allows short-term, medium-term, long-term, or even permanent shut-off (or explanting) of the electronic pacemaker.

In several embodiments, there is also provided a method of generating a biological pacemaker using transcription factors to treat a cardiac arrhythmia comprising identifying a subject suffering from cardiac arrhythmia, wherein the subject has cardiac tissue comprising quiescent cells, wherein the quiescent cells comprise one or more of cardiomyocytes and stem cells, wherein the quiescent cells do not exhibit spontaneous, repetitive electrical activity; and administering one or more transcription factors to the quiescent cells to generate treated cells, wherein the treated cells exhibit spontaneous, repetitive electrical activity; thereby treating the cardiac arrhythmia.

In several embodiments, the subject is mammalian, and in several embodiments is a human. In several embodiments, the stem cells that are converted into pacemaker cells are embryonic stem cells, while in additional embodiments, they are adult stem cells, induced stem cells, or resident stem cells.

There is also provided herein a method of treating a dysfunction in cardiac electrical activity comprising obtaining cells converted into pacemaker cells according to the methods disclosed herein and administering the converted cells to a subject suffering from a dysfunction in cardiac electrical activity, wherein the converted cells exhibit spontaneous, repetitive electrical activity, thereby treating the dysfunction in cardiac electrical activity.

In several embodiments, the dysfunction in cardiac electrical activity comprises a cardiac arrhythmia. In several embodiments, the method further comprises isolating the converted cells prior to the administration.

In several embodiments the spontaneous, repetitive electrical activity is within about 65% to about 100% of the normal activity of pacemaker cells. In several embodiments, the administration of transcription factors causes a change in the rhythm of the heart of the subject. In several embodiments, the changed rhythm of the heart corresponds to a new heart rate within about 25% to about 35% of a normal heart rate.

Additionally provided are compositions for the generation of a biological pacemaker comprising: a DNA delivery system, the system comprising, a viral vector encoding Tbx18, Shox-2, Tbx3, Tbx5, functional fragments thereof, or combinations thereof, and a eukaryotic promoter.

In several embodiments, the viral vector is an adenoviral vector. In several embodiments, the adenoviral vector further comprises the following operably linked components in sequence, a first inverted terminal repeat sequence (ITR), a first lox P site, a packaging site ($\psi$, psi), a cytomeglovirus promoter, a sequence encoding Tbx18, Shox2, or combinations thereof, an internal ribosome entry site (IRES), a polyadenylation signal (An), a second lox P site, a sequence encoding the adenovirus early region 2 and early region 4 genes; and a second inverted repeat sequence (ITR).

Several embodiments disclosed herein relate to a population of cells for the generation of a biological pacemaker comprising a plurality of stem cells, wherein the stem cells have been contacted with one or more transcription factors selected from the group consisting of Tbx18, Shox-2, Tbx3, Tbx5, functional fragments thereof, and combinations thereof, wherein the one or more transcription factors induce an increase in the spontaneous, repetitive electrical activity of the cells, wherein the increase in the spontaneous, repetitive electrical activity of the cells is capable of generating an ectopic contraction of the cells, and wherein the stem cells are suitable for administration to a subject in need of biological pacemaker function.

In several embodiments, the stem cells are selected from the group consisting of embryonic stem cells, non-embryonic stem cells, bone marrow-derived stem cells, adipose-derived stem cells, induced pluripotent stem cells, and cardiac stem cells.

There is also provided for herein a use of one or more transcription factors selected from the group consisting of Tbx18, Shox-2, Tbx3, Tbx5, functional fragments thereof, and combinations thereof to convert quiescent cells that do not exhibit spontaneous, repetitive electrical activity into pacemaker cells that exhibit spontaneous, repetitive electrical activity.

In several embodiments, there are provided methods for generating a biological pacemaker using transcription factors comprising identifying a subject having cardiac tissue comprising quiescent cells that do not exhibit spontaneous, repetitive electrical activity and administering one or more transcription factors to the quiescent cells to generate treated cells, wherein the treated cells exhibit spontaneous, repetitive electrical activity, thereby treating said cardiac arrhythmia. In several embodiments, the subject was previously suffering from cardiac arrhythmia.

In several embodiments, there is also provided a method for treating cardiac arrhythmia comprising identifying a subject having cardiac tissue comprising quiescent cells, the subject suffering from cardiac arrhythmia, wherein the quiescent cells do not exhibit spontaneous repetitive electrical activity, and administering one or more of Tbx18 and/or Shox2 (or fragments thereof) to the quiescent cells to generate treated cells, wherein the treated cells exhibit spontaneous repetitive electrical activity, thereby treating the cardiac arrhythmia.

In several embodiments, the quiescent cells comprise cardiomyocytes. In other embodiments, the quiescent cells comprise stem cells. In still additional embodiments, the quiescent cells comprise malfunctioning sinoatrial node cells (e.g. sinoatrial node cells that signal at levels that are too fast or too slow relative to normal functioning pacemaker cells). In other embodiments, the quiescent cells comprise other cells found in the heart and/or other somatic cells not found in the heart.

In several embodiments, there is also provided a method of converting a population of stem cells into cells suitable for generation of a biological pacemaker, the method comprising obtaining a population of stem cells, culturing the stem cells in vitro, wherein the cultured stem cells comprise quiescent cells that do not exhibit spontaneous repetitive electrical activity, and administering one or more transcription factors to the quiescent cells to generate converted cells. In several embodiments, the converted cells exhibit spontaneous repetitive electrical activity, and thus are capable of generating a biological pacemaker in vivo. In several embodiments, the stem cells comprise cardiac stem cells. In several embodiments, in vitro conversion can be performed on cardiomyocytes, other cells found in the heart, and/or other somatic cells not found in the heart.

In several embodiments, there are also provided methods of treating a cardiac arrhythmia by generating a biological pacemaker using transcription factors, the method comprising identifying a subject suffering from cardiac arrhythmia, obtaining a population of converted stem cells, wherein, prior to the conversion, the stem cells comprised quiescent cells that did not exhibit spontaneous repetitive electrical activity, wherein one or more of Tbx18 and Shox2 (or fragments thereof) were administered to the quiescent cells to generate converted cells, the converted cells exhibiting spontaneous repetitive electrical activity, and administering the converted cells to the subject, wherein the converted cells engraft into the cardiac tissue of the subject and continue to exhibit spontaneous repetitive electrical activity, thereby generating a biological pacemaker and treating the cardiac arrhythmia. In several embodiments, the converted cells are isolated, purified, selected for, or otherwise concentrated prior to administration to the subject. As discussed above, in several embodiments, instead of, or in conjunction with stem cells, other quiescent cells types are converted to pacemaker cells. In several embodiments, cells converted in vitro to cells that exhibit spontaneous repetitive electrical activity include cardiomyocytes.

In several embodiments, the methods provided herein utilize mammalian stem cells to treat mammalian subjects. In several embodiments, the subject is a human.

In several embodiments, the one or more transcription factors are regulators of embryonic sinoatrial node development. In several embodiments, the one or more transcription factors promote de novo cellular differentiation into sinoatrial nodal cells. In still additional embodiments, the one or more transcription factors not only regulate embryonic sinoatrial node development but also promote de novo cellular differentiation of precursor cells into sinoatrial nodal cells. In further embodiments, the one or more transcription factors provide a positive or negative regulatory input on such development or differentiation pathways. In several embodiments, the one or more transcription factors define the sinus venosus during cardiac development. In some embodiments, the one or more transcription factors are negative regulators of Nkx2.5 in the sinus venosus (or other regions of the developing heart). For example, the one or more transcription factors may negatively regulate a pathway in which Nkx2.5 signaling is involved. Further, the one more transcription factors may negatively regulate the expression (either at the RNA or protein level) of Nkx2.5. Moreover, the one or more transcription factors may indirectly regulate Nkx2.5, or a signaling pathway related thereto (e.g., the one or more transcription factors regulate a pathway that thereafter negatively regulates Nkx2.5).

In several embodiments, the one or more transcription factors is selected from the group consisting of Tbx18, Shox2, Tbx3, Tbx5 or combinations thereof. In several embodiments, variants of Tbx18, Shox2, Tbx3, Tbx5 are used alone or in combination. In some embodiments, functional fragments of Tbx18, Shox2, Tbx3, Tbx5 are used either alone or in combination. In additional embodiments, related family members of these transcription factors may also be used. In some embodiments, human transcription factors are used, while in other embodiments homologs from different species are used (either in place of or in conjunction with the human transcription factor(s)). In further embodiments, additional transcription factors, proteins, biologic molecules, or pharmacological agents are administered prior to, concurrently with, or subsequently to the one or more transcription factors in order to enhance the effect of the one or more transcription factors in generation of a biological pacemaker or conversion of stem cells. In some embodiments, for example, a traditional pharmacological agent that is used to treat cardiac arrhythmia is administered concurrently with the one or more transcription factors in order to provide a short-term bridge to allow the generated biological pacemaker to take full functional effect in a subject. In several embodiments, the one or more transcription factors comprises Tbx18 while in some embodiments, the one or more transcription factors comprises Shox-2. In still additional embodiments, Tbx18 and Shox2 are both used. However, in some embodiments, these two transcription factors are administered at discrete time frames (that optionally overlap in some embodiments). Additionally, Tbx18 and Shox2, are administered separately in some embodiments (e.g., different delivery systems are used). In several embodiments, a functional fragment of one transcription factor is used in conjunction with one (or more) full length transcription factors. In still additional embodiments, combinations of functional fragments of transcription factors are used.

In some embodiments, administration of the one or more transcription factors comprises administration of a DNA delivery system comprising a polynucleotide encoding the one or more transcription factors. In several embodiments, the DNA delivery system comprises a viral vector. A variety of different viral vectors are used, depending on the embodiment, based on the transcription factor(s) to be delivered, the size of the polynucleotide(s), the route of administration, and the general health status of the patient, among other variables. In some embodiments, the viral vector is selected from the group consisting of adenovirus, adeno-associated virus, lentivirus, retrovirus, HJV, HIV, and HSV. As discussed above, more than a single transcription factor is administered in certain embodiments. In some embodiments, each of the transcription factors delivered is delivered in the same type of virus. In some embodiments, however, a first transcription factor is delivered in a first type of virus, while a second transcription factor is delivered in a second type of virus. In this manner, a desired expression profile of each of the transcription factors can be generated based on the characteristics of the virus chosen (e.g., the time from infection with the virus to expression of the transgene carried by the virus). For example, certain viruses provide longer-term expression of the polynucleotides that they carry as compared to other viruses. In still other embodiments, more than one viral vector can be used to deliver a single transcription factor.

Alternatively, in several embodiments, the DNA delivery system comprises a non-viral vector. Non-viral vectors, in some embodiments, are selected from liposomal vectors, cationic polymers, and/or DNA binding polymers. In additional embodiments naked DNA encoding the one or more transcription factors is delivered. In still additional embodiments wherein more than one transcription factor is administered, a combination of viral and non-viral delivery systems may be used.

In several embodiments, the methods disclosed herein result in the generation of cells that exhibit spontaneous, repetitive, electrical activity. In some embodiments that spontaneous, repetitive, electrical activity is between about 50% to about 100% of the normal activity of healthy pacemaker cells. In some embodiments, a biological pacemaker can be generated even when the generated cells exhibit spontaneous, repetitive, electrical activity that is between about 5% to about 50% of the normal activity of healthy pacemaker cells. Thus, the methods disclosed herein are suitable for generating a biological pacemaker when the generated cells exhibit spontaneous, repetitive, electrical activity between about 5% to about 15%, about 15% to about 25%, about 25% to about 35%, about 35% to about 45%, about 45% to about 55%, about 55% to about 65%, about 65% to about 75%, about 75% to about 85%, about 85% to about 95%, or about 95% to about 100% of the normal activity of healthy pacemaker cells. In several embodiments, the generated cells exhibit spontaneous, repetitive, electrical activity of greater than 100% of the normal activity of healthy pacemaker cells.

In addition to changing the electrical activity of the target cells, in several embodiments administration of one or more transcription factors (or cells converted into biological pacemaker cells) causes a subsequent change in the rhythm of the heart. In several embodiments, the resultant heart rhythm is within about 5% to about 15%, about 15% to about 25%, about 25% to about 35%, about 35% to about 45%, about 45% to about 55%, about 55% to about 65%, about 65% to about 75%, about 75% to about 85%, about 85% to about 95%, or about 95% to about 100% of normal heart rhythm (taking into account the age and health history of a particular patient). In several embodiments, increases in heart rhythm of greater than 100% are achieved.

In several embodiments, the administration of one or more transcription factors (or cells converted into biological pacemaker cells) is to a subject having an implanted electronic pacemaker. In some embodiments, the generation of a biological pacemaker due to set administration reduces the dependence of the subject on the implanted electronic pacemaker. In some embodiments, generation of the biological pacemaker is for the purpose of providing a bridge therapy during which time all or a portion of the electronic pacemaker can be replaced (e.g., if a portion of the electronic pacemaker has become infected). In still additional embodiments, the generation of a biological pacemaker obviates the need for an implanted electronic pacemaker, and as such, the implanted electronic pacemaker can be permanently removed from the subject. In further embodiments, an electronic pacemaker may be implanted in conjunction with administration of one or more transcription factors (or converted biological pacemaker cells) such that reliance on the electronic pacemaker is reduced.

Multiple routes of administration may optionally be used, depending on the embodiment. Various factors determine what target site will be used including, but not limited to, where healthy tissue is available to generate a biological pacemaker, if the methods disclosed herein are to be used to re-functionalize a malfunctioning pacemaker cell, if one or more transcription factors are to be administered or if converted cells are to be administered. In some embodiments, administration is into the apex of the heart. In some embodiments, administration is to the inter-ventricular septum. In some embodiments, administration is to the right ventricular free wall. In some embodiments, administration is to the left ventricular free wall. In some embodiments, administration is via the right ventricle. In some embodiments, administration is via the right atrium. In several such embodiments, a right-sided approach advantageously reduces the risk of embolism and/or stroke. In some embodiments, administration is made via more than one of the above routes, either concurrently or at different times.

As discussed above, in some embodiments, the methods disclosed herein are used to restore (either partially or fully) the function of an existing pacemaker cell, or a cell within the cardiac conduction system. In some embodiments, administration is to the right or left branch of the Bundle of His. In some embodiments, administration is to the Purkinje fibers. In still additional embodiments, administration is to the SA node and/or to the AV node.

In certain embodiments wherein converted cells are delivered, intravenous administration is used. In some embodiments, intra-coronary administration is used.

Depending on the circumstance, in some embodiments administration (of one or more transcription factors or of converted biological pacemaker cells) is made by accessing the heart directly (e.g., injection during removal of an electronic pacemaker). In some embodiments, a catheter is used for administration. In some embodiments, the catheter comprises a map guided catheter injection system. In some embodiments, fluoroscopy guidance is used to guide a catheter (or other administration system) to the target tissue within the heart. In some embodiments, x-ray guidance is used. Echocardiography guidance is used in additional embodiments as well as magnetic resonance imaging, in certain embodiments. In some embodiments, more than one of the above modes of guidance vehicles are used concurrently or at different times during administration.

In addition to the methods disclosed above, there is also provided herein a composition for the generation of a biological pacemaker comprising a DNA delivery system, the system comprising a viral vector encoding Tbx18, Shox2, or combinations thereof, and a eukaryotic promoter. In one embodiment, the viral vector is an adenoviral vector however, as discussed above a variety of different viral vectors may also be used, depending on the embodiment. In several embodiments, the adenoviral vector further comprises the following operably linked components in sequence: a first inverted terminal repeat sequence (ITR), a first lox P site, a packaging site ($\psi$, psi), a cytomeglovirus promoter, a sequence encoding Tbx18, Shox2, or combinations thereof, an internal ribosome entry site (IRES), a polyadenylation signal (An), a second lox P site, a sequence encoding the adenovirus early region 2 and early region 4 genes, and a second inverted repeat sequence (ITR).

In several embodiments, the dose of a viral construct to be administered is based on plaque-forming units, which is a well-established unit of measurement in the viral arts. In some embodiments, a dose of between about $1\times10^8$ and $1\times10^{10}$ pfu (in volumes ranging from 50 to 200 microliters) are used. With respect to delivery of cells converted to be biological pacemaker cells, doses of cells range between $1\times10^5$ and $1\times10^8$ cells. Higher or lower doses may be used, depending (among other factors) on the severity of cardiac arrhythmia in the subject, the presence or absence of an electronic pacemaker, and/or the size of the heart of the subject.

Also provided for herein is a population of cells for the generation of a biological pacemaker comprising a plurality of stem cells, wherein the stem cells have been contacted with one or more transcription factors selected from the group consisting of Tbx18, Shox2, and combinations thereof, wherein the one or more transcription factors induce an increase in the spontaneous, repetitive electrical activity of the cells, wherein the increase in the spontaneous, repetitive electrical activity of the cells generates spontaneous, repetitive ectopic contractions, and wherein the stem cells are suitable for administration to a subject in need of biological pacemaker function.

In several embodiments, the stem cells are selected from the group consisting of embryonic stem cells, non-embryonic stem cells, bone marrow-derived stem cells, adipose-derived stem cells, induced pluripotent stem cells, and cardiac stem cells. In one embodiment, the population of cells comprises harvested adult cardiac stem cells that have been converted to cells with the biological pacemaker phenotype.

Also provided for herein is the use of one or more transcription factors selected from the group consisting of Tbx18 and Shox2 to convert quiescent cells that do not exhibit spontaneous, repetitive electrical activity into pacemaker cells that exhibit spontaneous, repetitive electrical activity.

BRIEF DESCRIPTION OF THE DRAWINGS

FIG. 2A depicts a significant increase in the number of spontaneously beating NRVM cultures. Each "n" represents one well of a 24-well plate. FIG. 2B shows representative action potential (AP) traces from GFP-(2B left) and Tbx18-NRVMs (2B right). FIG. 2C depicts the maximum diastolic potential (left), index of automaticity (center), and the total cell number (right) of spontaneously-oscillating $Ca^{2+}$ transients are summarized. FIG. 2D depicts representative $I_{K1}$ raw traces on the left and the summarized $I_{K1}$ densities at −140 mV are on the right. FIG. 2E depicts HCN4 immunostaining (HCN4-white, nuclei-blue) in GFP-(left) or Tbx18-NRVMs (middle). Summary data are shown on the right. FIG. 2F (left) depicts that Tbx18 transduction leads to a 3.8-fold increase in the number of NVRMs expressing HCN4 while 2F (right) depicts a 1.4-fold increase in HCN4 protein levels in Tbx18-NRVMs. FIG. 2G depicts that Tbx18-transduced cells exhibited $I_f$ at a density (−5.2±1.3 pA/pF at −140 mV, n=3) consistent with that reported in rabbit SAN cells. FIGS. 2H and 2I depict the changes of relative mRNA levels of selected genes comparing Tbx18-NRVMs normalized to GFP-NRVMs (left) and SAN normalized to LV (right). SAN and Tbx18-NRVMs demonstrate similar pattern of normalized transcript levels.

FIG. 3A depicts line-scan confocal imaging of Tbx18-NRVMs resolved localized $Ca^{2+}$ release events (LCRs) preceding each whole-cell $Ca^{2+}$ transient (n=8 out of 10 cells), recapitulating the LCRs observed in native SAN pacemakers. FIG. 3B depicts LCRs in control cells. Occasional randomly-distributed sparks were observed. FIG. 3C depicts that LCRs had an average period of 72±1% of that of the cycle length. FIG. 3D depicts spatially averaged $dF/F_0$ plots of changes in $Ca^{2+}$ concentration which depict a 2.3 fold increase in the caffeine (20 mM) induced $Ca^{2+}$ transients in the Tbx18-NRVMs compared to the controls. FIG. 3E depicts the spontaneous $Ca^{2+}$ transients were suppressed by 47±6% on superfusion with the RyR blocker, ryanodine (10 μM) in Tbx18-NRVMs in comparison to only 12±2% suppression in controls. FIG. 3F depicts Western blot experiments demonstrated a decrease in the total PLB levels and an increase in phosphorylated PLB (se16) akin to the adult rat SAN. FIG. 3G indicates that no changes in the protein levels of SERCA2A, NCXI and RyR were observed in the Tbx18-NRVMs in comparison to the controls. The relative p-PLB (Ser16) level was 65-fold higher in Tbx18-NRVMs in comparison to GFP-NRVMs (FIG. 3F, left panel), mimicking the augmentation of pPLN found in the SAN compared to that in the ventricular myocardium (FIG. 3F, right panel). Differences in the protein levels of SERCA2a, NCX1 and ryanodine receptor (RyR) were not detectable between Thx18- and GFP-NRVMs (FIG. 3G), consistent with findings in the rabbit SAN versus left ventricle. FIG. 3H depicts data related to the intracellular cAMP levels in GFP-NVRMs (open bars) and Tbx18-NVRMs (hatched bars). Intracellular cAMP levels were significantly higher in Tbx18-NRVMs compared to GFP-NRVMs, which mimics the increase known to exist between the rabbit SAN compared to ventricular myocardium. FIG. 3I depicts data related to $Ca^{2+}$ transients in GFP- or Tbx18 NVRMs. Application of the PKA inhibitor (PKI, 15 μM) led to cessation of spontaneous whole-cell $Ca^{2+}$ transients in Tbx-NRVMs, but had no effect on GFP-NRVMs. FIG. 3J indicates LCRs from Tbx18-NRVMs are longer and wider than spontaneous $Ca^{2+}$ release events from GFP-NRVMs, measured as full width at half-maximal duration (FWHD, left panel) and full duration at half-maximal width (FDHW, left panel) and. Amplitudes of the $Ca^{2+}$ signals (measured in arbitrary units of $F/F_o$, right panel) are similar between the two groups.

FIG. 4A depicts neonatal rat SANs, demarcated by HCN4 expression (top middle), that exhibit weaker and unstructured sarcomeric α-actinin (α-SA) expression (top panel). Bottom left: Zoom-in image of the boxed area in top left. FIG. 4B indicates a 28% reduction in cell area and a 33% reduction (left and right, respectively) in Tbx18-NRVMs membrane capacitance compared to control. FIG. 4C: tri-methylation level on H3K27 (left) indicates that Tbx18 increased the inactivity of Cx43, Kir2.1, and α-SA promoters while relieving its repressive epigenetic pressure on HCN4 promoter normalized to control. H3K4me3 levels (right) indicate that ratio of active HCN4 promoter regions increased upon Tbx18 expression while the transcriptionally active promoter regions of Cx43, Kir2.1, and a-SA have decreased upon Tbx18 expression.

FIGS. 5A-5H depict investigations of genes and cell markers characteristic of the fetal heart. The data supports Tbx18-induced specific re-engineering rather than dedifferentiation to an embryonic/fetal state. FIGS. 5A-5B depict the expression of atrial natriuretic peptide (ANP) in NRVMs induced by 24-hour stimulation with endothelin-I (100 nM). ANP expression was suppressed by Tbx18 expression (B, bottom panel) while GFP had no effect (A, bottom panel). FIG. 5C depicts the expression of skeletal α-actin (αSkA) in Tbx18-NRVMs. FIG. 5D depicts expression of phosphohistone 3 (H3P, a mitotically-active cell marker) and incorporation of EdU (an analog of BrdU, a marker for mitosis and nascent DNA synthesis) in GFP- and Tbx18-NRVMs (n=3). Immunohistochemical data are shown in the top panels and summary data in the corresponding lower panels. Expression and incorporation of these markers in Tbx18- and GFP-NRVMs is comparable, supporting the conclusion that the Tbx18-NRVMs did not dedifferentiate to an embryonic/fetal state. FIGS. 5E and 5G indicate the existence of only minor global differences between Tbx18- and GFP-NRVMs in a comparison of expression of 84 genes related to chromatin remodeling. FIGS. 5F and 5H show a similar comparison between iPS cells and their parental fibroblasts.

FIG. 6A indicates that the focal expression of Tbx18 in the apex of guinea pig hearts in vivo created ectopic ventricular beats (right panel) as compared to GFP (left panel). FIG. 6B indicates that the rate of ectopic ventricular beats in Tbx18-injected animals at day 3-5 after gene delivery is significantly higher than the control.

FIG. 9A depicts a Tbx18-transduced induced SAN (iSAN) cell (GFP-positive cell, top photographs) versus a native cell (bottom). FIG. 9B depicts SAN myocytes compared to Tbx18-VMs and GFP-VMs. The upper panels are bright field images, while the lower fields are fluorescent images. Immunostaining against α-SA revealed disorganized myofibrillar structure in Tbx18-VMs similar to that of native SAN myocytes. FIG. 9C depicts representative bight field images of freshly-isolated, living SAN myocytes, Tbx18-VMs (reported by GFP expression), and GFP-VMs (top panels) and immunostained, fixed myocytes (lower panels). FIG. 9D depicts an analysis of myocyte length-to-width ratio and whole-cell capacitance as measures of cell shape and size from freshly-isolated, living myocytes.

Tbx18-VMs are smaller in size and spindle-shaped compared to GFP-VMs (n=53 for Tbx18-VMs and 80 for GFB-VMs and non-transduced VMs, p<0.01), but are similar to native SAN myocytes (n=24). FIG. 9E depicts spontaneous action potentials recorded from freshly-isolated single Tbx18-VMs (n=5, middle panels) using a perforated-patch current-clamp technique. These data indicate that Tbx18 display robust and rhythmic APs with prominent diastolic depolarization, similar to the native SAN myocytes (left panels). The same recordings are expanded in the lower panels to show prominent diastolic depolarization in Tbx18-VMs and native SAN myocytes. The right panels depicts GFP-VMs displaying a stable resting membrane potential and firing a single action potential only upon electrical stimulation. FIG. 9F indicates the action potential parameters of Tbx18-VMs (n=5) were closer to native SAN myocytes (n=6) than to GFP-VMs (n=6). FIG. 9G depicts length-to-width ratio of Tbx18-VMs at 1 week, 3 weeks, and 6 weeks, compared to native SAN myocytes, GFP-VMs at 1 week, and a no-virus control.

FIGS. 10A and 10B depict scatter plots for Tbx18-NVRMs vs. GFP-NVRMs and iPS vs. parental fibroblasts (Fibs), respectively. The scatter plot depicts no discernible changes to transcripts levels related to stemness in Tbx18-NRVMs compared to control. FIGS. 10C and 10D depict RT-PCR array of 84 gene transcripts related to related to the identification, growth and differentiation of stem cells.

FIG. 25A depicts the layout of the 6-well multi-electrode array (MEA, left panel) and a representative image of NRVMs cultured as a monolayer on such a well. FIG. 25B depicts the average firing rates recorded from the MEAs demonstrating a significantly faster baseline chronotropy in Tbx18-NRVMs compared to that in control. Firing rates of Tbx18-NRVMs increased significantly upon β-adrenergic stimulation by changing the basal media with one containing 1 μM isoproterenol (ISO). Subsequent cholinergic challenge with 1 μM acetylcholine (ACh) significantly slowed the firing rates of Tbx18-NRVMs. In contrast, the chronotropy of GFP-NRVMs responded little to the autonomic inputs. FIG. 25C depicts representative raw traces from an electrode of a 6-well MEA plated with Tbx18-NRVMs. FIG. 25D depicts immunostaining on Tbx18-NRVMs (GFP$^+$ cells), demonstrating robust expression of β-adrenergic receptors and M$_2$ muscarinic receptors. FIGS. 25E and 25F depict electrocardiographic recordings of an intact perfused heart injected with Tbx18 at the apex, in vivo. As discussed below, other sites of administration are used, depending on the embodiment. Seven days post-injection, the heart was harvested, perfused, and cryoablated at the AV junctional region. The polarity and morphology of the ectopic beats (FIG. 25E, left panel) is identical to those of electrode-paced beats at the site of transgene injection (FIG. 25E, right panel). In contrast, most control hearts (7/10) showed a narrow-QRS junctional escape rhythm (FIG. 25F, left panel), which were opposite in polarity and morphology to those of electrode-paced beats at the apex (FIG. 25F, right panel). FIG. 25G indicates the chronotropic response of Tbx18-injected hearts to autonomic inputs, assessed by changing the perfusate (normal Tyrode's solution) to one containing 1 μM isoproterenol for β-adrenergic stimulation followed by one containing 1 μM acetylcholine for cholinergic suppression.

FIG. 26A depicts Tbx18-transduced ventricular myocytes assayed three days after in vivo gene transfer to validate the sensitivity of single-cell transcript detection by RT-qPCR. The data indicates Tbx18 transcript levels could be reliably detected over a wide range from very low (2.6% of GAPDH, cell 1) to very high (168% of GAPDH, cell 8). FIG. 26B depicts RT-qPCR results of VMs freshly isolated from the guinea pigs 6-8 weeks after the initial in vivo gene transfer, indicating that the transcript levels of Tbx18 in spontaneously-beating cells were either small (cells 1 and 2) or negligible (cells 3 and 4). A Tbx18-Vm with a strong GFP signal (cell 5) exhibited a larger relative amount of Tbx18.

FIG. 26C depicts a negative control (VMs expressing GFP alone were assayed for Tbx18).

FIG. 29A indicates an ectopic idioventricular rhythm at 165±14 bpm (n=3/3). FIG. 29B depicts electrocardiograms consistent with biological pacing from the Tbx18 injection site. FIG. 29C indicates the hearts responded to autonomic regulation in a manner similar to the short-term, Tbx18-injected hearts (FIG. 25G).

DETAILED DESCRIPTION

Figure 1A:
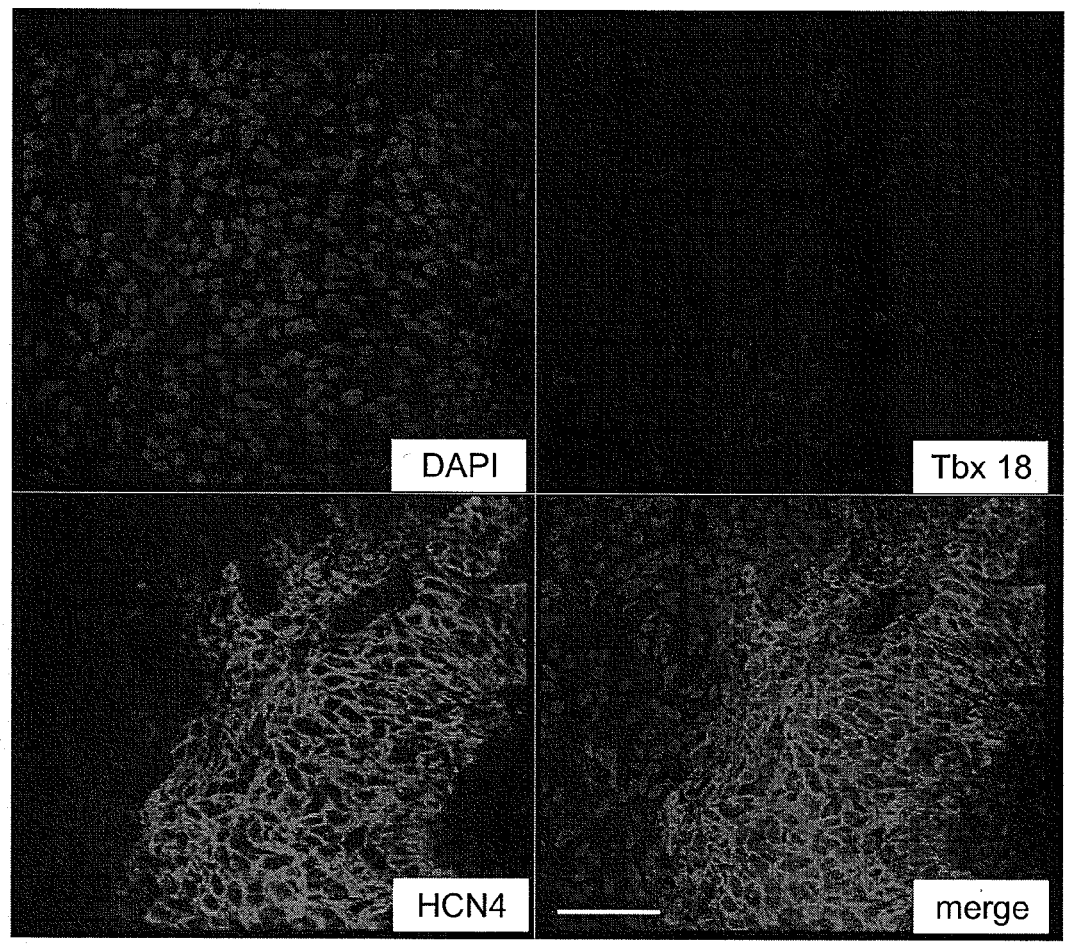
FIGS. 1A-1B depict the immunohistochemistry of neonatal (1A) and adult (1B) rat heart SAN cells. The SAN is demarcated by HCN4 co-staining and separated from the surrounding atria. Scale bar: 50 µm.

Background
Abnormalities of Excitable Tissue

Cardiac arrhythmias belong to a heterogeneous group of conditions in which there is abnormal electrical activity in the heart. As the result of an arrhythmia, heart rate may be too fast, too slow and/or may be regular or irregular. Normal electrical activity in the heart results from an electrical impulse that originates from the right atrium of the heart, in particular the sinus node (also referred to as the sino-atrial node, the SA node and/or SAN). This impulse induces contraction of both atria. The impulse then passes through the atrioventricular (or AV) node and through both ventricles via the Bundle of His and the Purkinje fibers. The result is a synchronized contraction of the heart muscle, and thus, blood flow. Normal adult heart rates range from 60 to 80 beats per minute, while the resting heart rate in children is typically much faster.

Bradycardias (HR of <60 bpm) have multiple possible etiologies, namely slowed signals from the sinus node (sinus bradycardia), pauses in the normal activity of the sinus node (sinus arrest), or blockages of the electrical impulse from the atria to the ventricles (AV block). Tachycardias (resting HR of >100 bpm) may cause mere palpitations (a subject becomes abnormally aware their heart beat) and may simply be the result of sympathetic nervous system stimulation of the sinus node (known as sinus tachycardia), for example during exercise or physical stress. Tachycardia that is not sinus tachycardia may result from abnormal impulses in addition to the normal cardiac cycle. Abnormal impulses can begin by one of three mechanisms: automaticity, reentry or triggered activity.

Certain cardiac tissues are capable of initiating an electrical impulse on their own, which is known as automaticity. Normally, such automatic cells are located in the conduction system of the heart (the SA node, AV node, Bundle of His and Purkinje fibers). The sinoatrial node is a single specialized location in the atrium which has a higher automaticity (a faster pacemaker) than the rest of the heart, and therefore is usually responsible for setting the heart rate, and initiating each heartbeat.

Re-entry arrhythmias occur when an electrical impulse recurrently circulates through a small region of the heart, rather than propagating from the atria to the ventricles. If conduction is abnormally slow in some areas of the heart, for example due to damaged or diseased cardiac tissue, impulse propagation times will vary, and certain impulses may potentially be treated as an entirely new impulse. Such disjointed impulse propagation can produce sustained abnormal circuit rhythms, which are responsible for atrial flutter, most paroxysmal supraventricular tachycardia, and dangerous ventricular tachycardia.

When an entire chamber of the heart has multiple reentry circuits, the chamber is considered to be in fibrillation, and quivers due to the chaotic electrical stimulation, rather than smoothly contracting and delivering blood. The lack of smooth and sustained blood and chaotic contraction can result in cardiogenic shock, cessation of effective blood circulation, and sudden cardiac death. Fibrillation can affect the atrium (atrial fibrillation) or the ventricle (ventricular fibrillation); ventricular fibrillation is imminently life-threatening.

Conventional Treatments for Abnormalities of Excitable Tissue

Traditional arrhythmia treatments include pharmacological therapy, electronic pacemakers, implantable cardioverter-defibrillators (ICDs), ablation, and combinations thereof. While these traditional treatments have been used in the past to treat various types of cardiac arrhythmias, these approaches have several shortcomings Implanted pacemakers and ICDs may cause complications from device implantation, malfunction or hardware infection. Pharmacological therapies may not be tolerated well in some patients, and have the capacity to induce additional arrhythmias during treatment. Thus, there is a need for alternatives or supplements to pharmacological therapies and implantable devices to modulate cardiac contractility and/or conductance.

There exist various approaches to generation of biological pacemakers that are distinct from those disclosed herein, in that several such methods employ delivery of ion channels, or subunits of ion channels to cardiac cells. In particular, dominant negative ion channels (or subunits thereof) have been investigated. Generally, as a result of expression of a dominant negative ion channel in cardiac cells, the ionic current across the cell membrane is altered, thereby resulting in pacemaker-like firing in these cells. Such methods generally rely on the delivery of genes that effectively manipulate the function of the treated cells by altering the ability of the cell with respect to conduction of certain ions. In other words, such approaches typically take the existing cell, and augment or alter its existing structures (e.g., ion channels) to change its function.

In contrast, several embodiments of the invention result in quiescent cells that are reprogrammed to become biological pacemaker cells. Several embodiments of the invention are particularly advantageous because the reprogramming of quiescent cells converts cells to their natural state, rather than treating cells with genetic sequences that did not exist naturally in the cell make-up. For example, several embodiments are advantageous because the reprogramming of the quiescent cells with transcription factors (e.g., not with ion channels) reduces the risk of induced abnormalities in the reprogrammed cell. In some embodiments, the transcription factors are less bulky (e.g., smaller genetic sequences can be used) which reduces logistical complications and opens up additional delivery options. Some embodiments of the invention are particularly beneficial because, by converting a cell to a natural (or native) pacemaker state, that cell will have a higher likelihood of success in generating and maintaining an appropriate pacemaker rhythm with reduced possibilities of side effects that may occur with other approaches (e.g., induction of arrhythmias due to the treatment itself). Further, several embodiments of the invention are beneficial in that they reduce the need for "fine-tuning" of the desired effect (e.g., requiring increased dose or number of treatments to achieve a particular result) as the conversion of the cells to a natural pacemaker-state enables the cells to operate at naturally defined, and therefore balanced, frequencies. As a result, several embodiments of the methods require fewer administrations (or doses) of the compositions in order to achieve conversion of a sufficient number of cells to generate a new pacemaker in the heart. Thus, in several embodiments, the methods disclosed herein may be less invasive to a patient, requiring fewer administration procedures, thereby presenting fewer risks to the patient and lowering morbidity due to the therapy itself.

Moreover, several embodiments of the methods disclosed herein are advantageous in that they do not rely on modification (by "non-native" sequences) of existing complex functional units of cardiac cells (e.g., the ion channels), rather, the conversion of the cells to a pacemaker state results in the generation of a complete complement of functional endogenous pacemaker channels. The reduced requirement for modification of existing channels reduces the likelihood that adverse results occur (e.g., mis-formation of channels or formation of channels that produce a greater or lesser impact on function than anticipated).

Additionally, several embodiments advantageously reduce the risk of unwanted side effects due to unbalanced electrical activity in the cells, as the cells converted to pacemakers by the methods herein have a complete and functionally balanced complement of ionic currents (and hence electrical activity), rather than cells having had a single current that was been exogenously manipulated.

As disclosed herein, the delivery of transcription factors involved in the early natural development of pacemaker cells (whose expression is reduced after development is complete) can unexpectedly reprogram non-pacemaker cells into pacemaker cells. These approaches are unexpected because the general view of cardiac cells is that they are terminally differentiated (e.g., once a contractile cell, always a contractile cell). However, several embodiments of the present methods allow the reprogramming of these cells, without direct exogenous alteration of their ion channels. Thus, rather than manipulating the functional units (ion channels) of the non-pacemaker cells, several embodiments of the methods disclosed herein change the functional fate and functional identity of the cells into pacemaker cells. As such, several embodiments of the methods and compositions disclosed herein result in the generation of a reprogrammed biological pacemaker, which lessens or obviates the need for such traditional pharmacological therapies, ablation, or artificial pacemakers.

Transcription Factors to Generate Biological Pacemakers

The use of transcription factor based biological pacemakers reduces and/or obviates the need for traditional arrhythmia therapies. In several embodiments, generation of a biological pacemaker is used to supplement traditional therapies for bradycardias or other arrhythmias. In several embodiments, generation of a biological pacemaker reduces dependence (e.g., patients are weaned from) on traditional therapies. In several embodiments, cardiac arrhythmias are treated by generating a biological pacemaker that drives the heart at a normal or substantially normal rhythm that was not possible when a subject was untreated or when treated with a non-biological therapy (e.g., pharmaceutical or electronic pacemaker therapy). In several embodiments, generation of a biological pacemaker is used as a bridge therapy (e.g., for patients with cardiac damage sufficient to necessitate a transplant).

In several embodiments, the generation of a biological pacemaker comprises inducing the conversion of quiescent cardiac cells into pacemaker cells by transfer of transcription factors to cells (transfer can occur, for example, through the use of gene delivery techniques used to deliver polynucleotides that encode one or more of the transcription factors disclosed herein). As used herein the term "quiescent cardiac cells" shall be given its ordinary meaning and shall also refer to cardiac cells that exhibit no, little, or an inappropriate firing rate and/or cardiac cells are not spontaneously active. It shall be appreciated that identification of quiescent cardiac cells depends, in some embodiments, on the cell type being targeted. For example, ventricular and/or atrial myocardium normally responds to electrical signals generated by pacemaker cells, and thus typically has lower spontaneous firing rates as compared to normal pacemaker cells. Thus, if targeting the ventricular and/or atrial myocardium quiescent cells having little firing rate comprise, in some embodiments, cells having less than about 20%, less than about 15%, or less than about 10% of the spontaneous firing as compared to normal pacemaker cells. Alternatively, certain embodiments disclosed herein target a malfunctioning region (or regions) of the conduction system of the heart. For example, in several embodiments a malfunctioning region of the sinoatrial node is target, in for example, sick sinus syndrome. In additional embodiments, the atrioventricular (AV) node is targeted, for example, in patients having AV block. In still additional embodiments, the secondary conduction pathways of the heart (e.g., the His-Purkinje system and/or Bundle of His) are targeted. In such tissues that normally exhibit spontaneous repetitive electrical activity, quiescent cells are those that fire at a reduced rate compared to a normal cell in that region of the heart, with said reduced rate being insufficient to maintain an appropriate cardiac firing rate and/or cardiac output. Thus, quiescent cells, in some embodiments, are recognized as those cells which, if responsible for driving the electrical activity of the heart, would do so at a level of electrical firing that is insufficient to maintain appropriate blood flow throughout the cardiovascular system (e.g., those cells firing at a hemodynamically non-sustainable rate).

In several embodiments, the generation of a biological pacemaker results from delivery of transcription factors to cardiac tissue in vivo, resulting in the conversion of quiescent cardiomyocytes, endogenous cardiac stem cells, or combinations thereof, to pacemaker cells. In several embodiments, the generation of a biological pacemaker is performed by delivery of transcription factors in vitro resulting in the conversion of cultured somatic cells, cardiomyocytes, stem cells (including embryonic, induced pluripotent, pluripotent, multipotent, unipotent and/or adult stem cells), or combinations thereof to pacemaker cells. In several embodiments, these generated pacemaker cells can subsequently be implanted in vivo to treat abnormalities of cardiac rhythm.

Figure 1B:
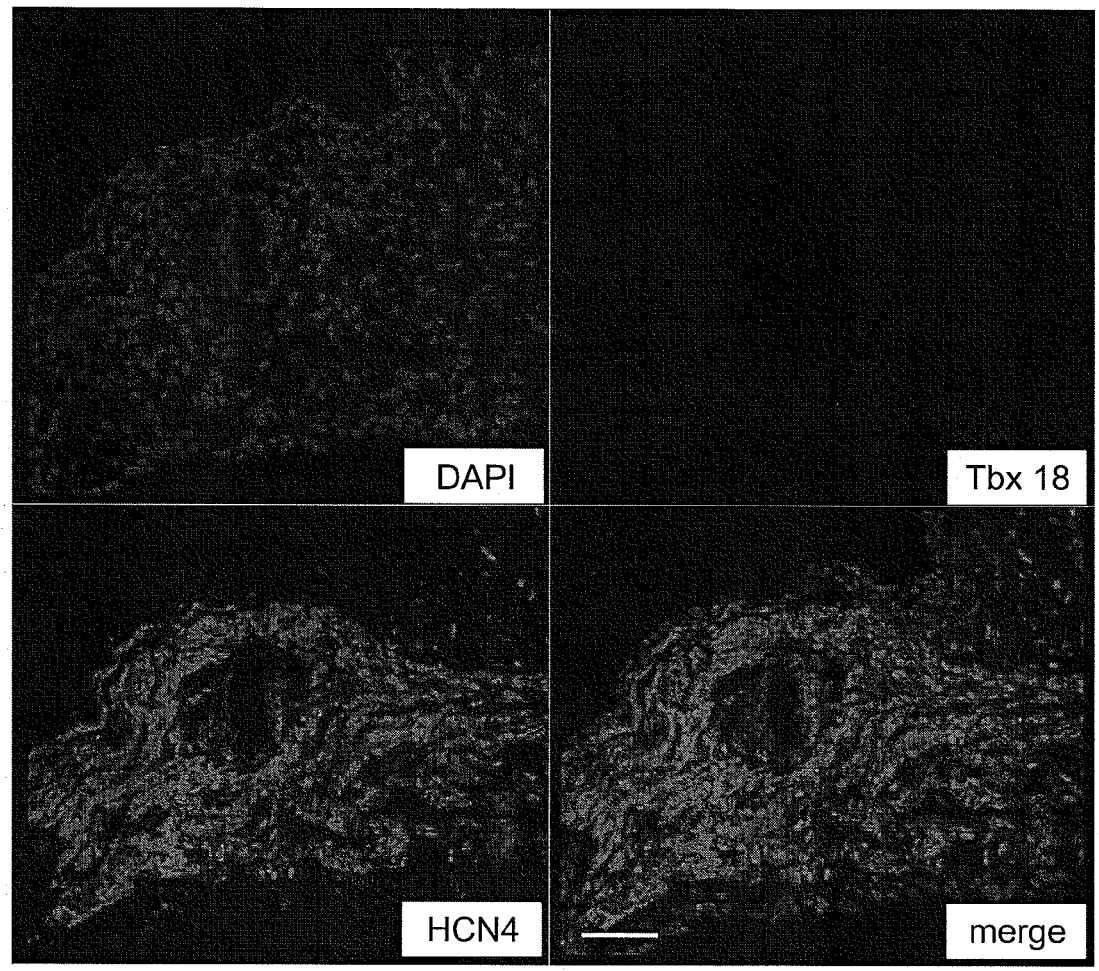

In several embodiments, the conversion of somatic cells, cardiomyocytes, and/or stem cells to pacemaker cells is achieved using transcription factors that are regulators of embryonic sinoatrial node (SAN) development. Potential transcription factors that are regulators of embryonic SAN development include, but are not limited to: Tbx18, Shox2, Tbx3, and/or Tbx5. Tbx18 is a transcription factor that is required for embryonic development of the SAN head area, but, as discussed in more detail below, typically becomes undetectable by birth and remains undetectable in adulthood (FIG. 1). Shox2 is a negative regulator of Nkx2.5 in the sinus venosus. This protein is critical for tissue differentiation. Further, Shox2-deficient mouse and zebrafish embryos display bradycardia. Tbx3 is a potent regulator of SAN specialization, with developmental errors resulting from either deficiency or ectopic expression. Tbx5, which shows an inverse correlation between its dosage and abnormal cardiac morphogenesis in Holt-Oram syndrome, is a positive regulator of Shox2 and Tbx3.

As described above, several embodiments of biological pacemaker generation are based on in vivo therapy. In several embodiments Shox2, Tbx18, or combinations thereof are delivered in vivo to induce ectopic pacemaker activity in non-pacemaker somatic cells, cardiomyocytes, endogenous stem cells, or combinations of the three. In several embodiments other combinations of SAN regulating transcription factors (or transcription factors that are related to cardiac development, but not specifically SAN regulation) can be used with or without Shox2 and Tbx18, or Shox2 and Tbx18 individually to convert cells in vivo to pacemaker cells. Those other transcription factors include, but are not limited to Tbx3 and Tbx5. Sequences for Tbx3, Tbx5, Tbx18, Shox2, and variants thereof are shown in Appendix A, B, C, and D, respectively.

In several embodiments, Tbx18, Shox2, or a combination of Tbx-18 and Shox2 are delivered to cardiomyocytes or stem cells in vitro, which, as discussed below, yields cultured pacemaker cells. These cells can subsequently be administered to patients as a cell therapy for biological pacemaker generations. In several embodiments, administration comprises direct administration of the cells to the heart of a subject (e.g., injection). Other administration routes disclosed herein are used. For example, in some embodiments, catheter-based administration is employed. In additional embodiments, the generated pacemaker cells are incorporated into a matrix, graft, or other biomaterial that aids in cell retention at a target site within the heart. Cells used for in vitro generation of biological pacemakers, are, in some embodiments, harvested from healthy tissue of the patient that they are to be transplanted into (e.g., autologous transplant of induced pacemaker cells). Then these cells can be converted to pacemaker cells by transcription factors in vitro and can be reinserted into the same patient for the treatment of arrhythmias. In other embodiments, allogeneic transplant of induced pacemaker cells is performed (e.g., cells are harvested from a first subject, cultured in vitro, contacted with one or more of the transcription factors disclosed herein, and then transplanted to a second subject). In several embodiments other SAN regulating transcription factors or combinations of such transcription factors are used (e.g., transcription factors in addition to or in place of Tbx18, Shox2, and/or Tbx-18+Shox2) to convert cells in vitro to pacemaker cells. Those other transcription factors include, but are not limited to Tbx3 and Tbx5.

Patients having abnormalities of excitable tissue that may be treated with the methods disclosed herein include mammals and in particular humans. Patients include those suffering from or diagnosed with one or more of the cardiac conditions disclosed herein or other conditions known in the art to affect cardiac activity, conductivity, rhythm, and the like.

Gene Delivery Vectors

Reprogramming cardiomyocytes is accomplished, in several embodiments disclosed herein by using gene delivery as a means of delivering exogenous genetic material to somatic cells, cardiomyocytes, stem cells, or combinations thereof. In several embodiments, polynucleotides are administered in a nucleic acid delivery system. In several embodiments, a nucleic acid delivery system comprises a non-viral vector linked to the polynucleotide. Examples of such non-viral vectors include the polynucleotide alone (e.g., naked DNA) or the polynucleotide in combination with a suitable protein, polysaccharide or lipid formulation.

In several embodiments, the nucleic acid delivery systems comprise one or more viral vectors, including but not limited to adenovirus, adenovirus-associated virus (AAV), helper-dependent adenovirus, lentivirus, retrovirus, or hemaglutinating virus of Japan-liposome (HVJ) complex. Various serotypes of adenovirus and/or AAV are also used in several embodiments. In several embodiments the viral vector comprises a eukaryotic promoter. In several embodiments cytomegalovirus (CMV) promoters are used. Other promoters, including tissue-specific promoters are well-established in the art and may be used in certain embodiments. Additional vectors include retroviral vectors such as moloney murine leukemia viruses and HIV-based viruses. In one embodiment, an HIV-based viral vector comprises at least two vectors wherein the gag and pol genes are from an HIV genome and the env gene is from another virus. DNA viral vectors are used in some embodiments, which include, but are not limited to pox vectors such as orthopox or avipox vectors, herpes virus vectors such as a herpes simplex I virus (HSV) vector.

In several embodiments, polynucleotides (e.g. those encoding one or more transcription factors) are administered in vivo and/or in vitro to convert cells (stem, cardiomyocytes, and/or other somatic cells) into pacemaker cells. In some embodiments, polynucleotides that encode a functional fragment of the transcription factor are delivered in addition to, or in place of, the entire transcription factor. As used herein, the terms "fragment", "functional fragment" or similar terms shall be given their ordinary meaning and shall refer to a portion of an amino acid sequence (or polynucleotide encoding that sequence) that has at least about 70%, preferably at least about 80%, more preferably at least about 90%, 95%, 96%, 97%, 98% or 99% of the function of the corresponding full-length amino acid sequence (or polynucleotide encoding that sequence). Methods of detecting and quantifying functionality of such fragments are established in the art.

Delivery Methods

In several embodiments, administration of the compositions (being transcription factors or cells) disclosed herein to modulate cardiac electrical activity is via direct cardiac injection (e.g., during electronic pacemaker implantation or explantation). In some embodiments, systemic injection is used. Intracoronary injection is used in some embodiments. In still additional embodiments, catheter-directed administration is used. In some embodiments, a map-guided catheter system (e.g., NOGA®) is used, in order to focally administer the compositions. Other mapping or guidance techniques are used in some embodiments. For example, in several embodiments fluoroscopy-based guidance is used. Electroanatomical guidance is also used in some embodiments. Mapping of specific structures (including but not limited to the His Bundle, the right or left portions of the bundle, the Purkinje fibers, etc) by intracardiac electrograms are also used in some embodiments. Moreover, X-rays or magnetic catheters are also used in some embodiments to guide delivery of a catheter, needle, or other delivery device(s) to a desired target location.

In several embodiments, a focal delivery approach advantageously reduces the time to generation of an active biological pacemaker. In some embodiments, the tissue-specific (or cell type-specific) delivery of several of the constructs disclosed herein is advantageous in that the construct is particularly suited for facilitating the generation of a biological pacemaker based on the expression profile of endogenous tissues. In some such embodiments, combinations of transcription factors are delivered to the same target site, while in other embodiments, individual constructs are delivered to distinct target sites, with the overall effect resulting in biological pacemaker generation.

In several embodiments, transduction is achieved by focal injection into the apex of the heart. In several embodiments, transduction is achieved by focal injection to the left ventricular apex. In several embodiments, a right-sided (e.g., right side of the heart, either atrium or ventricle) approach is used, in order to reduce the risk of stroke or other embolism. However, in several embodiments, left-sided approaches are used. In several embodiments, an injection catheter is introduced via the right atrium (rather than the right ventricle), in order to access the Bundle of His or AV node from above. In several embodiments, trans-septal catheter methods are used to introduce an injection catheter into the left atrium or left ventricle without the need for arterial access, thereby reducing stroke risk. In still additional embodiments, the introduction of an injection catheter is by way of the cardiac veins via the sinus of Valsalva for injection of a biologic as disclosed herein into various targets of the ventricles. Such an approach is similar to that used for the placement of pacer leads in cardiac resynchronization therapy.

Thus, in several embodiments, the compositions as disclosed herein can be used to deliver one or more transcription factors (or cells that have been previously contacted with the transcription factors) to either the right atrium, right ventricle, SA node, AV node, bundle of his, and/or left and right bundle branches. Moreover, through cannulation of the coronary sinus and its venous branches delivery to multiple left ventricular sites is achieved in several embodiments. Advantageously, in those patients with unfavorable coronary venous anatomy, access to the left side is achieved, in several embodiments, from the right side through a trans-septal puncture which allows direct access to left sided structures without the need of arterial access.

Supplemental methods are used in several embodiments and include administration of compounds to increase the microvascular permeability of the cardiac tissue. Suitable vascular permeability agents (administered prior to, during, or after administration of a gene transfer vector) include a solution having less than about 500 micromolar calcium: substance P, histamine, acetylcholine, an adenosine nucleotide, arachidonic acid, bradykinin, endothelin, endotoxin, interleukin-2, nitroglycerin, nitric oxide, nitroprusside, a leukotriene, an oxygen radical, phospholipase, platelet activating factor, protamine, serotonin, tumor necrosis factor, vascular endothelial growth factor, a venom, a vasoactive amine, or a nitric oxide synthase inhibitor, serotonin, vascular endothelial growth factor (VEGF), or a functional VEGF fragment.

Biological Pacemaker Effect on Tissues

In several embodiments, administration of transcription factors (or cells contacted with those transcription factors in vitro) disclosed herein induces or otherwise causes the spontaneous repetitive electrical signals to be generated in cells that previously responded to such signals, but did not generate them. For example, for treated myocardial cells that exhibited little (e.g., an index of automaticity between about 40% to about 30%, about 30% to about 20%, about 20% to about 10%, or about 10% to about 0%, or overlapping ranges thereof) or no firing rate, exhibit an increased frequency of firing rate or electrical signal output post-administration (e.g., an index of automaticity of between about 5% to about 15%, about 15% to about 25%, about 25% to about 35%, about 35% to about 45%, about 45% to about 55%, about 55% to about 65%, about 65% to about 75%, about 75% to about 85%, about 85% to about 95%, about 95% to about 100%, or more) as compared to the cells pre-administration.

The resultant changes in cardiac contraction and/or an electrical property of converted pacemaker cells, by the methods disclosed herein, modulate cardiac rhythm in several embodiments. In several embodiments, the methods and compositions disclosed herein achieve a heart rate within about 25%, within about 20%, within about 15%, within about 10%, within about 5%, within about 2%, or within about 1% of a clinically desired heart rate. In several embodiments, the methods and compositions disclosed herein are used to treat subjects suffering from or susceptible to a disease or disorder such as a cardiac-related syncope (e.g., Stokes-Adam syncope), an abnormality of sinus node function such as persistent sinus bradycardia, sino-atrial (S-A) block manifested as S-A Wenckebach, complete S-A block or sinus arrest, and high-grade atrioventricular block; or bradycardia-tachycardia syndrome or other bradycardia related condition. In several embodiments, modulation is used to increase or slow down the function of an implanted pacemaker (e.g., to achieve a desired heart rate that the implanted pacemaker fails to provide on its own).

Changes to the Cells as a Result of Administration of Transcription Factors

In several embodiments, the administration of Tbx18, Shox2, or a combination thereof produces several physiological changes to the contacted cells in addition to or separate from the generation of spontaneous repetitive electrical signals discussed above. In some embodiments, these physiological changes even if first seen in vitro, are also detectable in vivo, where they may serve as supplemental markers of the efficacy of biological pacemaker generation (e.g., they are recognized as characteristics or hallmarks of pacemaker cells). In some embodiments, the administration of one or more transcription factors results in an increased percentage of spontaneously beating monolayer cultures compared to control. In several embodiments, the presence, or amount, of spontaneous beating is use to screen cultures for functionality prior to transplant or to evaluate other combinations of transcription factors for their utility in generating pacemaker cells in vitro. In some embodiments, the administration of one or more transcription factors results in spontaneous intracellular $Ca^{2+}$ oscillations of myocardial cells are administered. In some embodiments, the administration of one or more transcription factors results in a gradual phase-4 depolarization. In some embodiments, the delivery of one or more transcription factors disclosed herein increases or decreases the expression of HCN4 in cells. Because calcium flux is a primary component of cardiac electrical signaling and HCN4 expression is important in pacemaker cell function, changes in these endpoints correspond, in some embodiments, to more SAN-like behavior in induced biological pacemaker cells. In some embodiments, the administration of one or more transcription factors results in modulation of sub-sarcolemmal, spontaneous localized $Ca^{2+}$ release events. In some embodiments, the administration of one or more transcription factors results in modulation of intracellular cAMP levels. Thus, as a result of administration of one or more of the above types of transcription factors, cardiac electrical activity can be modulated and abnormalities in excitable cardiac tissue can be treated.

In several embodiments, the administration of Tbx18, Shox2, or a combination thereof will result in cells new phenotypes of the contacted cells in addition to or separate from the generation of spontaneous repetitive electrical signals. In some embodiments, the administration of one or more transcription factors results in disorganized and markedly lower sarcomeric α-actin expression in transduced cells, which is indicative of pacemaker cells. In some embodiments, the administration of one or more transcription factors results in a change in cell size. In some embodiments, the administration of one or more transcription factors results in changes to the chromatin state. In some embodiments, the administration of one or more transcription factors results in chromatin modification and will cause lower or higher expression and or activity of one or more of the following genes: Cx43, Kir2.1, Actc2, and HCN4. These phenotypic changes, mirror those of natural SAN cells and as a result of the administration of one or more of these transcription factors, can be used, in several embodiments, as an additional means to evaluate the generation of biological pacemaker cells.

In several embodiments, the administration of the one or more transcription factors to the heart will result in frequent ectopic ventricular beats that originate from the site of gene injection resulting in targeted generation of pacemaker activity. In some embodiments, the administration of one or more transcription factors results in gene-related epigenetic changes in cells and de novo pacemaker activity. This pacemaker activity, in some embodiments, is a result of somatic reprogramming, and not due to dedifferentiation to a progenitor state. Somatic to somatic transdifferentiation will lower the threat of neoplasia from transduced cells (e.g., teratoma formation is reduced). In other embodiments, however, the administration of one or more transcription factors may result in dedifferentiation to a progenitor state. In certain such embodiments, differentiation into pacemaker cells is induced using one or more of the transcription factors disclosed herein. Using such methods, biological pacemaker cells can safely and effectively be made from a wide variety of cells.

EXAMPLES

Examples provided below are intended to be non-limiting embodiments of the invention.
Methods:
Heterologous Transduction of NRVMs The human Tbx18 gene with a C-terminal myc/FLAG tag was excised from pCMV6-Tbx18 (Origene, Rockville, Md.) by digestion with FseI and SalI. The Tbx18 gene was then sub cloned into a NotI- and XhoI digested lentiviral expression vector with the desired reporter gene, pLVX-IRES-ZsGreen1 (Clontech, Mountain View, Calif.), thus generating the pLV-Tbx18-IRES-ZsGreen1 (~10.1 kb) vector. ZsGreen1 was used as the reporter protein for Tbx18-transduced cardiomyocytes, due to its similar spectral characteristics as the commonly used GFP. Thus, throughout the disclosure, the terms ZsGreen1 and GFP are used interchangeably. The recombinant target gene was then introduced to an adenovirus vector backbone by Gateway recombination cloning using Gateway-adapted vectors (Invitrogen, Carlsbad, Calif.). An LR recombination reaction was performed between the entry clone and the destination vector, pAd/CMV/V5-DEST (~36.7 kb), to generate the desired adenoviral expression construct, pAd-CMV-TBX18-IRES-GFP (~39.8 kb). Positive constructs were verified to have the correct target gene by DNA sequencing (Laragen, Los Angeles, Calif.).
Electrophysiology Whole-cell electrophysiology recordings were performed as described below. Experiments were carried out using standard microelectrode whole-cell patch-clamp techniques with an Axopatch 200B amplifier (Axon instruments) with a sampling rate of 20 kHz and low-pass Bessel-filtered at 5 kHz. All experiments were performed at a room temperature. Cells were washed with a normal Tyrode's solution containing (mmol/L): NaCl 138, KCl 5, $CaCl_2$, 2, glucose 10, $MgCl_2$ 0.5, and HEPES 10; pH 7.4. The micropipette electrode solution was composed of (mmol/L): K-glutamate 130, KCl 9, NaCl 8, $MgCl_2$ 0.5, HEPES 10, EGTA 2, and Mg-ATP 5; pH 7.2. Microelectrodes had tip resistances of 2 to 4 MΩ when filled with the internal recording solution. Voltage-clamp experiments were performed with an interepisode interval of 2.5 seconds. Action potentials were either initiated by short depolarizing current pulses (2 to 3 ms, 500 to 800 pA) on GFP-NRVMs or recorded with I=0 mode on Tbx18-NRVMs. Data were corrected for the measured liquid junction potential (-mV). A xenon arc lamp was used to view GFP fluorescence at 488/530 nm (excitation/emission).
Adenovirus Construction and Purification The expression constructs as discussed above were digested with PacI to expose inverted terminal repeats before transfecting into 293A cells to produce adenoviral stocks for use in subsequent expression of the transgene. Adenoviruses were plaque-purified, amplified, and affinity-column purified using Adenopure kit (Puresyn, Inc), and stored at −80° C.
Myocyte Isolation and Transduction NRVMs were isolated from 1-2 day old rat pups and cultured as a monolayer using established culture methods. Only the lower one third of the heart (from the apex to the midline) was excised in order to minimize contaminating atrioventricular nodal cells. In some embodiments, other portions of the heart are used, including the lower third, the middle third, and combinations of these portions, or whole hearts (or portions thereof) where endogenous pacemaker cells are selectively removed. In some embodiments, biopsies (e.g., guided biopsies) are used to obtain non-pacemaker tissue). A monolayer of NRVMs was transduced with either Ad-Tbx18-IRES-GFP or Ad-GFP (control vector; moi=1-10) one day after cell isolation, and cultured for 2-5 days. Tbx20, known to be critical for cardiac chamber differentiation, was employed in order to control for non-specific, embryonic transcription factor-related effects.
Isolation of SA Myocytes SA nodal myocytes were isolated from adult Sprague-Dawley rats.

Animals were anesthetized with isoflurane. Hearts were quickly removed, the atria separated from the ventricles, and the sinoatrial node region dissected in Tyrode solution, which consisted of (in mM) 140 NaCl, 5.4 KCl, 1.2 $KH_2PO_4$, 5 HEPES, 5.55 glucose, 1 $MgCl_2$, 1.8 $CaCl_2$; pH adjusted to 7.4 with NaOH. The rat sinoatrial node region was defined by the borders of the crista terminalis, the interatrial septum, and the superior and inferior vena cavae.

Embryonic Stem Cell Transduction

Mouse embryonic stem cells were transfected with an adenoviral vector expressing Shox2 or a control gene. Established embryoid body methods were used for differentiation. Pooled data are n>3 with p<0.05 for all reported differences.

Intracellular Calcium Recordings and Analyses

For measurements of intracellular $Ca^{2+}$ oscillations, $2 \times 10^6$ NRVMs were plated in 35-mm glass bottom dishes (MatTek Cultureware) or 22 mm fibronectin-coated glass coverslips, transduced, and analyzed 4 days post-transduction. Cells were loaded with Rhod2-AM (2 µmol/L) (Molecular Probes) for 18 minutes, then washed once and subsequently placed in normal Tyrode's solution with 2 mmol/L calcium. Calcium transients were recorded at 37° C. from AdTbx18IS-IRES-GFP and Ad-GFP transduced NRVMs. Images were acquired on an inverted confocal laser-scanning microscope (Perkin Elmer/Nikon) or Leica SP5 confocal microscope. Offline analysis was performed using Ultraview (Perkin Elmer) and ImageJ. Whole-cell $Ca^{2+}$ transients were obtained from confocal line scan images through single NRVMs by averaging the signal of an individual cell. $Ca^{2+}$ transients are presented as background-subtracted, normalized fluorescence ($F/F_o$). For 2-D confocal $Ca^{2+}$ imaging calcium transients were obtained by averaging the signal through the entire cell.

Immunostaining

Frozen sections of neonatal rat sinoatrial node and NRVMs 4 days post adenoviral transduction were fixed with 4% paraformaldehyde and permeabilized with 0.1% Triton-X 100 and then incubated with the appropriate primary antibody: sarcomeric α-actinin (Sigma-Aldrich; A5044; 1:800), ANP (AbCam; ab-14348; 1:1000), HCN4 (Abcam; ab85023; 1:500) and Alexa Fluor-conjugated secondary antibodies (Invitrogen).

Immunoblotting

Western blots were performed using specific antibodies against to Cx43 (Sigma-Aldrich, C6219; 1:1000), PLN (Alomone; A010-14: 1:5000), p-PLB (Alomone; A010-12: 1:5000) HCN4 (AbCam; ab85023; 1:500) Briefly, Ad-Tbx18, Ad-GFP transduced NRVMs, rat SAN and Left ventricle were homogenized in RIP A buffer containing a protease inhibitor cocktail (Sigma). Protein content was quantified by BCA assay and cell lysates (15 µg per lane) were run on a 12% SDS-PAGE gel and transferred onto a PVDF membrane. Then the transferred membrane was incubated with a primary antibody overnight at 4° C., followed by 1-hour incubation with a peroxidase-conjugated secondary antibody. Immunoreactivity was detected by chemiluminescence (ECL Western Blotting Analysis System, Amersham). Equal protein loading of the gels was assessed by re-probing the membrane with monoclonal anti-GAPDH antibody (Abeam; ab9482; 1:10000) or anti-β-actin (Sigma-Aldrich; A3848: 1:25000).

In Vivo Gene Transfer

Adenoviruses were injected into the left ventricular apex of guinea pigs. Adult female guinea pigs (weight, 250 to 300 g; Charles River) were anesthetized with 4% isoflurane, intubated, and placed on a ventilator with a vaporizer supplying 1.5% to 2% isoflurane. After lateral thoracotomy, a 30-gauge needle was inserted at the free wall apex of the left ventricle. 100 µl of adenovirus containing $1 \times 10^9$ plaque-forming units of Ad-Tbx18-IRES-GFP or Ad-GFP (control group) was injected into the left ventricle apex. As discussed above, other delivery routes are used in some embodiments.

In Vivo and Ex Vivo Electrocardiographs (ECGs)

Figure 3A:
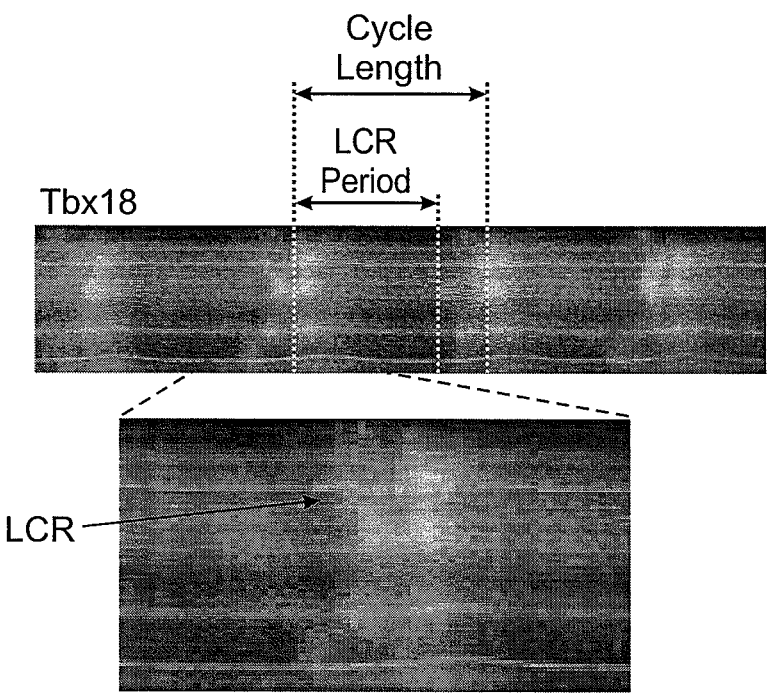
FIGS. 3A-3J depict the effects of Tbx18 expression on various aspects of cardiac calcium signaling in NRVMs.
Figure 3B:
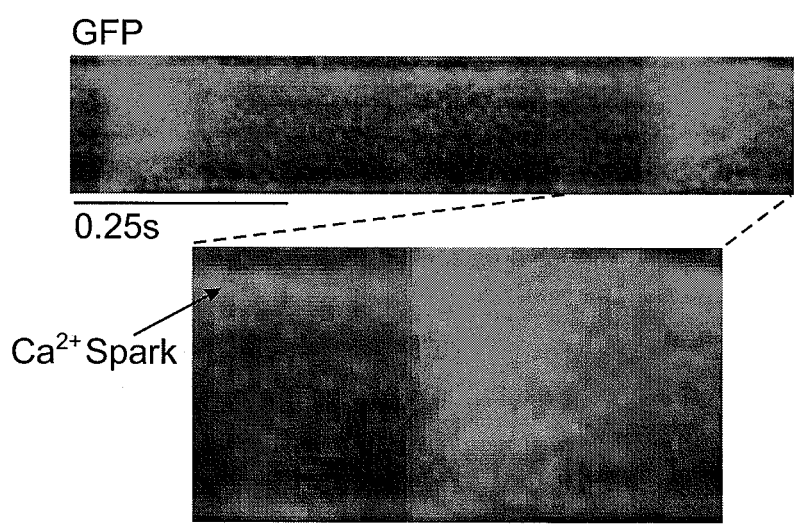
Figure 3C:
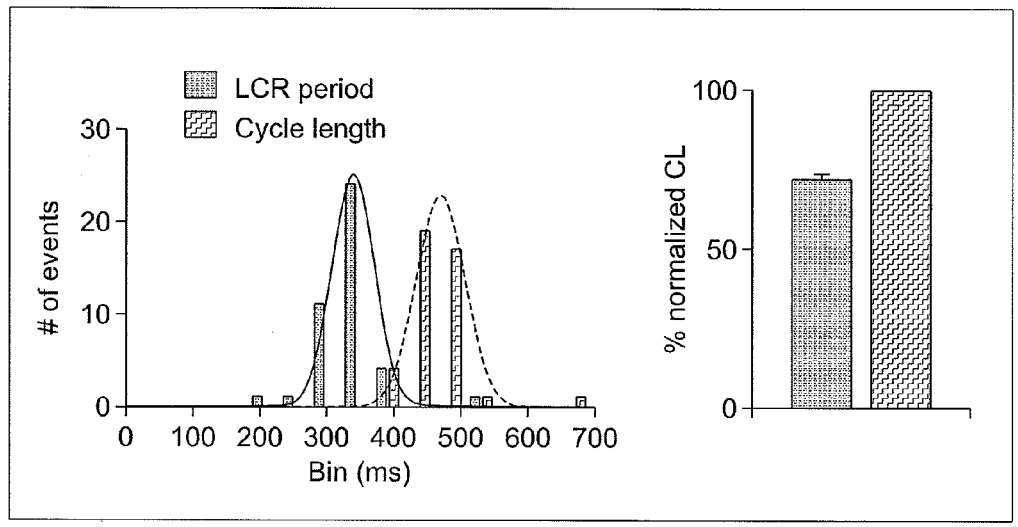
Figure 3D:
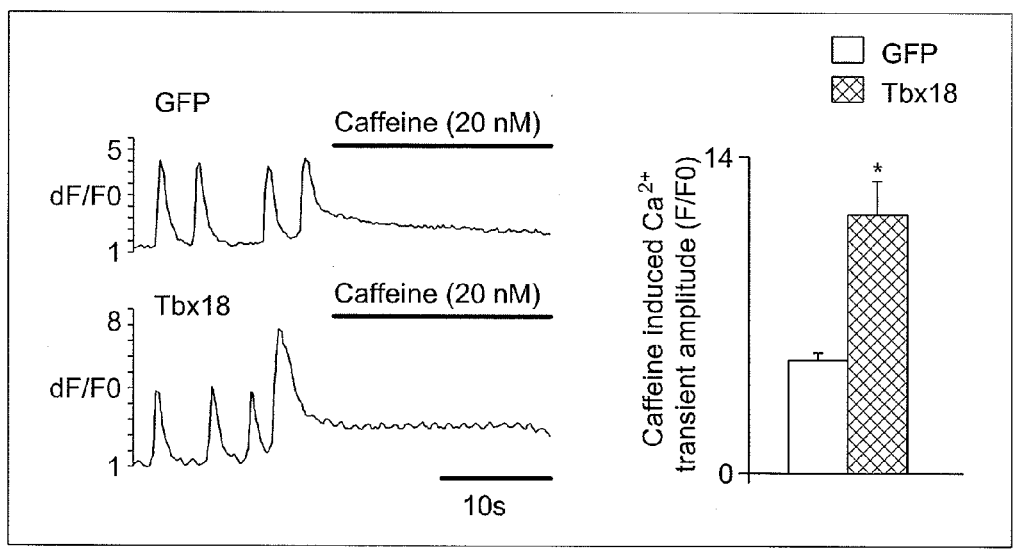

Methacholine (0.1-0.5 mg per kg of body weight in saline, Sigma-Aldrich, St. Louis, Mo.) was delivered via the jugular vein in order to slow the animals' sinus rhythm prior to ECG recordings under general anesthesia (2% isoflurane, 98% O2). ECGs were recorded using a 2-lead digital ECG system at 2 kHz (Lead I and Lead 3, BIOPAC Systems, Goleta, Calif.) and Lead 2 was offline calculated by Einthoven's triangle using Acqknowlege 3.7.3 software (BIOPAC Systems, Goleta, Calif.). In all animals, methacholine was administered until complete heart block was achieved. Heart block was accompanied by a reduction of the animals' sinus rhythm to <100 bpm. In most of the Tbx18-injected guinea pigs, ectopic ventricular rhythms were manifested well before the sinus rhythm reached 100 bpm (FIG. 3D, right panel). In contrast, control animals exhibited no evidence of such ectopic ventricular beats even when the sinus rhythm was brought to <100 bpm (FIG. 3D, left panel). FIG. 3D highlights the lack of any ectopic ventricular rhythm in the control animals even at a very slow escape rate compared to Tbx18-injected animals.

Figure 28A:
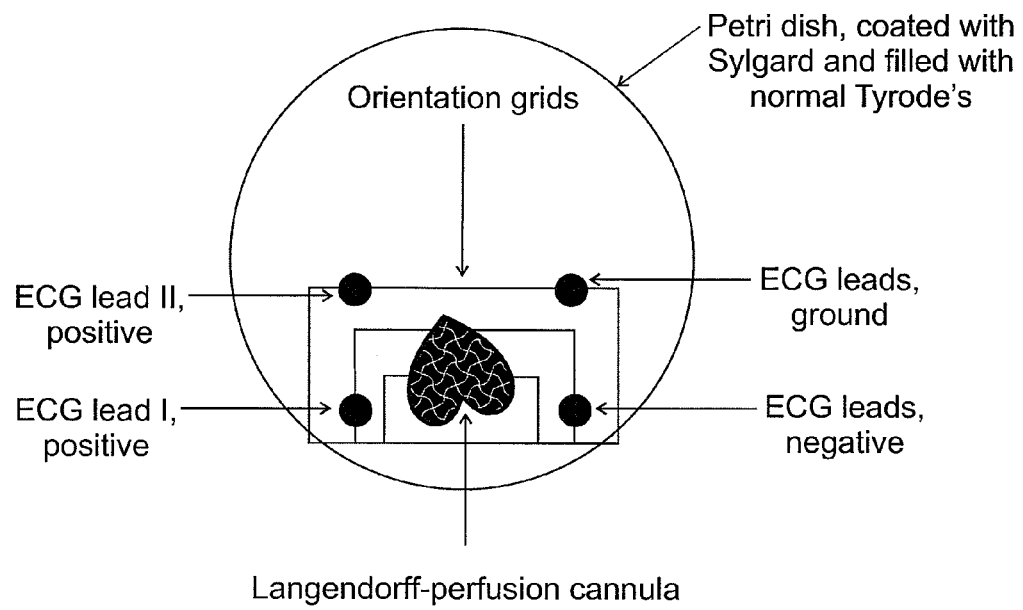
FIGS. 28A and 28B depict the placement of leads for ex vivo intact whole-heart ECG recordings. The heart was retrograde-perfused via aorta at 60 mmHg with oxygenated Tyrode's solution at 36° C. The perfused heart was placed in a sylgard-coated plate filled with warm Tyrode's solution. ECG leads were stationed at appropriate sites to record leads I and II.
Figure 28B:
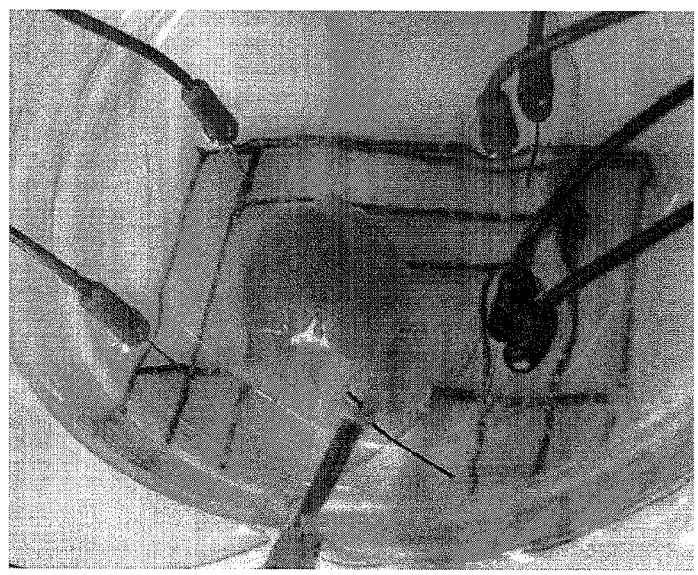

For ex vivo, intact whole-heart ECG recordings, the heart was retrograde-perfused via the aorta at 60 mmHg with oxygenated Tyrode's solution at 36° C. The perfused heart was placed in a sylgard-coated plate filled with warm Tyrode's solution. ECG leads were stationed at appropriate sites to record leads I and II (FIG. 28). After a 20-minute equilibration period, the region of the atrioventricular node was ablated with a cryogun (Brymill Cryogenic Systems, Ellington, Conn.) filled with liquid $N_2$. Electrode-pacing was performed at the site of transgene injection (anterior, left ventricular apex) at 200-ms intervals with a platinum electrode connected to an isolated pulse stimulator (Model 2100, A-M Systems, Carlsborg, Wash.).

RT-PCR for Gene Arrays

Rat sinoatrial node, left ventricle and Tbx18- and GFP-transduced NRVMs (4 days post transduction) were collected and mRNA was extracted (Qiagen mRNA Isolation Kit,). The mRNA samples were converted to first strand cDNA, using the RT2 First Strand Kit (SA Biosciences). Then, the cDNA template was mixed with the RT2 qPCR Master Mix and the mixture was aliquoted into each well of the same plate containing pre-dispensed gene specific primer sets. PCR was performed on a 7900HT Fast Real-Time PCR System (Applied Biosystems/Life Technologies Corporation, Carlsbad, Calif.) and the relative expression of the genes was calculated.

cAMP Assay

The Cyclic AMP Elisa Assay Kit (catalog # STA-501; Cell Biolabs, INC) was used to determine cAMP levels in NRVMs transduced with Ad-Tbx18 or Ad-GFP. Briefly, 50 µl Tbx18- and GFP-NRVM cell lysates were added to the Goat Anti-Rabbit Antibody Coated Plate 96 well plate. 25 µl of diluted Peroxidase cAMP Tracer Conjugate was added to each tested well. Then, 50 µl of diluted Rabbit Anti-cAMP Polyclonal Antibody was added to each tested well and the plate was incubated at room temperature for 30 minutes with shaking. After washing 100 µl of Chemiluminescent Reagent was added to each well. After incubation at room temperature for 5 minutes on an orbital shaker, the plate was read for luminescence of each microwell on a plate luminometer. Measurement of light emission (RLU) allowed calculating the amount of cAMP in samples which were then normalized to β-actin for comparison of the samples.

Solutions

Tyrode solution containing (min): NaCl 140, KCl 5.4, $CaCl_2$ 1.5, $MgCl_2$ 1.5, glucose 10 and Hepes 5; pH adjusted to 7.38 with NaOH. Ryanodine and Protein kinase I (PKI) were purchased from Tocris biosciences and caffeine was purchased from Sigma. Rhod-2/AM and was purchased from Invitrogen.

Chromatin Immunoprecipitation

NRVMs transduced with either Tbx18 or GFP were fixed two- to four-days after viral vector transduction with 10% formaldehyde for 8 min at room temperature. Cells were sheared using a sonicator with ten pulses of 20 seconds each, with a 30-second rest on ice between each pulse. Chromatin immunoprecipitation was performed using ChIP-IT® Express Chromatin Immunoprecipitation kit (Active Motif, Carlsbad, Calif.) following the manufacturer's protocol. Primary antibodies for the H3K4me3 and H3K27me3 were purchased from Active Motif.

qPCR after Chromatin Immunoprecipitation

Gene specific (Cx43, Kir2.1, α-SA, HCN4) primers, already validated for qPCR in rat, were purchased from SA Biosciences. For each gene, three sets of primers were employed corresponding to −2 kb (upstream), −1 kb, and +1 kb (downstream) of the transcription start site. The ΔCt values from the three tiles were averaged from each experiment for data analyses.

Single-cell Quantitative Real-time PCR

Figure 30A:
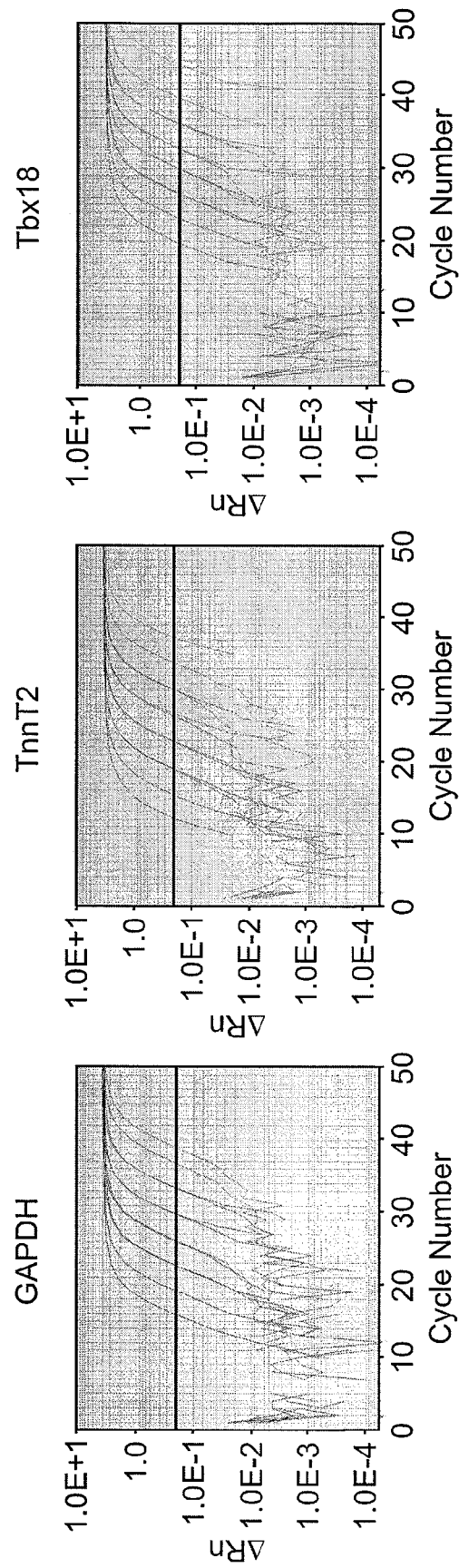
FIGS. 30A and 30B depict results of real-time PCR to examine Tbx18 mRNA levels in individual myocytes. Standard curves for each of the 3 primer sets were constructed with serial dilutions of input DNA templates and validated comparable amplification efficiencies (curve slopes: −3.32 to −3.64). Relative mRNA levels of human Tbx18, guinea pig GAPDH, and guinea pig TnnT2 were obtained by extrapolation of Ct values with the slopes of the standard curve for each primer sets. Tbx18 mRNA amount in each cell was then normalized to GAPDH or TnnT2 level.
Figure 30B:
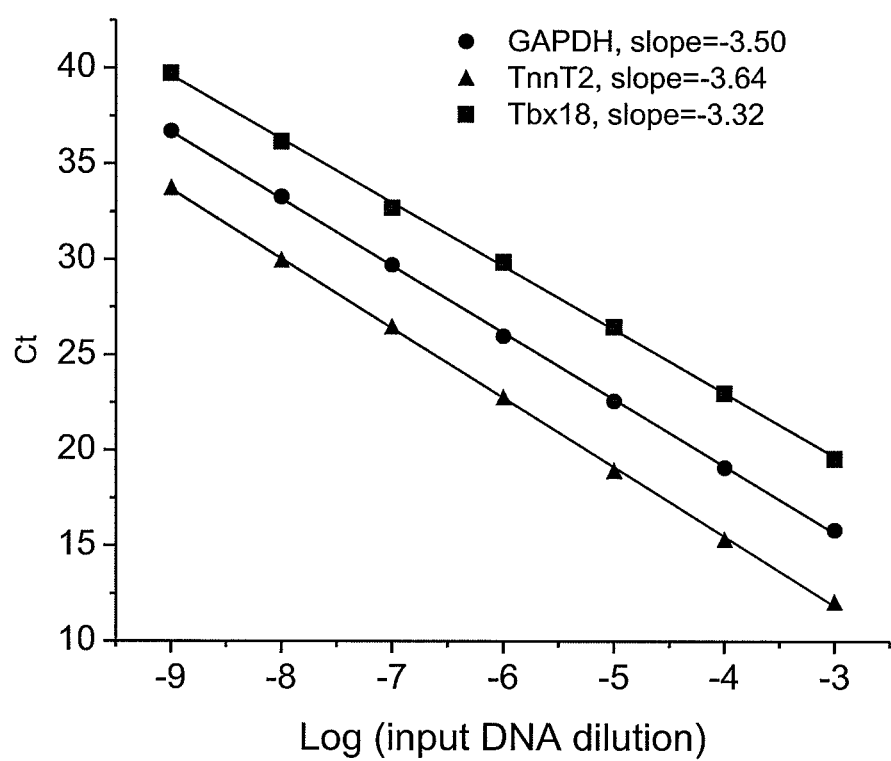

Single myocytes were collected in PBS with a wide-opening patch pipette, placed on dry ice and then stored at −80° C. Tbx18 mRNA levels in individual myocytes were examined by quantitative real-time PCR with an Ambion® Single Cell-to-CT™ Kit (Life Technologies) according to manufacturer's instructions. Briefly, single cells were treated with cell lysis solution and DNase I for 5 minutes at room temperature. Reverse transcription was performed at 25° C. for 10 minutes, at 42° C. for 60 minutes and at 85° C. for 5 minutes after addition of SupersScript RT and VILO RT mix. Preamplification was performed with 14 cycles of 95° C. for 15 seconds and 60° C. for 4 minutes with addition of PreAmp mix and 0.2× TaqMan Gene Expression Assays, containing primers for human Tbx18 (assay ID:Hs01385457_m1), guinea pig GAPDH (assay ID:Cp03755742_g1), and guinea pig TnnT2 (assay ID:Cp04182357_g1). The custom primers were synthesized by Applied Biosystems (Carlsbad, Calif.). Preamplification products (1:20 dilution) were used for real-time PCR with TaqMan Gene Expression Assays using an Applied Biosystems 7900HT Fast Real-Time PCR System. Standard curves for each of the 3 primer sets were constructed with serial dilutions of input DNA templates (FIG. 30) and validated comparable amplification efficiencies (curve slopes: −3.32 to −3.64). Relative mRNA levels of Tbx18, GAPDH, and TnnT2 were obtained by extrapolation of Ct values with the slopes of the standard curve for each primer sets. Tbx18 mRNA expression in each cell was then normalized to GAPDH or TnnT2 level.

Statistical Analyses

Data were analyzed for mean, standard deviation and standard error of the mean (SEM). The quantitative figures in this work represent the mean±SEM. Data sets were statistically evaluated using an unpaired t test. $p<0.05$ was considered significant unless indicated otherwise.

Example 1

Pacemaker Cells Created by Gene Delivery to NVRMs

As discussed above, present therapies for cardiac arrhythmias caused by abnormalities of excitable tissue rely primarily on pharmacotherapy, radiofrequency ablation, implantable devices, and other such related approaches. These methods, while useful for the treatment of some forms of arrhythmias, have limitations (as discussed above). Biological pacemakers offer advantages over the use of traditional pacemakers and can be used instead of, or in conjugation with traditional pacemakers. The present study evaluated the use of transcription factor inducing agents for the generation of biological pacemakers.

Figure 2A:
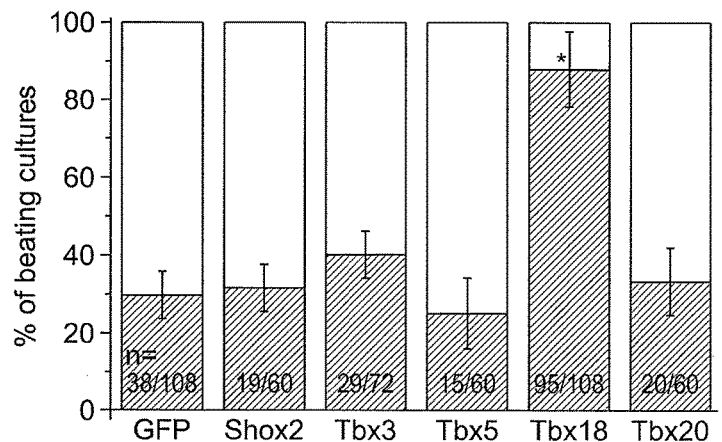
FIGS. 2A-2I depict the effects of Tbx18 transduction into neonatal rat ventricular myocytes (NRVM).

To demonstrate that transduction of transcription factors to cardiac cells produces biological pacemakers, singular, heterologous transduction of selected transcription factors in bicistronic adenoviral vectors was performed in freshly-isolated NRVMs. As an initial screen, the number of spontaneously-beating cultures 36-48 hrs post-transduction was analyzed. Tbx18-transfected NRVMs (Tbx18-NRVMs) exhibited an increased percentage of spontaneously-beating monolayer cultures compared to control and other transcription factors screened (minimum of five different cell isolations per group, FIG. 2A). Beyond two days of culture, multiple, spontaneously-beating foci were observed in individual Tbx-NRVM monolayers, as expected from the downregulation of Cx43 (but not Cx45 or Cx40) by Tbx. Accordingly, Tbx was selected as a candidate for converting ventricular cardiomyocytes to pacemaker cells. Thus, in several embodiments, Tbx18 is used to create a biological pacemaker. However, in several embodiments, other transcription factors are used, including one or more of those screened in the current experiment. In several embodiments, combinations of two or more transcription factors will be used. In several embodiments, Shox2 will be used in conjugation with Tbx18 to achieve these results. In several embodiments, one or more of the following transcription factors will be selected for use: Tbx18, Shox 2, Tbx3, and Tbx5.

Figure 2B:
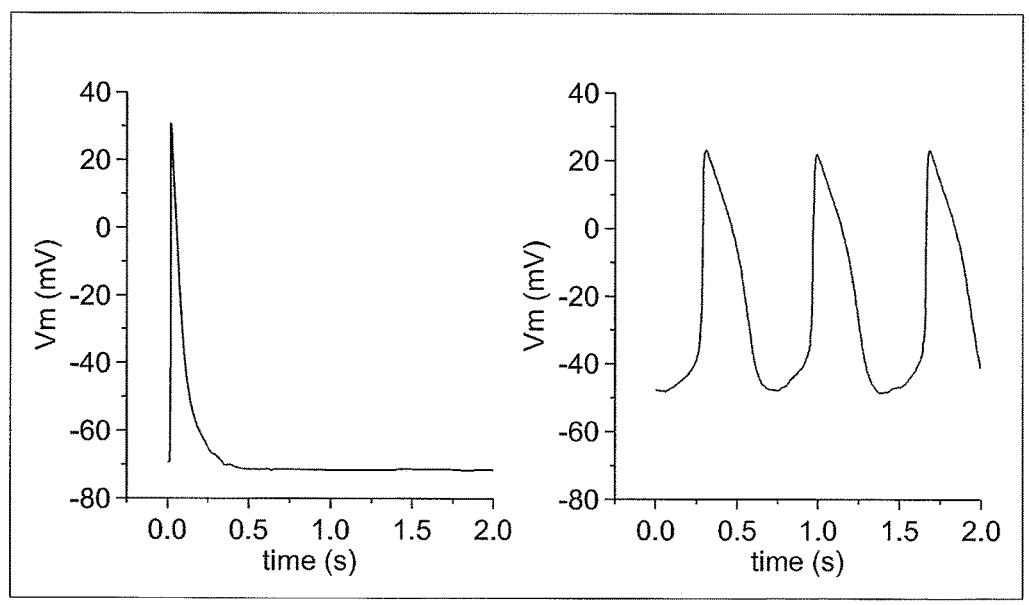

Although NRVMs exhibit spontaneous, syncytial contractions when cultured as monolayers, such a phenomenon is driven by a relatively small number of autonomously-beating cells. FIG. 2B shows representative action potential (AP) traces. When sparsely plated at a density of ~4 NRVMs/mm$^2$ such that a given cell is unlikely to make physical contact with neighboring cells, a majority of the control (GFP) ventricular myocytes were quiescent (7 of 9), firing single action potentials only upon stimulation (FIG. 2B, left). Tbx18 expression transformed the electrical phenotype to that of SAN cells; most Tbx18-NRVMs (7 of 9) beat autonomously and spontaneously (FIG. 2B, right). It will be appreciated that, in several embodiments, Shox2 could be used instead of or in conjunction with Tbx18. In several embodiments, one or more of the following transcription factors will be selected for use: Tbx18, Shox2, Tbx3, and Tbx5. The Tbx18-NRVMs exhibited spontaneous APs with prominent gradual phase-4 depolarization. Gradual phase-4 depolarization underlies automaticity in SAN pacemaker cells, and is prominent in Tbx-NRVMs (FIG. 2B). This increase in autonomous beats and gradual depolarization indicates that these cells are functioning in a manner consistent with natural sinoatrial node cells, which suggests that Tbx18 (alone or in combination with other transcription factors) is generating pacemaker cells. In some embodiments, similar functions are detected in stem cells, and which therefore indicates that the cells are useful in the generation of biological pacemakers and in the treatment of arrhythmias.

Figure 2C:
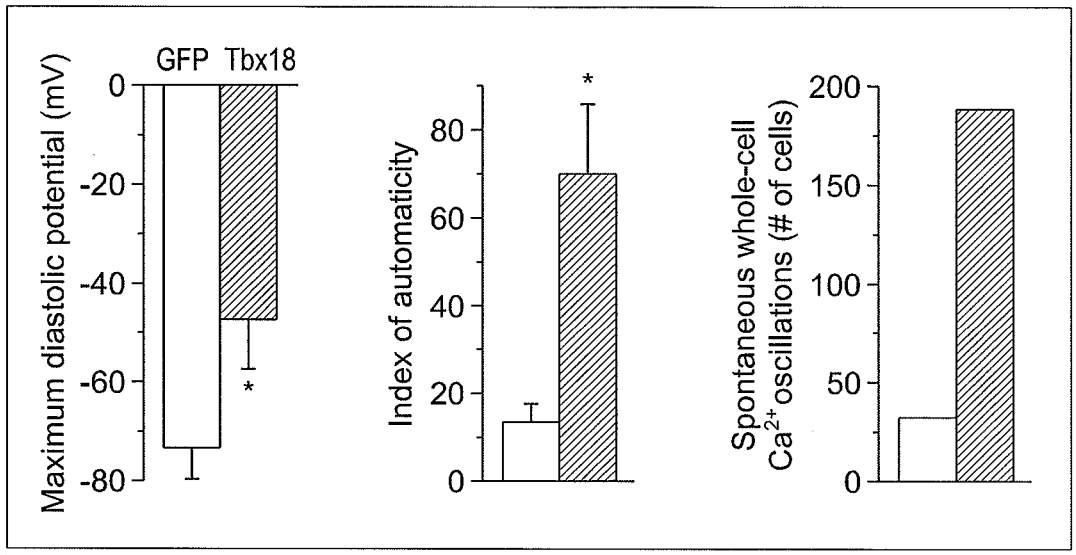

The maximum diastolic potential (MDP) of −47±10 mV (n=6) in Tbx18-NRVMs was depolarized relative to the resting membrane potential (RMP) of −73±6 mV in GFP- NRVMs (n=5, FIG. 2C, left). This suggests that Tbx-18 transduced cells will fire more frequently than the control cells, much like pacemaker cells are expected to. GFP- and Tbx18-groups are indicated by white and cross-hatched bars, respectively, throughout the data presented. As used herein, the term "index of automaticity" shall be given its ordinary meaning and shall also be defined as the percentage of autonomously-beating cells multiplied by the frequency of action potential (AP) oscillations in those cells, was much larger in Tbx-NRVMs (70±16% bpm) compared to control (13±4% bpm, FIG. 2C, middle). As shown in FIG. 2C middle, automaticity increased relative to the GFP control by around 60%. In some embodiments, the increase in index of automaticity will be 5% to about 15%, about 15% to about 25%, about 25% to about 35%, about 35% to about 45%, about 45% to about 55%, about 55% to about 65%, about 65% to about 75%, about 75% to about 85%, about 85% to about 95%, about 95% to about 100%, and overlapping ranges thereof, relative to the automaticity of normal pacemaker cells. The number of cells having spontaneous $Ca^{2+}$ oscillations also increased relative to the controls (FIG. 2C, right). The number of Tbx18-NRVMs exhibiting spontaneous intracellular $Ca^{2+}$ oscillations was about 6-fold higher relative to control (FIG. 2C, right). Because $Ca^{2+}$ is necessary for the generation of an action potential in pacemaker cells, these data also demonstrate that transduction of cells with Tbx18 (alone or in combination with other transcription factors) can be successfully used in the generation of pacemaker cells.

Figure 2D:
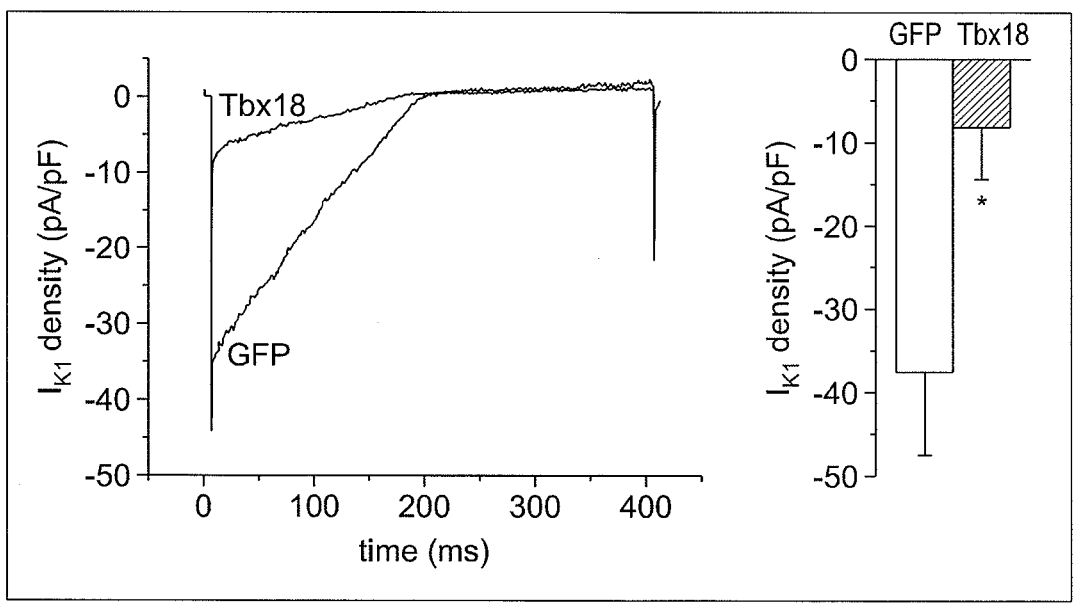

The change in diastolic potential, automaticity, and $Ca^{2+}$ oscillation was complemented by a 78% reduction in $I_{K1}$ density in Tbx18-NRVMs (FIG. 2D). Left: representative $I_{K1}$ raw traces elicited by a ramp protocol from −140 to −20 mV. The summarized $I_{K1}$ densities at −140 mV are shown in 2D right. In several embodiments the reduction in $I_{K1}$ density will be between about 5% to about 15%, about 15% to about 25%, about 25% to about 35%, about 35% to about 45%, about 45% to about 55%, about 55% to about 65%, about 65% to about 75%, about 75% to about 85%, about 85% to about 95%, about 95% to about 100%, and overlapping ranges thereof. The reduction in $I_{K1}$ density also indicates that the transduced cells will fire with higher frequency relative to untreated cells (e.g., non-pacemaker cells). This increase in firing indicates that these transduced cells are functioning as pacemaker cells. Thus, the methods used to generate these cells, or methods used to generate pacemaker cells from stem cells, can be used in the treatment of cardiac arrhythmias, or other maladies that are associated with a disrupted cardiac cell firing rate.

Figure 2E:
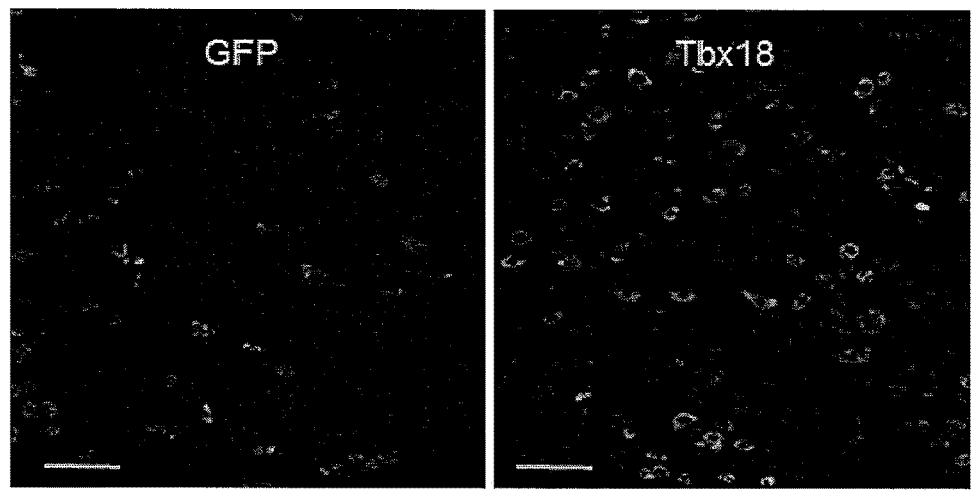
Figure 2F:
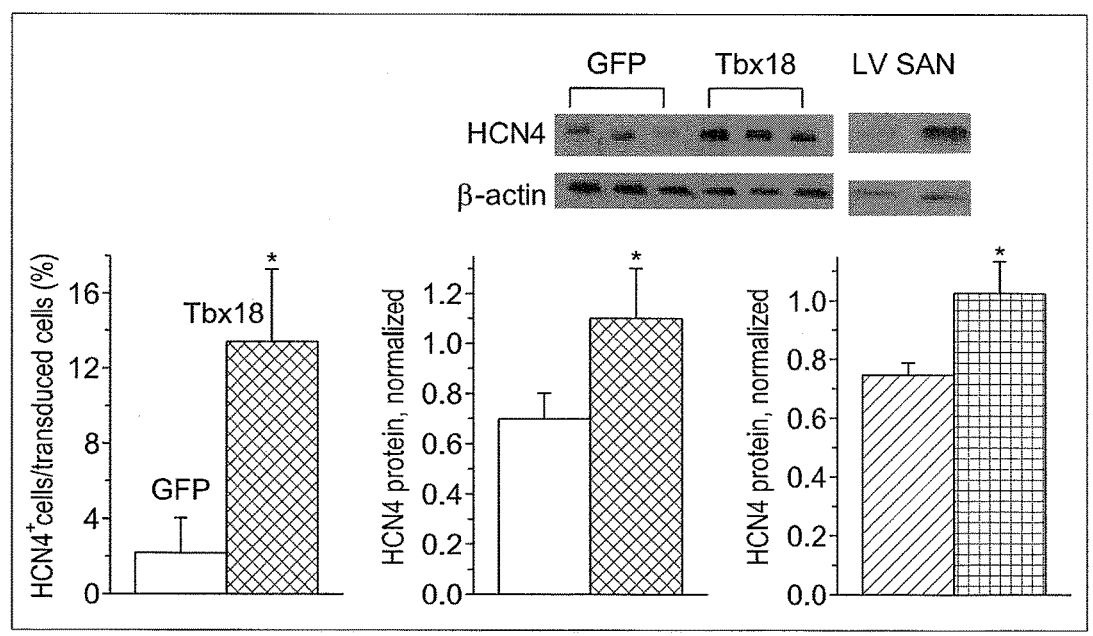
Figure 2G:
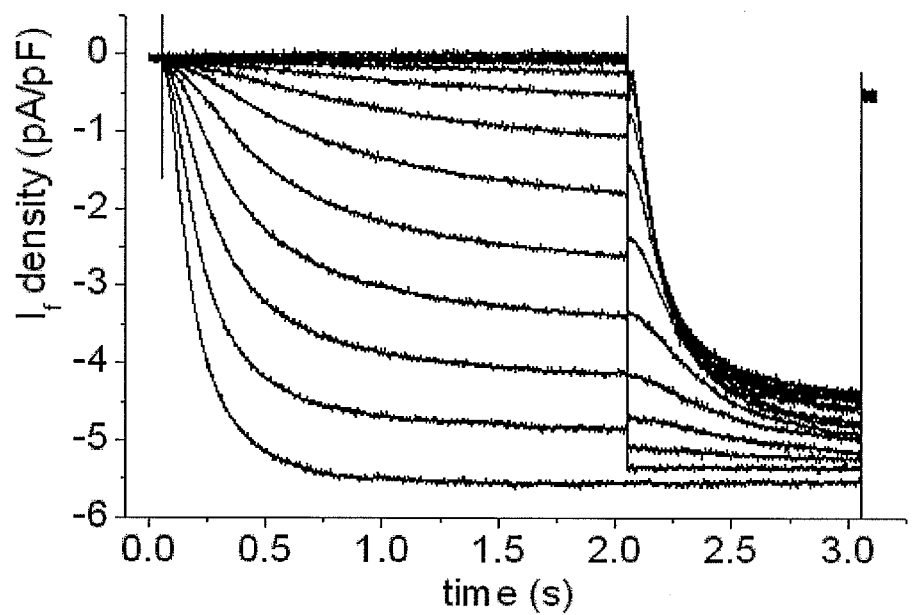
Figure 2H:
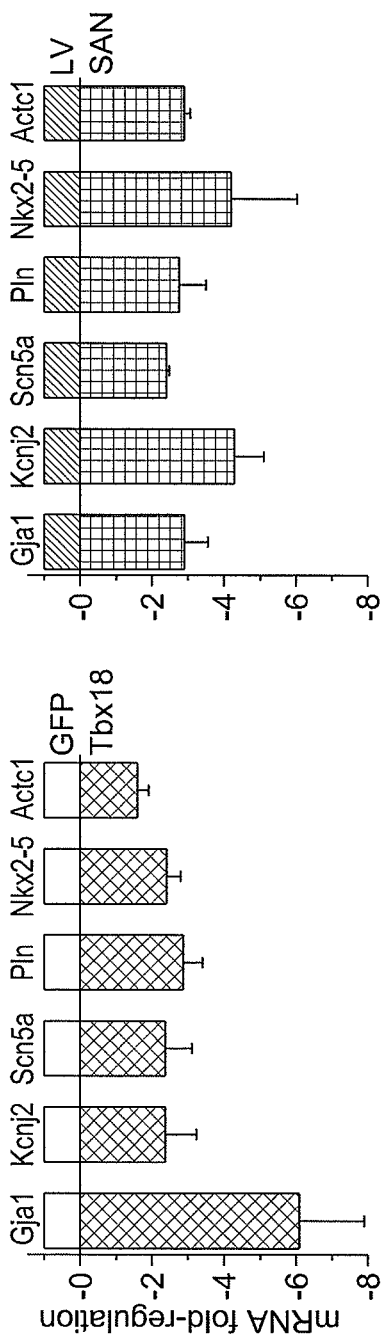

HCN4 is the molecular correlate of the hyperpolarization-activated current, If, which contributes to pacemaker activity in the SAN. Tbx18 transduction led to a 3.8-fold increase in the number of cells expressing HCN4 (FIG. 2E). HCN4 immunostaining image (HCN4-white, nuclei-blue) of GFP- or Tbx18-NRVMs are shown in left and middle, respectively. Scale bar: 200 μm. Right panel: summary of the percent HCN4-positive cells per GFP- or Tbx18-transduced cells. Tbx18 expression also led to a 1.4-fold increase in HCN4 protein level (FIG. 2F) in Tbx18-NRVMs. Such cells also exhibited If (FIG. 2G) at a density (−5.2±1.3 pA/pF at −140 mV, n=3) consistent with that reported in rabbit SAN cells. Western blot indicates higher HCN4 protein level in Tbx18-NRVMs relative to control (left) comparable to the level HCN4 observed in adult rat SAN (right). $Ca^{2+}$ cycling events complement and couple with sarcolemmal ionic currents to generate automaticity. Comparison of transcript levels for selected components of the voltage- and calcium-dependent mechanisms revealed differences in Tbx18-vs. GFP-NRVMs which closely recapitulate those between native SAN and ventricular myocardium, used here as positive controls (FIG. 2H). Changes of relative mRNA levels of selected genes comparing Tbx18-NRVMs normalized to GFP-NRVMs (left) and SAN normalized to LV (right). SAN and Tbx18-NRVMs demonstrate similar pattern of normalized transcript levels. Thus, in several embodiments, Tbx18 also elicits gene and protein expression changes that are associated with biological pacemaker formation.

FIG. 2B shows Tbx18 cells were more likely to fire and fire in a manner (with slow depolarization) like that of native SAN cells. FIG. 2C shows that Tbx18 cells have a lower diastolic potential (middle) resulting in a higher index of automaticity (middle) and more spontaneous whole-cell oscillations of $Ca^{2+}$ (left). FIG. 2D shows that the current density of the Tbx18 cells have less repolarization time, and thus a higher chance of firing. Together these data indicated that, in some embodiments, Tbx18 changes the electrical properties of cells and make them SAN-like. Each of these results indicates a higher likelihood that these cells will fire automatically when implanted into or generated in the living heart. Thus, in several embodiments, these induced pacemaker cells are able to beat and can modulate heart rhythm to treat cardiac arrhythmias, or other maladies associated with abnormal cardiac rhythm.

While membrane-delimited electrophysiological pathways contribute to pacemaking, SAN cells are triggered to fire rhythmically by finely-orchestrated, distinctive intracellular $Ca^{2+}$ cycling events. Sub-sarcolemmal, spontaneous localized $Ca^{2+}$ release events (LCRs) are a hallmark of automaticity in sinoatrial node cells. During late diastole, LCRs activate Na+—$Ca^{2+}$ exchanger currents (INCX), which then contribute to the exponential phase of phase-4 depolarization. LCR measurements were performed on Tbx18-NRVMs to characterize their $Ca^{2+}$ cycling profiles.

During late diastole, LCRs activate Na+—$Ca^{2+}$ exchanger currents (INCX), which then contribute to the exponential phase of phase-4 depolarization. Line-scan confocal imaging of Tbx18-NRVMs resolved LCRs preceding each whole-cell $Ca^{2+}$ transient (FIG. 3A, n=8 out of 10 cells), recapitulating the LCRs observed native SAN pacemakers. Representative confocal line-scan images of changes in $[Ca^{2+}]_i$ in Rhod2/AM loaded Tbx18-NRVMs (FIG. 3A) and GFP-NRVMs (FIG. 3B) 4 days post transduction depict LCRs preceding the whole cell $Ca^{2+}$ transient only in the Tbx18-NRVMs whereas occasional $Ca^{2+}$ sparks could be detected in the GFP-NRVMs. The LCR period is defined as the period between the start of the $Ca^{2+}$ transient to the beginning of the subsequent LCR. Cycle length is defined as the period between the start of the whole cell $Ca^{2+}$ transient to the start of the subsequent $Ca^{2+}$ transient. LCRs depicted periodicity with an average period of 72±1% of that of the cycle length (FIG. 3C). Thus, Tbx18 alone or with other transcription factors, functionally converts cardiomyocytes into cells having pacemaker-like $Ca^{2+}$ activities.

The LCRs in Tbx18-NRVMs occurred at an average period of 343±8 ms, which was 72±1% of the whole-cell $Ca^{2+}$ transient cycle length (474±7 ms, FIG. 3D). In some embodiments the LCR will occur between about 5% to about 15%, about 15% to about 25%, about 25% to about 35%, about 35% to about 45%, about 45% to about 55%, about 55% to about 65%, about 65% to about 75%, about 75% to about 85%, about 85% to about 95%, about 95% to about 100%, and overlapping ranges thereof, of the whole-cell $Ca^{2+}$ transient cycle length. Spatially averaged F/F0 plots of changes in $[Ca^{2+}]_i$ depicted a 2.3 fold increase in the caffeine (20 mM) induced $Ca^{2+}$ transients in the Tbx-NRVMs compared to the controls. In contrast, LCRs were not detected in control cells (n~12 out of 12 cells, FIG. 3D), although occasional randomly-distributed sparks were observed (e.g., FIG. 3B). Larger $Ca^{2+}$ stores in the sarcoplasmic reticulum (SR) would be likely to promote automaticity. The amplitude of caffeine-induced $Ca^{2+}$ transients was 2.3-fold larger in Tbx18-NRVMs compared to control (FIG. 3D).

Figure 3E:
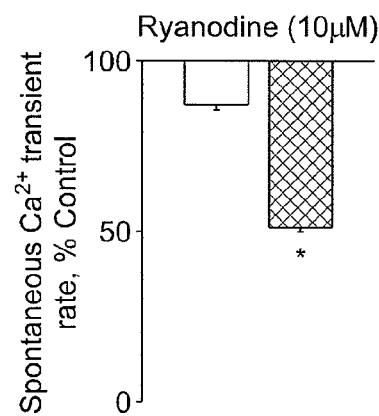
Figure 3F:
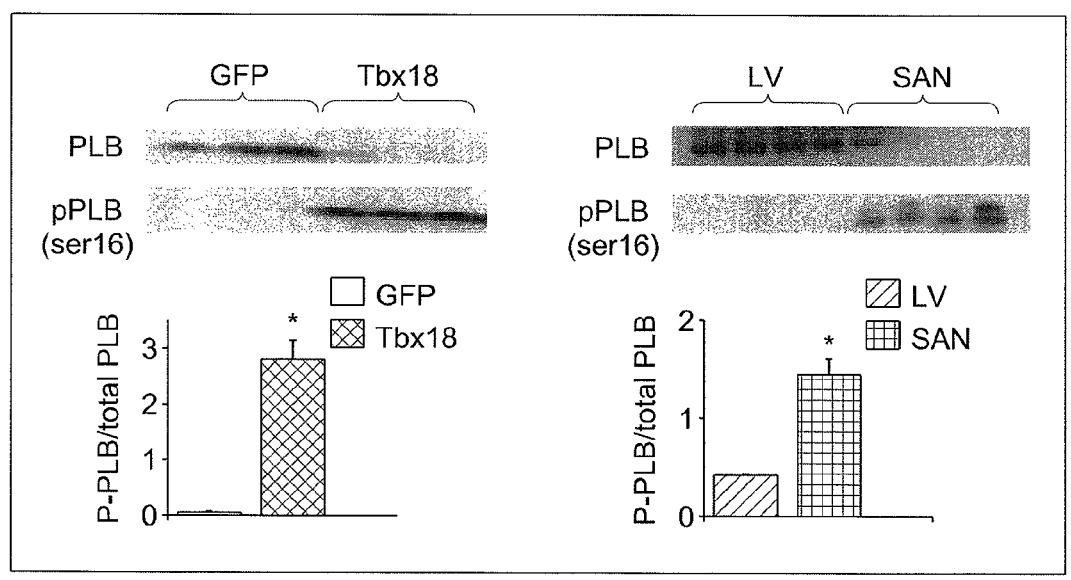
Figure 3G:
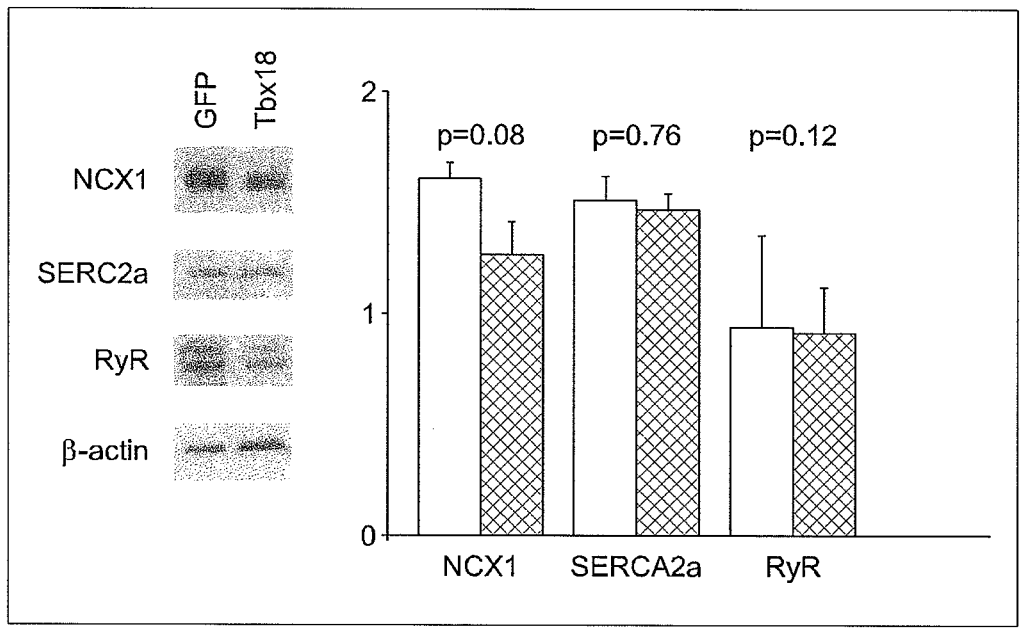

Western blot experiments demonstrated a decrease in the total PLB levels and an increase in phosphorylated PLN (se16) akin to the adult rat SAN (FIG. 3F). No changes in the protein levels of SERCA2A, NCXI and RyR were observed in the Tbx18-NRVMs in comparison to the controls (FIG. 3G). The $Ca^{2+}$ release channel blocker, ryanodine (10 μM), suppressed the rate of spontaneous $Ca^{2+}$ transients by 47±6% in Tbx-NRVMs but only by 12±2% in control (FIG. 3E). These results indicate that transduction with Tbx18 (alone or in combination with other transcription factors) can be used, in several embodiments, to generate biological pacemakers, or in some embodiments, used to generate cells which can later be implanted to function as biopacemakers.

Figures 3H, 3I:
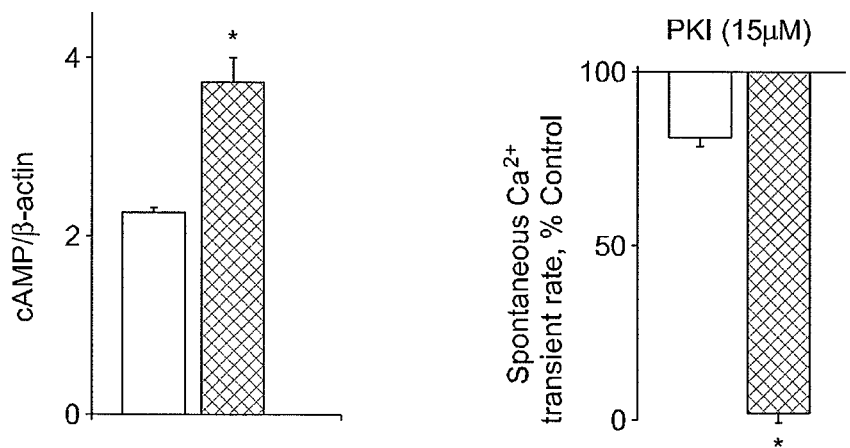
Figure 3J:
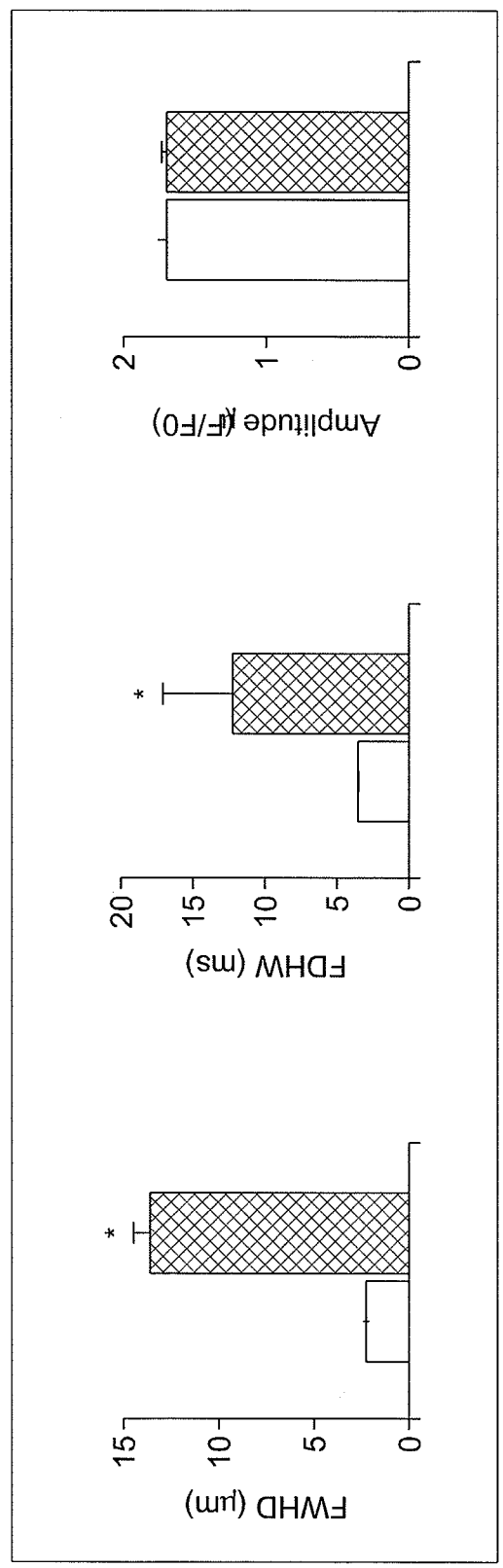

Phospholamban (PLN), in its unphosphorylated state, inhibits sarcoplasmic reticulum $Ca^{2+}$-ATPase 2a (SERCA2a), thereby suppressing the reuptake of $Ca^{2+}$ by internal stores. Such inhibition is relieved upon phosphorylation of the protein (P-PLB). The relative p-PLN (Ser16) level was 65-fold higher in Tbx-NRVMs in comparison to GFP-NRVMs (FIG. 3F, left panel), mimicking the augmentation of p PLN found in the SAN compared to that in the ventricular myocardium (FIG. 3F, right panel). Meanwhile, differences in the protein levels of SERCA2a, NCX1 and ryanodine receptor (RyR) were not detectable between Tbx- and GFP-NRVMs (FIG. 3G), consistent with findings in the rabbit sinoatrial node versus left ventricle. Intracellular cAMP levels were 1.7 fold higher in Tbx18-NRVMs compared to GFP-NRVMs (FIG. 3H), reproducing the higher $[cAMP]_i$ observed in the rabbit SAN compared to ventricular myocardium as known in the art. Application of a PKA inhibitor (PKI, 15 μM) led to cessation of spontaneous whole-cell $Ca^{2+}$ transients in Tbx-NRVMs, but had no effect on GFP-NRVMs (FIG. 3I). Thus, Tbx18 expression in NRVMs produced changes in key $Ca^{2+}$ cycling components which recapitulate key features of sinoatrial node pacemaker cells, thereby allowing, in several embodiments, transduction of cells with Tbx18 (alone or in combination with other transcription factors, depending on the embodiment) to be used in therapeutic methods for treating cardiac arrhythmias.

Phenotypic Changes to the Reprogrammed Cell

In addition to the electrophysiological changes, cellular reprogramming replicates key features of cell structure in pacemaker tissue. Native sinoatrial node pacemaker cells are distinctive in their morphology: they are smaller and exhibit less-organized myofibrils than working cardiomyocytes. To test whether Tbx18-NRVMs had phenotypic changes, the morphology of the cells was investigated.

Figure 4A:
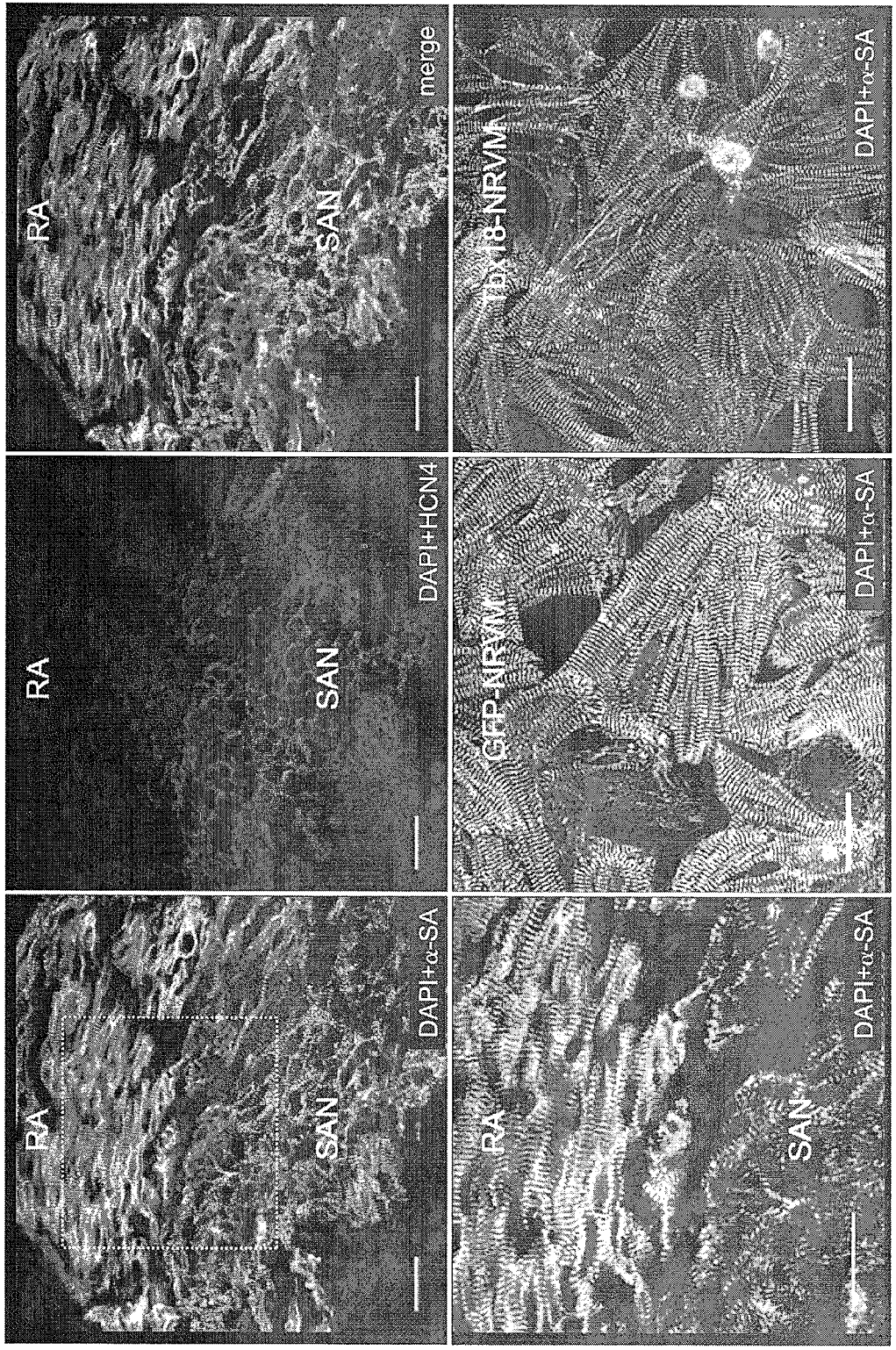
FIGS. 4A-4C depict data related to the expression of various cardiac proteins, function and channel expression after Tbx-18 transduction.
Figure 4B:
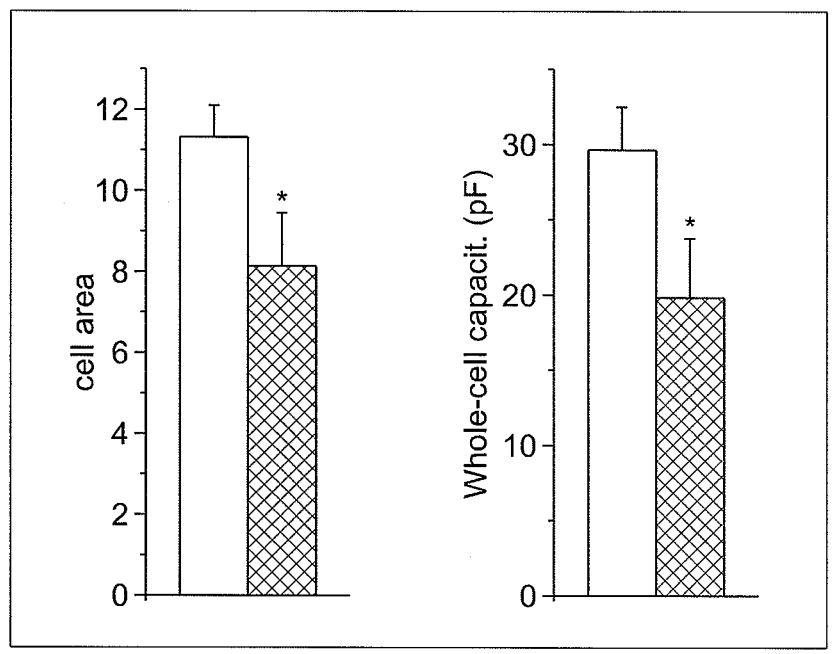

Sections of neonatal rat heart demonstrate that cardiac sarcomeric α-actinin (α-SA) expression is markedly lower and disorganized in the sinoatrial node compared to the adjacent right atrium (RA, FIG. 4A, top left and bottom left). Tbx18-NRVMs resembled native sinoatrial node cells in their morphology, with myofibrillar disorganization and weak expression of a-SA (FIG. 4A, bottom right). Neonatal rat sinoatrial node, demarcated by HCN4 expression (top middle), exhibits weaker and unstructured sarcomeric α-actinin (α-SA) expression (top panel). Bottom left: Zoom-in image of the boxed area in top left. The pattern is faithfully recapitulated in Tbx18-NRVMs compared to GFP-NRVMs (bottom right and middle, respectively). Scale bar: 30 μm. The data are corroborated by the observed downregulation of α-SA transcript levels in Tbx18-NRVMs (FIG. 2H). Cell size, measured by two complementary methods, is 28-33% smaller in Tbx18-NRVMs than in control NRVMs (FIG. 4B), recapitulating the smaller size of SAN cells relative to working cardiomyocytes. Thus, Tbx18-NRVMs underwent both structural (morphology) as well as functional (electrophysiology) reprogramming.

Figure 4C:
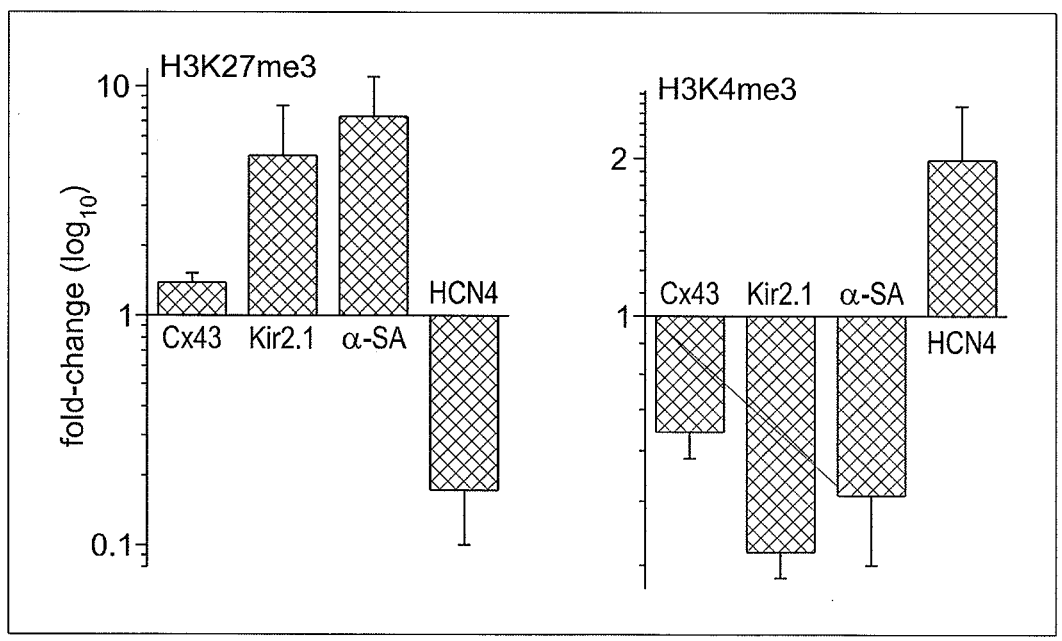

Whether the shifts to sinoatrial node-like phenotype are associated with a sinoatrial node-like chromatin state in Tbx18-NRVMs was then investigated. Trimethylation of lysine 27 in histone 3 (H3K27me3) is a heterochromatin mark which promotes the recruitment of Polycomb group proteins for gene silencing. Conversely, trimethylation of lysine 4 (H3K4me3) marks genes transcriptionally active. Histone modification profiles in the promoter regions of four genes, Cx43, Kir2.1, Actc2, and HCN4, were then investigated. Tbx18 is a transcription factor that is required for embryonic development of the sinoatrial node head area. Shox2 is a negative regulator of Nkx2.5 in the sinus venosus (as discussed above). Tbx3 is a potent regulator of sinoatrial node specialization, with developmental errors resulting from either deficiency or ectopic expression. Tbx5 is a positive regulator of Shox2 and Tbx3. These genes exhibit relevant molecular and functional changes in Tbx18-NRVMs. Tri-methylation level on H3K27 indicates that Tbx18 increased inactivity of Cx43, Kir2.1, and a-SA promoters while relieving its repressive epigenetic pressure on HCN4 promoter normalized to control. These results were measured by chromatin immunoprecipitation followed by qPCR. Meanwhile, H3K4me3 (FIG. 4C right) levels indicate that ratio of active HCN4 promoter regions increased upon Tbx18 expression while the transcriptionally active promoter regions of Cx43, Kir2.1, and a-SA have decreased upon Tbx18 expression. Cx43, Kir2.1, and Actc2 became epigenetically inactive (higher H3K27me3 and lower H3K4me3) in Tbx18-NRVMs compared to control (FIG. 4C). As a result, these data suggest that Tbx18 expression would reduce one or more of Cx43, Kir2.1, and a-SA expression while HCN4 would be upregulated. As HCN4 is involved in repetitive signals, these data are consistent with biological pacemaker formation. Moreover, the chromatin histone modifications are consistent with durable epigenetic reprogramming rather than transient functional re-engineering.

In FIG. 5, the expression of atrial natriuretic peptide (ANP) in NRVMs was induced by 24-hour stimulation with endothelin-1 (100 nM), a vasoconstrictor. However, induced ANP expression was suppressed by Tbx18 expression (5B, bottom panel) while GFP had no effect (5A, bottom panel). Scale bar: 20 μm. Each of these phenotypic changes show that Tbx18-transduced cells appear to be more sinoatrial node-like than cardiomyocytes that are untreated. This reflects a reprogramming of the cell that is structural as well as physiological, thus generating a biological pacemaker cell that is similar to sinoatrial node cells.

In several embodiments, at least one of Cx43, Kir2.1, and Actc2 may become epigenetically inactive in iSAN cells as compared to the quiescent cells. In several embodiments, expression of sarcomeric α-actinin in iSAN cells may be weak as compared to the quiescent cells. Furthermore, in several embodiments, the iSAN cells may exhibit myofibrillar disorganization. Only one of such changes may occur, or combinations thereof may occur, depending on the embodiment; however, each of the above are consistent with a shift of a cell towards a sinoatrial node-like phenotype. Moreover, in several embodiments pacemaker cells are generated without the induced alteration expression of ion-channel proteins, the genetic introduction of which may be contrary to the data above (e.g., the reduction in Kir2.1 that contributes, at least in part, to iSAN formation, would potentially be offset by genetic introduction of Kir2.1 channels).

Example 2

In Vivo Application of Transcription Factor Induced Biological Pacemakers

The prior example established the ability of Tbx18 to induce changes in gene/protein expression and function in vitro. Thus, the possibility of reprogramming adult ventricular myocytes into pacemaker cells in vivo was also investigated. An adenoviral vector encoding Tbx18 was directly and focally injected into the apex of guinea pig hearts. In some embodiments, the injection will be to other areas of the heart and sometimes in several areas at once. It shall be appreciated that the guinea pig is an accepted model for use in cardiovascular studies, and data can be readily extrapolated to other mammals, including the human. In some embodiments, the administration of the Tbx18 adenoviral vector will be performed on various mammalian hearts, including that of the human heart.

Figure 6B:
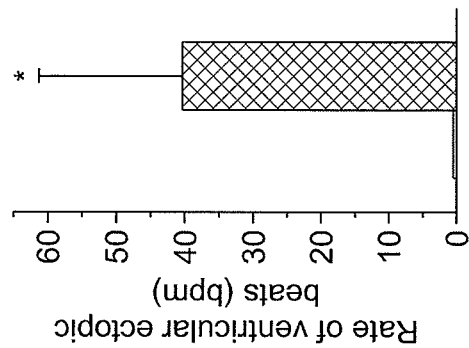
FIGS. 6A-6B depict data related to ventricular ectopic beats.
Figure 6A:
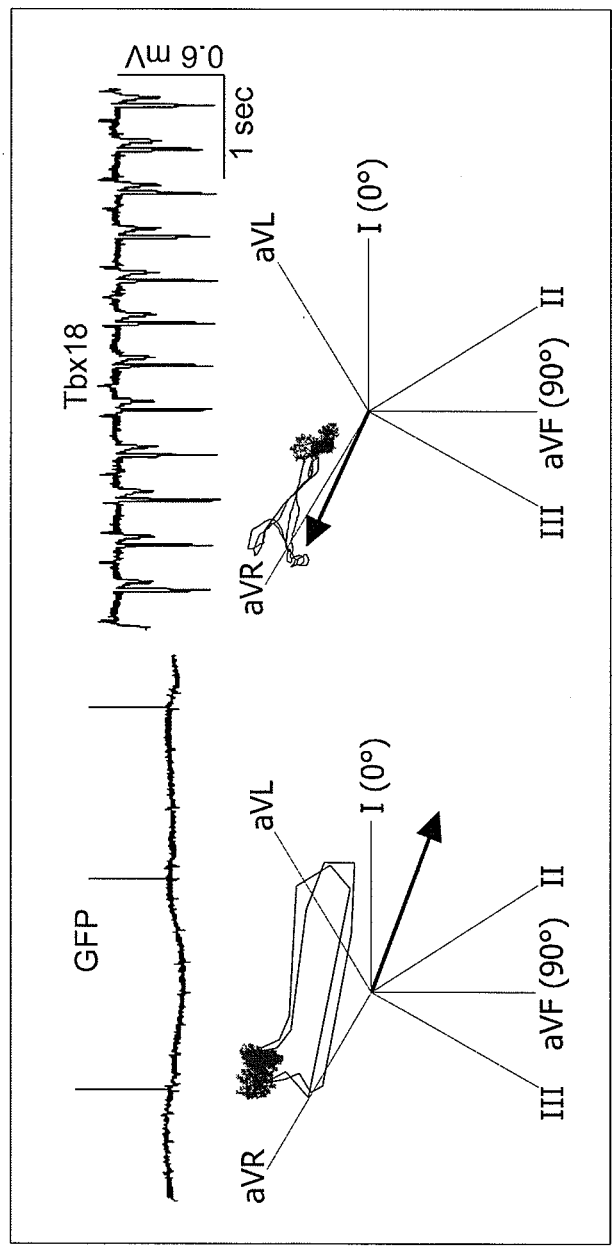
Figure 7A:
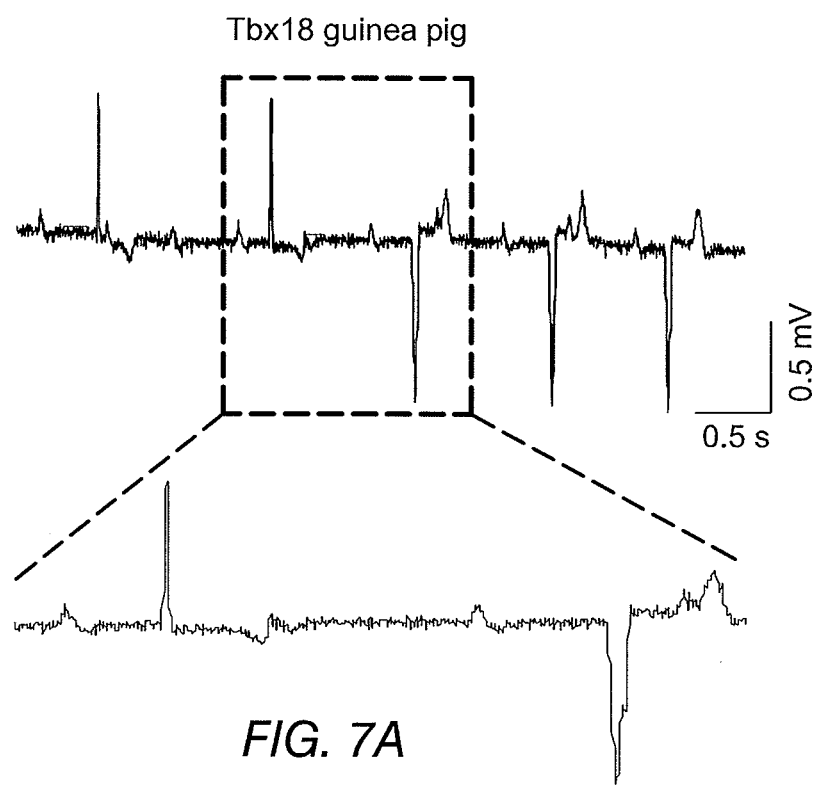
FIGS. 7A-7D indicate that the focal expression of Tbx18 (7A) in the apex of guinea pig hearts in in vivo created ectopic ventricular beats (as compared to GFP controls (7B)). These data are also represented in EKG traces from TBX18 animals (7C) and GFP controls (7D).
Figure 7B:
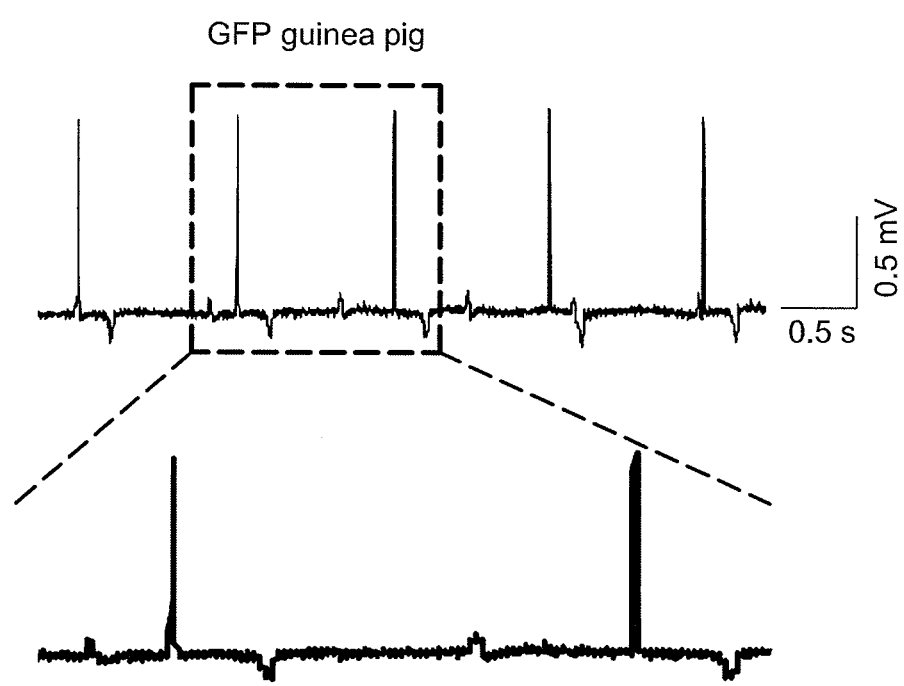
Figure 7C:
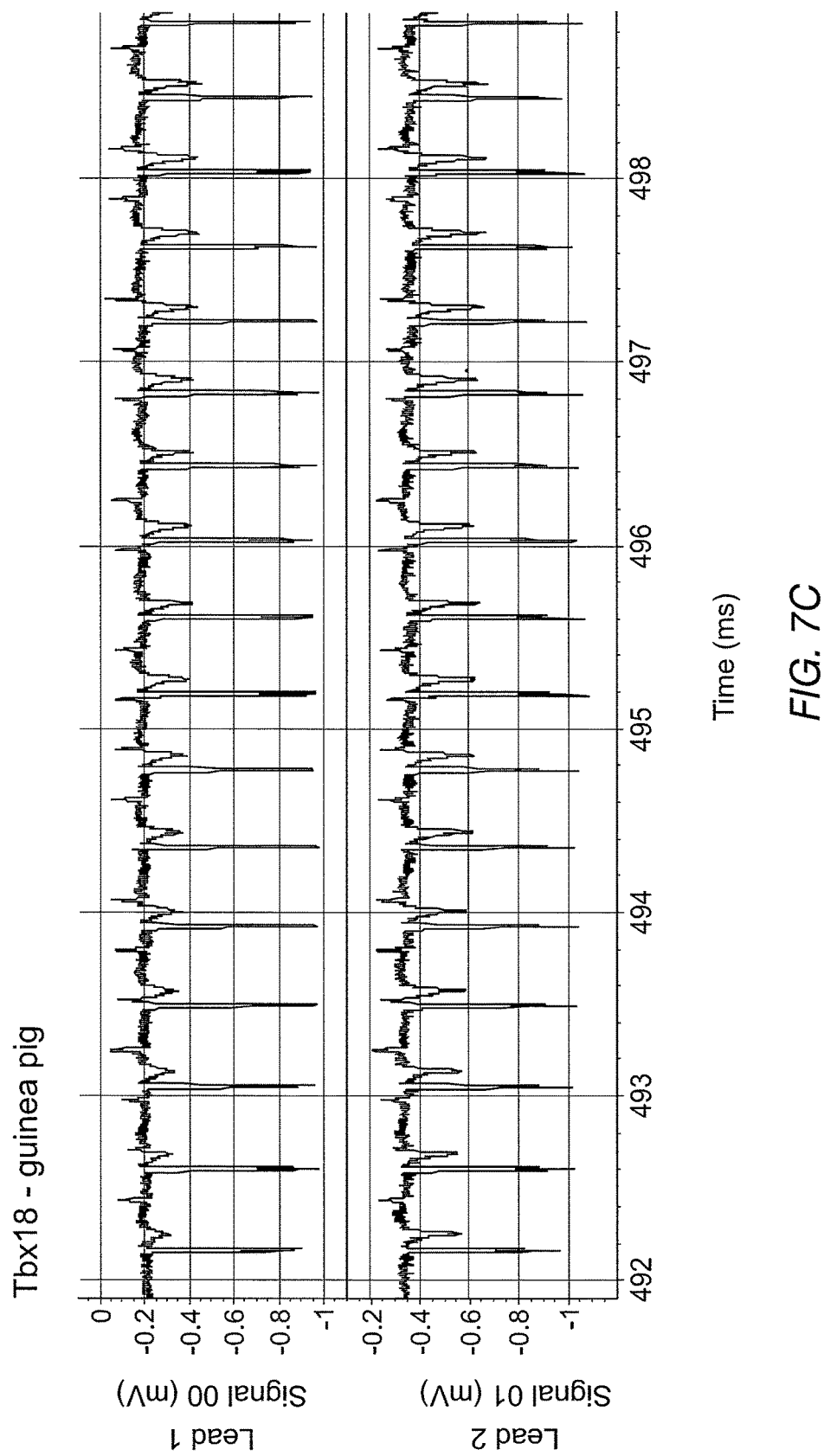
Figure 7D:
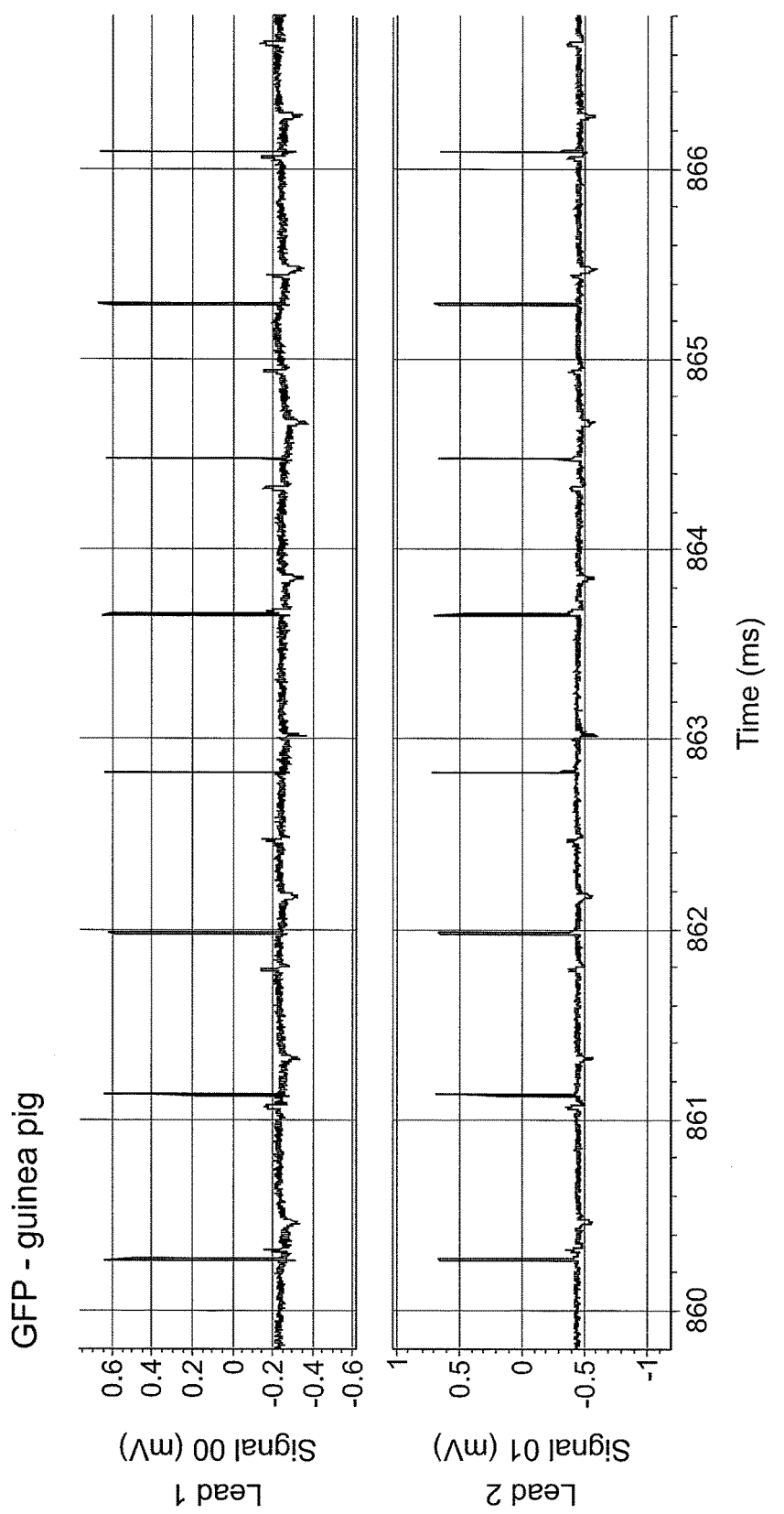

Two to four days after injection into the guinea pig hearts, the hearts were checked for pacemaker-like signals originating from the site of injection. Upon slowing of the sinus rhythm, none of the seven control (GFP-injected) animals exhibited wide-complex escape rhythms, which would indicate pacemaker function (FIG. 6A left). Under the same conditions, 5 of 7 Tbx18-injected animals demonstrated frequent ectopic ventricular beats (wider QRS complexes with negative polarity in Lead II, FIG. 7A) at a rate of 40±21 bpm (FIG. 6B). The rate of ectopic ventricular beats in Tbx18-injected animals at day 3-5 after gene delivery is significantly higher than the control (FIG. 6B). In some embodiments, the rate of beating of the pacemaker cells will be between about 5% to about 15%, about 15% to about 25%, about 25% to about 35%, about 35% to about 45%, about 45% to about 55%, about 55% to about 65%, about 65% to about 75%, about 75% to about 85%, about 85% to about 95%, about 95% to about 100%, and overlapping ranges thereof, of the normal beating rate of healthy pacemaker cells. This beating will correspond to a new heart rate of the mammal, including the human, of about 5% to about 15%, about 15% to about 25%, about 25% to about 35%, about 35% to about 45%, about 45% to about 55%, about 55% to about 65%, about 65% to about 75%, about 75% to about 85%, about 85% to about 95%, about 95% to about 100%, or overlapping ranges thereof, of the normal heart. Electrocardiographic vector analysis revealed that ectopic beats originated at the site of gene injection (apex) and propagated towards the base (FIG. 6A, right). In contrast, the rare escape beats seen in controls did not originate from the site of injection: they were narrow and propagated toward the apex from the atrioventricular junction (FIG. 6A, left). Thus, in vivo transduction of the ventricles with Tbx18 induced ectopic pacemaker activity, which indicates that Tbx18 can be used in treat abnormalities of excitable tissue. In several embodiments, Shox2 could be used instead of or in addition to Tbx18. In several embodiments, one or more of the following transcription factors will be selected for use: Tbx18, Shox2, Tbx3, and Tbx5. It will also be appreciated that, in several embodiments, stem cells, progenitor cells, somatic cells, and/or cardiomyocytes could be transfected with genes for the above transcription factors. Then these cells, after verifying generation of pacemaker activity, can be implanted in vivo to treat abnormalities of excitable tissues.

Morphological Changes

The fidelity of reprogramming was tested by expressing Tbx18 in adult guinea pig ventricles and comparing the properties of Tbx18-transduced ventricular myocytes (Tbx18-VMs) with those of GFP-transduced ventricular myocytes (as controls; control-VMs) and native SAN cells. Adenoviruses co-expressing Tbx18 and GFP, or GFP alone, were directly injected in the apex of the guinea pig heart ($4\times10^7$ cfu/heart). Five days after injection, the heart was harvested and cardiomyocytes were isolated from the site of gene injection.

Figure 8:
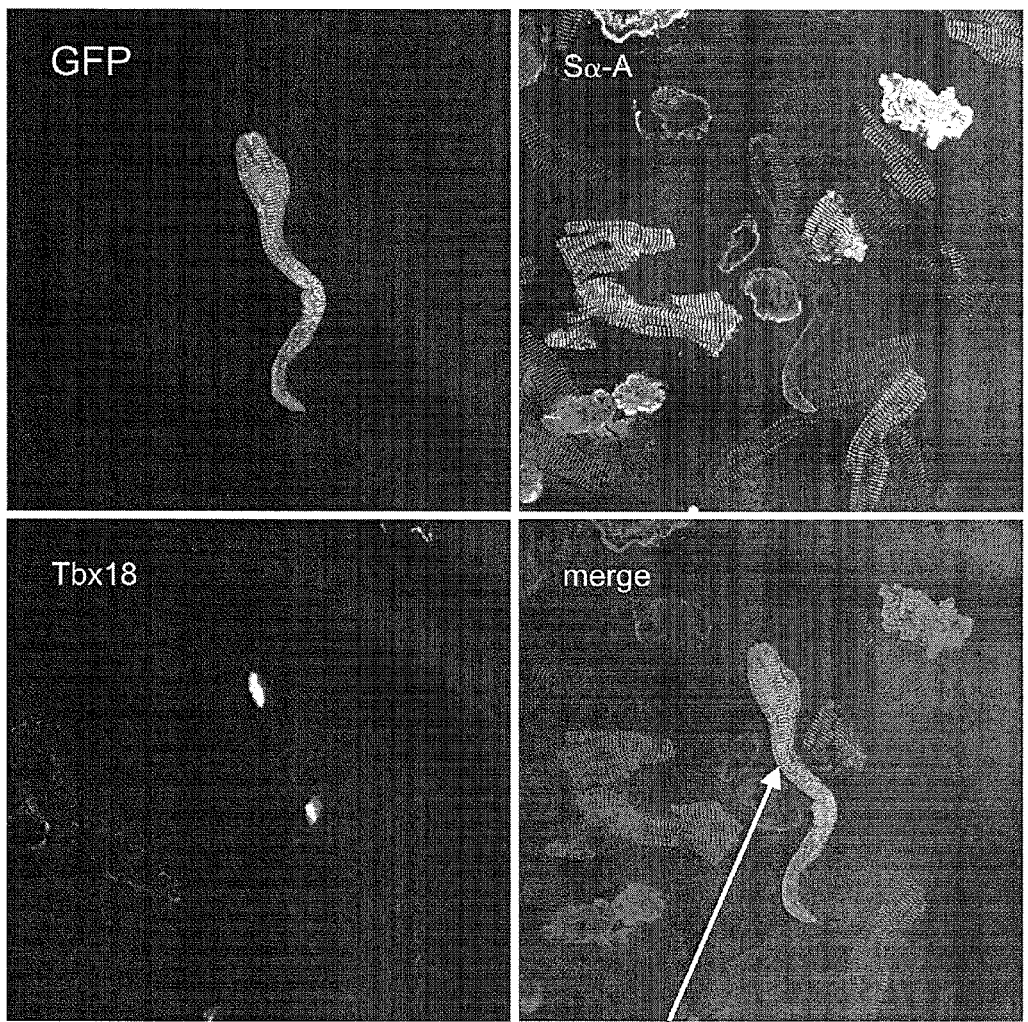
FIG. 8 depicts a Tbx18-injected adult guinea pig heart where a single myocyte is isolated five days after injection. The induced SAN pacemaker cells are created by Tbx18 somatic reprogramming (lower right panel).

Native sinoatrial node cells are smaller and leaner than nontransduced ventricular myocytes: length-to-width (LtW) ratios equal 14.7±1.5 (n=24) and 7.6±0.7 (n=9, p<0.05), respectively. Freshly-isolated control-ventricular myocytes maintained their native shape (with LtW=7.4±0.9, n=4); in contrast, Tbx18-ventricular myocytes were leaner (LtW=16.0±1.0, n=12, p<0.05) than control-ventricular myocytes and were often spindle-shaped, reproducing the morphological hallmark of SAN cells. Control-ventricular myocytes had stable resting potentials at −76 mV, with action potentials elicited only upon electrical stimulation. In contrast, Tbx18-VMs demonstrated diastolic depolarization (maximal diastolic potential=−59 mV) and fired spontaneous action potentials at 26 bpm. Thus the Tbx18 transduced cells function more like pacemaker cells. Whole-cell capacitance, a measure of cell size, was smaller in Tbx18-ventricular myocytes vs. control-ventricular myocytes (40.8±3.6 vs. 119±16 pF, respectively). The electrophysiological and morphological features of Tbx18-VMs generally resembled those of native SAN cells (FIGS. 8 and 9). These data show that somatic gene transfer of Tbx18 in the ventricle in vivo yielded induced SAN (iSAN) cells which faithfully recapitulate the key phenotypic properties of genuine SAN cells. The in situ reprogramming was effective and rapid in speed (as little as five days), offering a novel approach to creating a biological pacemaker as an alternative to electronic devices. The data indicates that in several embodiments the iSAN cells will have a length-to-width ratio greater than the nontransduced ventricular myocytes. In several embodiments, this LtW ratio will be greater than about 2, about 4, about 6, about 8, or about 10. In several other embodiments, this LtW ratio will be about equal to 15. In still additional embodiments, the ratio will range from about 10 to about 12, about 12 to about 14, about 14 to about 16, about 16 to about 20, or greater. In several embodiments, other phenotypic characteristics of the iSAN cells resemble that of native pacemaker cells (e.g., more closely than nontransduced ventricular cells).

Example 3

Testing for Somatic to Somatic Transformation Instead of Dedifferentiation

Figure 2I:
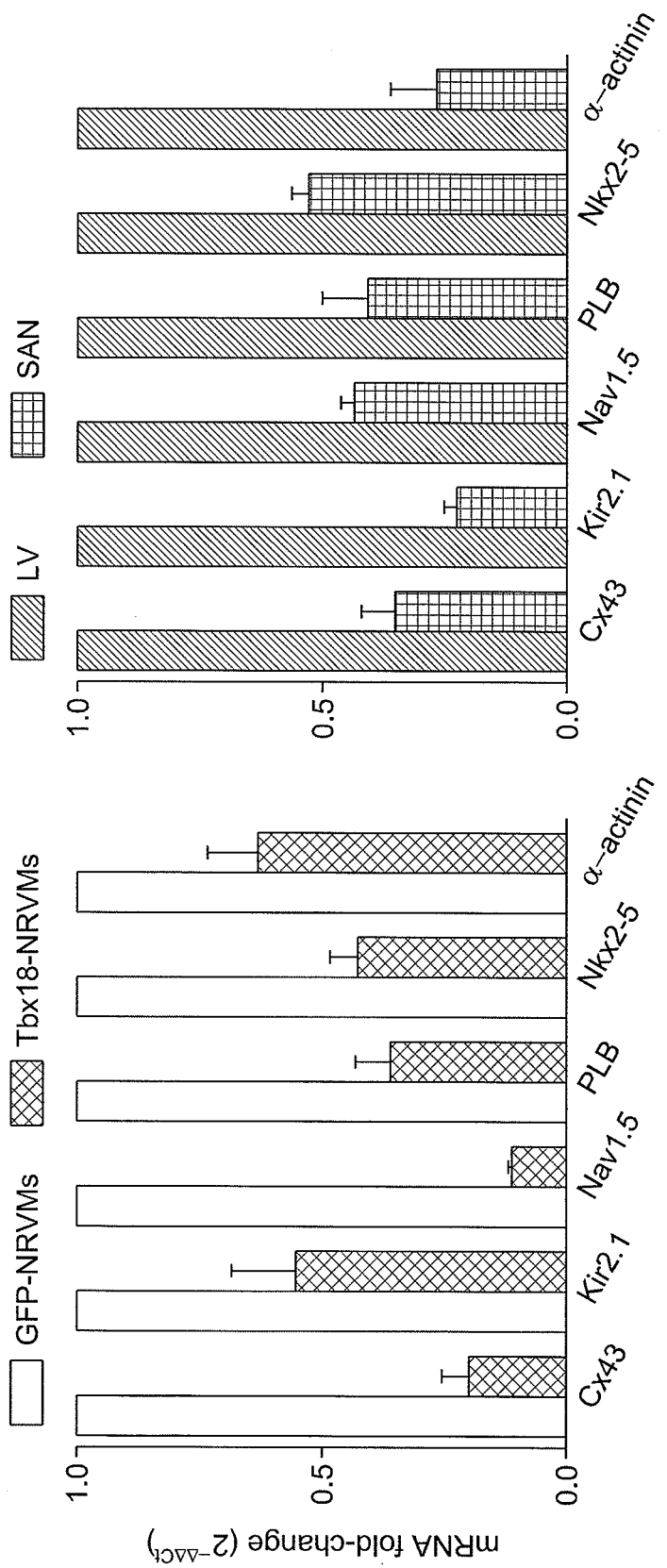
Figure 5C:
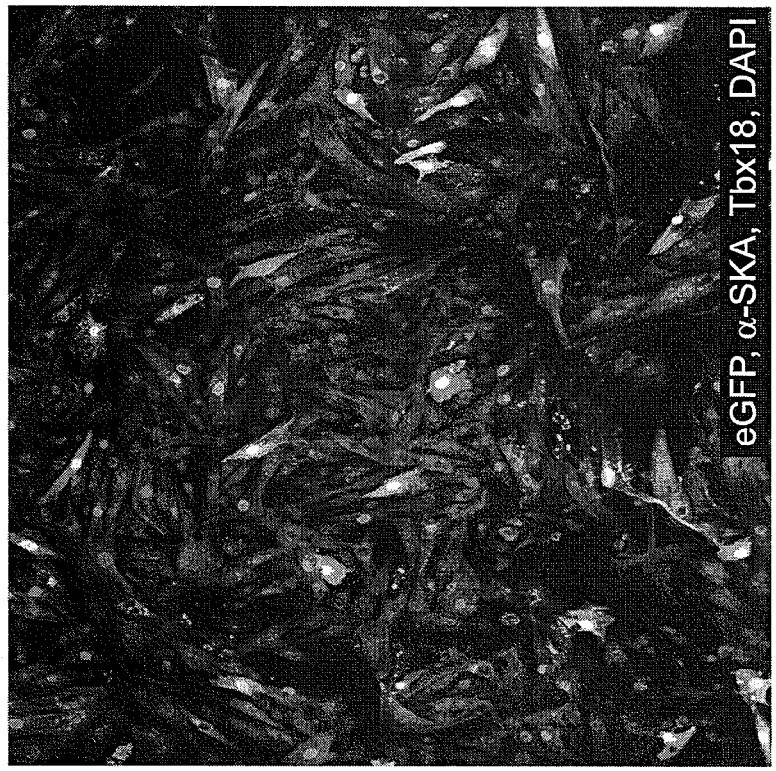
Figure 5D:
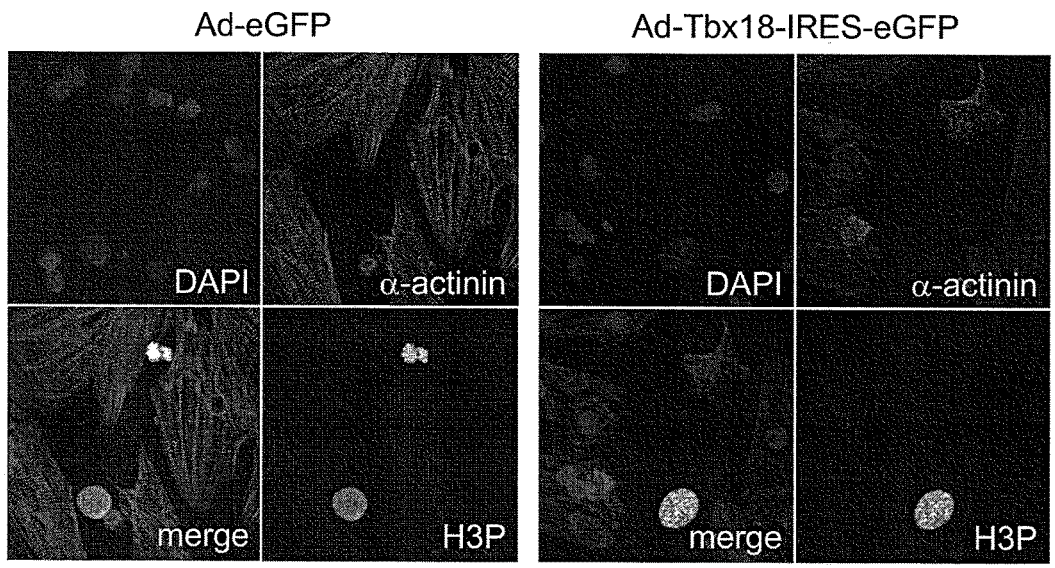
Figure 5D:
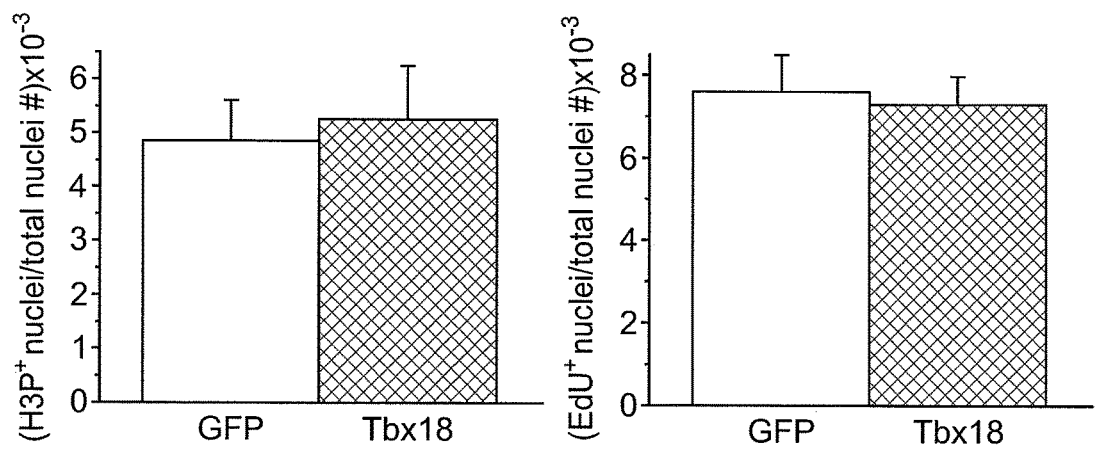
Figure 5E:
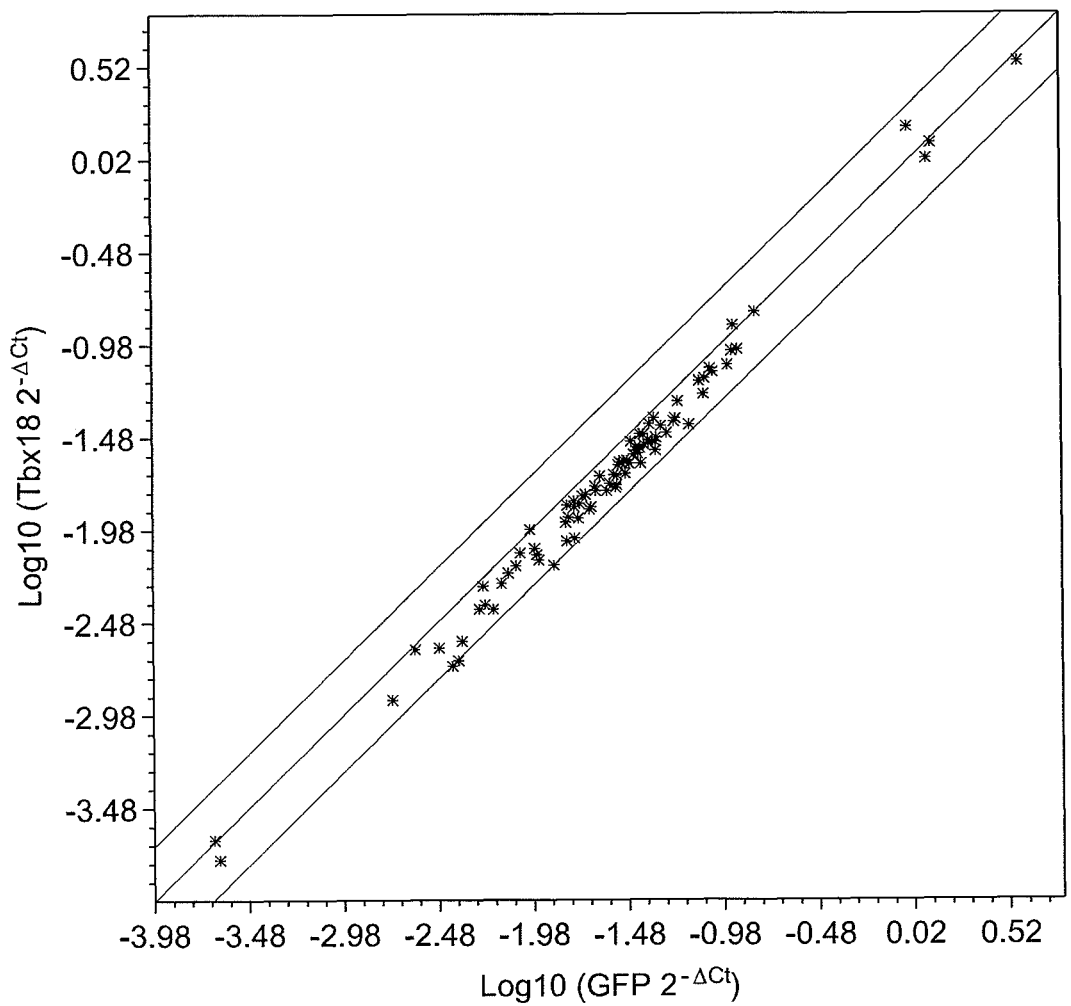
Figure 5F:
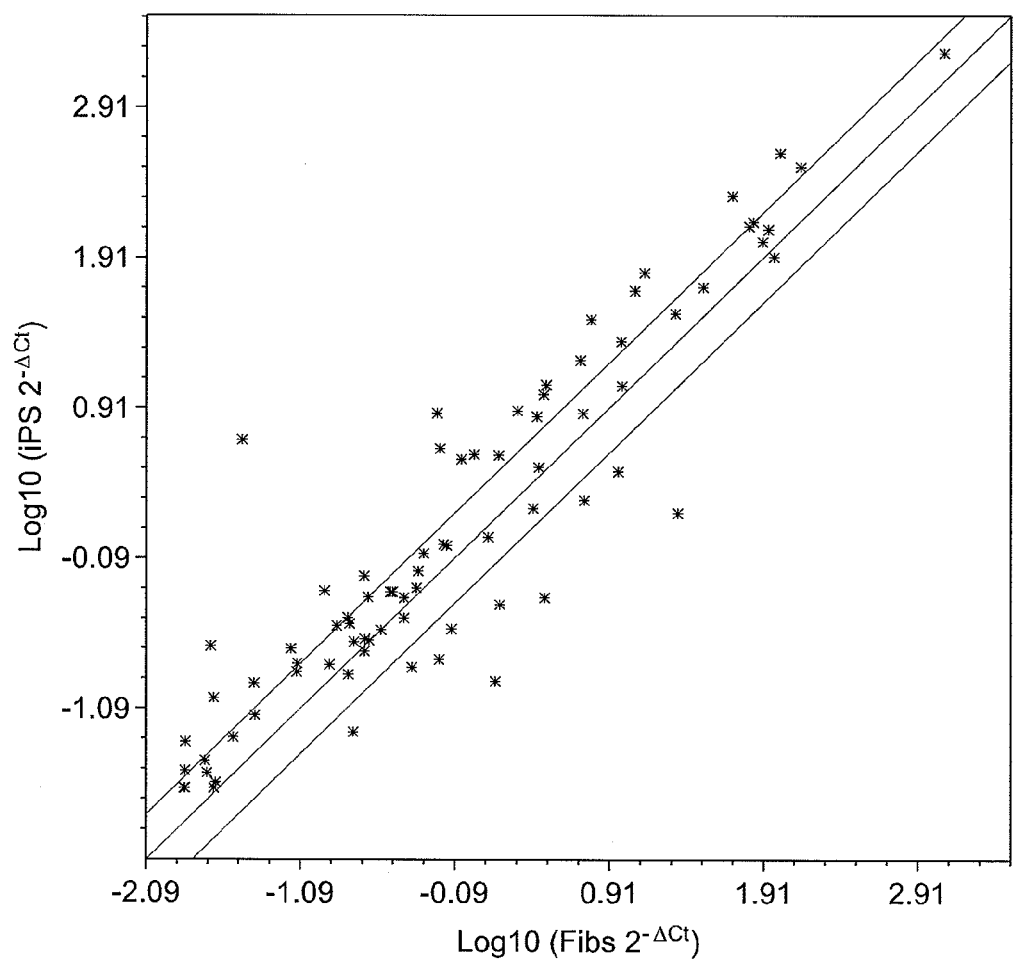
Figure 5G:
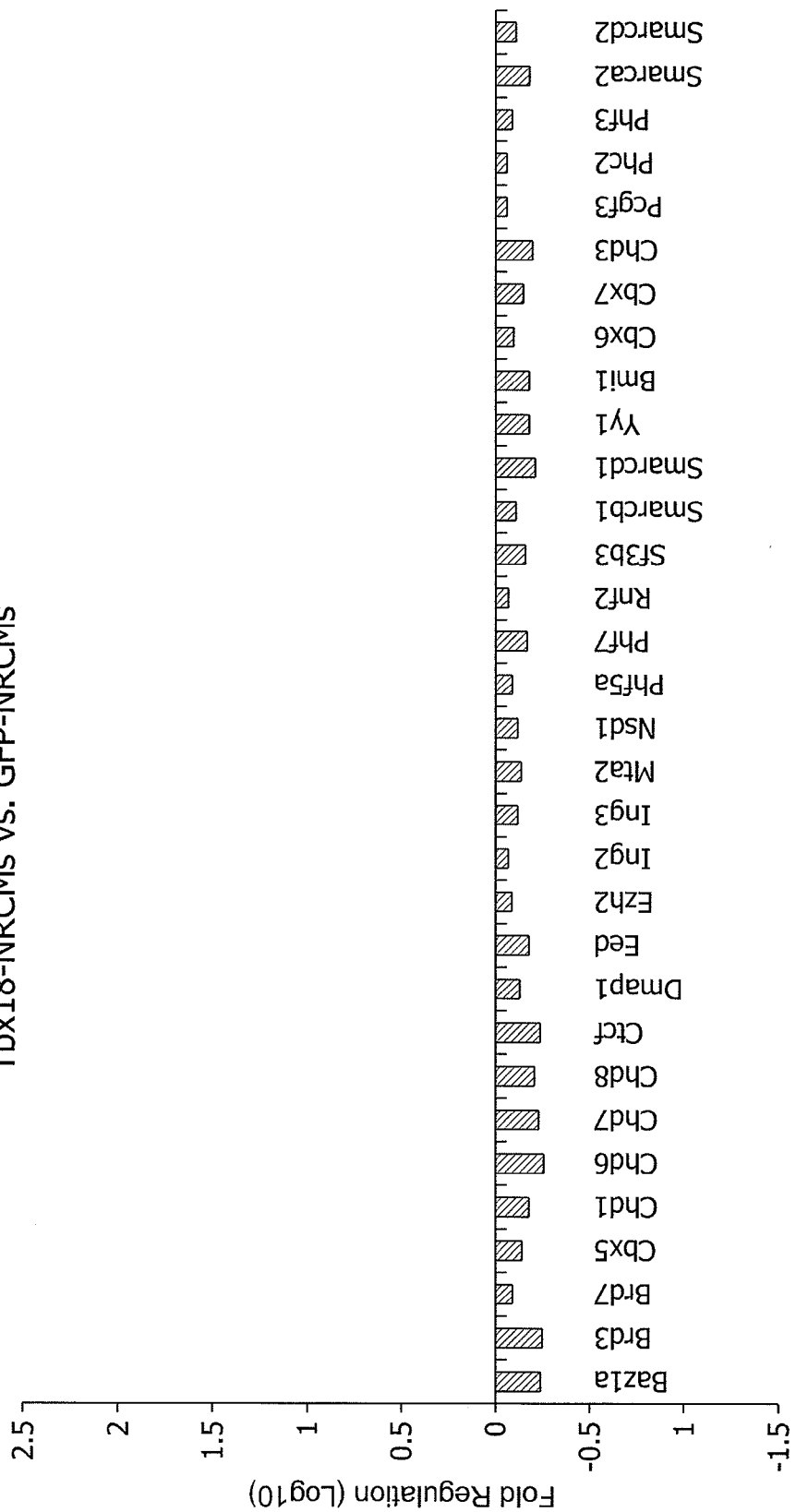
Figure 5H:
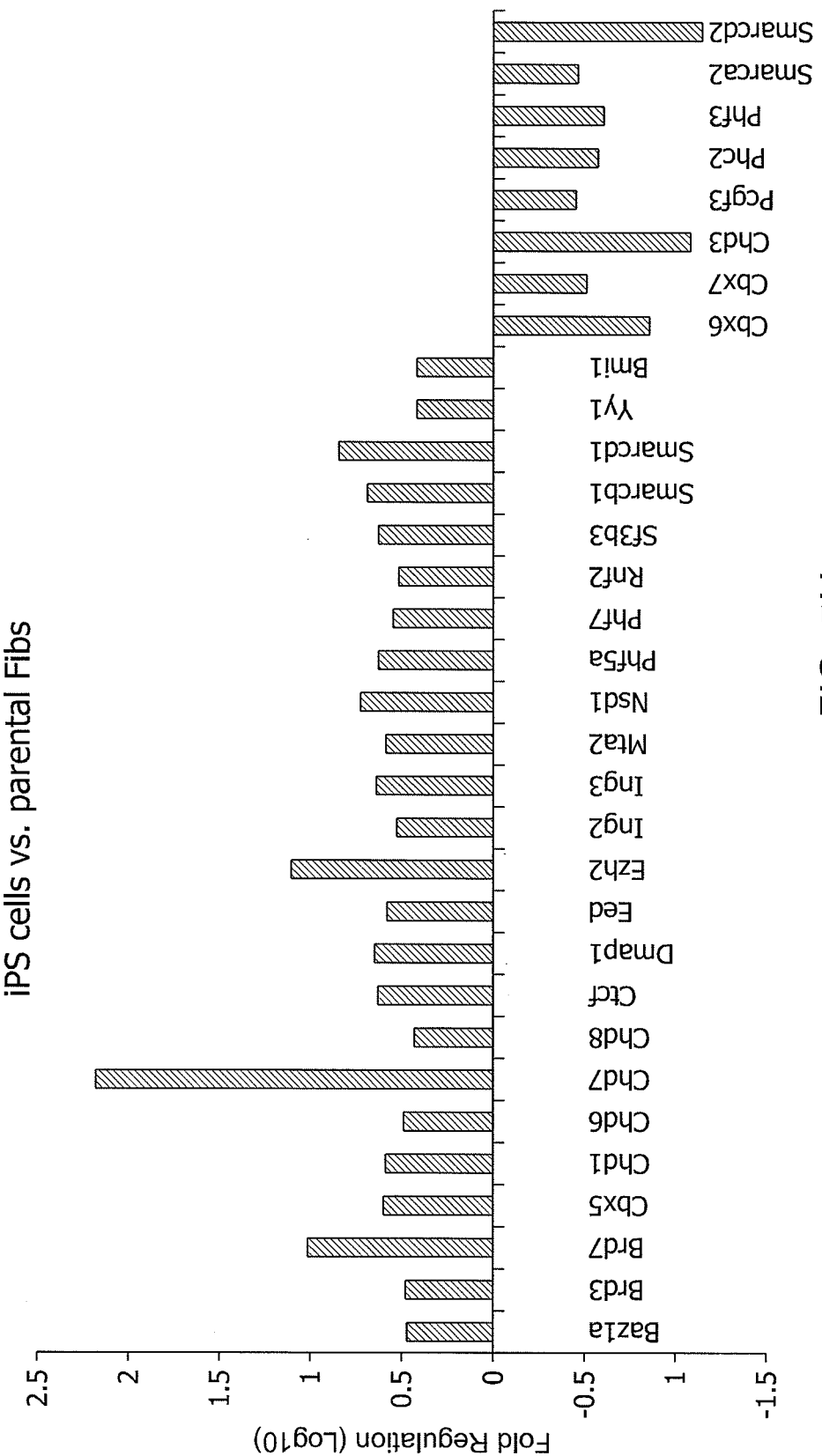
Figure 10A:
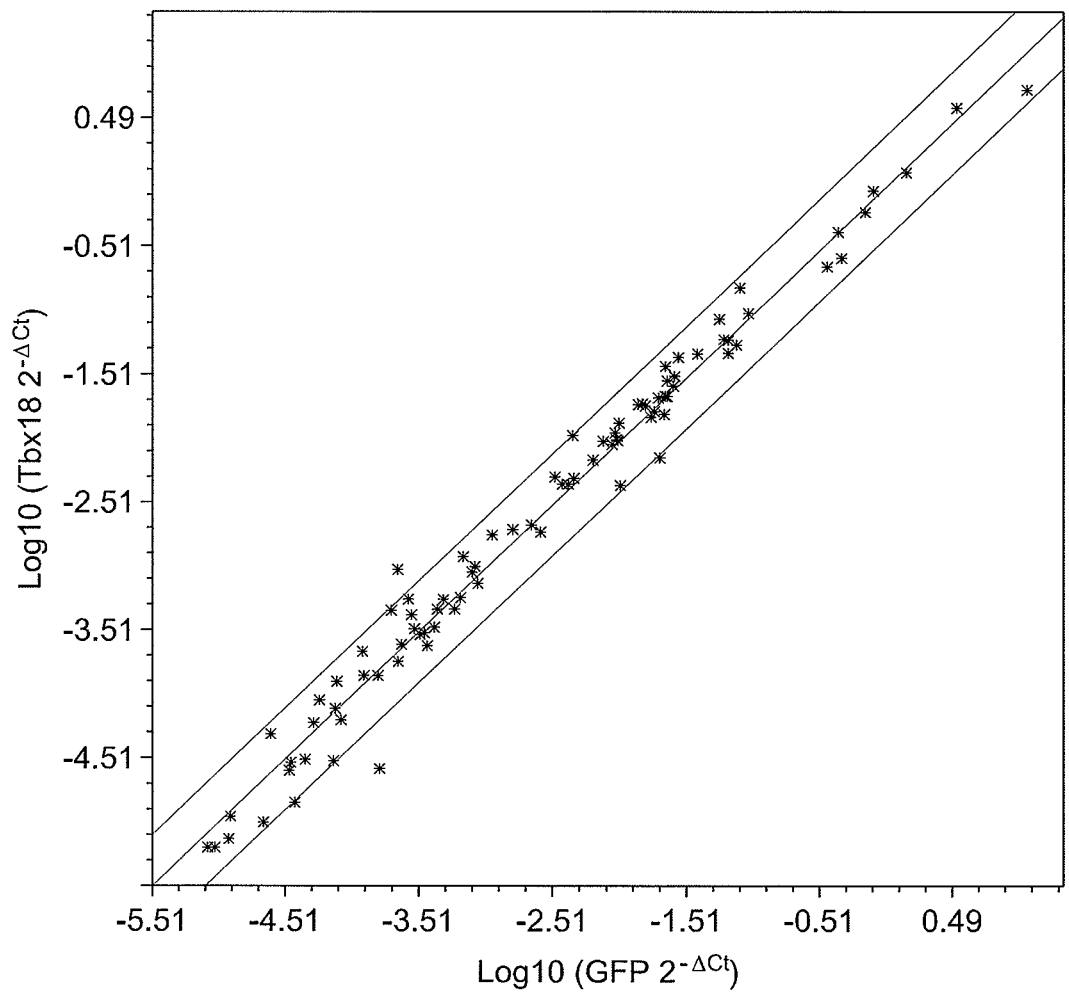
FIGS. 10A-10D depict data related to stemness of Tbx-18 transduced cells.
Figure 10B:
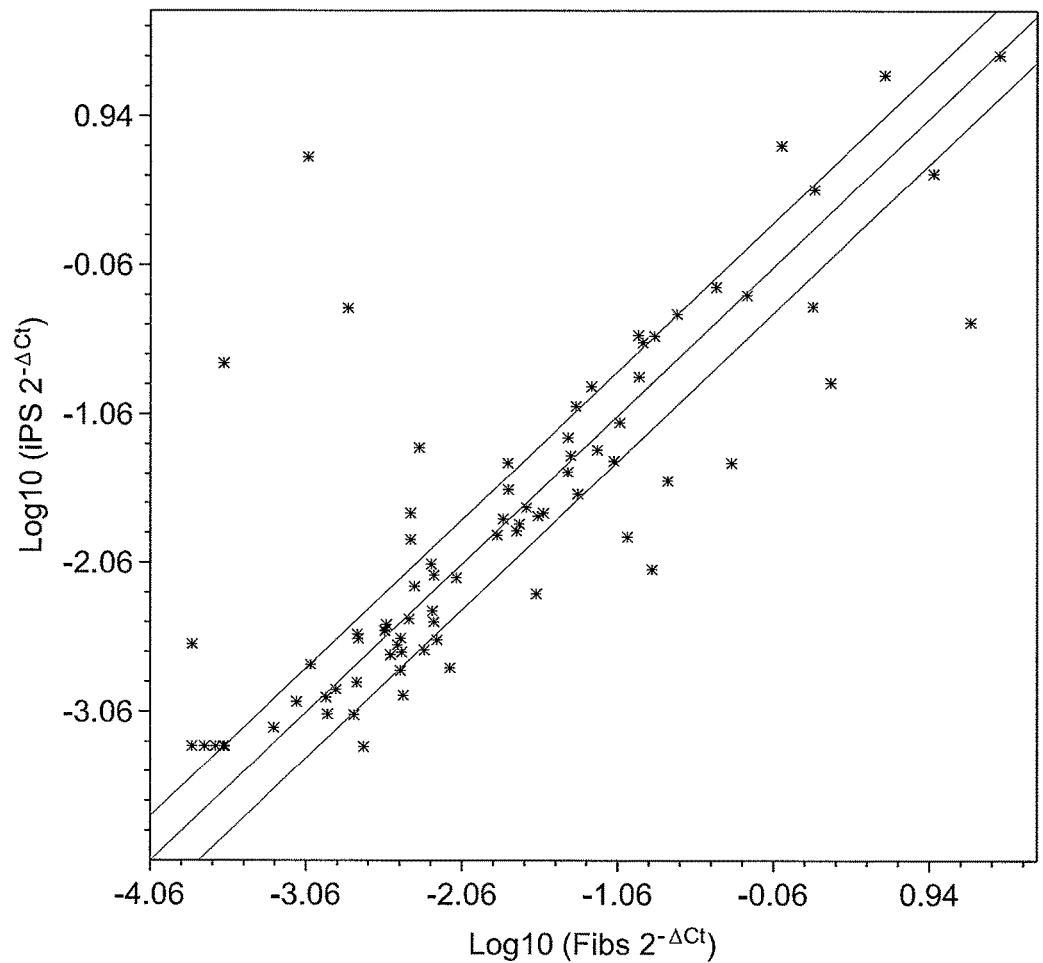
Figure 10C:
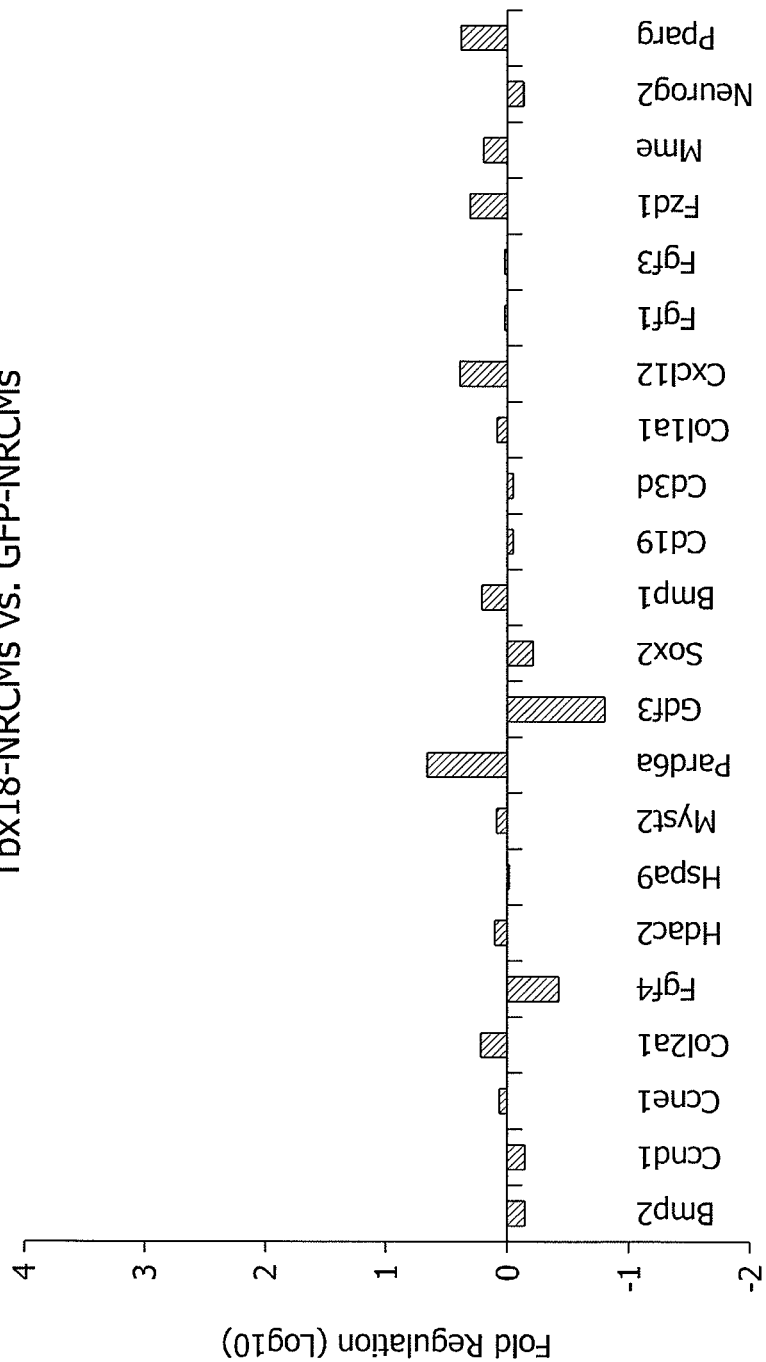
Figure 10D:
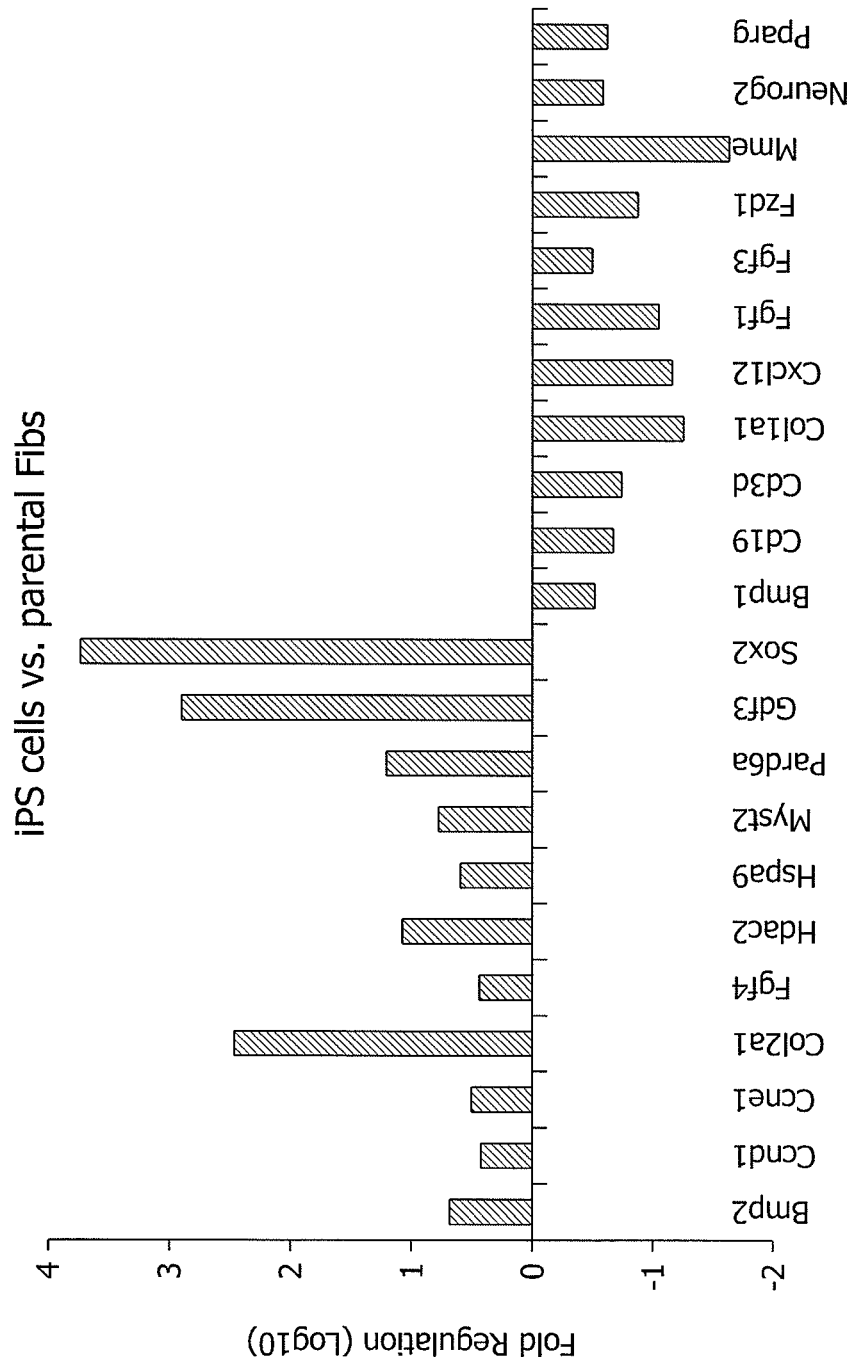

Tbx18 is a marker of multipotent progenitors in cardiac development, and has been associated with neoplasia. Pluripotent stem cells (embryonic or induced) are known to differentiate spontaneously into pacemaker cells. Thus, to reduce concern with neoplasia, testing was performed to ensure that Tbx18 transduction did not produce pacemaker cells via a pluripotent/neoplastic state, which could occur by accelerating the dedifferentiation known to occur in cultured cardiomyocytes. However, the data presented herein indicate that the SAN-like morphology of Tbx18-VMs is not indicative of nonspecific regression. For example, dedifferentiating adult VMs lose the longitudinal, 'bricklike' shape and become rather circular, similar to their neonatal counterparts, but do not become thinner. Further indicating that Tbx18 induces specific re-engineering rather than reversion to a fetal state are the following. First, dedifferentiation is accompanied by re-expression of genes characteristic of the fetal heart, including atrial natriuretic peptide (ANP) and skeletal α-actin (αSkA). Neither ANP nor αSkA was re-expressed in Tbx18-NRVMs (iSAN cells); in fact, ANP expression was strongly suppressed (FIGS. 5C and 5A, B, respectively). Second, dedifferentiation would bring the transduced myocytes closer to a progenitor state, and expression of early ventricular transcription factors such as Nkx2-5 would be enhanced. Instead, Tbx18 lowered the transcript level of Nkx2-5 (FIG. 2I), consistent with conversion to mature pacemaker cells but not reversion to a fetal state. Third, if the de novo automaticity of Tbx18-NRVMs were a consequence of dedifferentiation to an embryonic/fetal state, the proliferative index of those cells would be expected to increase. This is because the embryonic ventricle grows by hyperplasia, an ability which plummets after birth. On the contrary, phosphohistone 3 (H3P, a mitotically-active cell marker) expression and EdU (an analog of BrdU, a marker for mitosis and nascent DNA synthesis) incorporation were comparable in Tbx18- and GFP-NRVMs (n=3, FIG. 5D). Finally, reversion to an embryonic state would be expected to require extensive epigenetic changes. Investigation of 84 genes related to chromatin remodeling identified only minor global differences between Tbx18-NRVMs and GFP-NRVMs (FIG. 5E-H). Furthermore, the investigation expression of 84 genes related to stemness verified that Tbx18-NRVMs remained differentiated with no discernible increase in stemness factors 2-4 days post-transduction (FIG. 10A). These findings contrasted sharply with the increased stemness and decreased differentiation seen in induced pluripotent stem cells relative to their parental dermal fibroblasts (FIG. 10B). In light of the specific gene-related epigenetic changes (FIG. 4C), it was concluded that the de novo pacemaker activity in Tbx18-NRVMs arises from straightforward somatic reprogramming without dedifferentiation to a progenitor state. Fold changes in specific genes are represented as bar graphs for Tbx18 (relative to GFP) and iPSCs (relative to parental fibroblasts) in FIG. 10C and FIG. 10D, respectively. It will be appreciated that, in several embodiments, Shox2 could be used instead of or in conjugation with Tbx18. In several embodiments, one or more of the following transcription factors will be selected for use to achieve transdifferentiation: Tbx18, Shox2, Tbx3, and Tbx5.

From these data it shall be appreciated that, in several embodiments, the quiescent cells will transdifferentiate to iSAN cells without first dedifferentiating to an embryonic/fetal state. Thus, in several embodiments the iSAN cells may exhibit similar morphology to that of native SAN cells consistent with conversion from quiescent cells to iSAN cells without dedifferentiation. Likewise, in several embodiments, expression of ANP and αSkA will be suppressed in the iSAN cells. Additionally, in several embodiments, iSAN cells may exhibit transcript levels of Nkx2.5 similar to that of mature native pacemaker cells. In several embodiments the iSAN cells will remain differentiated without any discernible increase in stemness factors. In several embodiments this transdifferentiation may occur in vitro, while in other embodiments this transdifferentiation may occur in vivo. In several embodiments, the quiescent cells will be mammalian, including several embodiments in which the quiescent cell is human.

Example 4

Differentiation of Embryonic Stem Cells using Shox2 to a Pacemaker Phenotype

Figure 11A:
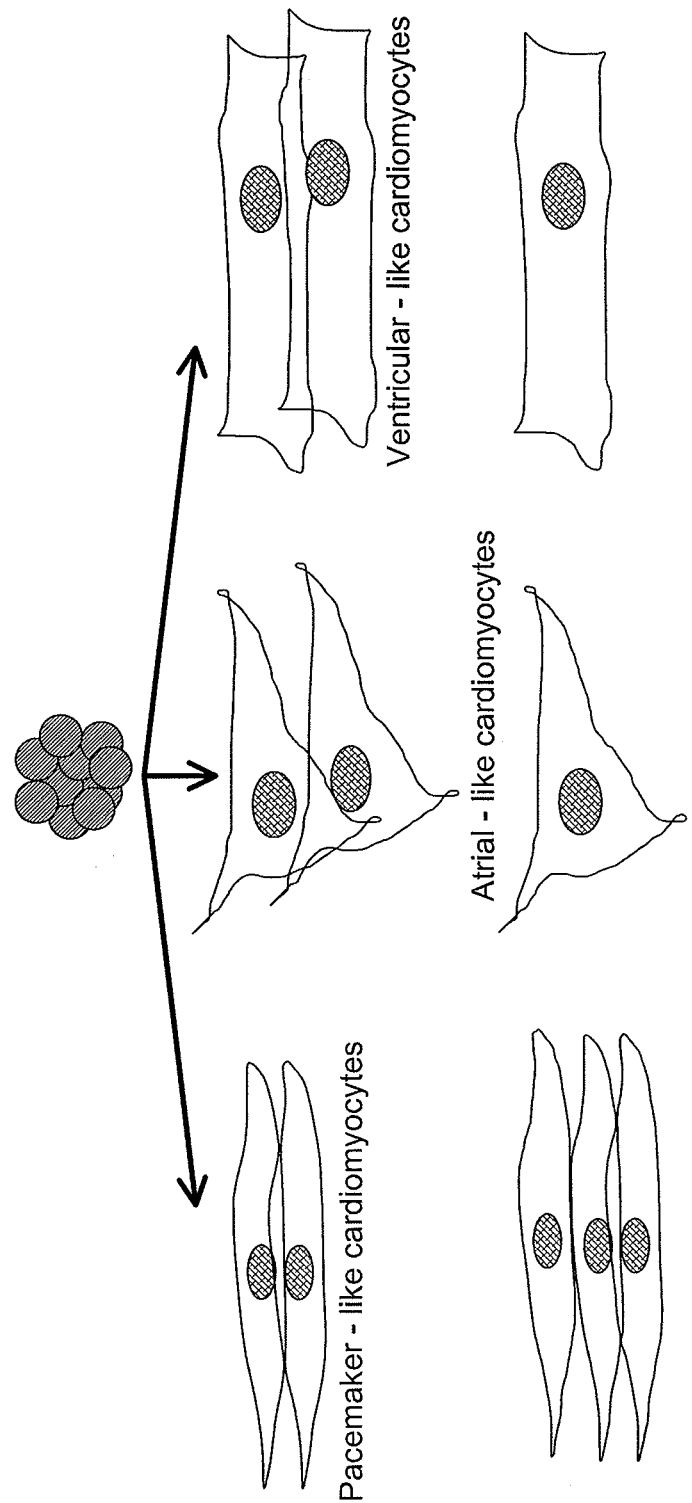
FIG. 11A depicts a schematic of the cells derived from the growth of embryoid bodies (EB).
Figure 11B:
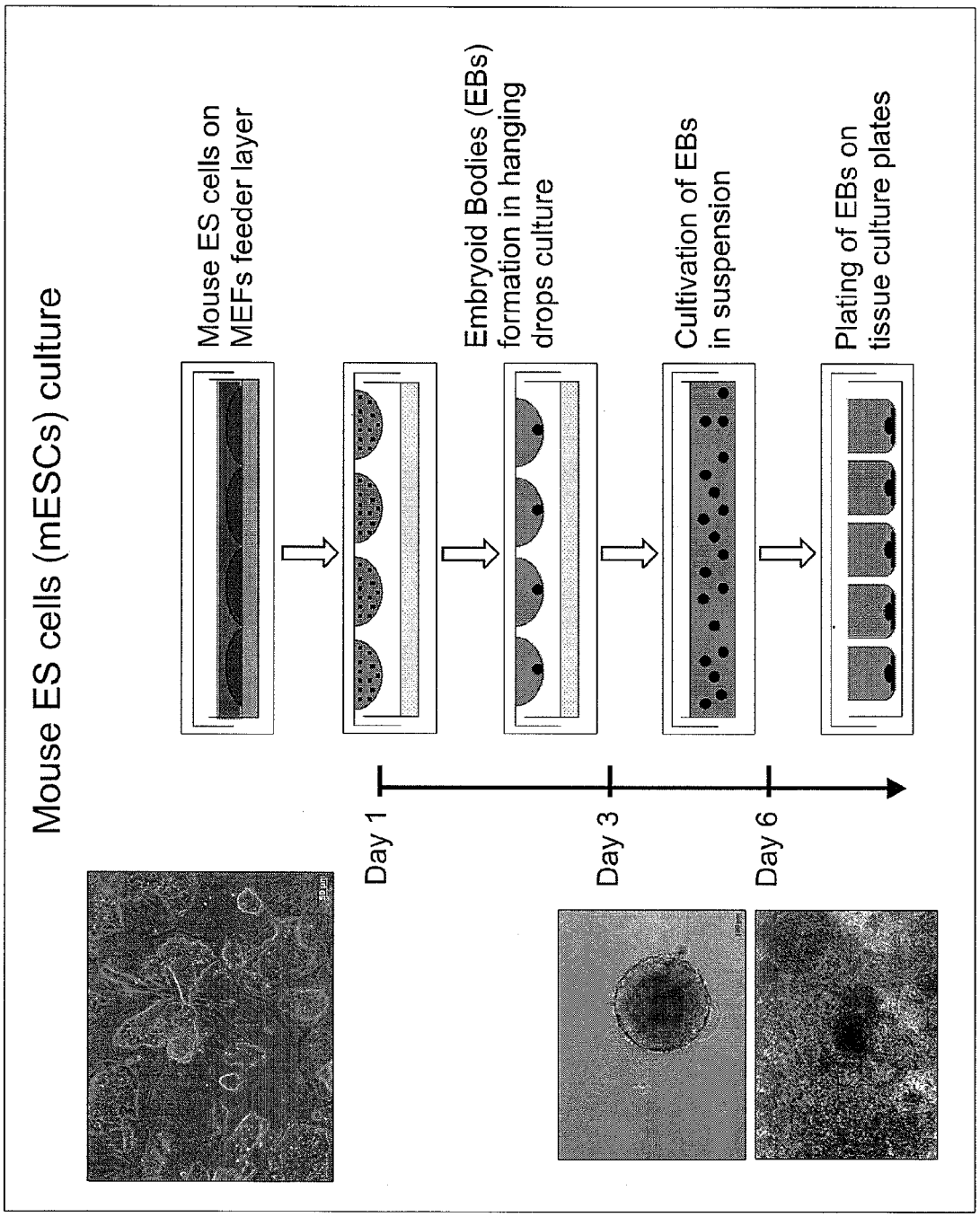
FIG. 11B depicts a schematic for embryoid body (EB) EB growth. On day 3 the hanging EBs were cultivated in suspension. On day 6 the EBs were plated in tissue culture plates.

Embryonic stem cells can spontaneously differentiate into heterogeneous aggregates of cardiomyocytes with atrial, ventricular, and pacemaker properties. Experiments were thus performed to test whether Embryonic stem cells could be biased from random cardiogenesis toward a dominant pacemaker phenotype. Shox2 is an embryonic transcription factor essential for the patterning of pacemaker cells in the sinoatrial node. Using Shox2 overexpression, the developmental program for the embryonic stem cells was tilted and dominated toward pacemaker myocytes. It will be appreciated that, in several embodiments, Tbx18 could be used instead of or in conjugation with Shox2. In several embodiments, one or more of the following transcription factors could be selected for use: Tbx18, Shox2, Tbx3, and Tbx5.
Results:

Mouse embryonic stem cells were cultured on a MEFs feeder layer. Embryoid body formation was cultivated using established hanging drop culture methods. On day 3, cultivation of embryoid bodies was performed. On day 6, plating of embryoid bodies on tissue culture plates was performed (FIG. 11).

Figure 12A:
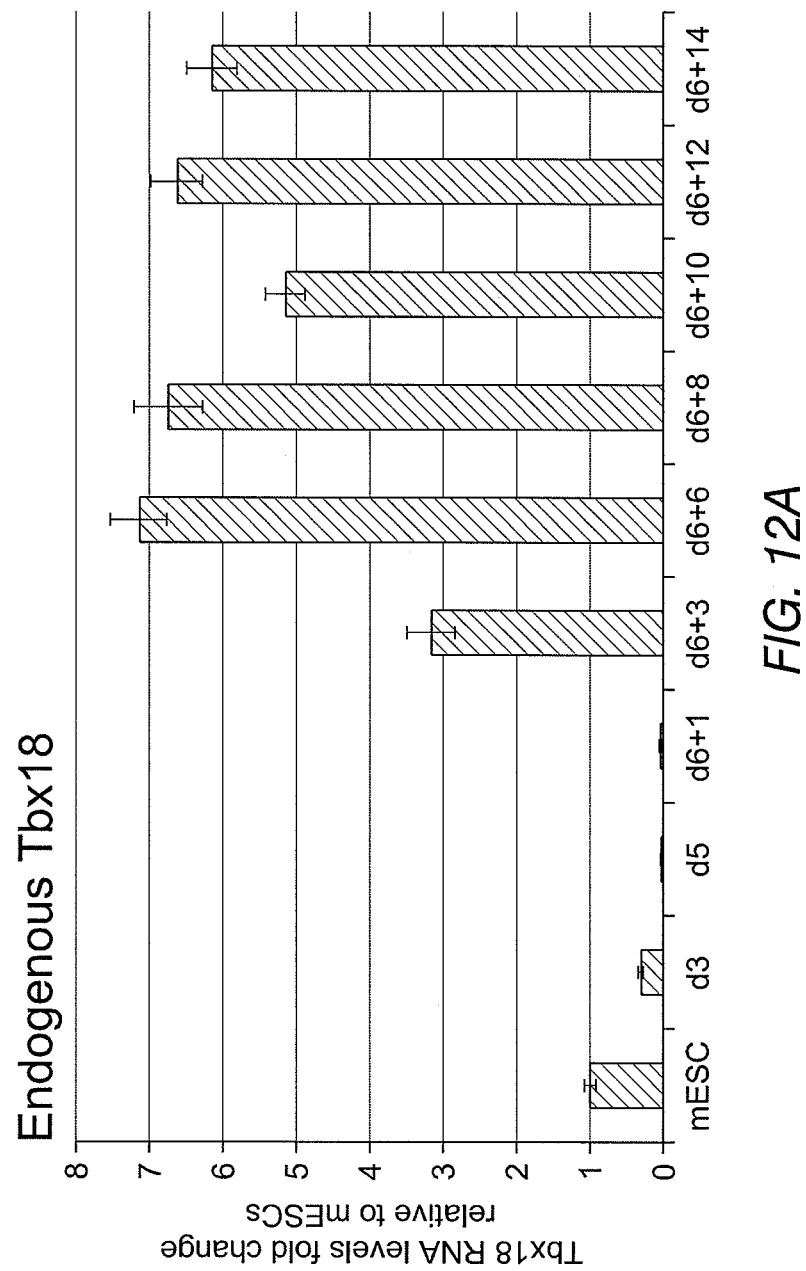
FIGS. 12A-12B depict endogenous expression of Tbx18 (A) and Tbx3 (B) relative to control murine embryonic stem cells (mESCs) during the growth of EBs.
Figure 12B:
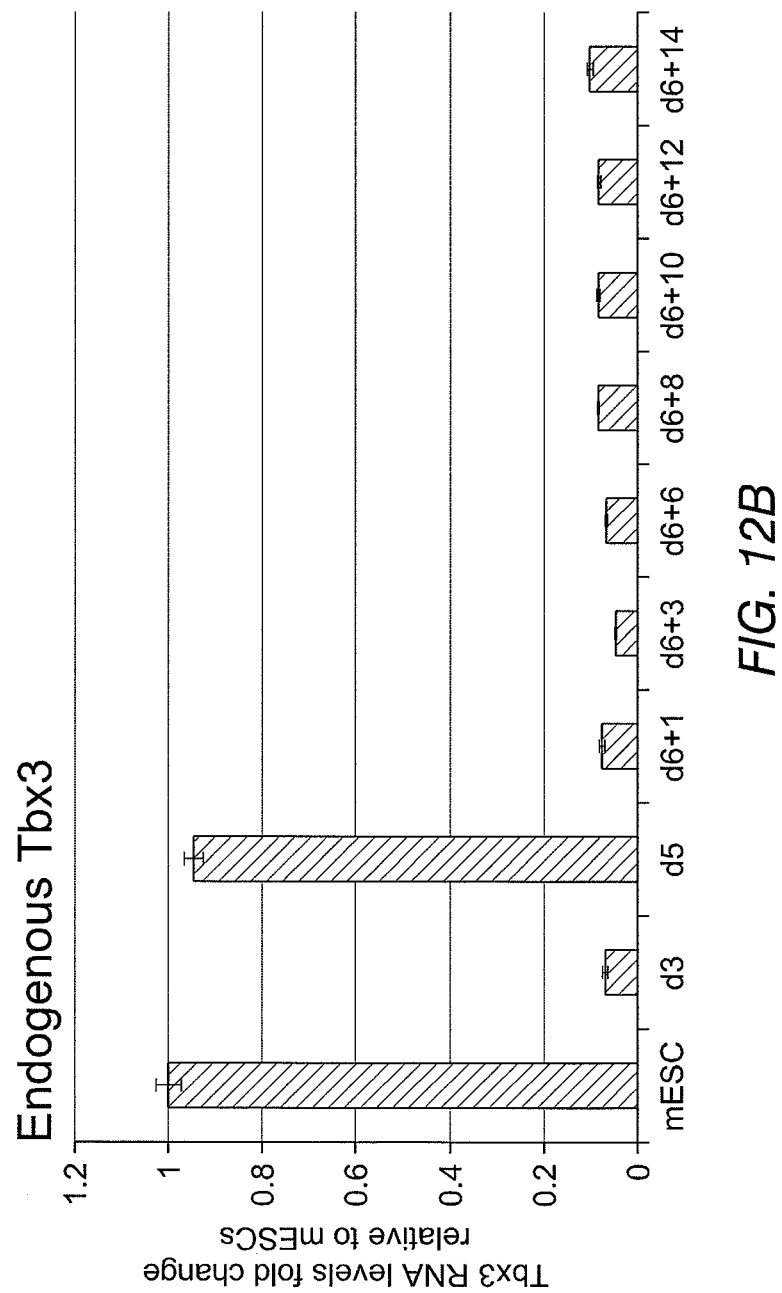
Figure 13A:
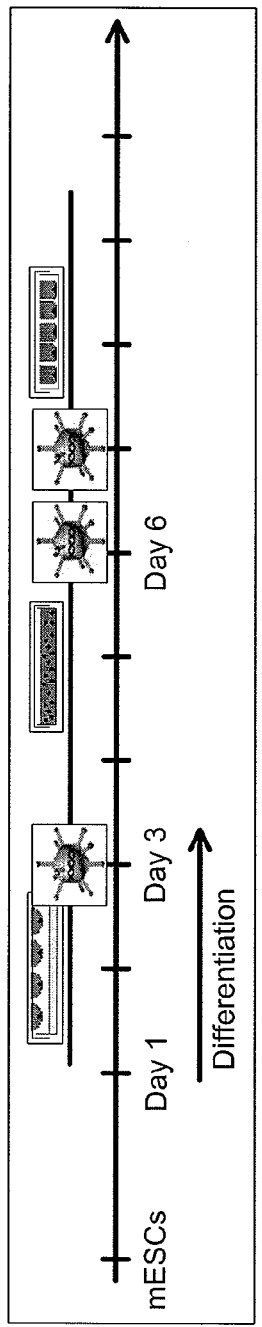
FIG. 13A depicts a treatment schedule of cells with Shox2. Treatment with vectors carrying the Shox2 gene occur at day three (in this general scheme), then twice at day 6.
Figure 13B:
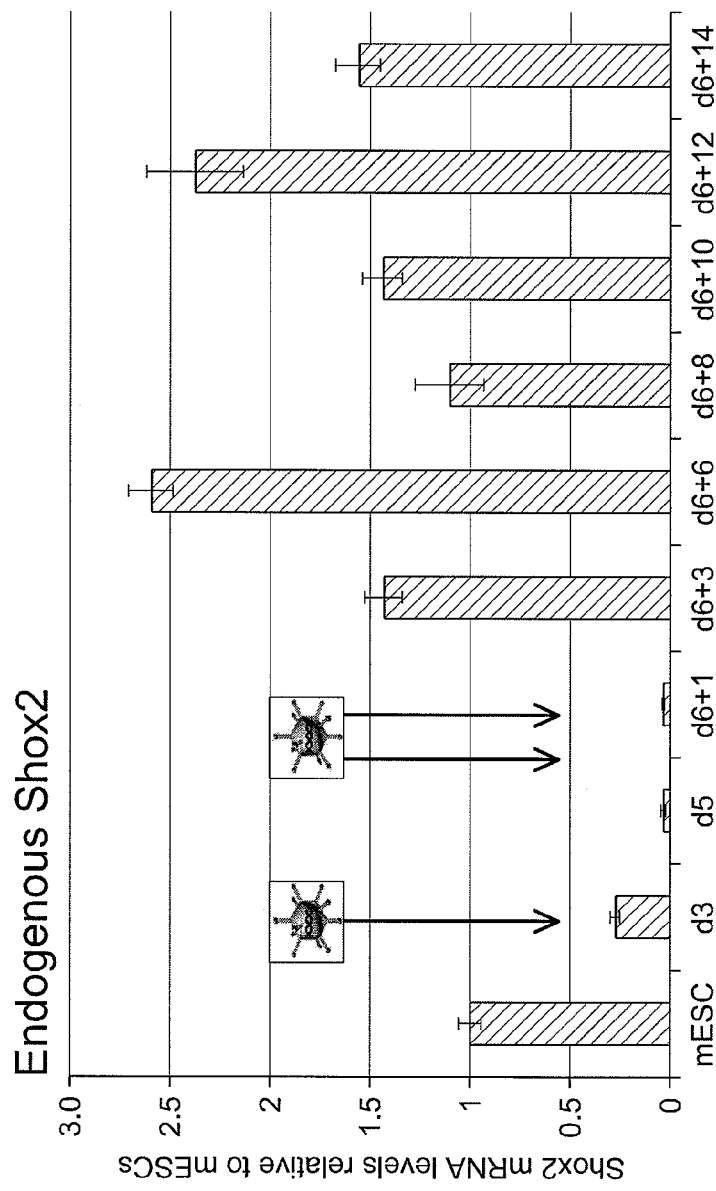
FIG. 13B depicts endogenous Shox2 mRNA expression at differing time points after transduction.

Endogenous levels of transcription factor RNA were measured at several time points. As shown in FIG. 12, endogenous levels of Tbx18 RNA increased sharply upon formation of embryoid bodies and leveled after plating of the embryoid bodies. Endogenous Tbx3 RNA however, decreased relative to mouse embryonic stem cells. FIG. 13 shows the administration of Shox2 expression vectors. As shown by the graph in 13B, the level of mRNA relative to control mouse embryonic stem cells increased after the third administration of Shox2-vector to levels higher than for control mouse embryonic stem cells.

Figure 14A:
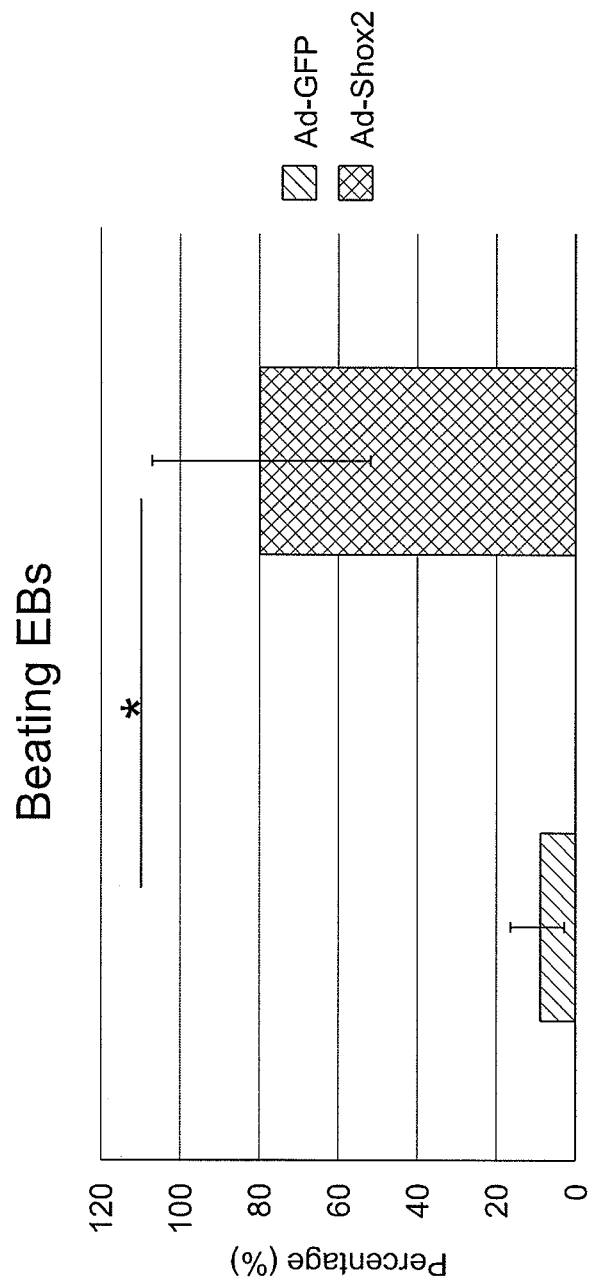
FIG. 14A depicts the percentage of beating EBs that were transduced with Shox2 relative to a control that was treated only with GFP.
Figure 14B:
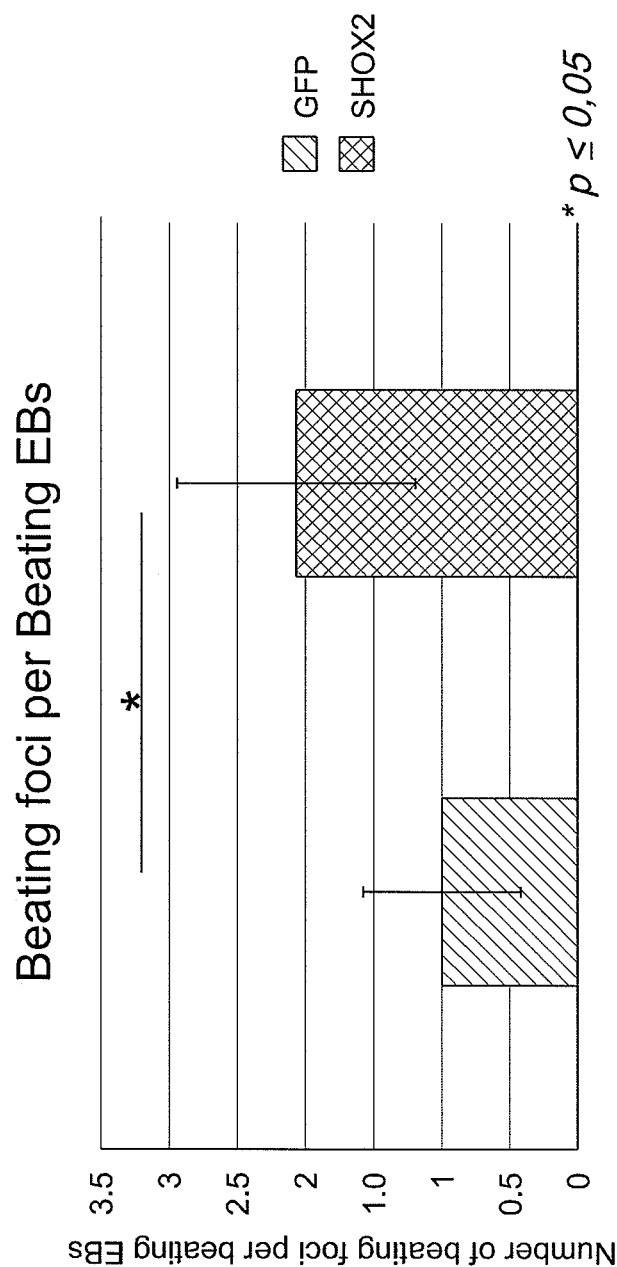
FIG. 14B depicts the number of beating foci per beating EB.
Figure 15A:
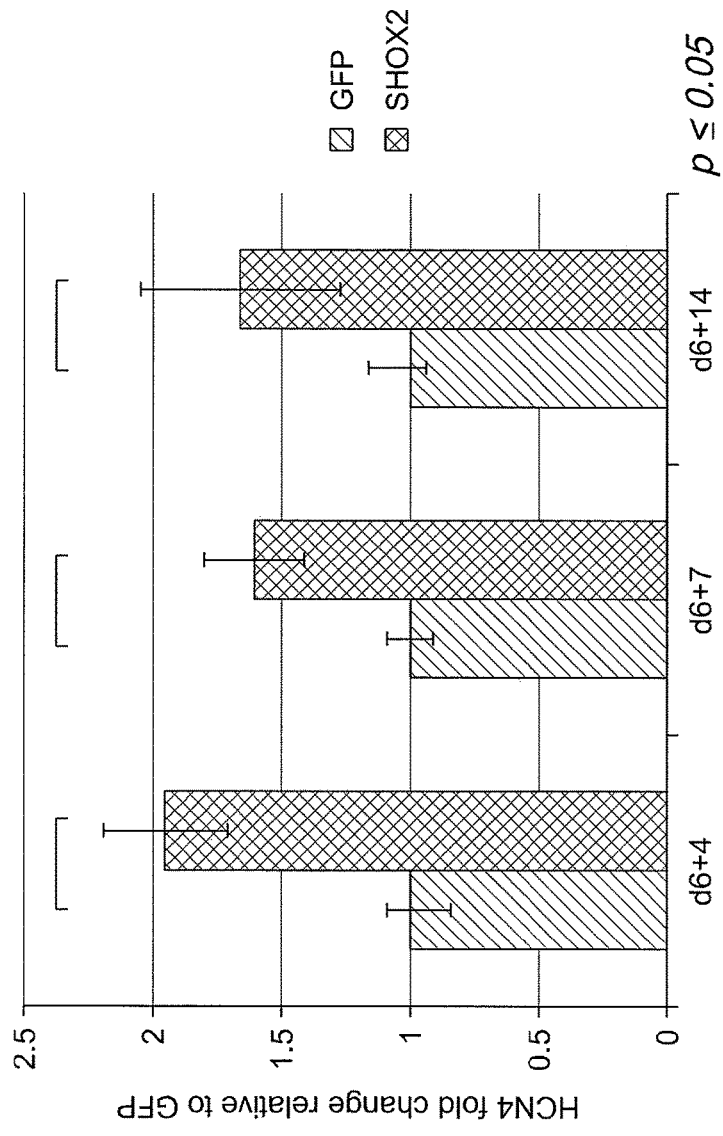
FIG. 15A depicts the increase in HCN4 mRNA expression for cells treated with Shox2 expression factors relative to cells treated with GFP.
Figure 15B:
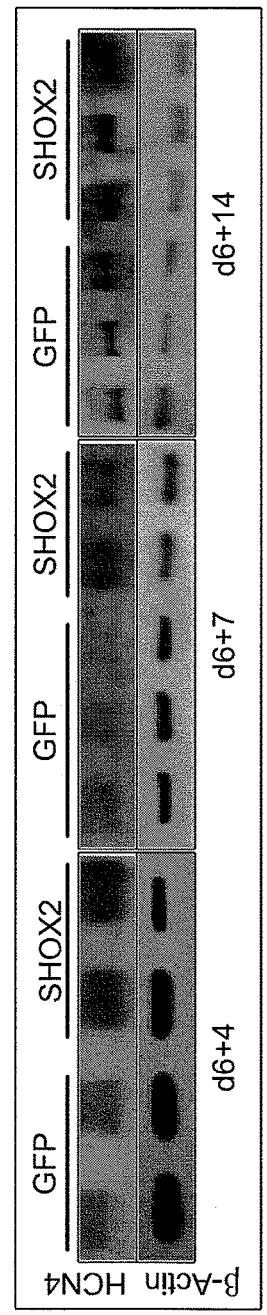
FIG. 15B shows the Western Blot analysis for the corresponding time points in FIG. 15A.
Figure 16A:
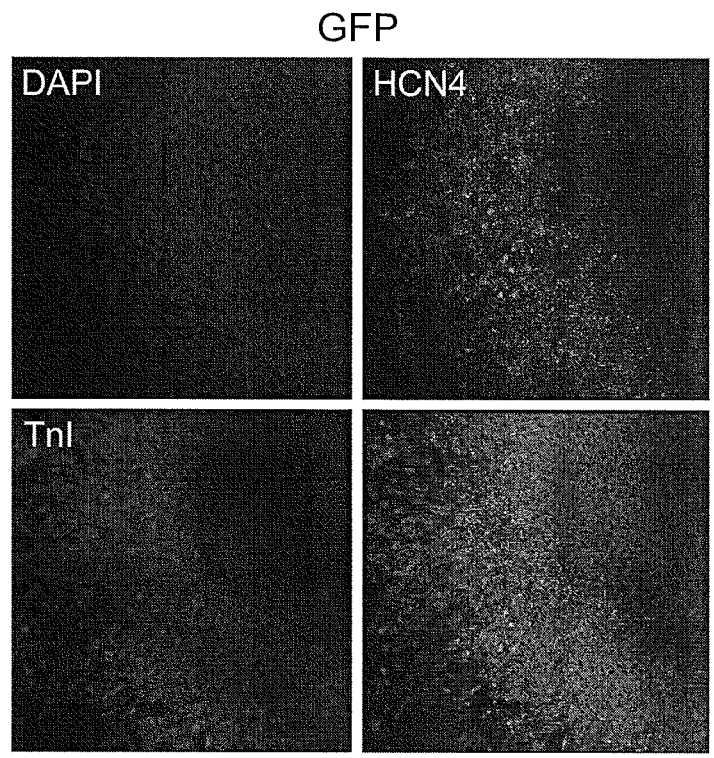
FIG. 16 depicts the HCN4 co-expression with troponin I in Shox2 transduced mESCs-derived cardiomyocytes (B) as compared to GFP controls (A).
Figure 16B:
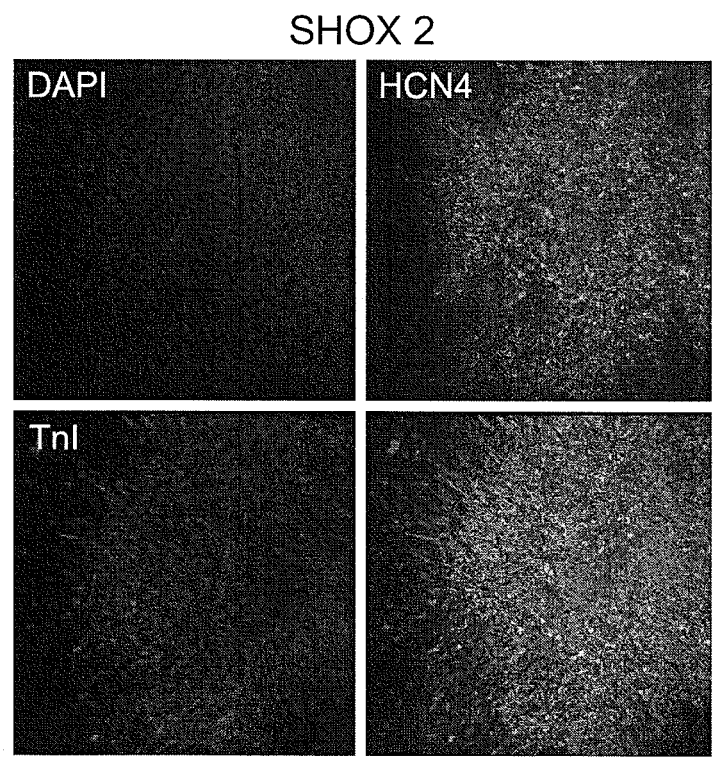
Figure 17A:
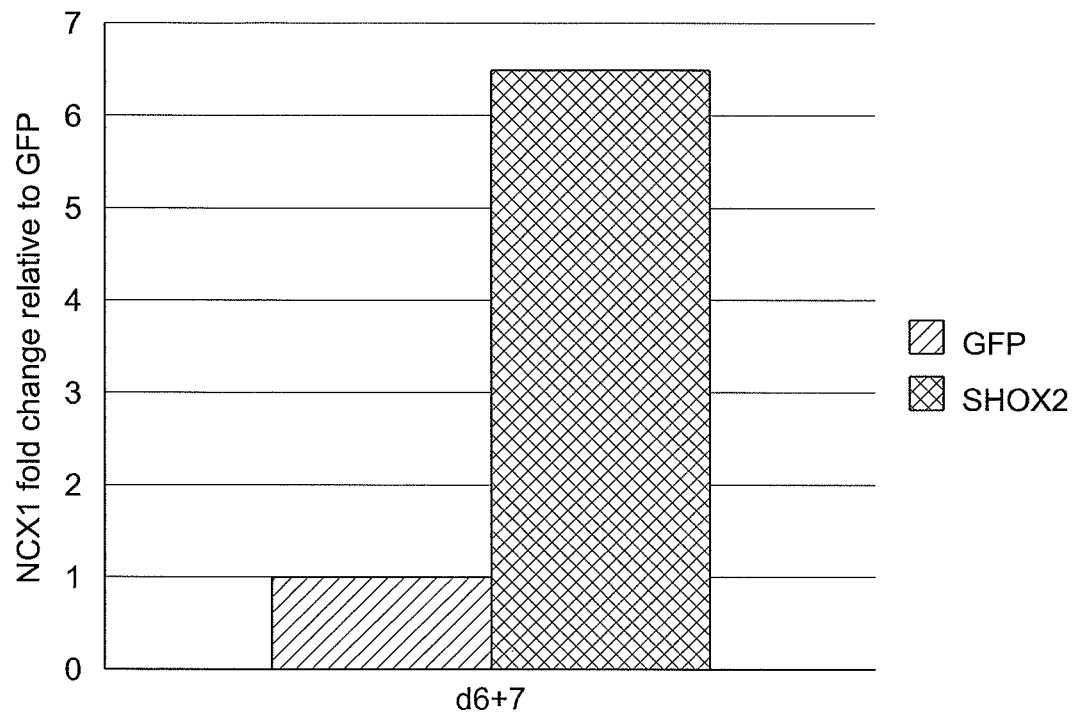
FIG. 17 depicts the NCX1 mRNA (A) and protein levels (B) in Shox2 transduced cells versus a GFP control at day 6+7 (post transduction).
Figure 17B:
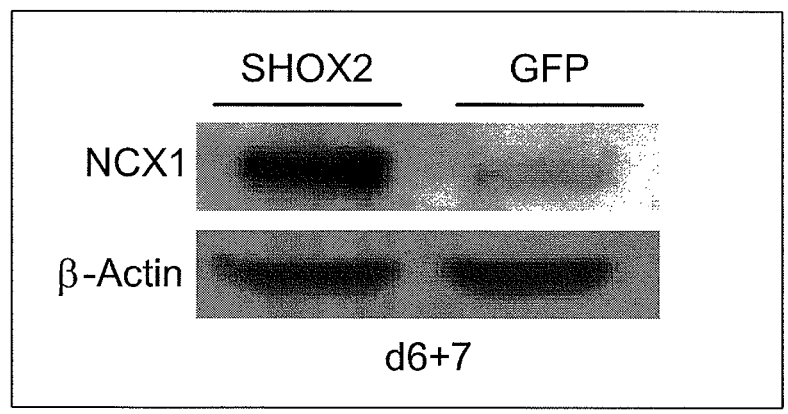
Figure 18A:
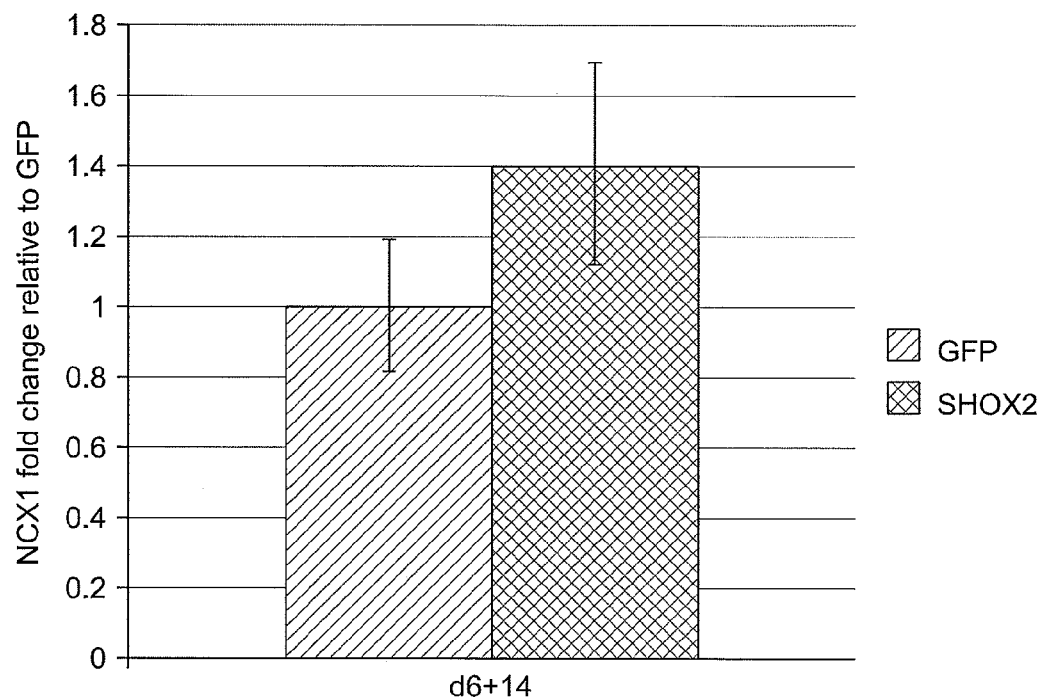
FIG. 18 depicts the NCX1 mRNA (A) and protein levels (B) in Shox2 transduced cells versus a GFP control at day 6+14 (post transduction).
Figure 18B:
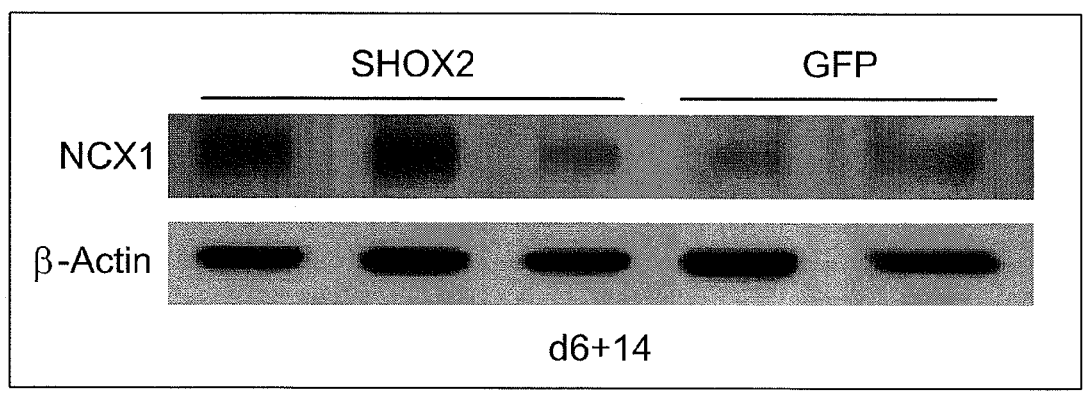
Figure 19A:
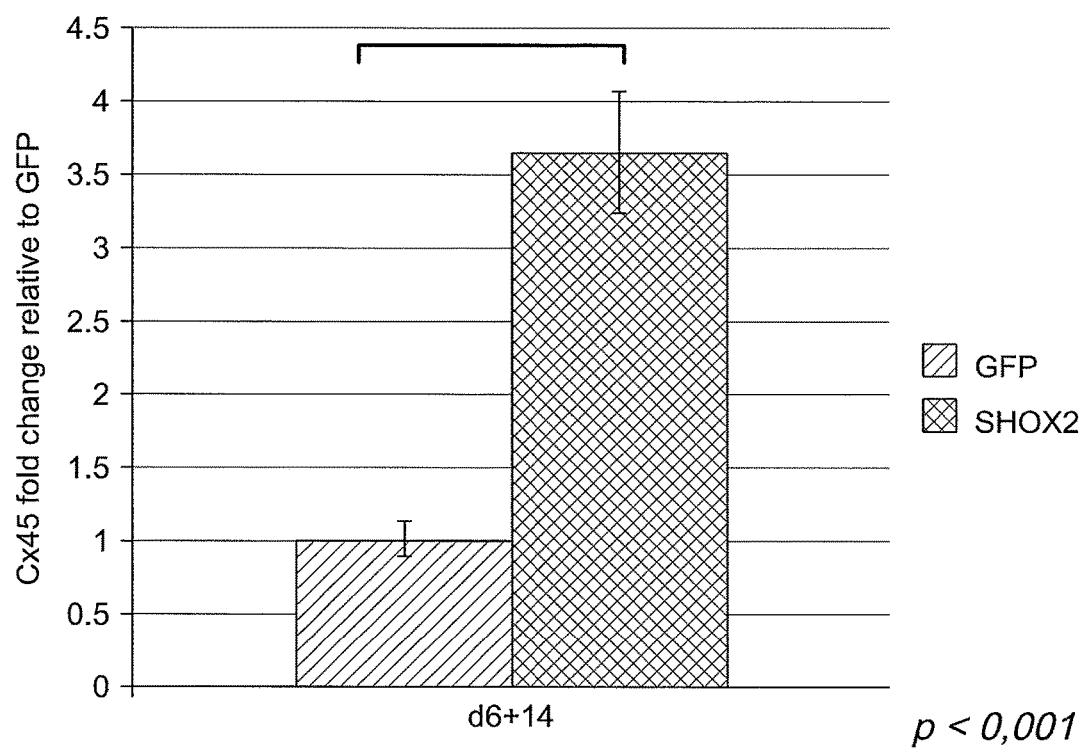
FIG. 19 depicts the Cx45 mRNA (A) and protein levels (B) in Shox2 transduced cells versus a GFP control at day 6+14 (post transduction).
Figure 19B:
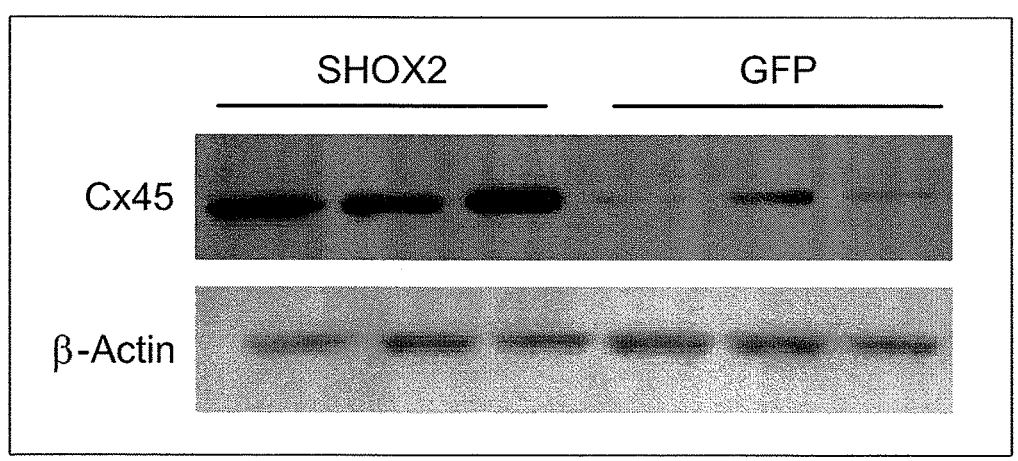
Figure 20A:
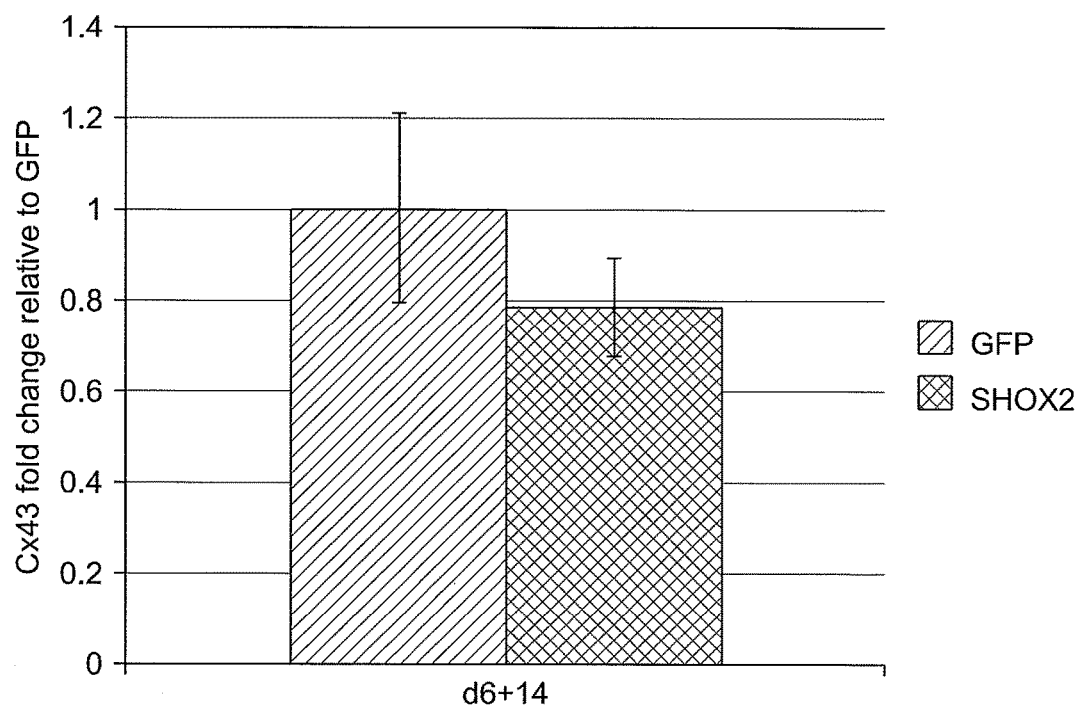
FIG. 20 depicts the Cx43 mRNA (A) and protein levels (B) in Shox2 transduced cells versus a GFP control at day 6+14 (post transduction).
Figure 20B:
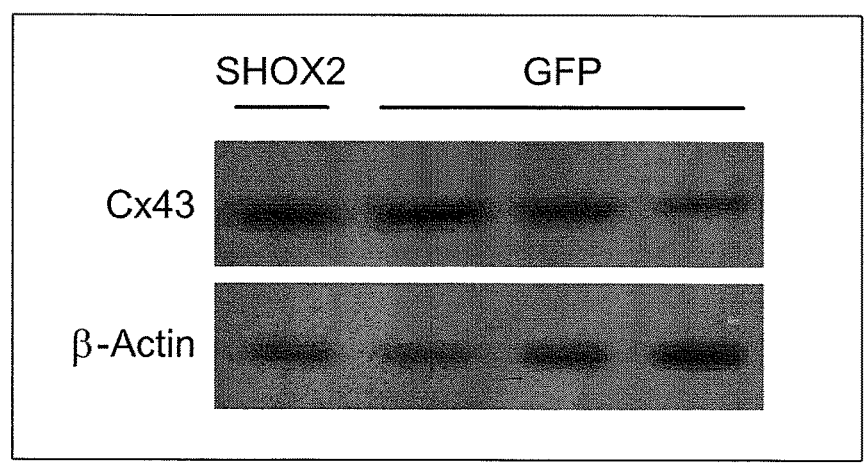
Figure 21A:
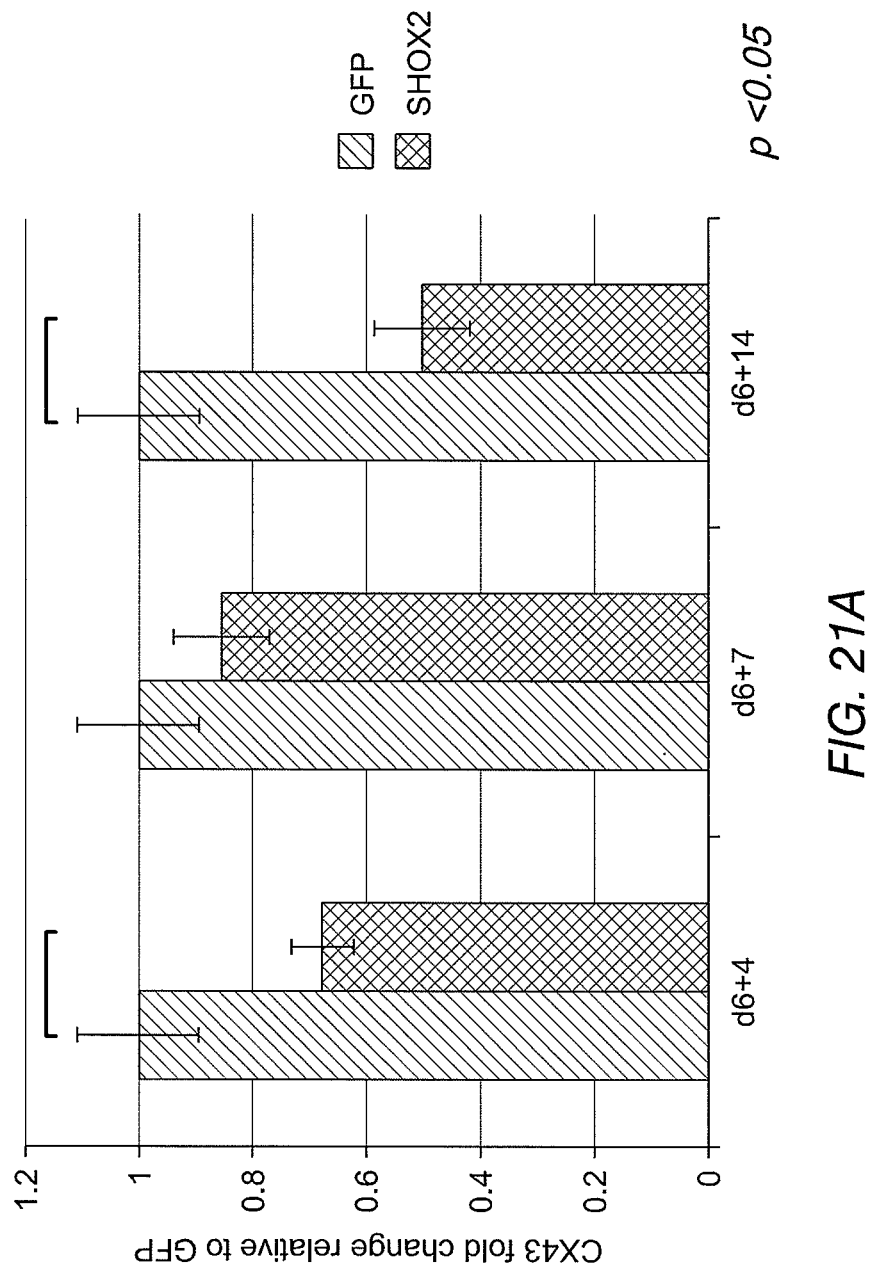
FIG. 21A depicts the Cx43 mRNA fold change in Shox2 transduced cells versus a GFP control.
Figure 21B:
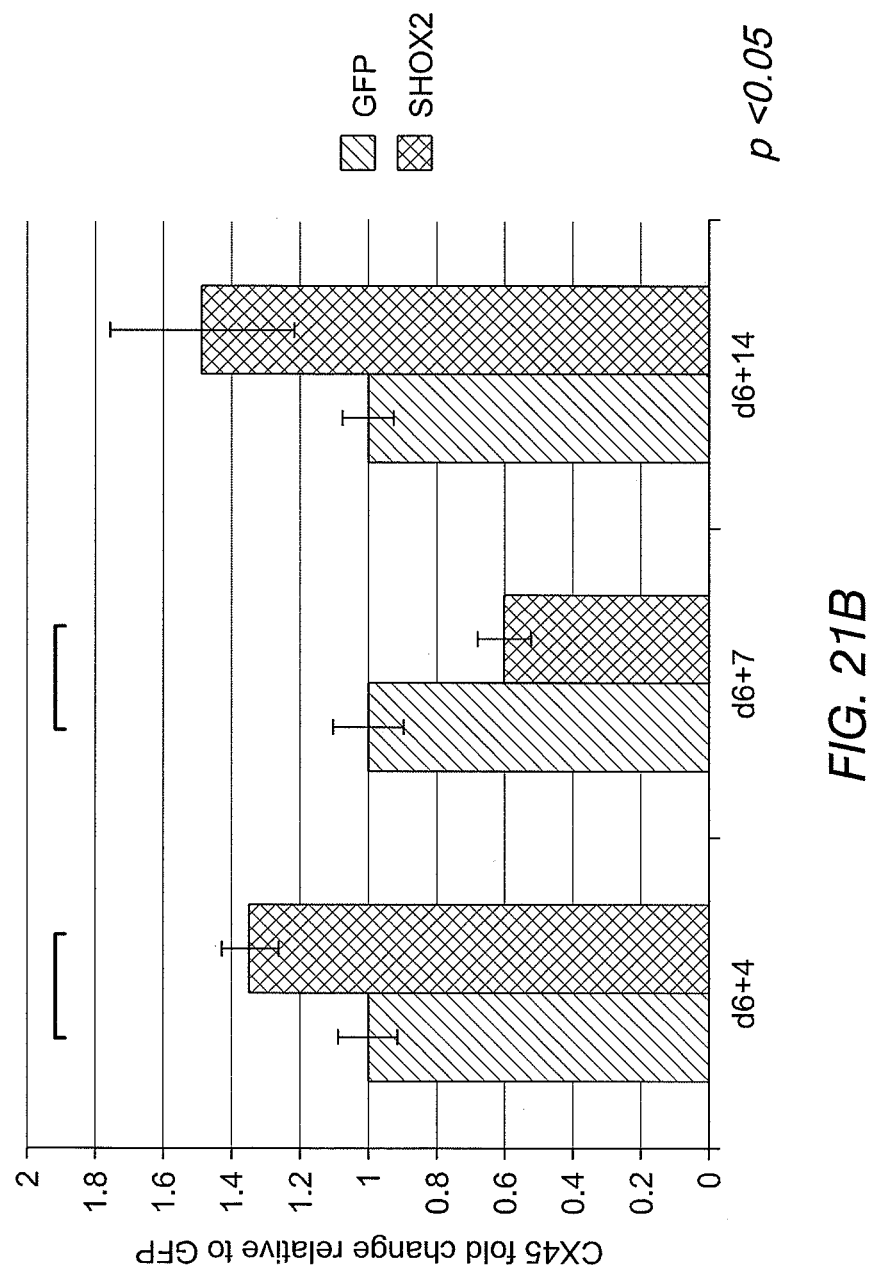
FIG. 21B depicts the Cx45 mRNA fold change in Shox2 transduced cells versus a GFP control.
Figure 22:
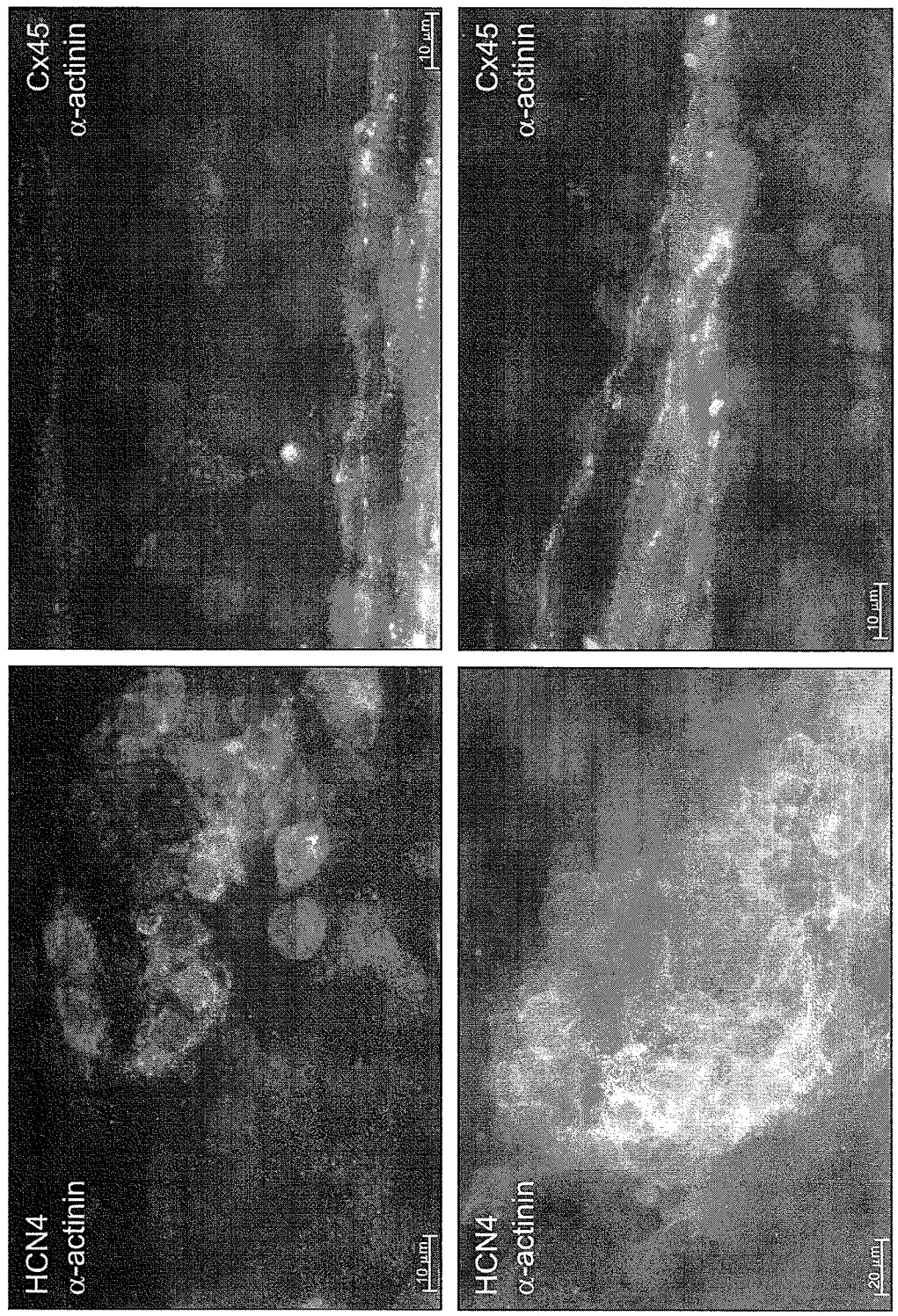
FIG. 22 depicts HCN4 and Cx45 expression in Shox2 transduced mESCs-derived cardiomyocytes.
Figure 23A:
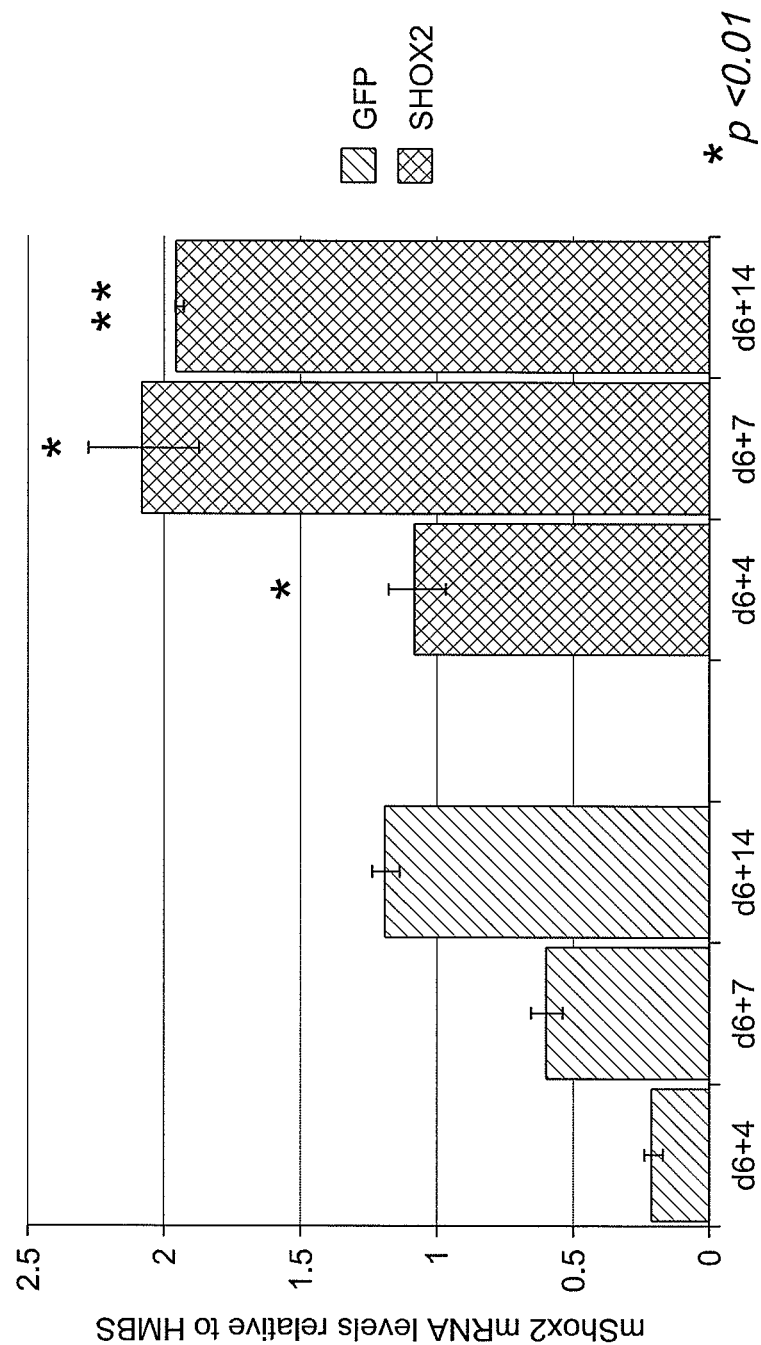
FIG. 23A shows that endogenous mouse Shox2 mRNA is upregulated in respect to transduction of ESC-derived cardiomyocytes with exogenous Shox2.
Figure 23B:
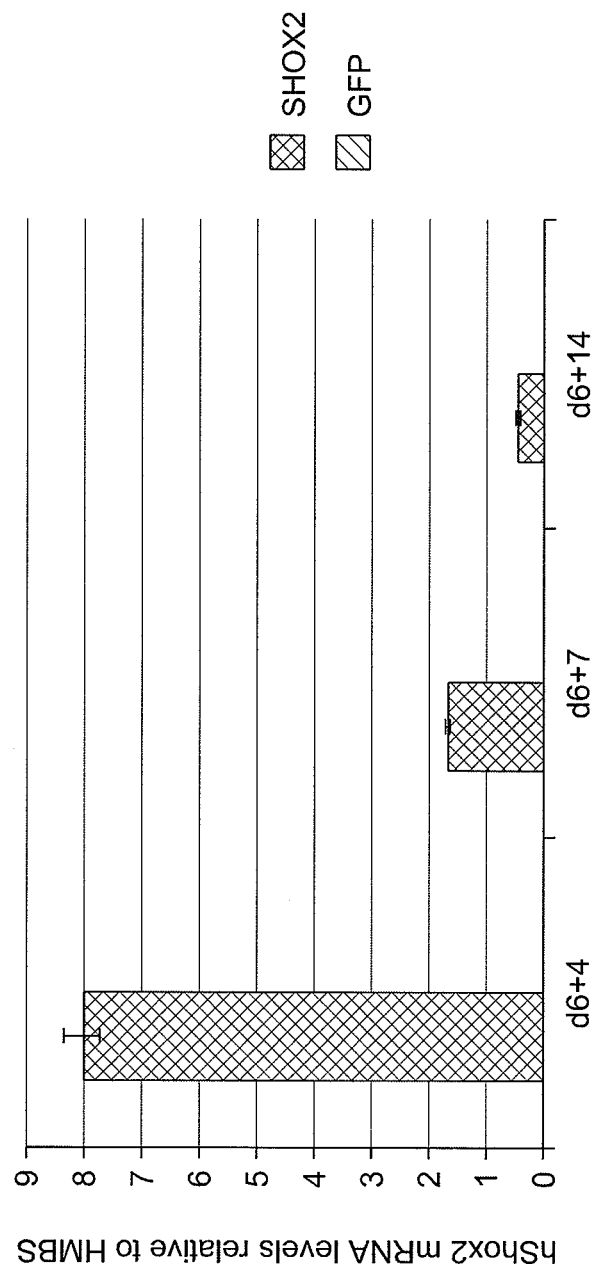
FIG. 23B shows endogenous human Shox2 mRNA is upregulated in respect to transduction of ESC-derived cardiomyocytes with exogenous Shox2.
Figure 24A:
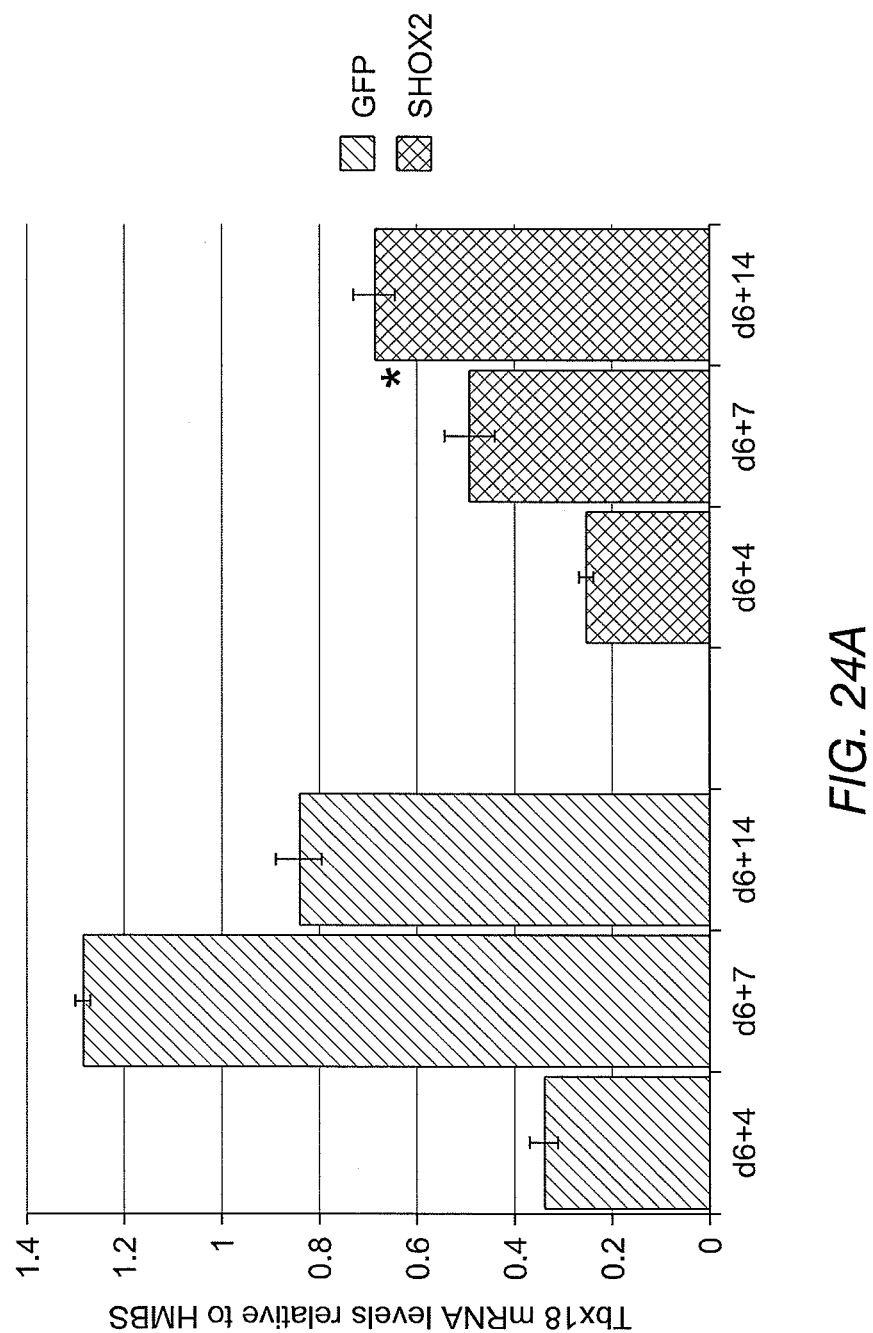
FIG. 24A shows Tbx18 mRNA levels relative to hydroxymethylbilane synthase (HMBS).
Figure 24B:
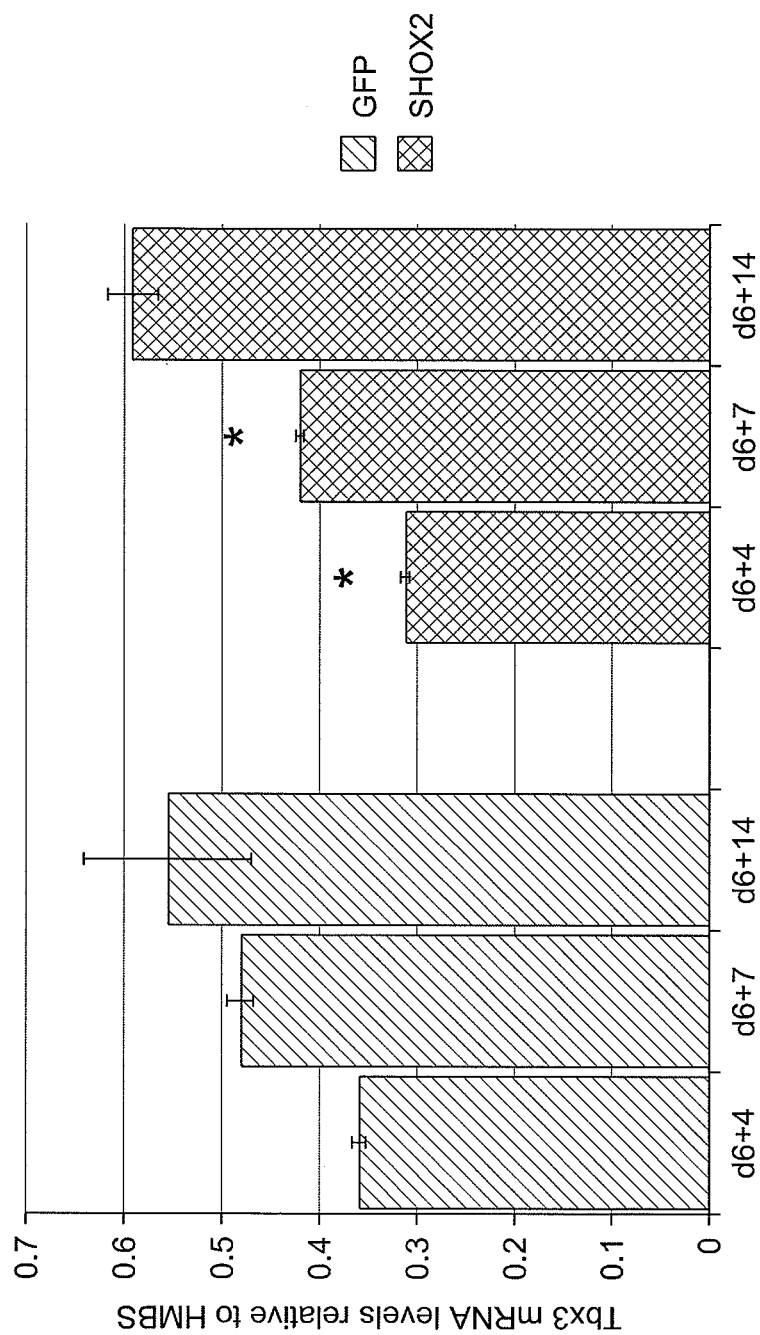
FIG. 24B shows Tbx3 mRNA levels relative to HMBS.

Transient overexpression of Shox2 in embryonic stem cells increased the quantity of spontaneously-beating embryoid bodies by 8-fold (80±27%) compared to control (9±6%)(FIG. 14A). Within each beating embryoid body, twice as many beating foci (2.1±0.8 per embryoid body) were found in Shox2-embryoid bodies compared to control (1.0±0.6 per embryoid bodies) (FIG. 14B). $Na^+/Ca^{2+}$ exchanger (NCX1) and HCN4 are important for pacemaker electrophysiology. As shown in FIG. 15, HCN4 protein level was up-regulated at all differentiation stages, with heightened cell surface expression in Shox2-embryoid bodies. Confocal imaging in FIG. 16, also shows an increase in HCN4 expression relative to GFP control cells. NCX1 protein level increased >6-fold in Shox2-embryoid bodies compared to control at the early and late stages of differentiation (FIG. 17). This level began to decrease and by day 14 after the last administration of Shox2 gene, the NCX1 was 1.4 fold higher than the control. Action potentials are mainly propagated by connexin (Cx) 45 but not Cx43 in the sinoatrial node, which is mirrored in the atrial/ventricular myocardium, Shox2-overexpression led to an increase in the transcript (~1.5-fold) and protein (~3-fold) levels of Cx45. In contrast, Cx43 transcript and protein levels were reduced in Shox2-embryoid bodies by 33±5% and 30±10%, respectively, compared to control (FIG. 20). This decrease in Cx43 transcript remained below the control for the 14 day time period of the experiment (FIG. 21A). In contrast, Cx45 remained increased relative to the control until day 14, with a decline at day 7 after the administration of the Shox2 vector (FIG. 21B). The increased level of HCN4 expression and Cx45 is also apparent from confocal imaging of cells that were transduced (FIG. 22). The Shox2 expression after transfection also remained at elevated levels relative to control HMBS and GFP transfected cells (FIG. 23). The hShox2 mRNA decreased after transduction of the Shox2 gene eventually falling below the level of control cells. Tbx18 and Tbx3 mRNA levels relative to HMBS are shown in FIG. 24. These data suggest that exogenous Shox2 induced an increase in endogenous Shox2 that resulted expression changes in a variety of genes that suggest pacemaker generation. For example, HCN4 is known to be important for pacemaker function and its upregulation the transduced cells indicates that these cells i) are taking on characteristics of pacemakers due to Shox2 and/or, ii) may be useful themselves as biological pacemaker cells (e.g., transplanted cells). Further the upregulation of Cx45, which is primarily responsible for the propagation of action potentials, indicates that these Shox2-transduced stem cells were biased in their differentiation toward a pacemaker lineage. As such, these data indicate that Shox2 (alone, as tested here, or in combination with other transcription factors, e.g., Tbx18) are useful in the in vivo and/or in vitro generation of biological pacemaker cells.

Shox2 overexpression singularly biased embryonic stem cell differentiation toward more pacemaker cells, increased expression of NCX1, HCN4, Cx45, and down-regulated Cx43. All of these features are hallmarks of SA nodal cell biology. In several embodiments, one or more of the following transcription factors will be selected for use in differentiating embryonic stem cells: Tbx18, Shox 2, Tbx3, and Tbx5. Further, it will be appreciated that the use of multipotent and/or other pluripotent stem cells will also afford hallmarks of sinatrial nodal cell biology and/or pacemaker function when contact with one or more of the transcription factors disclosed herein. The data provide a novel and efficient platform to develop biological pacemakers from pluripotent cells.

Example 5

Figure 25A:
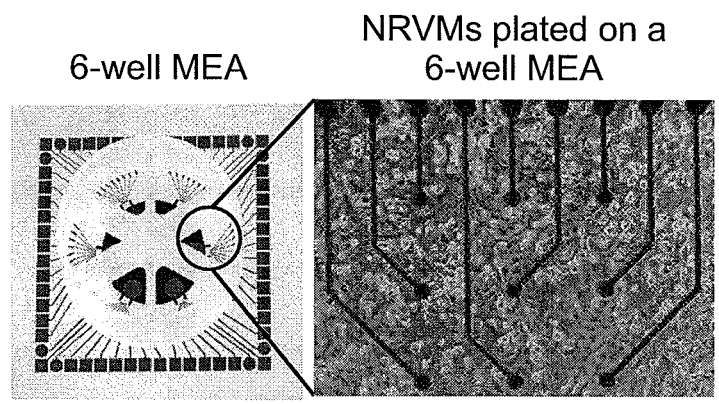
FIGS. 25A-25G indicate de novo automaticity in response to autonomic regulation.
Figure 25B:
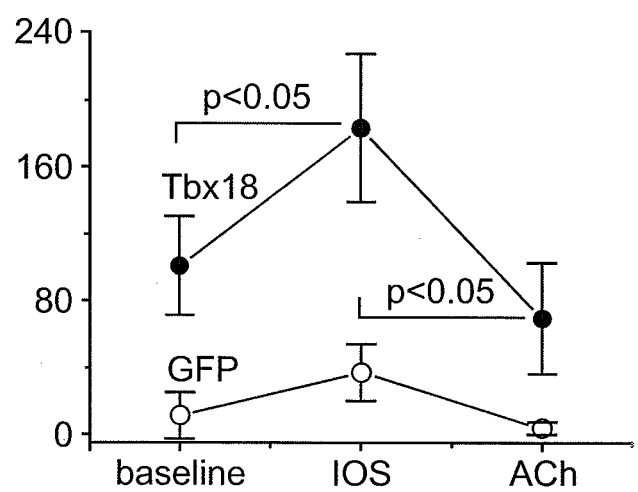
Figure 25C:
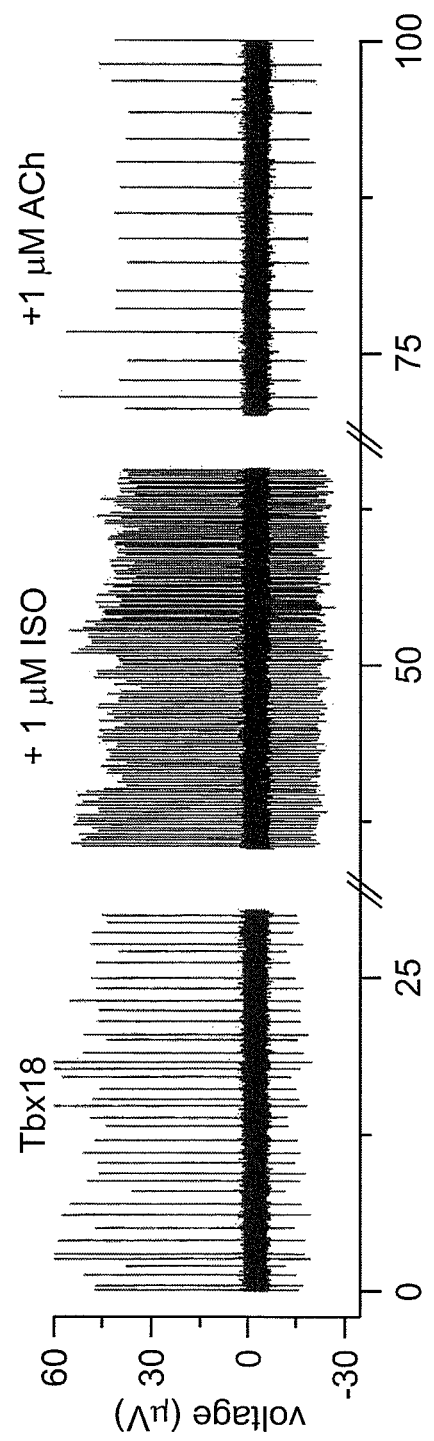
Figure 25D:
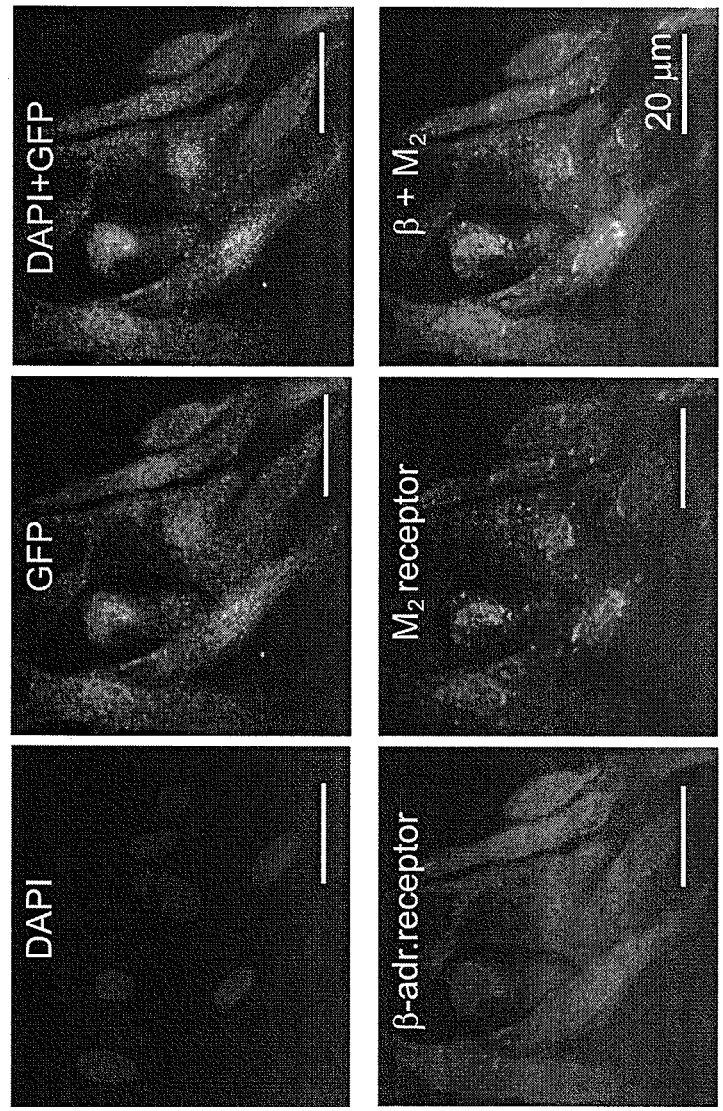

De Novo Automaticity Responds to Autonomic Regulation In Vitro and in the Intact Perfused Heart SAN pacemaker cells respond to autonomic inputs with altered firing rates. To assess adrenergic and muscarinic responses in iSAN cells, Tbx18- and GFP-NRVMs were plated on multi-electrode arrays (MEAs) to record extracellular field potentials from spontaneously-beating cells (FIG. 25A). Beta-adrenergic stimulation (with 1 μM isoproterenol) increased the firing rates of Tbx18-NRVMs from 101±30 bpm to 183±44 bpm (n=12, p<0.05). Subsequent exposure to a cholinergic agonist, acetylcholine (1 μM), suppressed the rate to 69±33 bpm (n=12, p<0.05, FIG. 25B, C). In contrast, GFP-NRVMs exhibited a very slow spontaneous beating rate which changed little with either isoproterenol or acetylcholine (FIG. 25B, C). Immunostaining confirmed prominent expression of β-adrenergic receptors and muscarinic receptor type 2 in Tbx18-NRVMs (FIG. 25D). Thus, Tbx18-NRVMs respond appropriately to adrenergic and muscarinic stimuli.

Figure 25E:
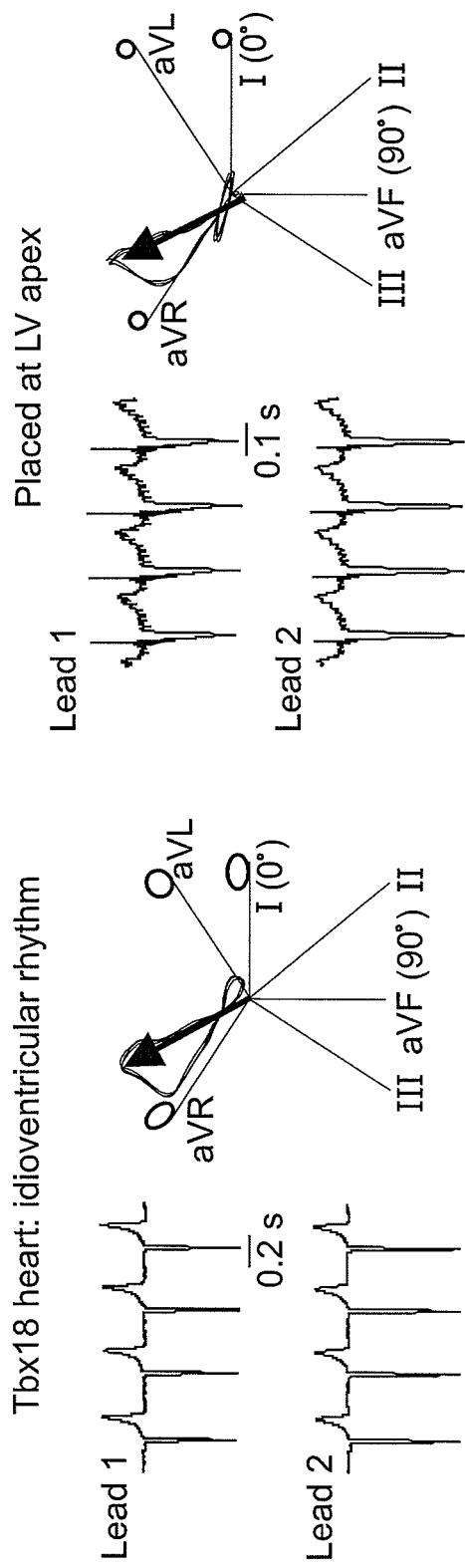
Figure 25F:
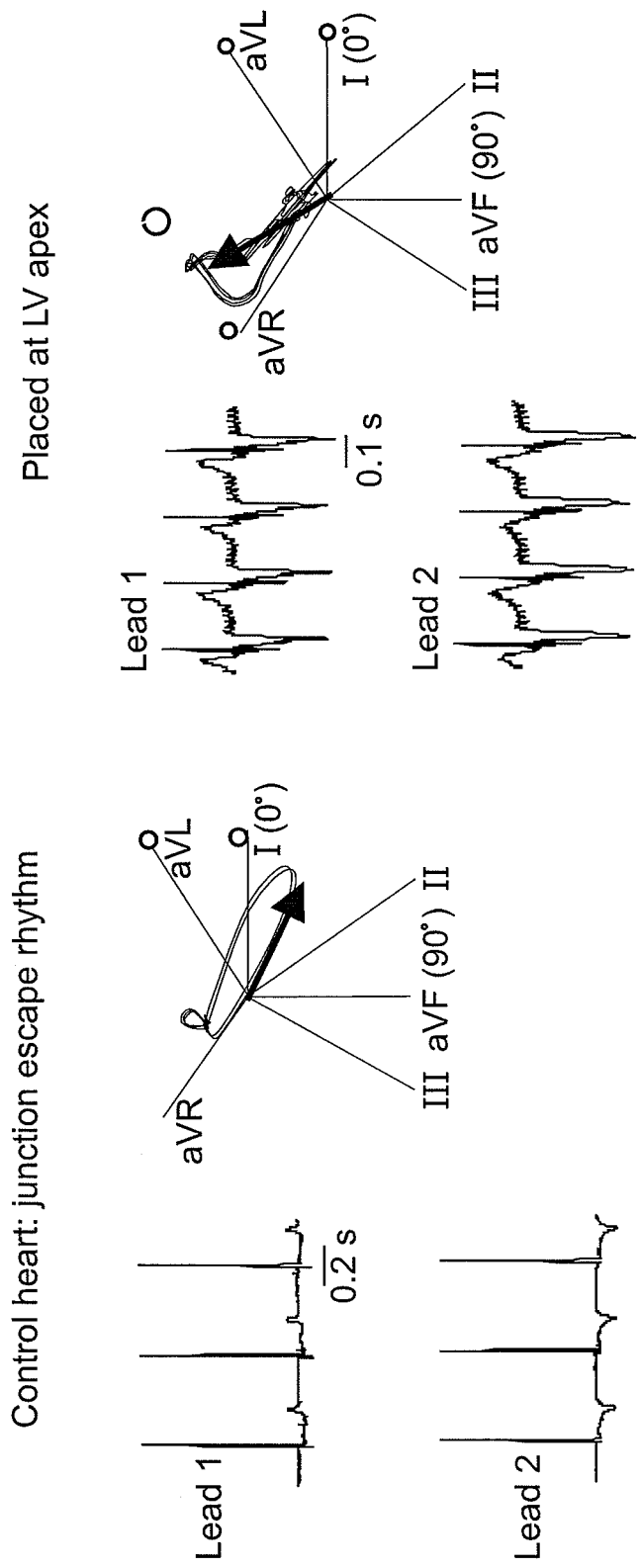

A disease model of atrioventricular (AV) block, which is a common indication for the placement of an electronic pacemaker, was created to investigate autonomic regulation of induced biological pacemakers in the intact heart. Electrocardiographic recordings of the beating hearts, perfused ex vivo (FIG. 28), revealed ectopic ventricular beats in 8 of 8 Tbx18-injected hearts, at a rate of 154±6 bpm. The polarity and morphology of the ectopic beats was identical to that of electrode-paced beats at the location of transgene injection (FIG. 25E), linking the origin of the ectopic beats to the site of Tbx18 transduction. Conversely, most control hearts showed a narrow-QRS junctional escape rhythm at an average rate of 120±7 bpm (n=7/10), which originated on the opposite end of the ventricle (FIG. 25F). Tbx18-injected hearts responded well to autonomic regulation; β-adrenergic stimulation followed by cholinergic suppression increased and then decreased the heart rate to 235±19 and then to 150±23 bpm, respectively (n=7, FIG. 25G). Collectively, the data demonstrate that Tbx18-NRVM cells respond to autonomic regulation in vitro and in the intact heart with proper chronotropy.

It shall be appreciated that, in several embodiments, Shox2 could be used instead of or in conjugation with Tbx18. In several embodiments, one or more of the following transcription factors could be selected for use: Tbx18, Shox2, Tbx3, and Tbx5. In several embodiments, the iSAN cells may generate ectopic ventricular beats. In several embodiments the Tbx18-NRVM cells (iSAN cells) may respond to autonomic regulation to alter the pacing ectopic beats in a way substantially similar to natural SAN cells. Thus, in several embodiments, iSAN cells will respond to autonomic regulation such as β-adrenergic stimulation and cholinergic suppression in vivo. In several other embodiments, iSAN cells converted from quiescent cells in vitro may be capable of responding to autonomic regulation. In several embodiments, the iSAN cells may generate ectopic beats at a rhythm controlled by autonomic regulation. It shall be appreciated that in several embodiments in which iSAN cells respond to autonomic regulation, the iSAN cells can function to treat a cardiac arrhythmia in a patient suffering from said arrhythmia. In several embodiments, iSAN cells responding to autonomic regulation can replace or supplement electronic pacemaker devices in a patient.

Example 6

Figure 9A:
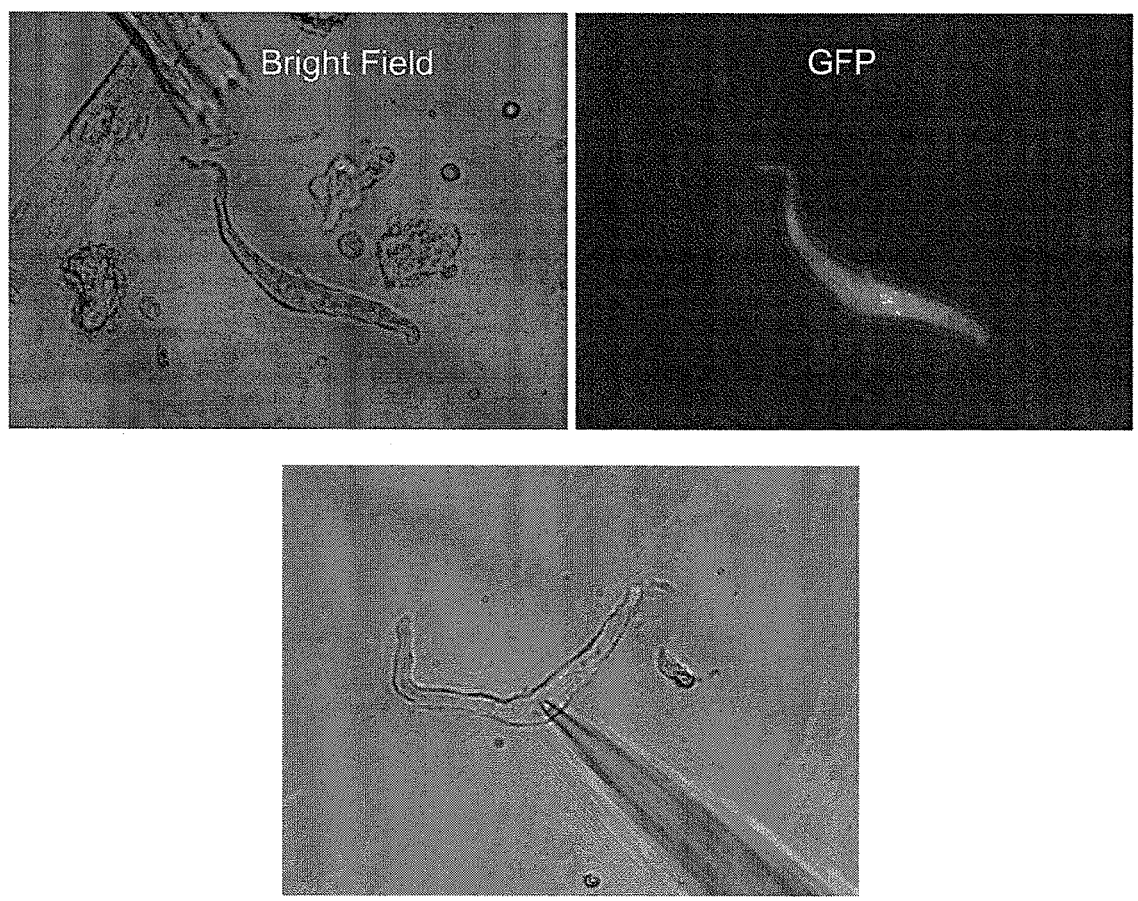
FIGS. 9A-9G depict various characteristics of Tbx18-transduced ventricular myocytes and GFP-ventricular myocytes (VM).
Figure 9B:
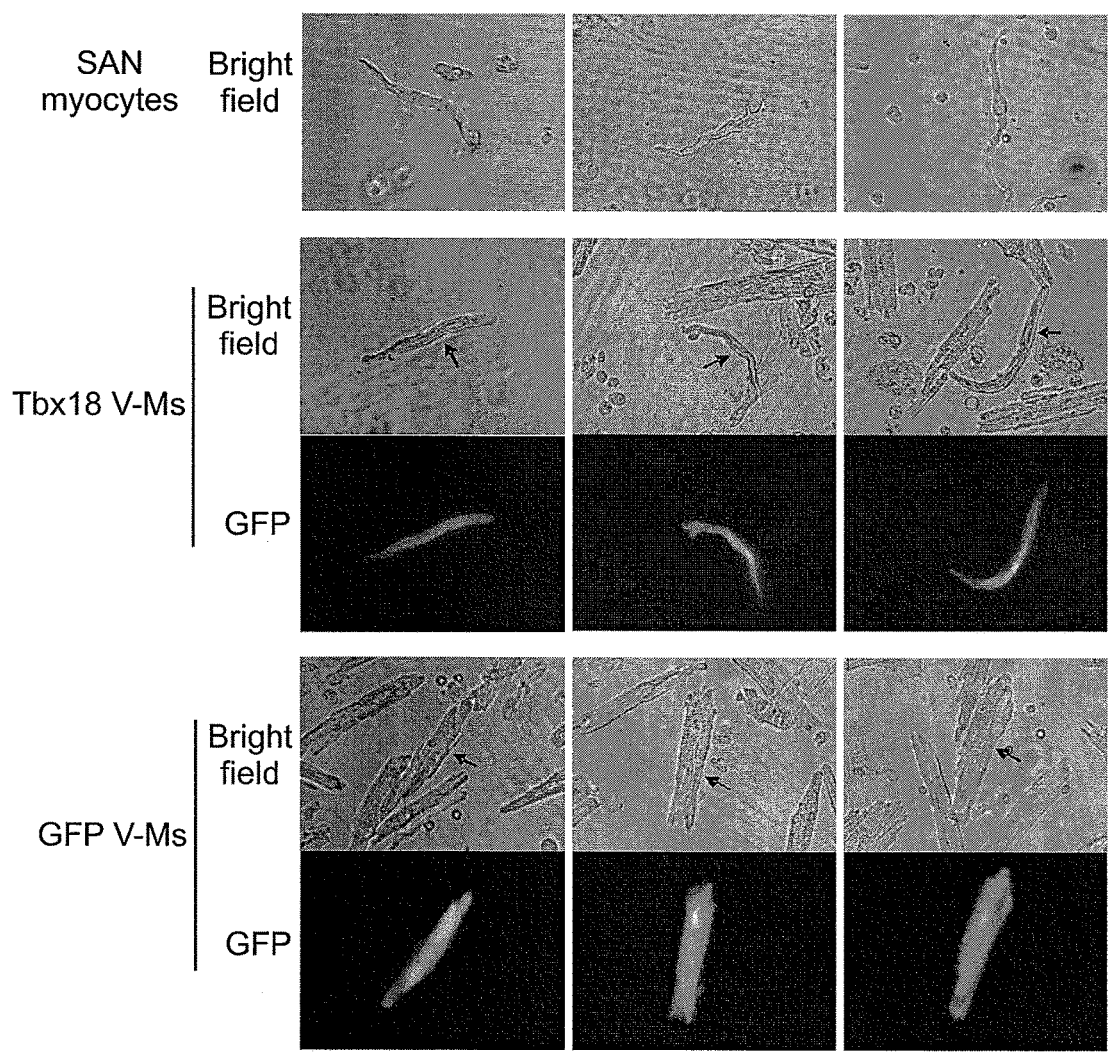
Figure 9C:
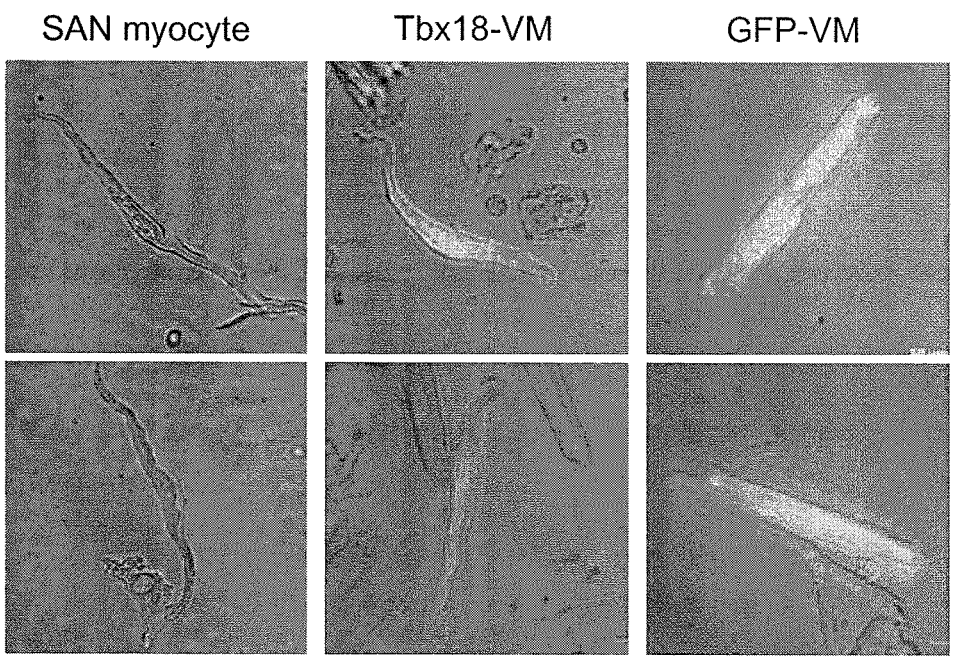
Figure 9C:
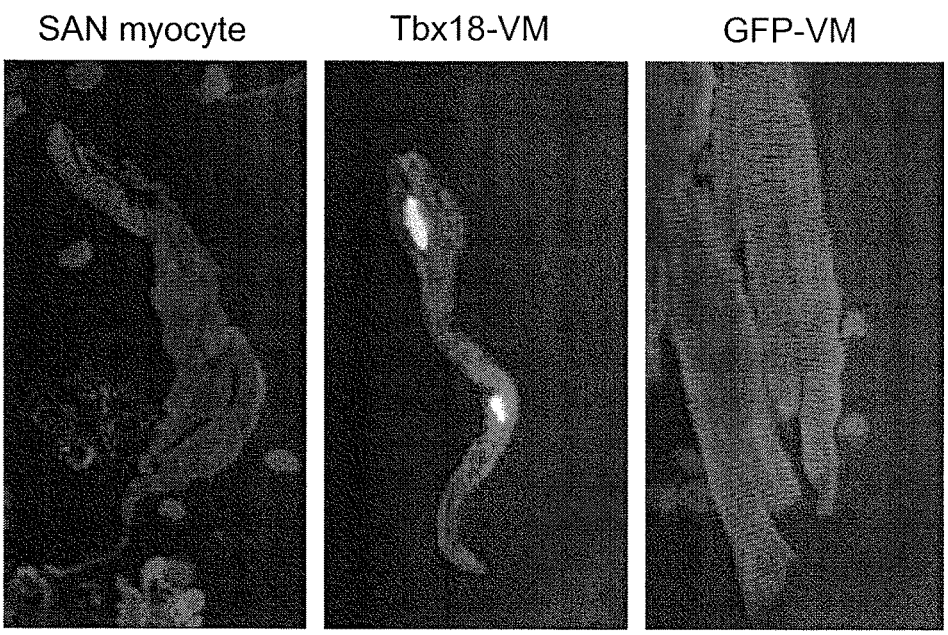
Figure 9D:
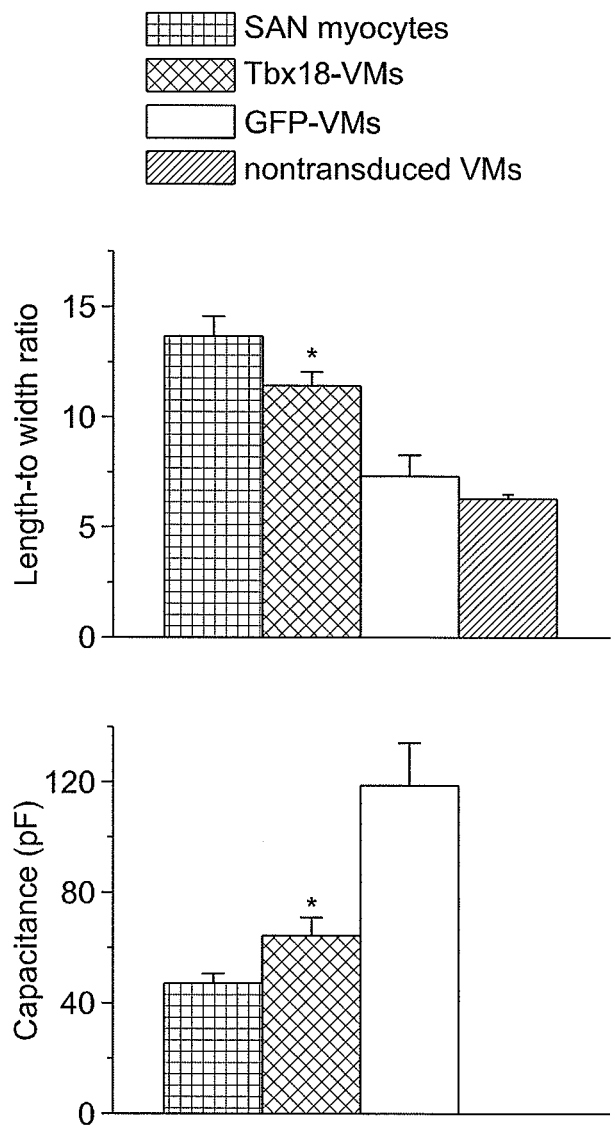
Figure 9E:
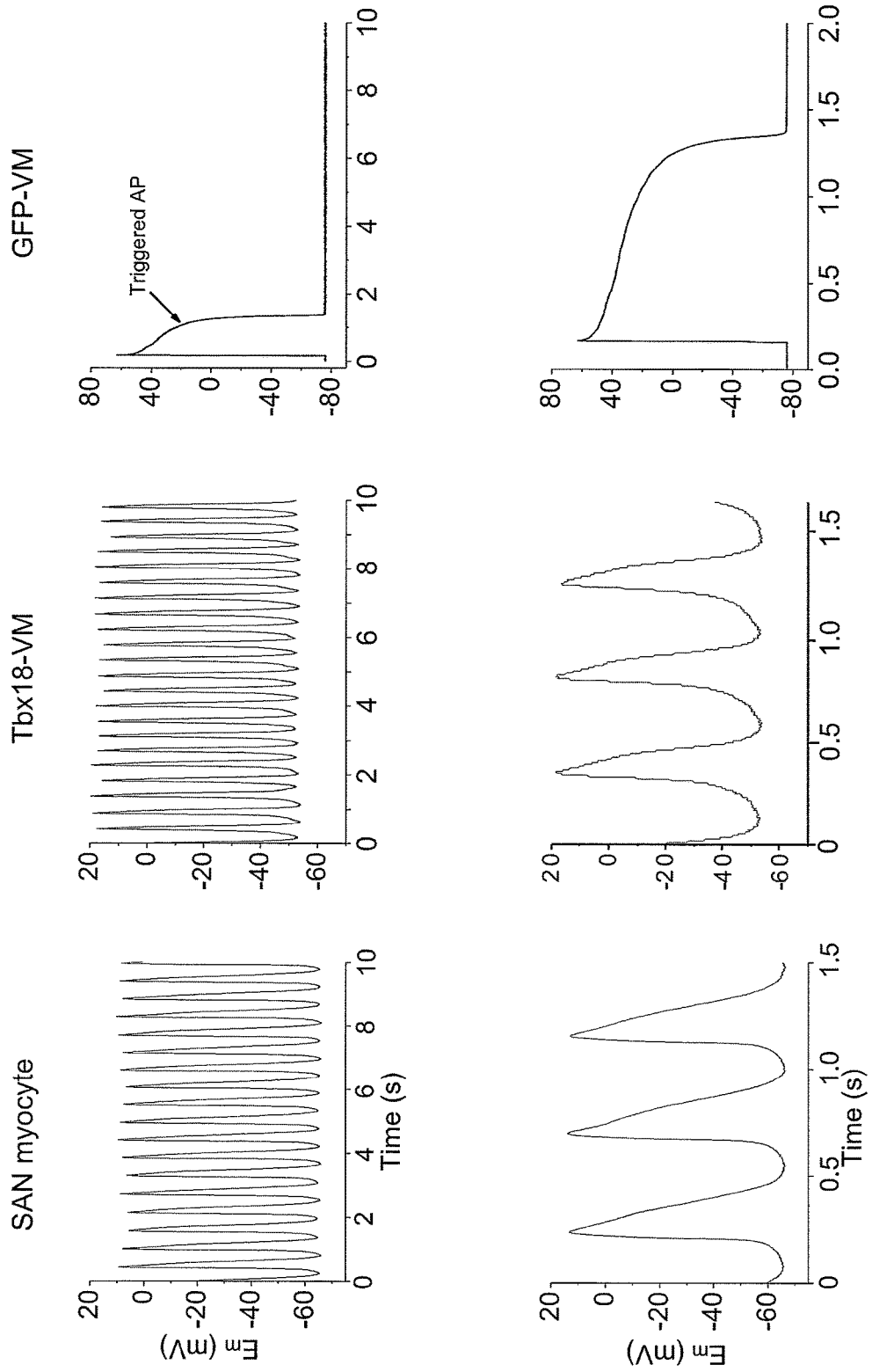
Figure 9F:
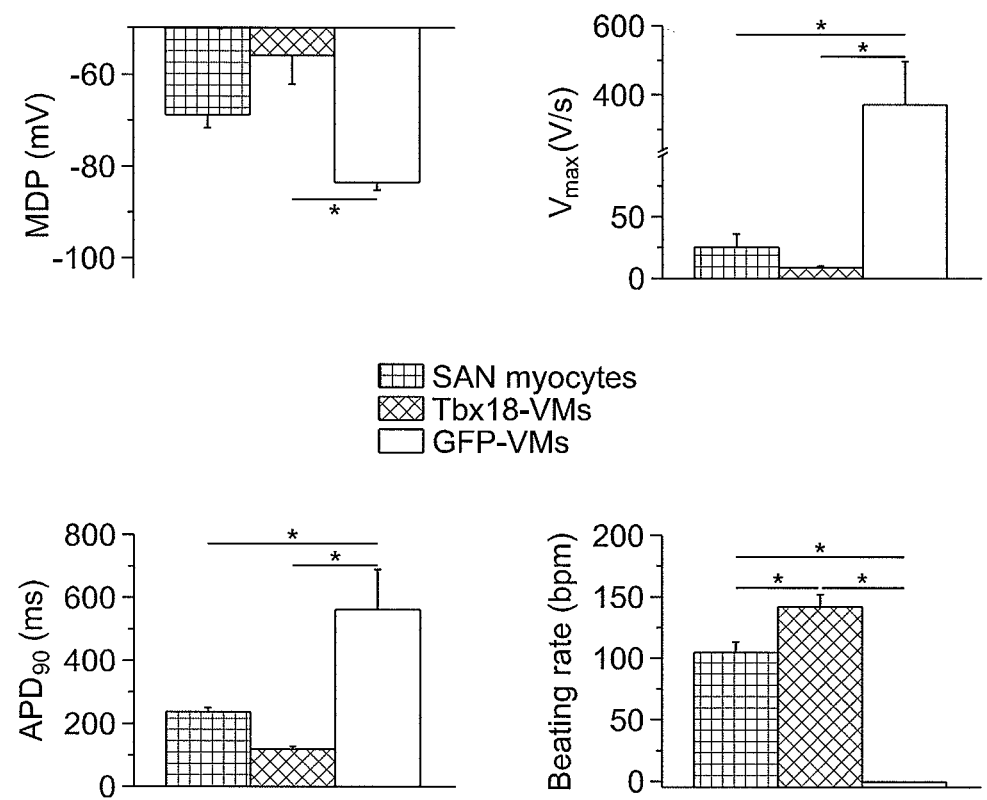
Figure 9G:
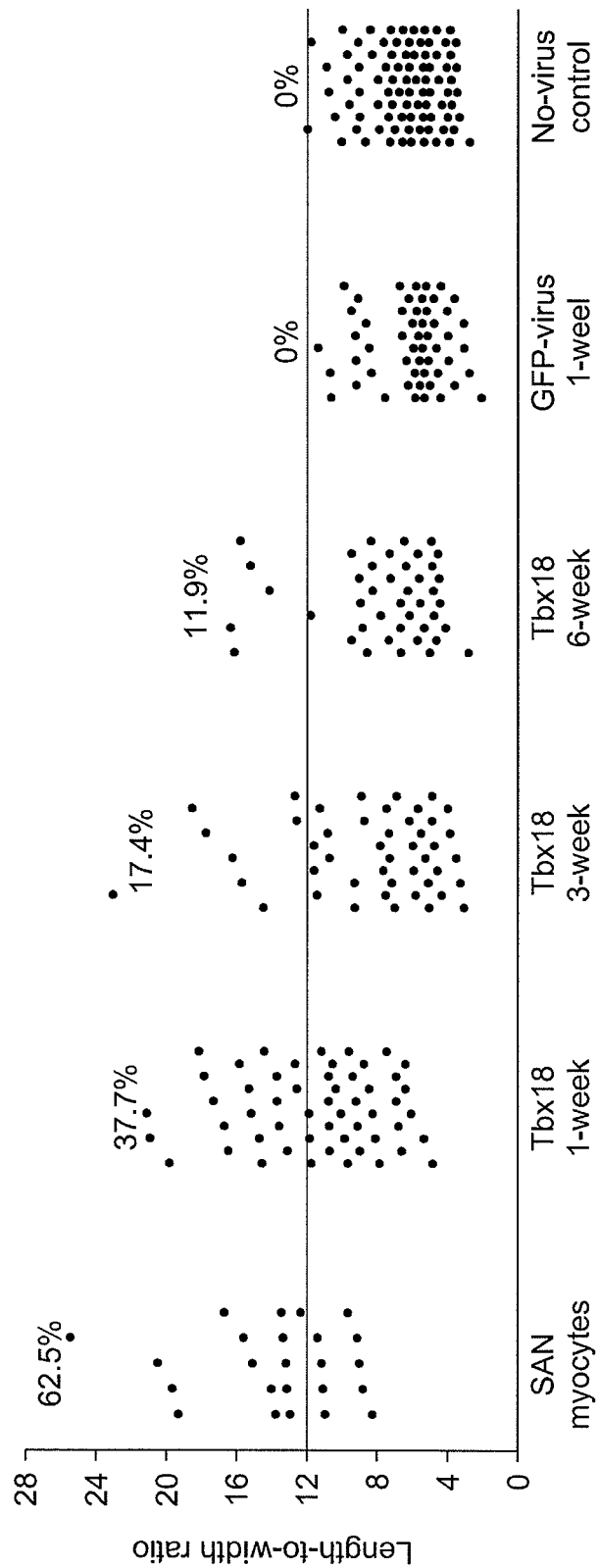
Figure 26A:
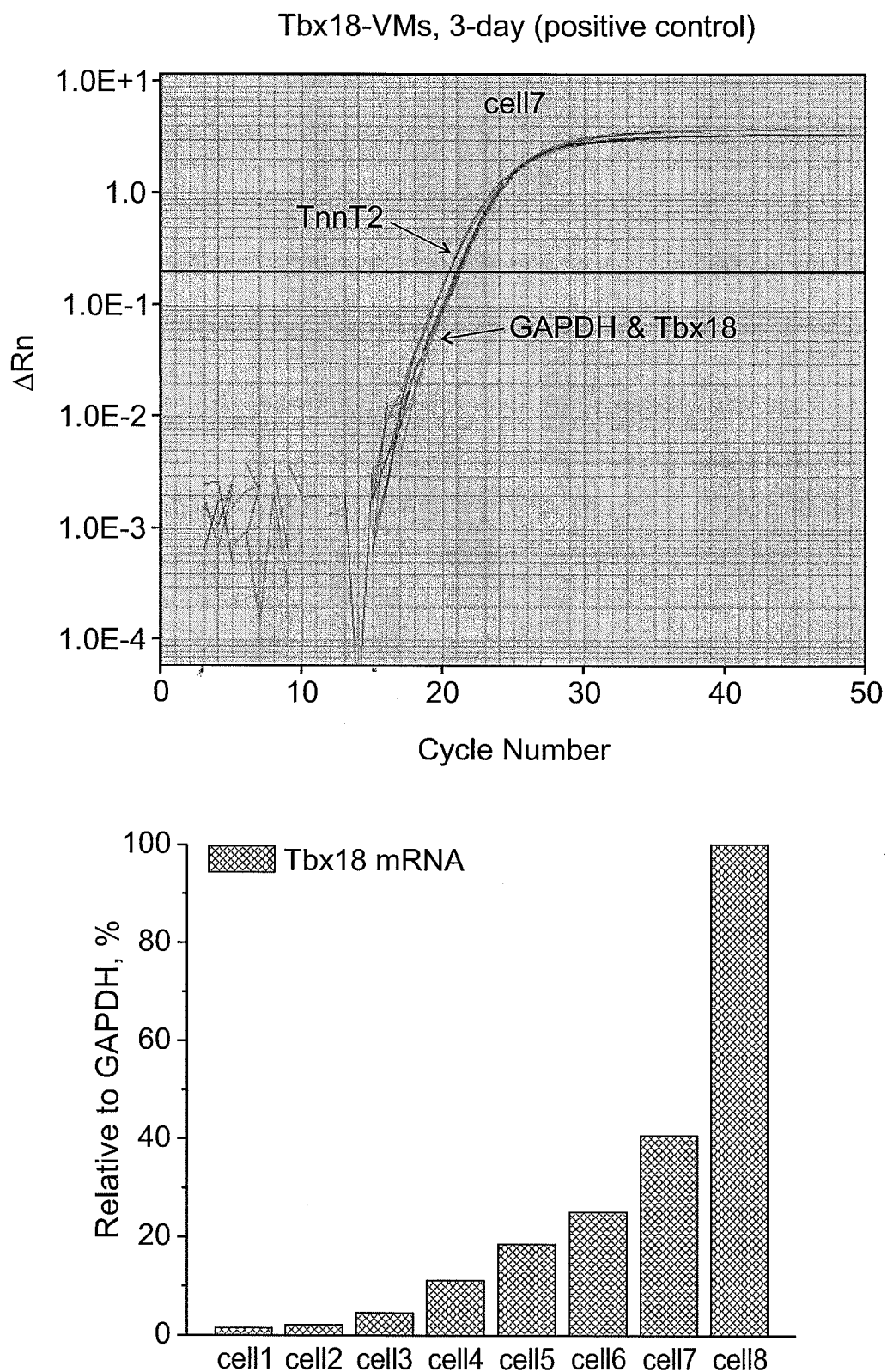
FIGS. 26A-26C depict results of single-cell, quantitative RT-PCR of long-term Tbx18-VMs. The data indicates persistent automaticity even after Tbx18 expression had waned.
Figure 26B:
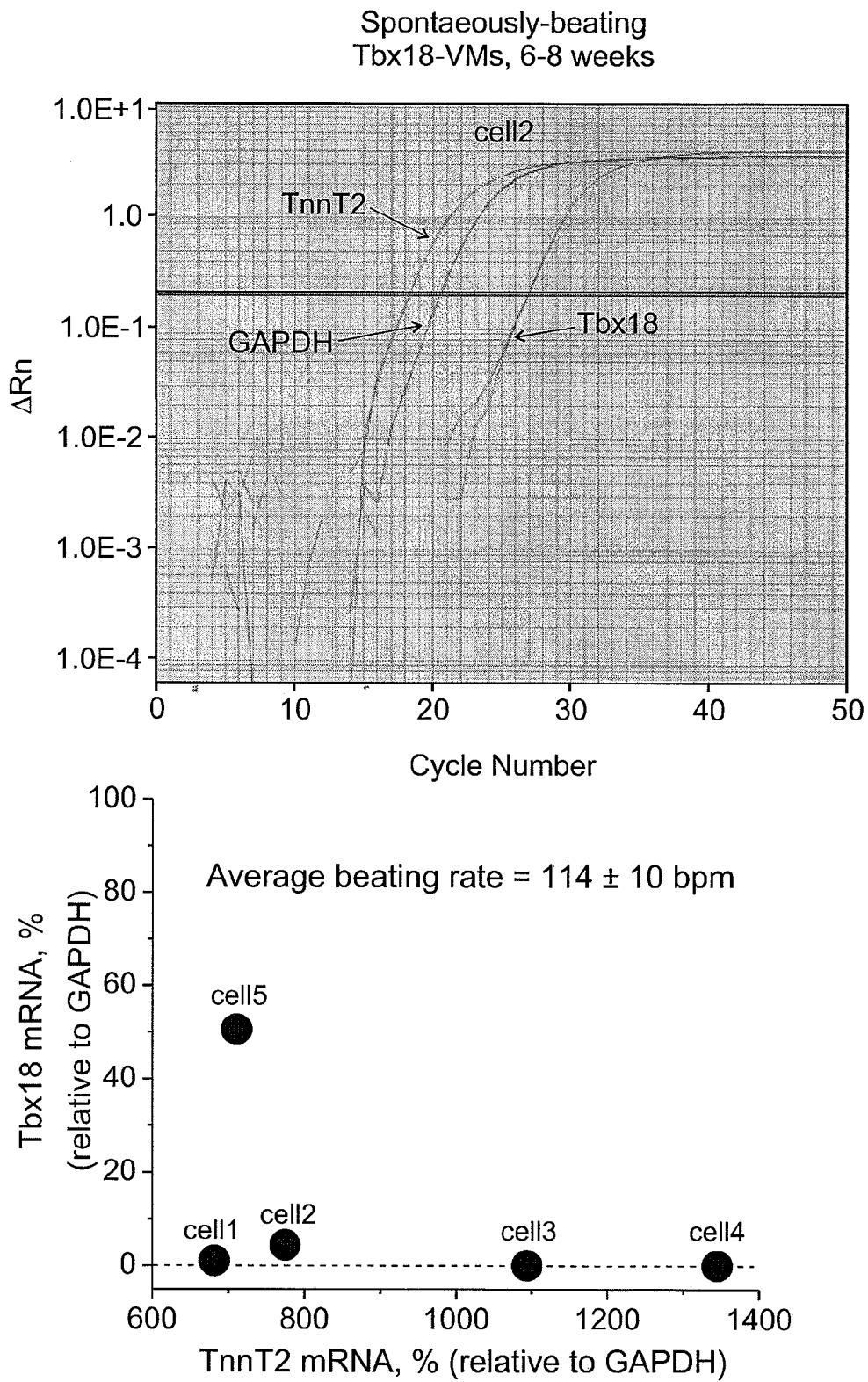
Figure 26C:
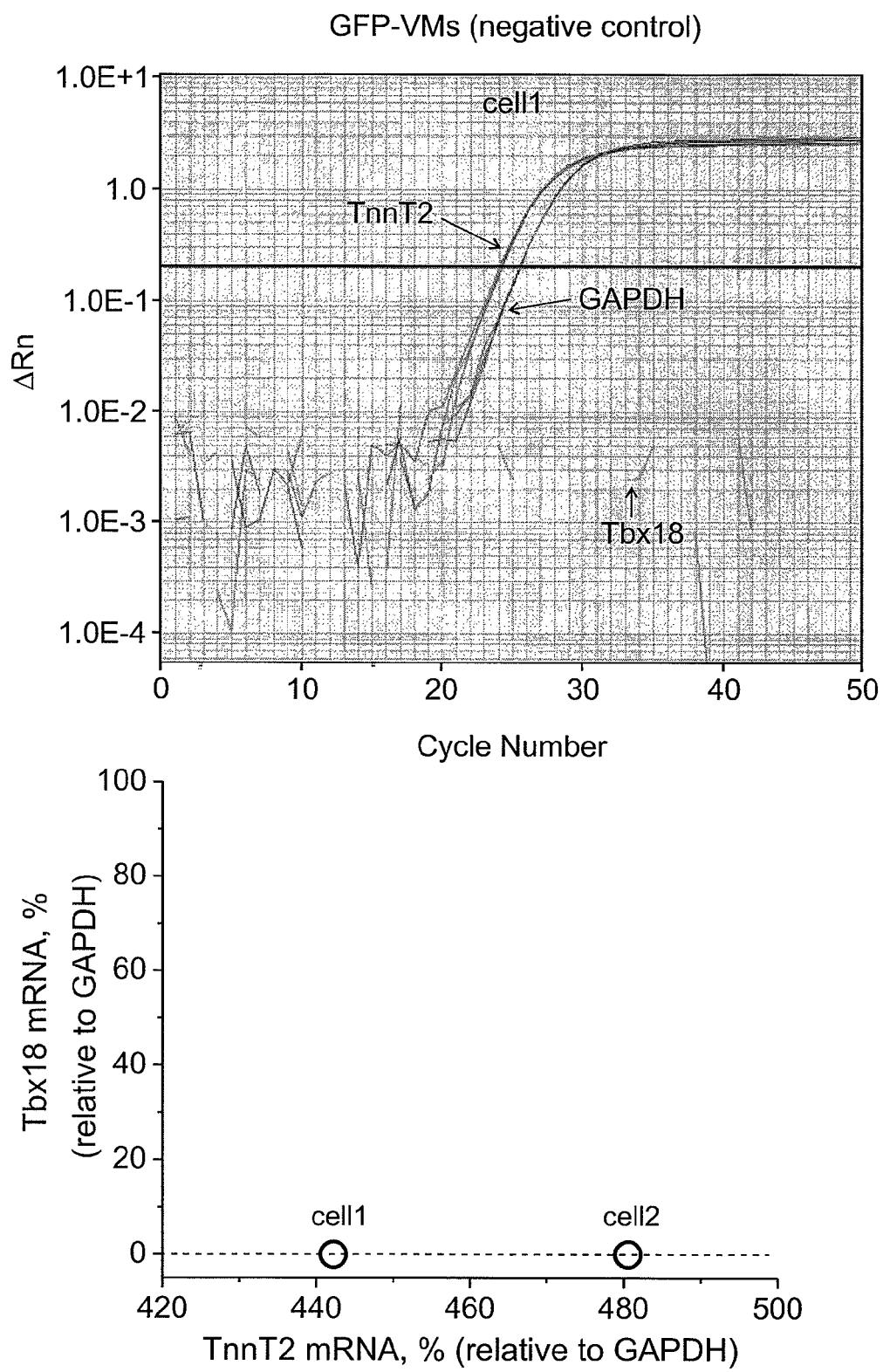
Figure 27A:
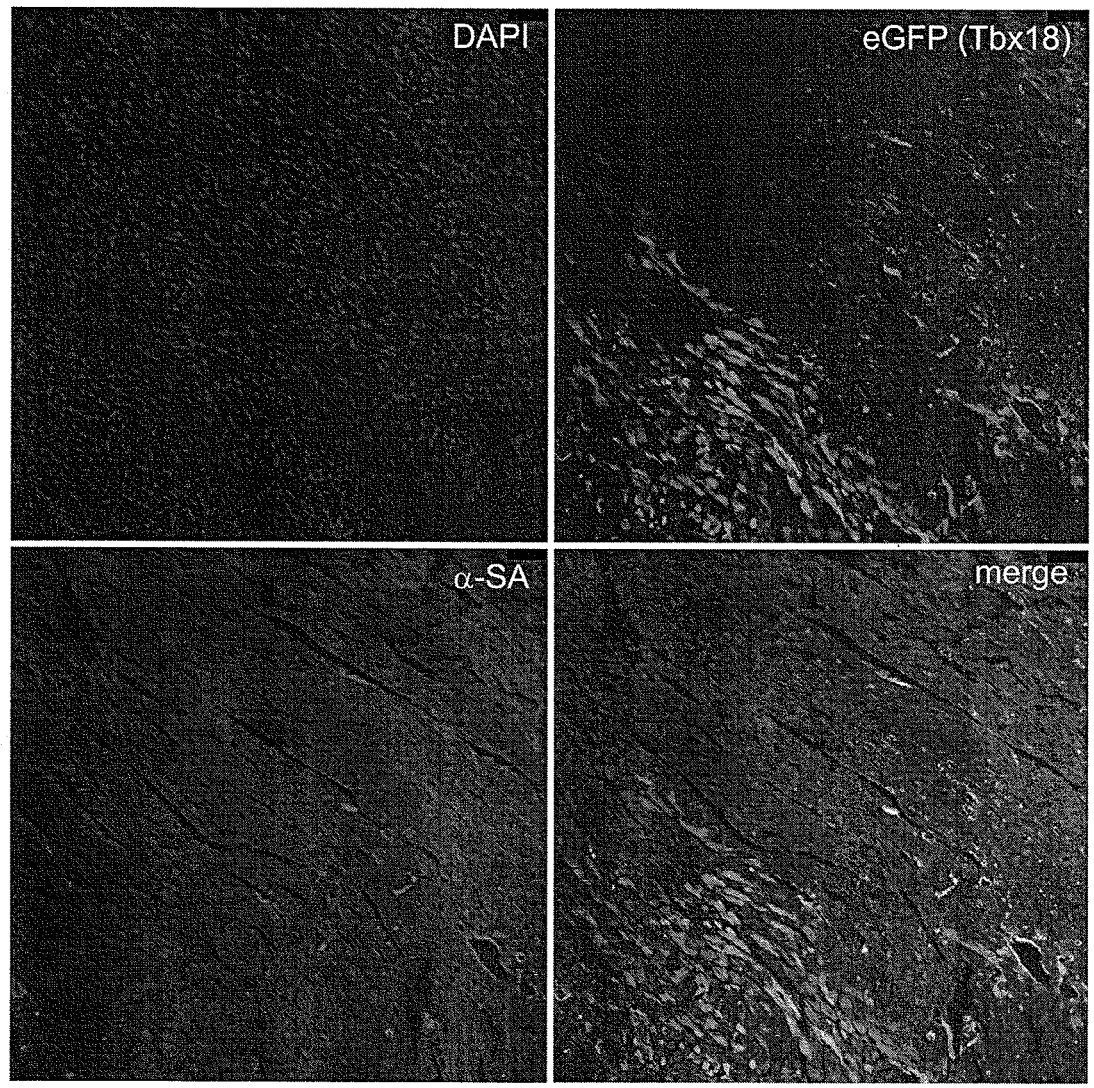
FIGS. 27A and 27B depict histological sections from a Tbx18-injected guinea pig heart, indicating strong and focal Tbx18 transduction in the injection region.
Figure 27B:
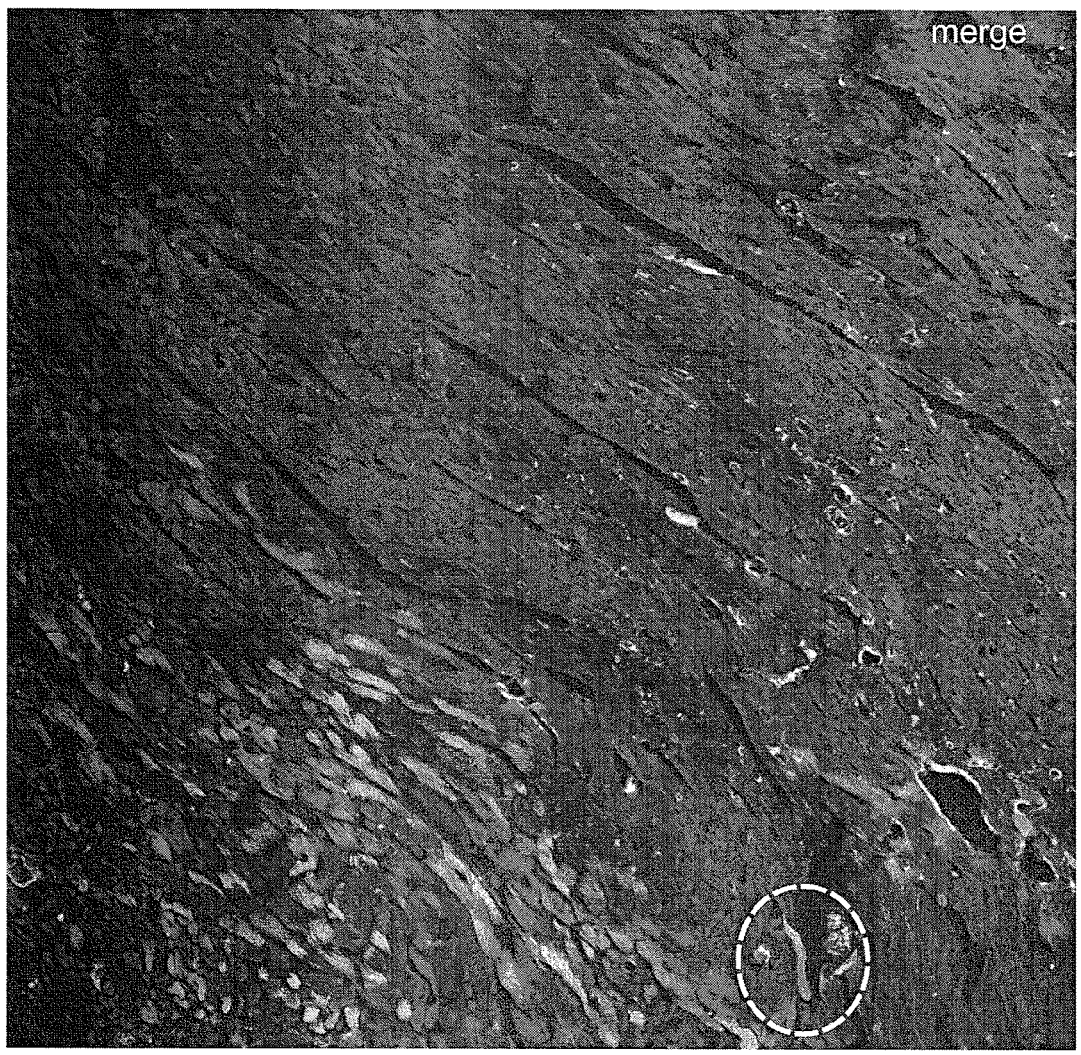

The Induced Pacemaker Phenotype is not Dependent upon Continued Expression of Tbx18 Transcript Reprogrammed cells remain altered without sustained transcription factor expression. In order to investigate the persistence of the SAN phenotype, Tbx18-VMs were isolated 6-8 weeks after the initial in vivo gene transfer, and the transcript levels of Tbx18 were quantified by single-cell, quantitative RT-PCR. Tbx18 transcripts exhibited a wide dynamic detection range in Tbx18-VMs isolated just 3 days after in vivo gene transfer (FIG. 26A, bottom panel). To examine the durability of conversion to SAN-like pacemaker cells, 5 spontaneously-beating ventricular myocytes (114±10 bpm, identified by live-cell video recording or whole-cell patch-clamp) isolated 6-8 weeks after in vivo gene transfer were examined. PCR primer sets were designed to detect Tbx18, cardiac troponin T (TnT2, to verify cardiomyocyte identity) and GAPDH. The levels of Tbx18 transcript in 4 of the 5 spontaneously-beating myocytes were negligible (FIG. 26B, cell 1, 2, 3 and 4, bottom panel), close to the negative control level (FIG. 26C) in ventricular myocytes expressing GFP alone. Taking the cell length-to-width (L-to-W) ratio as the criteria, the percentage of SAN-like Tbx18-VMs (iSAN cells) up to six weeks after initial gene transfer was examined A significant proportion of iSAN cells persists, although the percentage tends to decline over time (FIG. 9C). In several embodiments therefore, the persistent positive effects due to administration of iSAN cells (e.g., to treat cardiac arrhythmia) persists for an extended period of time after administration. For example, in several embodiments, the effects last from about 2 to about 4 weeks, about 3 to about 5 weeks, about 4 to about 6 weeks, about 5 to about 7 weeks, about 6 to about 8 weeks, post-administration, and overlapping ranges thereof. In several embodiments, longer periods of persistence are realized, depending on the embodiment.

Figure 25G:
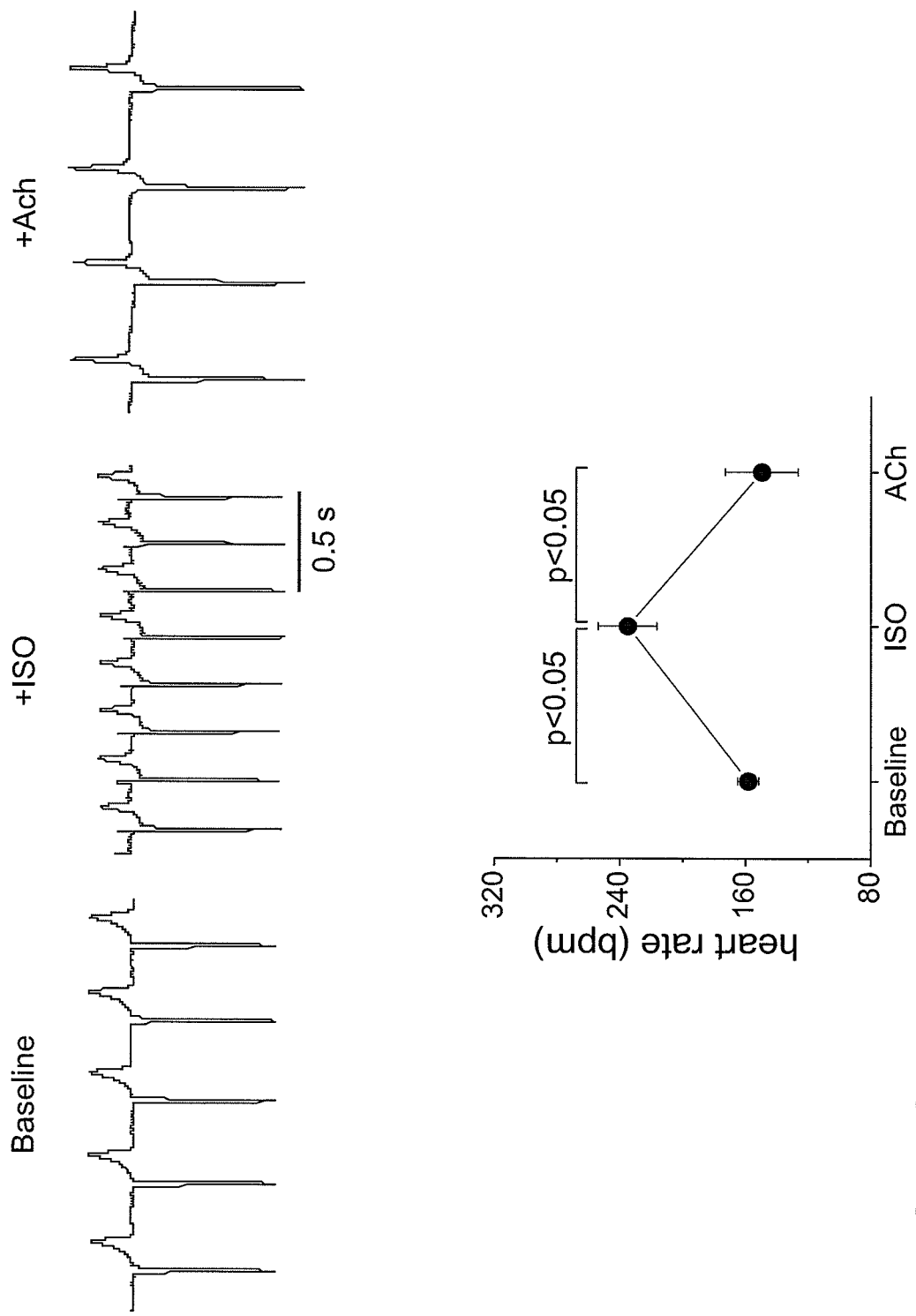
Figure 29A:
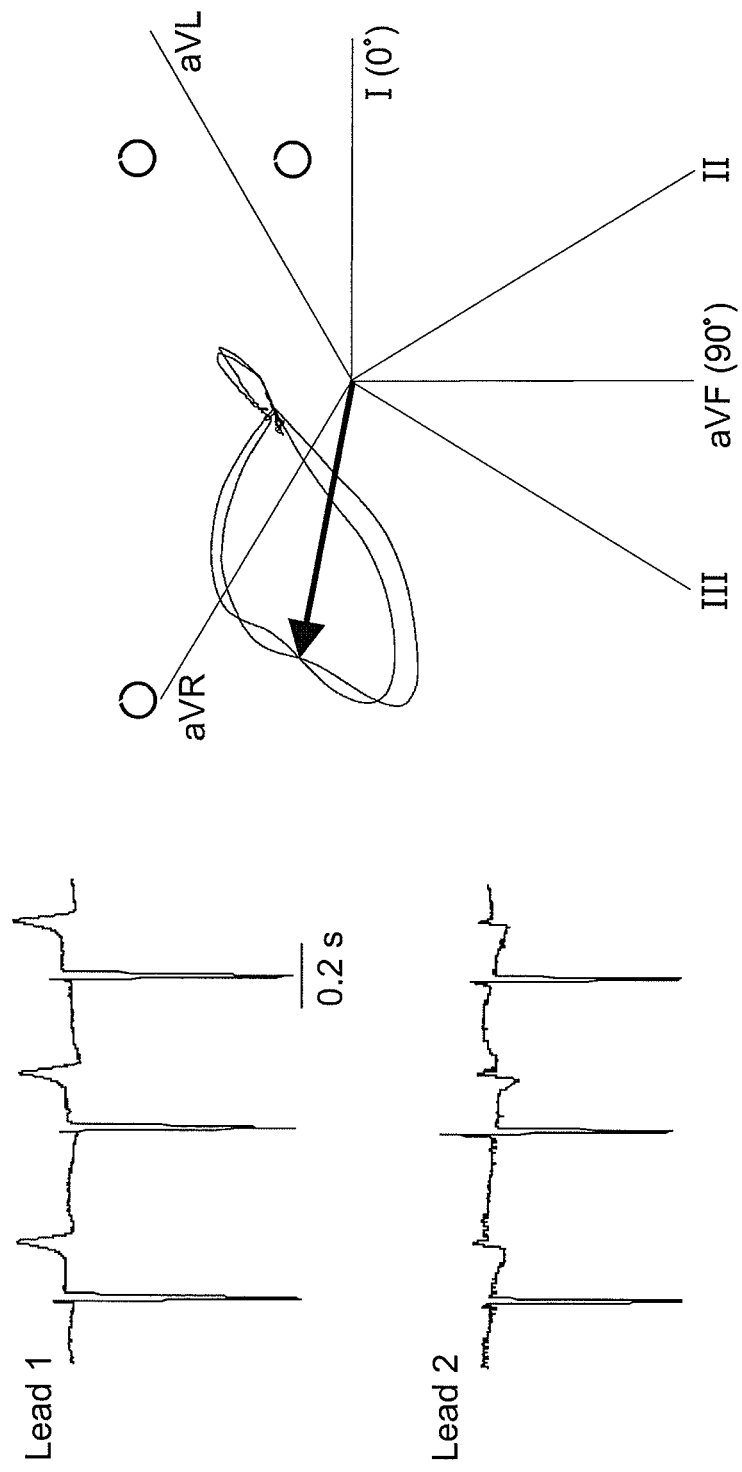
FIGS. 29A-29C depict electrocardiograms of Tbx18-injected hearts three to four weeks after gene transfer.
Figure 29B:
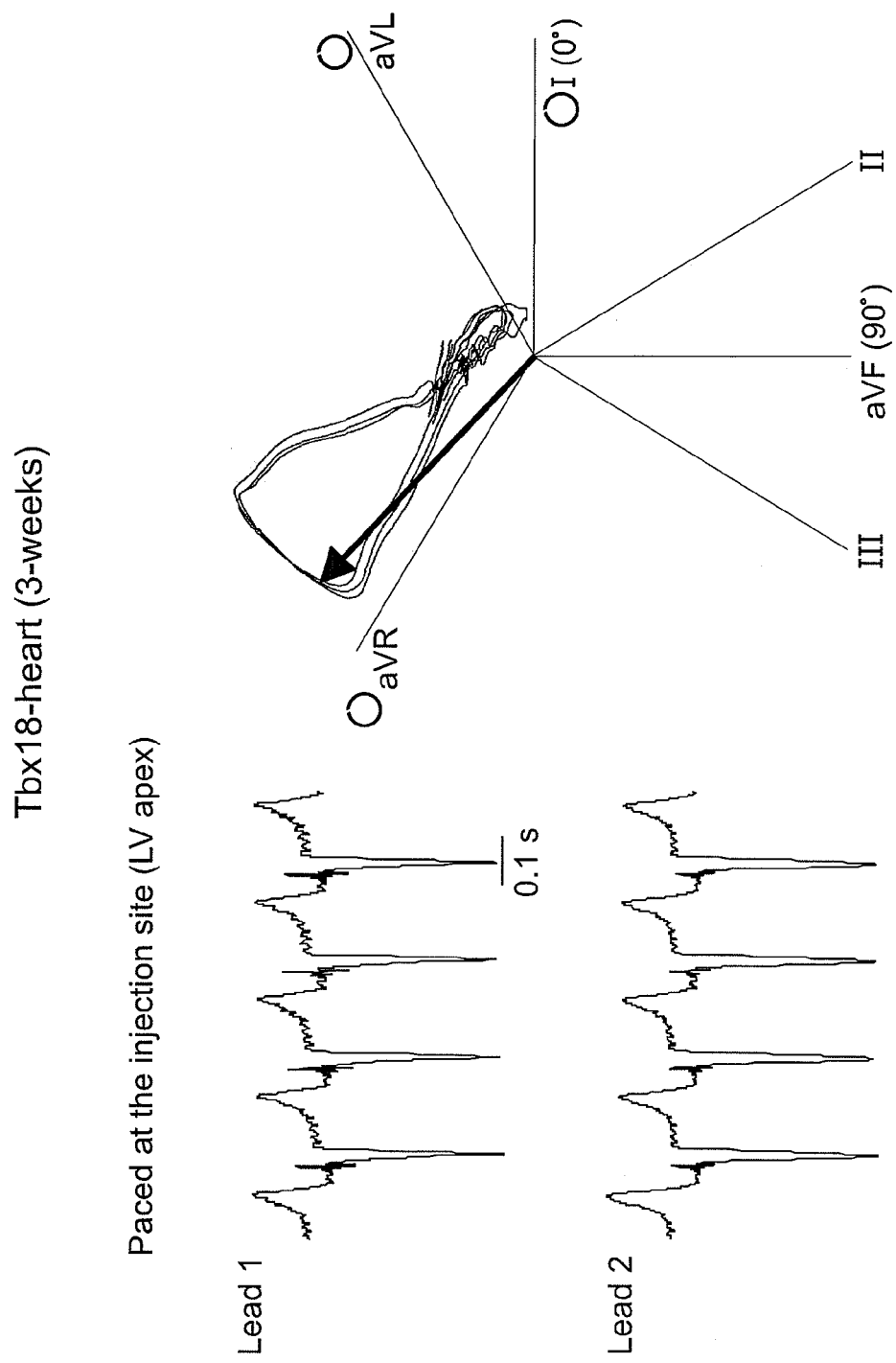
Figure 29C:
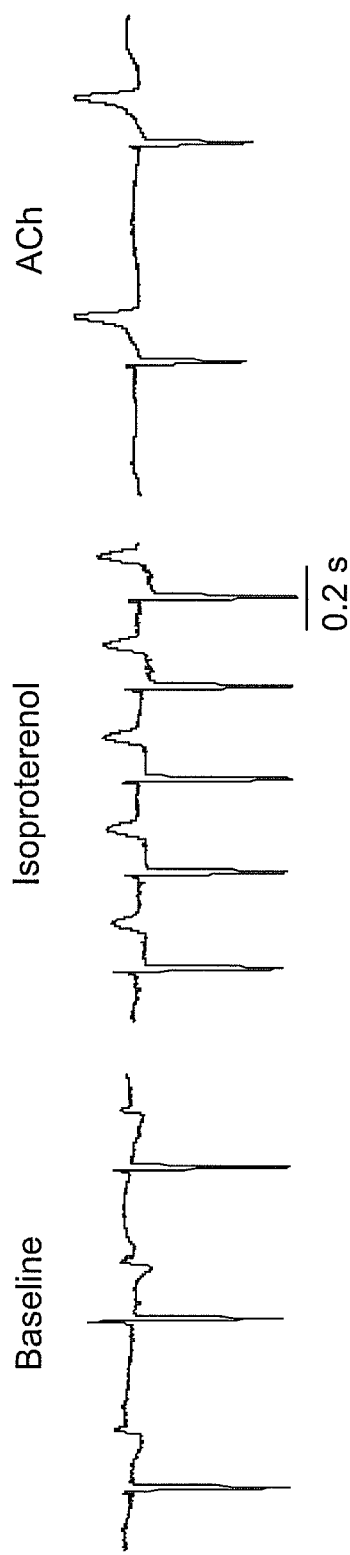

The persistence of the induced pacemaker phenotype beyond the first few days of transduction was examined using the perfused intact heart AV block model. Three to four weeks after gene transfer, Tbx18-injected hearts demonstrated ectopic idioventricular rhythm at 165±14 bpm (n=3/3, FIG. 29A), with electrocardiograms consistent with biological pacing from the Tbx18 injection site (FIG. 29B). Furthermore, these hearts responded to autonomic regulation (FIG. 29C) in a manner similar to the short-term, Tbx18-injected hearts (FIG. 25G). Taken together, the data indicate that SAN-like cells maintain pacemaker function even after exogenous Tbx18 expression has waned, indicative of genuine reprogramming.

From this data it shall be appreciated that in several embodiments the iSAN cells will not continue to express Tbx18 after conversion from quiescent cells to pacemaker-like cells. Thus, in several embodiments, it shall be appreciated that a single administration of Tbx18 to the quiescent cells may be sufficient to convert the quiescent cells to iSAN cells and for the iSAN cells to maintain their pacemaker function for a period of at least 6-8 weeks in vivo even if Tbx18 expression wanes in the iSAN cells. In some embodiments, this period during which the converted iSAN cells maintain pacemaker function could be a period of less than 6 weeks. In some embodiments, this period could be a period of more than 8 weeks. In some embodiments, more than one administration of Tbx18 transcript may be administered to the quiescent cells. Furthermore, it shall be appreciated that, in several embodiments, Shox2 could be used instead of or in conjugation with Tbx18. In several embodiments, one or more of the following transcription factors could be selected for use: Tbx18, Shox2, Tbx3, and Tbx5 and/or functional fragments or combinations thereof. In some embodiments, the administration of the transcription factor or transcription factors could occur in vitro. It shall be appreciated that in several embodiments the ability of the iSAN cell to generate an ectopic rhythm after expression of Tbx18 in the iSAN cell has waned indicates that the iSAN cell may be suitable to replace or supplement an electronic pacemaker in a subject with a cardiac arrhythmia or act to treat said cardiac arrhythmia in said subject.

Although the embodiments of the inventions have been disclosed in the context of a certain preferred embodiments and examples, it will be understood by those skilled in the art that the present inventions extend beyond the specifically disclosed embodiments to other alternative embodiments and/or uses of the inventions and obvious modifications and equivalents thereof. In addition, while a number of variations of the inventions have been shown and described in detail, other modifications, which are within the scope of the inventions, will be readily apparent to those of skill in the art based upon this disclosure. It is also contemplated that various combinations or subcombinations of the specific features and aspects of the embodiments may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. For all of the embodiments described herein the steps of the methods need not be performed sequentially. Thus, it is intended that the scope of the inventions herein disclosed should not be limited by the particular disclosed embodiments described above.

```
Homo sapiens T-box 3 (TBX3), transcript variant 1, mRNA
Accession Number - NM_005996.3
                                                            SEQ ID No. 1
GAATTCTAGAGGCGGCGGAGGGTGGCGAGGAGCTCTCGCTTTCTCTCGCTCCCTCCCTCTCCGACTCCGTCTCTC

TCTCTCTCTCTCTCTCTCCCCTCCCTCTCTTTCCCTCTGTTCCATTTTTTCCCCCTCTAAATCCTCCCTGCCCTG

CGCGCCTGGACACAGATTTAGGAAGCGAATTCGCTCACGTTTTAGGACAAGGAAGAGAGAGAGGCACGGGAGAAG

AGCCCAGCAAGATTTGGATTGAAACCGAGACACCCTCCGGAGGCTCGGAGCAGAGGAAGGAGGAGGAGGGCGGCG

AACGGAAGCCAGTTTGCAATTCAAGTTTTGATAGCGCTGGTAGAAGGGGGTTTAAATCAGATTTTTTTTTTTTA

AAGGAGAGAGACTTTTTCCGCTCTCTCGCTCCCTGTTAAAGCCGGGTCTAGCACAGCTGCAGACGCCACCAGCGA

GAAAGAGGGAGAGGAAGACAGATAGGGGCGGGGGAAGAAGAAAAAGAAAGGTAAAAAGTCTTCTAGGAGAACCT

TTCACATTTGCAACAAAAGACCTAGGGGCTGGAGAGAGATTCCTGGGACGCAGGGCTGGAGTGTCTATTTCGAGC

TCAGCGGCAGGGCTCGGGCGCGAGTCGAGACCCTGCTCGCTCCTCTCGCTTCTGAAACCGACGTTCAGGAGCGGC

TTTTTAAAAACGCAAGGCACAAGGACGGTCACCCGCGCGACTATGTTTGCTGATTTTTCGCCTTGCCCTCTTTAA

AAGCGGCCTCCCATTCTCCAAAAGACACTTCCCCTCCTCCCTTTGAAGTGCATTAGTTGTGATTTCTGCCTCCTT

TTCTTTTTTCTTTCTTTTTTGTTTTGCTTTTTCCCCCCTTTTGAATTATGTGCTGCTGTTAAACAACAACAAAAA
```

-continued

```
AACAACAAAACACAGCAGCTGCGGACTTGTCCCCGGCTGGAGCCCAGCGCCCCGCCTGGAGTGGATGAGCCTCTC
CATGAGAGATCCGGTCATTCCTGGGACAAGCATGGCCTACCATCCGTTCCTACCTCACCGGGCGCCGGACTTCGC
CATGAGCGCGGTGCTGGGTCACCAGCCGCCGTTCTTCCCCGCGCTGACGCTGCCTCCCAACGGCGCGGCGGCGCT
CTCGCTGCCGGGCGCCCTGGCCAAGCCGATCATGGATCAATTGGTGGGGCGGCCGAGACCGGCATCCCGTTCTC
CTCCCTGGGGCCCCAGGCGCATCTGAGGCCTTTGAAGACCATGGAGCCCGAAGAAGAGGTGGAGGACGACCCCAA
GGTGCACCTGGAGGCTAAAGAACTTTGGGATCAGTTTCACAAGCGGGGCACCGAGATGGTCATTACCAAGTCGGG
AAGGCGAATGTTTCCTCCATTTAAAGTGAGATGTTCTGGGCTGGATAAAAAAGCCAAATACATTTTATTGATGGA
CATTATAGCTGCTGATGACTGTCGTTATAAATTTCACAATTCTCGGTGGATGGTGGCTGGTAAGGCCGACCCCGA
AATGCCAAAGAGGATGTACATTCACCCGGACAGCCCCGCTACTGGGGAACAGTGGATGTCCAAAGTCGTCACTTT
CCACAAACTGAAACTCACCAACAACATTTCAGACAAACATGGATTTACTATATTGAACTCCATGCACAAATACCA
GCCCCGGTTCCACATTGTAAGAGCCAATGACATCTTGAAACTCCCTTATAGTACATTTCGGACATACTTGTTCCC
CGAAACTGAATTCATCGCTGTGACTGCATACCAGAATGATAAGATAACCCAGTTAAAAATAGACAACAACCCTTT
TGCAAAGGTTTCCGGGACACTGGAAATGGCCGAAGAGAAAAAAGAAAACAGCTCACCCTGCAGTCCATGAGGGT
GTTTGATGAAAGACACAAAAAGGAGAATGGGACCTCTGATGAGTCCTCCAGTGAACAAGCAGCTTTCAACTGCTT
CGCCCAGGCTTCTTCTCCAGCCGCCTCCACTGTAGGGACATCGAACCTCAAAGATTTATGTCCCAGCGAGGGTGA
GAGCGACGCCGAGGCCGAGAGCAAAGAGGAGCATGGCCCCGAGGCCTGCGACGCGGCCAAGATCTCCACCACCAC
GTCGGAGGAGCCCTGCCGTGACAAGGGCAGCCCCGCGGTCAAGGCTCACCTTTTCGCTGCTGAGCGGCCCCGGGA
CAGCGGGCGGCTGGACAAAGCGTCGCCCGACTCACGCCATAGCCCCGCCACCATCTCGTCCAGCACTCGCGGCCT
GGGCGCGGAGGAGCGCAGGAGCCCGGTTCGCGAGGGCACAGCGCCGGCCAAGGTGGAAGAGGCGCGCGCGCTCCC
GGGCAAGGAGGCCTTCGCGCCGCTCACGGTGCAGACGGACGCGGCCGCCGCGCACCTGGCCCAGGGCCCCCTGCC
TGGCCTCGGCTTCGCCCCGGGCCTGGCGGGCCAACAGTTCTTCAACGGGCACCCGCTCTTCCTGCACCCCAGCCA
GTTTGCCATGGGGGGCGCCTTCTCCAGCATGGCGGCCGCTGGCATGGGTCCCCTCCTGGCCACGGTTTCTGGGGC
CTCCACCGGTGTCTCGGGCCTGGATTCCACGGCCATGGCCTCTGCCGCTGCGGCGCAGGGACTGTCCGGGGCGTC
CGCGGCCACCCTGCCCTTCCACCTCCAGCAGCACGTCCTGGCCTCTCAGGGCCTGGCCATGTCCCCTTTCGGAAG
CCTGTTCCCTTACCCCTACACGTACATGGCCGCAGCGGCGGCCGCCTCCTCTGCGGCAGCCTCCAGCTCGGTGCA
CCGCCACCCCTTCCTCAATCTGAACACCATGCGCCCGCGGCTGCGCTACAGCCCCTACTCCATCCCGGTGCCGGT
CCCGGACGGCAGCAGTCTGCTCACCACCGCCCTGCCCTCCATGGCGGCGGCCGCGGGGCCCCTGGACGGCAAAGT
CGCCGCCCTGGCCGCCAGCCCGGCCTCGGTGGCAGTGGACTCGGGCTCTGAACTCAACAGCCGCTCCTCCACGCT
CTCCTCCAGCTCCATGTCCTTGTCGCCCAAACTCTGCGCGGAGAAAGAGGCGGCCACCAGCGAACTGCAGAGCAT
CCAGCGGTTGGTTAGCGGCTTGGAAGCCAAGCCGGACAGGTCCCGCAGCGCGTCCCCGTAGACCCGTCCCAGACA
CGTCTTTTCATTCCAGTCCAGTTCAGGCTGCCGTGCACTTTGTCGGATATAAAATAAACCACGGGCCCGCCATGG
CGTTAGCCCTTCCTTTTGCAGTTGCGTCTGGGAAGGGGCCCCGGACTCCCTCGAGAGAATGTGCTAGAGACAGCC
CCTGTCTTCTTGGCGTGGTTTATATGTCCGGGATCTGGATCAGATTCTGGGGGCTCAGAAACGTCGGTTGCATTG
AGCTACTGGGGGTAGGAGTTCCAACATTTATGTCCAGAGCAACTTCCAGCAAGGCTGGTCTGGGTCTCTGCCCAC
CAGGCGGGGAGGTGTTCAAAGACATCTCCCTCAGTGCGGATTTATATATATATTTTTCCTTCACTGTGTCAAGTG
GAAACAAAAACAAATCTTTCAAAAAAAAAATCGGGACAAGTGAACACATTAACATGATTCTGTTTGTGCAGATT
AAAAACTTTATAGGGACTTGCATTATCGGTTCTCAATAAATTACTGAGCAGCTTTGTTTGGGGAGGGAAGTCCCT
ACCATCCTTGTTTAGTCTATATTAAGAAAATCTGTGTCTTTTTAATATTCTTGTGATGTTTTCAGAGCCGCTGTA
GGTCTCTTCTTGCATGTCCACAGTAATGTATTTGTGGTTTTTATTTTGAACGCTTGCTTTTAGAGAGAAAACAAT
ATAGCCCCCTACCCTTTTCCCAATCCTTTGCCCTCAAATCAGTGACCCAAGGGAGGGGGGATTTAAAGGGAAGG
AGTGGGCAAAACACATAAAATGAATTTATTATATCTAAGCTCTGTAGCAGGATTCATGTCGTTCTTTGACAGTTC
```

-continued

TTTCTCTTTCCTGTATATGCAATAACAAGGTTTTAAAAAAATAATAAAGAAGTGAGACTATTAGACAAAGTATTT
ATGTAATTATTTGATAACTCTTGTAAATAGGTGGAATATGAATGCTTGGAAAATTAAACTTTAATTTATTGACAT
TGTACATAGCTCTGTGTAAATAGAATTGCAACTGTCAGGTTTTGTGTTCTTGTTTTCCTTTAGTTGGGTTTATTT
CCAGGTCACAGAATTGCTGTTAACACTAGAAAACACACTTCCTGCACCAACACCAATACCCTTTCAAAAGAGTTG
TCTGCAACATTTTTGTTTTCTTTTTTAATGTCCAAAAGTGGGGGAAAGTGCTATTTCCTATTTTCACCAAAATTG
GGGAAGGAGTGCCACTTTCCAGCTCCACTTCAAATTCCTTAAAATATAACTGAGATTGCTGTGGGGAGGGAGGAG
GGCAGAGGCTGCGGTTTGACTTTTTAATTTTTCTTTGTTATTTGTATTTGCTAGTCTCTGATTTCCTCAAAACG
AAGTGGAATTTACTACTGTTGTCAGTATCGGTGTTTTGAATTGGTGCCTGCCTATAGAGATATATTCACAGTTCA
AAAGTCAGGTGCTGAGAGATGGTTTAAAGACAAATTCATGAAGGTATATTTTGTGTTATAGTTGTTGATGAGTTC
TTTGGTTTTCTGTATTTTTCCCCCTCTCTTTAAAACATCACTGAAATTTCAATAAATTTTTATTGAAATGTCTAA
AAAAAAAAAAAAAAAAAAAAAAAAAAA

Homo sapiens T-box 3 (TBX3), transcript variant 2, mRNA
Accession Number - NM_016569.3

SEQ ID. No. 2

GAATTCTAGAGGCGGCGGAGGGTGGCGAGGAGCTCTCGCTTTCTCTCGCTCCCTCCCTCTCCGACTCCGTCTCTC
TCTCTCTCTCTCTCTCCCCTCCCTCTCTTTCCCTCTGTTCCATTTTTTCCCCCTCTAAATCCTCCCTGCCCTG
CGCGCCTGGACACAGATTTAGGAAGCGAATTCGCTCACGTTTTAGGACAAGGAAGAGAGAGAGGCACGGGAGAAG
AGCCCAGCAAGATTTGGATTGAAACCGAGACACCCTCCGGAGGCTCGGAGCAGAGGAAGGAGGAGGAGGGCGGCG
AACGGAAGCCAGTTTGCAATTCAAGTTTTGATAGCGCTGGTAGAAGGGGGTTTAAATCAGATTTTTTTTTTTTA
AAGGAGAGAGACTTTTTCCGCTCTCTCGCTCCCTGTTAAAGCCGGGTCTAGCACAGCTGCAGACGCCACCAGCGA
GAAAGAGGGAGAGGAAGACAGATAGGGGGCGGGGGAAGAAGAAAAAGAAAGGTAAAAAGTCTTCTAGGAGAACCT
TTCACATTTGCAACAAAAGACCTAGGGGCTGGAGAGAGATTCCTGGGACGCAGGGCTGGAGTGTCTATTTCGAGC
TCAGCGGCAGGGCTCGGGCGCGAGTCGAGACCCTGCTCGCTCCTCTCGCTTCTGAAACCGACGTTCAGGAGCGGC
TTTTTAAAAACGCAAGGCACAAGGACGGTCACCCGCGCGACTATGTTTGCTGATTTTTCGCCTTGCCCTCTTTAA
AAGCGGCCTCCCATTCTCCAAAAGACACTTCCCCTCCTCCCTTTGAAGTGCATTAGTTGTGATTTCTGCCTCCTT
TTCTTTTTTCTTTCTTTTTTGTTTTGCTTTTTCCCCCCTTTTGAATTATGTGCTGCTGTTAAACAACAACAAAAA
AACAACAAAACACAGCAGCTGCGGACTTGTCCCCGGCTGGAGCCCAGCGCCCCGCCTGGAGTGGATGAGCCTCTC
CATGAGAGATCCGGTCATTCCTGGGACAAGCATGGCCTACCATCCGTTCCTACCTCACCGGGCGCCGGACTTCGC
CATGAGCGCGGTGCTGGGTCACCAGCCGCCGTTCTTCCCCGCGCTGACGCTGCCTCCCAACGGCGCGGCGGCGCT
CTCGCTGCCGGGCGCCCTGGCCAAGCCGATCATGGATCAATTGGTGGGGCGGCCGAGACCGGCATCCCGTTCTC
CTCCCTGGGGCCCCAGGCGCATCTGAGGCCTTTGAAGACCATGGAGCCCGAAGAAGAGGTGGAGGACGACCCCAA
GGTGCACCTGGAGGCTAAAGAACTTTGGGATCAGTTTCACAAGCGGGGCACCGAGATGGTCATTACCAAGTCGGG
AAGGCGAATGTTTCCTCCATTTAAAGTGAGATGTTCTGGGCTGGATAAAAAAGCCAAATACATTTTATTGATGGA
CATTATAGCTGCTGATGACTGTCGTTATAAATTTCACAATTCTCGGTGGATGGTGGCTGGTAAGGCCGACCCCGA
AATGCCAAAGAGGATGTACATTCACCCGGACAGCCCCGCTACTGGGGAACAGTGGATGTCCAAAGTCGTCACTTT
CCACAAACTGAAACTCACCAACAACATTTCAGACAAACATGGATTTACTTTGGCCTTCCCAAGTGATCACGCTAC
GTGGCAGGGGAATTATAGTTTTGGTACTCAGACTATATTGAACTCCATGCACAAATACCAGCCCCGGTTCCACAT
TGTAAGAGCCAATGACATCTTGAAACTCCCTTATAGTACATTTCGGACATACTTGTTCCCCGAAACTGAATTCAT
CGCTGTGACTGCATACCAGAATGATAAGATAACCCAGTTAAAAATAGACAACAACCCTTTTGCAAAAGGTTTCCG
GGACACTGGAAATGGCCGAAGAGAAAAAGAAACAGCTCACCCTGCAGTCCATGAGGGTGTTTGATGAAAGACA
CAAAAAGGAGAATGGGACCTCTGATGAGTCCTCCAGTGAACAAGCAGCTTTCAACTGCTTCGCCCAGGCTTCTTC
TCCAGCCGCCTCCACTGTAGGGACATCGAACCTCAAAGATTTATGTCCCAGCGAGGGTGAGAGCGACGCCGAGGC

-continued

```
CGAGAGCAAAGAGGAGCATGGCCCCGAGGCCTGCGACGCGGCCAAGATCTCCACCACCACGTCGGAGGAGCCCTG

CCGTGACAAGGGCAGCCCCGCGGTCAAGGCTCACCTTTTCGCTGCTGAGCGGCCCCGGGACAGCGGGCGGCTGGA

CAAAGCGTCGCCCGACTCACGCCATAGCCCCGCCACCATCTCGTCCAGCACTCGCGGCCTGGGCGCGGAGGAGCG

CAGGAGCCCGGTTCGCGAGGGCACAGCGCCGGCCAAGGTGGAAGAGGCGCGCGCGCTCCCGGGCAAGGAGGCCTT

CGCGCCGCTCACGGTGCAGACGGACGCGGCCGCCGCGCACCTGGCCCAGGGCCCCCTGCCTGGCCTCGGCTTCGC

CCCGGGCCTGGCGGGCAACAGTTCTTCAACGGGCACCCGCTCTTCCTGCACCCCAGCCAGTTTGCCATGGGGGG

CGCCTTCTCCAGCATGGCGGCCGCTGGCATGGGTCCCCTCCTGGCCACGGTTTCTGGGGCCTCCACCGGTGTCTC

GGGCCTGGATTCCACGGCCATGGCCTCTGCCGCTGCGGCGCAGGGACTGTCCGGGGCGTCCGCGGCCACCCTGCC

CTTCCACCTCCAGCAGCACGTCCTGGCCTCTCAGGGCCTGGCCATGTCCCCTTTCGGAAGCCTGTTCCCTTACCC

CTACACGTACATGGCCGCAGCGGCGGCCGCCTCCTCTGCGGCAGCCTCCAGCTCGGTGCACCGCCACCCCTTCCT

CAATCTGAACACCATGCGCCCGCGGCTGCGCTACAGCCCCTACTCCATCCCGGTGCCGGTCCCGGACGGCAGCAG

TCTGCTCACCACCGCCCTGCCCTCCATGGCGGCGGCCGCGGGGCCCCTGGACGGCAAAGTCGCCGCCCTGGCCGC

CAGCCCGGCCTCGGTGGCAGTGGACTCGGGCTCTGAACTCAACAGCCGCTCCTCCACGCTCTCCTCCAGCTCCAT

GTCCTTGTCGCCCAAACTCTGCGCGGAGAAAGAGGCGGCCACCAGCGAACTGCAGAGCATCCAGCGGTTGGTTAG

CGGCTTGGAAGCCAAGCGGACAGGTCCCGCAGCGCGTCCCCGTAGACCCGTCCCAGACACGTCTTTTCATTCCA

GTCCAGTTCAGGCTGCCGTGCACTTTGTCGGATATAAAATAAACCACGGGCCCGCCATGGCGTTAGCCCTTCCTT

TTGCAGTTGCGTCTGGGAAGGGGCCCCGGACTCCCTCGAGAGAATGTGCTAGAGACAGCCCCTGTCTTCTTGGCG

TGGTTTATATGTCCGGGATCTGGATCAGATTCTGGGGGCTCAGAAACGTCGGTTGCATTGAGCTACTGGGGGTAG

GAGTTCCAACATTTATGTCCAGAGCAACTTCCAGCAAGGCTGGTCTGGGTCTCTGCCCACCAGGCGGGGAGGTGT

TCAAAGACATCTCCCTCAGTGCGGATTTATATATATATTTTTCCTTCACTGTGTCAAGTGGAAACAAAAACAAAA

TCTTTCAAAAAAAAATCGGGACAAGTGAACACATTAACATGATTCTGTTTGTGCAGATTAAAAACTTTATAGGG

ACTTGCATTATCGGTTCTCAATAAATTACTGAGCAGCTTTGTTTGGGGAGGGAAGTCCCTACCATCCTTGTTTAG

TCTATATTAAGAAAATCTGTGTCTTTTTAATATTCTTGTGATGTTTTCAGAGCCGCTGTAGGTCTCTTCTTGCAT

GTCCACAGTAATGTATTTGTGGTTTTTATTTTGAACGCTTGCTTTTAGAGAGAAAACAATATAGCCCCCTACCCT

TTTCCCAATCCTTTGCCCTCAAATCAGTGACCCAAGGGAGGGGGGGATTTAAAGGGAAGGAGTGGGCAAAACACA

TAAAATGAATTTATTATATCTAAGCTCTGTAGCAGGATTCATGTCGTTCTTTGACAGTTCTTTCTCTTTCCTGTA

TATGCAATAACAAGGTTTTAAAAAAATAATAAAGAAGTGAGACTATTAGACAAAGTATTTATGTAATTATTTGAT

AACTCTTGTAAATAGGTGGAATATGAATGCTTGGAAAATTAAACTTTAATTTATTGACATTGTACATAGCTCTGT

GTAAATAGAATTGCAACTGTCAGGTTTTGTGTTCTTGTTTTCCTTTAGTTGGGTTTATTTCCAGGTCACAGAATT

GCTGTTAACACTAGAAAACACACTTCCTGCACCAACACCAATACCCTTTCAAAAGAGTTGTCTGCAACATTTTTG

TTTTCTTTTTAATGTCCAAAAGTGGGGAAAGTGCTATTTCCTATTTTCACCAAAATTGGGGAAGGAGTGCCAC

TTTCCAGCTCCACTTCAAATTCCTTAAAATATAACTGAGATTGCTGTGGGGAGGGAGGAGGGCAGAGGCTGCGGT

TTGACTTTTTAATTTTTCTTTTGTTATTTGTATTTGCTAGTCTCTGATTTCCTCAAAACGAAGTGGAATTTACTA

CTGTTGTCAGTATCGGTGTTTTGAATTGGTGCCTGCCTATAGAGATATATTCACAGTTCAAAAGTCAGGTGCTGA

GAGATGGTTTAAAGACAAATTCATGAAGGTATATTTTGTGTTATAGTTGTTGATGAGTTCTTTGGTTTTCTGTAT

TTTTCCCCTCTCTTTAAAACATCACTGAAATTTCAATAAATTTTTATTGAAATGTCTAAAAAAAAAAAAAAAAAA

AAAAAAAAAAAAA
```

*Homo sapiens* T-box 5 (TBX5), transcript variant 1, mRNA
Accession Number - NM_000192.3

SEQ ID No. 3

```
CATGCCTTATGCAAGAGACCTCAGTCCCCGGAACAACTCGATTTCCTTCCAATAGAGGTCTGAGGTGGACTCCC

ACCTCCCTTCGTGAAGAGTTCCCTCCTCTCCCCCTTCCTAAGAAAGTCGATCTTGGCTCTATTTGTGTCTTATGT
```

-continued

```
TCATCACCCTCATTCCTCCGGAGAAAGCCGGGTTGGTTTATGTCTTTATTTATTCCCGGGGCCAAGACGTCCGGA
ACCTGTGGCTGCGCAGACCCGGCACTGATAGGCGAAGACGGAGAGAAATTTACCTCCCGCCGCTGCCCCCCAGCC
AAACGTGACAGCGCGCGGGCCGGTTGCGTGACTCGTGACGTCTCCAAGTCCTATAGGTGCAGCGGCTGGTGAGAT
AGTCGCTATCGCCTGGTTGCCTCTTTATTTTACTGGGGTATGCCTGGTAATAAACAGTAATATTTAATTTGTCGG
AGACCACAAACCAACCTTGAGCTGGGAGGTACGTGCTCTTCTTGACAGACGTTGGAAGAAGACCTGGCCTAAAGA
GGTCTCTTTTGGTGGTCCTTTTCAAAGTCTTCACCTGAGCCCTGCTCTCCAGCGAGGCGCACTCCTGGCTTTTGC
GCTCCAAAGAAGAGGTGGGATAGTTGGAGAGCAGAACCTTGCGCGGGCACAGGGCCCTGGGCGCACCATGGCCGA
CGCAGACGAGGGCTTTGGCCTGGCGCACACGCCTCTGGAGCCTGACGCAAAAGACCTGCCCTGCGATTCGAAACC
CGAGAGCGCGCTCGGGGCCCCCAGCAAGTCCCCGTCGTCCCCGCAGGCCGCCTTCACCCAGCAGGGCATGGAGGG
AATCAAAGTGTTTCTCCATGAAAGAGAACTGTGGCTAAAATTCCACGAAGTGGGCACGGAAATGATCATAACCAA
GGCTGGAAGGCGGATGTTTCCCAGTTACAAAGTGAAGGTGACGGGCCTTAATCCCAAAACGAAGTACATTCTTCT
CATGGACATTGTACCTGCCGACGATCACAGATACAAATTCGCAGATAATAAATGGTCTGTGACGGGCAAAGCTGA
GCCCGCCATGCCTGGCCGCCTGTACGTGCACCCAGACTCCCCCGCCACCGGGGCGCATTGGATGAGGCAGCTCGT
CTCCTTCCAGAAACTCAAGCTCACCAACAACCACCTGGACCCATTTGGGCATATTATTCTAAATTCCATGCACAA
ATACCAGCCTAGATTACACATCGTGAAAGCGGATGAAAATAATGGATTTGGCTCAAAAAATACAGCGTTCTGCAC
TCACGTCTTTCCTGAGACTGCGTTTATAGCAGTGACTTCCTACCAGAACCACAAGATCACGCAATTAAAGATTGA
GAATAATCCCTTTGCCAAAGGATTTCGGGGCAGTGATGACATGGAGCTGCACAGAATGTCAAGAATGCAAAGTAA
AGAATATCCCGTGGTCCCCAGGAGCACCGTGAGGCAAAAAGTGGCCTCCAACCACAGTCCTTTCAGCAGCGAGTC
TCGAGCTCTCTCCACCTCATCCAATTTGGGGTCCCAATACCAGTGTGAGAATGGTGTTTCCGGCCCCTCCCAGGA
CCTCCTGCCTCCACCCAACCCATACCCACTGCCCCAGGAGCATAGCCAAATTTACCATTGTACCAAGAGGAAAGA
GGAAGAATGTTCCACCACAGACCATCCCTATAAGAAGCCCTACATGGAGACATCACCCAGTGAAGAAGATTCCTT
CTACCGCTCTAGCTATCCACAGCAGCAGGGCCTGGGTGCCTCCTACAGGACAGAGTCGGCACAGCGGCAAGCTTG
CATGTATGCCAGCTCTGCGCCCCCCAGCGAGCCTGTGCCCAGCCTAGAGGACATCAGCTGCAACACGTGGCCAAG
CATGCCTTCCTACAGCAGCTGCACCGTCACCACCGTGCAGCCCATGGACAGGCTACCCTACCAGCACTTCTCCGC
TCACTTCACCTCGGGGCCCCTGGTCCCTCGGCTGGCTGGCATGGCCAACCATGGCTCCCCACAGCTGGGAGAGGG
AATGTTCCAGCACCAGACCTCCGTGGCCCACCAGCCTGTGGTCAGGCAGTGTGGGCCTCAGACTGGCCTGCAGTC
CCCTGGCACCCTTCAGCCCCCTGAGTTCCTCTACTCTCATGGCGTGCCAAGGACTCTATCCCCTCATCAGTACCA
CTCTGTGCACGGAGTTGGCATGGTGCCAGAGTGGAGCGACAATAGCTAAAGTGAGGCCTGCTTCACAACAGACAT
TTCCTAGAGAAAGAGAGAGAGAGGAGAAAGAGAGAGAAGGAGAGAGACAGTAGCCAAGAGAACCCCACGGACA
AGATTTTTCATTTCACCCAATGTTCACATCTGCACTCAAGGTCGCTGGATGCTGATCTAATCAGTAGCTTGAAAC
CACAATTTTAAAAATGTGACTTTCTTGTTTTGTCTCAAAACTTAAAAAAACAAACACAAAAAGATGAGTCCCACC
CCCCACTACCACCACACCCATCAACCAGCCACATTCACGCTACTCCCCAGATCTCTTCCCCCATTCCTTCTTTTG
GGCTCTAGAAAGTCTTGCCTCATTGAGTGTTTTTCCCTAGTGCGTAGTTGGAGTCTGTCCCTGTCTTGGTGTTAA
TGTTGACATTGTTATATAATAAATGATAATATATTTTTTCTTTCAATTTTCTTAATGGGACCCAGTCCCTTATT
TGGGGGGAGGTCTGAGGCAAGTATATTTCAAAATATGTACTTGCGGGATTCCCTTCAAGTAAACCATCCCTGAAA
CCTAAATTCACGTTTCCCCTTGACTAAGAAAAGCACCTACCTCTGCCATGTGATGTTTCTGAAAAGCCTCTGTAT
GTCCCCATTTGCTTTGGTTTTGTCCTGCCTTCTCCAATATCACGTGCTCAGTTTTGCCTCTACTTACCCATGGAG
TCAGGATAACACTGACGCTCCCTGGCATCCTATCTTATTCAGCCCTACCATCTTGCCAGCTCTGTCTTTCCAGCT
GTCTGTCGCTAAAACGTGGCCTATAGCTTCCCTTCCGGAAAGCTTGCTTTGAAAAACTTAAAAAGCCCCGTTTA
CATGTAGGCAGGACTGTGATAACAGTGCAAGCTCTGTGTTGACAAGAGTTGTGGACAAAAAGCCAAAATAAATAT
TCTTCCTGATTAAAAAAATTTTTTTTGAAAAAAACAAGGCCAGCCCCAACCTTCCAAACCTCCATCACCAACAAC
```

-continued

```
CCAAACTGGATGTCAAGCAAAATGCACAATTCCTACAGAAGAGGCAAGACACAGTCACCAATGATATCTCGCCAA

AGAAACCACGCCCACACCAATGCCAACACAAAACTGTGTTTACTGAAAGCCGAAAACAGTATTAAAAAAAGTGTG

TAAGTAAAGTGTTATGGTAGGGTTCTTCAGATGTAATATTTTACTGGTACTATTTATTTATAAATAGGAATTCTA

ATTAAGTAATAACATGAAATGAAACCCAGCATAGGAGCTGGCCAAGAGCTTTTAATTTTATTGATACTCAAAACC

AAGTTTGTGTTTTTTGTTTTTTTTGTTTTTTCCTCTTTCGAATGTGCTTTGCTTTTTTGATTAAAAGAAT

TTTTTTTTCCTTTTTTATAAACAGACCCTAATAAAGAGAACAGGGTAAGATGTGAGGCTGAGTGTGTTTAAGTA

CGTGAGAGAGTGTGAGTGTGTTTGTAAGTGAGTGTCCCTATGCGATTATGTCTCTTTACGTTGCTAAGGGGGAG

GGTGAGGATTAAGTACTCGTGCCTTATATTTGTGTGCCAATTAATGCCTAATAAATACCATGTGCTTAAACAAGT

AAAAAAAAAAAAAAAAAAAAAAAAAAAAAAAAAAAAAAAAAAAAAAAAAAAAAAAAAAAAAAAAAAAAAAAAAAA

AAAAAAAAAAAAAAAAAAAA
```

Homo sapiens T-box 5 (TBX5), transcript variant 2, mRNA
Accession Number - NM_080718.1

SEQ ID NO. 4

```
ATGGCCGACGCAGACGAGGGCTTTGGCCTGGCGCACACGCCTCTGGAGCCTGACGCAAAAGACCTGCCCTGCGAT

TCGAAACCCGAGAGCGCGCTCGGGGCCCCCAGCAAGTCCCCGTCGTCCCCGCAGGCCGCCTTCACCCAGCAGGGC

ATGGAGGGAATCAAAGTGTTTCTCCATGAAAGAGAACTGTGGCTAAAATTCCACGAAGTGGGCACGGAAATGATC

ATAACCAAGGCTGGAAGGCGGATGTTTCCCAGTTACAAAGTGAAGGTGACGGGCCTTAATCCCAAAACGAAGTAC

ATTCTTCTCATGGACATTGTACCTGCCGACGATCACAGATACAAATTCGCAGATAATAAATGGTCTGTGACGGGC

AAAGCTGAGCCCGCCATGCCTGGCCGCCTGTACGTGCACCCAGACTCCCCCGCCACCGGGGCGCATTGGATGAGG

CAGCTCGTCTCCTTCCAGAAACTCAAGCTCACCAACAACCACCTGGACCCATTTGGGCATATTATTCTAAATTCC

ATGCACAAATACCAGCCTAGATTACACATCGTGAAAGCGGATGAAAATAATGGATTTGGCTCAAAAAATACAGCG

TTCTGCACTCACGTCTTTCCTGAGACTGCGTTTATAGCAGTGACTTCCTACCAGAACCACAAGATCACGCAATTA

AAGATTGAGAATAATCCCTTTGCCAAAGGATTTCGGGGCAGTGATGACATGGAGCTGCACAGAATGTCAAGAATG

CAAAGTAAAGAATATCCCGTGGTCCCCAGGAGCACCGTGAGGCAAAAAGTGGCCTCCAACCACAGTCCTTTCAGC

AGCGAGTCTCGAGCTCTCTCCACCTCATCCAATTTGGGGTCCCAATACCAGTGTGAGAATGGTGTTTCCGGCCCC

TCCCAGGACCTCCTGCCTCCACCCAACCCATACCCACTGCCCCAGGAGCATAGCCAAATTTACCATTGTACCAAG

AGGAAAGGTGAGTGTGATCACCCCTGGTCAATTTGCTTTCTTTCTTACCTTTTCCTTTCCTTGGGTTGGGGGTGA
```

Homo sapiens T-box 5 (TBX5), transcript variant 3, mRNA
Accession Number - NM_080717.2

SEQ ID No. 5

```
CATGCCTTATGCAAGAGACCTCAGTCCCCCGGAACAACTCGATTTCCTTCCAATAGAGGTCTGAGGTGGACTCCC

ACCTCCCTTCGTGAAGAGTTCCCTCCTCTCCCCCTTCCTAAGAAAGTCGATCTTGGCTCTATTTGTGTCTTATGT

TCATCACCCTCATTCCTCCGGAGAAAGCCGGGTTGGTTTATGTCTTTATTTATTCCCGGGGCCAAGACGTCCGGA

ACCTGTGGCTGCGCAGACCCGGCACTGATAGGCGAAGACGGAGAGAAATTTACCTCCCGCCGCTGCCCCCCAGCC

AAACGTGACAGCGCGCGGGCCGGTTGCGTGACTCGTGACGTCTCCAAGTCCTATAGGTGCAGCGGCTGGTGAGAT

AGTCGCTATCGCCTGGTTGCCTCTTTATTTTACTGGGGTATGCCTGGTAATAAACAGTAATATTTAATTTGTCGG

AGACCACAAACCAACCTTGAGCTGGGAGGTACGTGCTCTTCTTGACAGACGTTGGAAGAAGACCTGGCCTAAAGA

GGTCTCTTTTGGTGGTCCTTTTCAAAGTCTTCACCTGAGCCCTGCTCTCCAGCGAGGCGCACTCCTGGCTTTTGC

GCTCCAAAGAAGAGGTGGGATAGTTGGAGGGCATGGAGGGAATCAAAGTGTTTCTCCATGAAAGAGAACTGTGGC

TAAAATTCCACGAAGTGGGCACGGAAATGATCATAACCAAGGCTGGAAGGCGGATGTTTCCCAGTTACAAAGTGA

AGGTGACGGGCCTTAATCCCAAAACGAAGTACATTCTTCTCATGGACATTGTACCTGCCGACGATCACAGATACA

AATTCGCAGATAATAAATGGTCTGTGACGGGCAAAGCTGAGCCCGCCATGCCTGGCCGCCTGTACGTGCACCCAG

ACTCCCCCGCCACCGGGGCGCATTGGATGAGGCAGCTCGTCTCCTTCCAGAAACTCAAGCTCACCAACAACCACC

TGGACCCATTTGGGCATATTATTCTAAATTCCATGCACAAATACCAGCCTAGATTACACATCGTGAAAGCGGATG
```

-continued

```
AAAATAATGGATTTGGCTCAAAAAATACAGCGTTCTGCACTCACGTCTTTCCTGAGACTGCGTTTATAGCAGTGA

CTTCCTACCAGAACCACAAGATCACGCAATTAAAGATTGAGAATAATCCCTTTGCCAAAGGATTTCGGGGCAGTG

ATGACATGGAGCTGCACAGAATGTCAAGAATGCAAAGTAAAGAATATCCCGTGGTCCCCAGGAGCACCGTGAGGC

AAAAAGTGGCCTCCAACCACAGTCCTTTCAGCAGCGAGTCTCGAGCTCTCTCCACCTCATCCAATTTGGGGTCCC

AATACCAGTGTGAGAATGGTGTTTCCGGCCCCTCCCAGGACCTCCTGCCTCCACCCAACCCATACCCACTGCCCC

AGGAGCATAGCCAAATTTACCATTGTACCAAGAGGAAAGAGGAAGAATGTTCCACCACAGACCATCCCTATAAGA

AGCCCTACATGGAGACATCACCCAGTGAAGAAGATTCCTTCTACCGCTCTAGCTATCCACAGCAGCAGGGCCTGG

GTGCCTCCTACAGGACAGAGTCGGCACAGCGGCAAGCTTGCATGTATGCCAGCTCTGCGCCCCCCAGCGAGCCTG

TGCCCAGCCTAGAGGACATCAGCTGCAACACGTGGCCAAGCATGCCTTCCTACAGCAGCTGCACCGTCACCACCG

TGCAGCCCATGGACAGGCTACCCTACCAGCACTTCTCCGCTCACTTCACCTCGGGGCCCCTGGTCCCTCGGCTGG

CTGGCATGGCCAACCATGGCTCCCCACAGCTGGGAGAGGGAATGTTCCAGCACCAGACCTCCGTGGCCCACCAGC

CTGTGGTCAGGCAGTGTGGGCCTCAGACTGGCCTGCAGTCCCCTGGCACCCTTCAGCCCCCTGAGTTCCTCTACT

CTCATGGCGTGCCAAGGACTCTATCCCCTCATCAGTACCACTCTGTGCACGGAGTTGGCATGGTGCCAGAGTGGA

GCGACAATAGCTAAAGTGAGGCCTGCTTCACAACAGACATTTCCTAGAGAAAGAGAGAGAGAGGAGAAAGAGA

GAGAAGGAGAGAGACAGTAGCCAAGAGAACCCCACGGACAAGATTTTTCATTTCACCCAATGTTCACATCTGCAC

TCAAGGTCGCTGGATGCTGATCTAATCAGTAGCTTGAAACCACAATTTTAAAAATGTGACTTTCTTGTTTTGTCT

CAAAACTTAAAAAAACAAACACAAAAAGATGAGTCCCACCCCCACTACCACCACACCCATCAACCAGCCACATT

CACGCTACTCCCCAGATCTCTTCCCCCATTCCTTCTTTTGGGCTCTAGAAAGTCTTGCCTCATTGAGTGTTTTTC

CCTAGTGCGTAGTTGGAGTCTGTCCCTGTCTTGGTGTTAATGTTGACATTGTTATATAATAAATGATAATATATT

TTTTTCTTTCAATTTTCTTAATGGGACCCAGTCCCTTATTTGGGGGGAGGTCTGAGGCAAGTATATTTCAAAATA

TGTACTTGCGGGATTCCCTTCAAGTAAACCATCCCTGAAACCTAAATTCACGTTTCCCCTTGACTAAGAAAAGCA

CCTACCTCTGCCATGTGATGTTTCTGAAAAGCCTCTGTATGTCCCCATTTGCTTTGGTTTTGTCCTGCCTTCTCC

AATATCACGTGCTCAGTTTTGCCTCTACTTACCCATGGAGTCAGGATAACACTGACGCTCCCTGGCATCCTATCT

TATTCAGCCCTACCATCTTGCCAGCTCTGTCTTTCCAGCTGTCTGTCGCTAAAACGTGGCCTATAGCTTCCCTTC

CGGAAAGCTTGCTTTGAAAAACTTAAAAAGCCCCGTTTACATGTAGGCAGGACTGTGATAACAGTGCAAGCTCT

GTGTTGACAAGAGTTGTGGACAAAAAGCCAAAATAAATATTCTTCCTGATTAAAAAAATTTTTTTTGAAAAAAC

AAGGCCAGCCCCAACCTTCCAAACCTCCATCACCAACAACCCAAACTGGATGTCAAGCAAAATGCACAATTCCTA

CAGAAGAGGCAAGACACAGTCACCAATGATATCTCGCCAAAGAAACCACGCCCACACCAATGCCAACACAAAACT

GTGTTTACTGAAAGCCGAAAACAGTATTAAAAAAAGTGTGTAAGTAAAGTGTTATGGTAGGGTTCTTCAGATGTA

ATATTTTACTGGTACTATTTATTTATAAATAGGAATTCTAATTAAGTAATAACATGAAATGAAACCCAGCATAGG

AGCTGGCCAAGAGCTTTTAATTTTATTGATACTCAAAACCAAGTTTGTGTTTTTTGTTTTTTTTGTTTTTTTC

CTCTTTCGAATGTGCTTTGCTTTTTTTGATTAAAAAGAATTTTTTTTTCCTTTTTTATAAACAGACCCTAATAA

AGAGAACAGGGTAAGATGTGAGGCTGAGTGTGTTTAAGTACGTGAGAGAGTGTGAGTGTGTTTGTAAGTGAGTGT

CCCTATGCGATTATGTCTCTTTACGTTGCTAAGGGGGAGGGTGAGGATTAAGTACTCGTGCCTTATATTTGTGT

GCCAATTAATGCCTAATAAATACCATGTGCTTAAACAAGTAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAA

Homo sapiens T-box 5 (TBX5), transcript variant 4, mRNA
Accession Number - NM_181486.1
                                                             SEQ ID No. 6
TTCAGAGAGAGAGAGAGGGAGAGAGAGTGAGAGAGACTGACTCTTACCTCGAATCCGGGAACTTTAATCCTGA

AAGCTGCGCTCAGAAAGGACTTCGACCATTCACTGGGCTTCCAACTTTCCCTCCCTGGGGGTGTAAAGGAGGAGC

GGGGCACTGAGATTATATGGTTGCCGGTGCTCTTGGAGGCTATTTTGTGTTCTTTGGCGCTTGCCAACTGGGAAG
```

-continued

```
TATTTAGGGAGAGCAAGCGCACAGCAGAGGAGGTGTGTGTTGGAGGTGGGCAGTCGCCGCGGAGGCTCCAGCGGT

AGGTGCGCCCTAGTAGGCAGCAGTAGCCGCTATTCTGGGTAAGCAGTAAACCCCGCATAAACCCCGGAGCCACCA

TGCCTGCTCCCCCGCCTCACCGCCGGCTTCCCTGCTAGGAGCAGCAGAGGATGTGGTGAATGCACCGGCTTCACC

GAACGAGAGCAGAACCTTGCGCGGGCACAGGGCCCTGGGCGCACCATGGCCGACGCAGACGAGGGCTTTGGCCTG

GCGCACACGCCTCTGGAGCCTGACGCAAAAGACCTGCCCTGCGATTCGAAACCCGAGAGCGCGCTCGGGGCCCCC

AGCAAGTCCCCGTCGTCCCCGCAGGCCGCCTTCACCCAGCAGGGCATGGAGGGAATCAAAGTGTTTCTCCATGAA

AGAGAACTGTGGCTAAAATTCCACGAAGTGGGCACGGAAATGATCATAACCAAGGCTGGAAGGCGGATGTTTCCC

AGTTACAAAGTGAAGGTGACGGGCCTTAATCCCAAAACGAAGTACATTCTTCTCATGGACATTGTACCTGCCGAC

GATCACAGATACAAATTCGCAGATAATAAATGGTCTGTGACGGGCAAAGCTGAGCCCGCCATGCCTGGCCGCCTG

TACGTGCACCCAGACTCCCCCGCCACCGGGGCGCATTGGATGAGGCAGCTCGTCTCCTTCCAGAAACTCAAGCTC

ACCAACAACCACCTGGACCCATTTGGGCATATTATTCTAAATTCCATGCACAAATACCAGCCTAGATTACACATC

GTGAAAGCGGATGAAAATAATGGATTTGGCTCAAAAAATACAGCGTTCTGCACTCACGTCTTTCCTGAGACTGCG

TTTATAGCAGTGACTTCCTACCAGAACCACAAGATCACGCAATTAAAGATTGAGAATAATCCCTTTGCCAAAGGA

TTTCGGGGCAGTGATGACATGGAGCTGCACAGAATGTCAAGAATGCAAAGTAAAGAATATCCCGTGGTCCCCAGG

AGCACCGTGAGGCAAAAAGTGGCCTCCAACCACAGTCCTTTCAGCAGCGAGTCTCGAGCTCTCTCCACCTCATCC

AATTTGGGGTCCCAATACCAGTGTGAGAATGGTGTTTCCGGCCCCTCCCAGGACCTCCTGCCTCCACCCAACCCA

TACCCACTGCCCCAGGAGCATAGCCAAATTTACCATTGTACCAAGAGGAAAGAGGAAGAATGTTCCACCACAGAC

CATCCCTATAAGAAGCCCTACATGGAGACATCACCCAGTGAAGAAGATTCCTTCTACCGCTCTAGCTATCCACAG

CAGCAGGGCCTGGGTGCCTCCTACAGGACAGAGTCGGCACAGCGGCAAGCTTGCATGTATGCCAGCTCTGCGCCC

CCCAGCGAGCCTGTGCCCAGCCTAGAGGACATCAGCTGCAACACGTGGCCAAGCATGCCTTCCTACAGCAGCTGC

ACCGTCACCACCGTGCAGCCCATGGACAGGCTACCCTACCAGCACTTCTCCGCTCACTTCACCTCGGGGCCCCTG

GTCCCTCGGCTGGCTGGCATGGCCAACCATGGCTCCCCACAGCTGGGAGAGGGAATGTTCCAGCACCAGACCTCC

GTGGCCCACCAGCCTGTGGTCAGGCAGTGTGGGCCTCAGACTGGCCTGCAGTCCCCTGGCACCCTTCAGCCCCCT

GAGTTCCTCTACTCTCATGGCGTGCCAAGGACTCTATCCCCTCATCAGTACCACTCTGTGCACGGAGTTGGCATG

GTGCCAGAGTGGAGCGACAATAGCTAAAGTGAGGCCTGCTTCACAACAGACATTTCCTAGAGAAAGAGAGAGAGA

GAGGAGAAAGAGAGAGAAGGAGAGAGACAGTAGCCAAGAGAACCCCACGGACAAGATTTTTCATTTCACCCAATG

TTCACATCTGCACTCAAGGTCGCTGGATGCTGATCTAATCAGTAGCTTGAAACCACAATTTTAAAAATGTGACTT

TCTTGTTTTGTCTCAAAACTTAAAAAAACAAACACAAAAAGATGAGTCCCACCCCCCACTACCACCACACCCATC

AACCAGCCACATTCACGCTACTCCCCAGATCTCTTCCCCCATTCCTTCTTTTGGGCTCTAGAAAGTCTTGCCTCA

TTGAGTGTTTTTCCCTAGTGCGTAGTTGGAGTCTGTCCCTGTCTTGGTGTTAATGTTGACATTGTTATATAATAA

ATGATAATATATTTTTTCTTTCAATTTTCTTAATGGGACCCAGTCCCTTATTTGGGGGGAGGTCTGAGGCAAGT

ATATTTCAAAATATGTACTTGCGGGATTCCCTTCAAGTAAACCATCCCTGAAACCTAAATTCACGTTTCCCCTTG

ACTAAGAAAAGCACCTACCTCTGCCATGTGATGTTTCTGAAAAGCCTCTGTATGTCCCCATTTGCTTTGGTTTTG

TCCTGCCTTCTCCAATATCACGTGCTCAGTTTTGCCTCTACTTACCCATGGAGTCAGGATAACACTGACGCTCCC

TGGCATCCTATCTTATTCAGCCCTACCATCTTGCCAGCTCTGTCTTTCCAGCTGTCTGTCGCTAAAACGTGGCCT

ATAGCTTCCCTTCCGGAAAGCTTGCTTTGAAAAACTTAAAAAGCCCCCGTTTACATGTAGGCAGGACTGTGATAA

CAGTGCAAGCTCTGTGTTGACAAGAGTTGTGGACAAAAAGCCAAAATAAATATTCTTCCTGATTAAAAAAATTTT

TTTTGAAAAAAACAAGGCCAGCCCCAACCTTCCAAACCTCCATCACCAACAACCCAAACTGGATGTCAAGCAAAA

TGCACAATTCCTACAGAAGAGGCAAGACACAGTCACCAATGATATCTCGCCAAAGAAACCACGCCCACACCAATG

CCAACACAAAACTGTGTTTACTGAAAGCCGAAAACAGTATTAAAAAAAGTGTGTAAGTAAAGTGTTATGGTAGGG

TTCTTCAGATGTAATATTTTACTGGTACTATTTATTTATAAATAGGAATTCTAATTAAGTAATAACATGAAATGA
```

-continued

```
AACCCAGCATAGGAGCTGGCCAAGAGCTTTTAATTTTATTGATACTCAAAACCAAGTTTGTGTTTTTTGTTTTT
TTTTGTTTTTTTCCTCTTTCGAATGTGCTTTGCTTTTTTTGATTAAAAAGAATTTTTTTTTTCCTTTTTTATAAA
CAGACCCTAATAAAGAGAACAGGGTAAGATGTGAGGCTGAGTGTGTTTAAGTACGTGAGAGAGTGTGAGTGTGTT
TGTAAGTGAGTGTCCCTATGCGATTATGTCTCTTTACGTTGCTAAGGGGGGAGGGTGAGGATTAAGTACTCGTGC
CTTATATTTGTGTGCCAATTAATGCCTAATAAATACCATGTGCTTAAACAAGTAAAAAAAAAAAAAAAAAAAAAA
AAAAAAAAAAAAAAAAAAAAAAAAAAAAAAAAAAAAAAAAAAAAAAAAAAAAAAAAAAAAAAAAAAAAAAA
```

*Homo sapiens* T-box 18 (TBX18), mRNA
Accession Number - NM_001080508.1

SEQ ID No. 7

```
ATGGCCGAGAAGCGAAGGGGCTCGCCGTGCAGCATGCTAAGCCTCAAGGCGCACGCTTTCTCGGTGGAGGCGCTG
ATCGGCGCCGAGAAGCAGCAACAGCTTCAGAAGAAGCGGCGAAAACTGGGCGCCGAAGAGGCGGCGGGGCCGTG
GACGACGGAGGCTGCAGCCGCGGCGGCGGCGCGGGCGAAAAGGGTTCTTCTGAGGGAGACGAAGGCGCTGCGCTC
CCGCCGCCGGCTGGGGCGACGTCTGGGCCGGCTCGGAGTGGCGCAGACCTGGAGCGCGGAGCCGCGGGCGGCTGT
GAGGACGGCTTCCAGCAGGGAGCTTCCCCTCTGGCGTCACCGGGAGGCTCCCCCAAGGGGTCTCCGGCGCGCTCC
CTGGCCCGGCCCGGGACCCCTCTGCCCTCGCCGCAGGCCCCGCGGGTGGATCTGCAGGGAGCCGAGCTCTGGAAG
CGCTTTCATGAGATAGGCACTGAGATGATCATCACCAAGGCCGGCAGGCGCATGTTTCCAGCAATGAGAGTGAAG
ATCTCTGGATTAGATCCTCACCAGCAATATTACATTGCCATGGATATTGTACCAGTGGACAACAAAAGATACAGG
TATGTTTACCACAGTTCGAAATGGATGGTGGCAGGTAATGCTGACTCGCCTGTGCCACCCCGTGTGTACATTCAT
CCAGACTCGCCTGCCTCGGGGGAGACTTGGATGAGACAAGTTATCAGCTTCGACAAGCTGAAGCTCACCAACAAT
GAACTGGATGACCAAGGCCATATTATTCTTCATTCTATGCACAAATACCAACCGCGAGTGCACGTCATCCGTAAA
GACTGTGGAGACGATCTTTCTCCCATCAAGCCTGTTCCATCCGGGGAGGGAGTAAAGGCATTCTCCTTTCCAGAA
ACTGTCTTCACAACCGTCACTGCCTATCAGAATCAGCAGATTACTCGCCTGAAGATAGATAGGAATCCATTTGCT
AAAGGCTTCCGAGACTCCGGGCGCAACAGAATGGGTTTGGAAGCCTTGGTGGAATCATATGCATTCTGGCGACCA
TCACTACGGACTCTGACCTTTGAAGATATCCCTGGAATTCCCAAGCAAGGCAATGCAAGTTCCTCCACCTTGCTC
CAAGGTACTGGGAATGGCGTTCCTGCCACTCACCCTCACCTTTTGTCTGGCTCCTCTTGCTCCTCTCCTGCCTTC
CATCTGGGGCCCAACACCAGCCAGCTGTGTAGTCTGGCCCCTGCTGACTATTCTGCCTGTGCCCGCTCAGGCCTC
ACCCTCAACCGATACAGCACATCTTTGGCAGAGACCTACAACAGGCTCACCAACCAGGCTGGTGAGACCTTTGCC
CCGCCCAGGACTCCCTCCTATGTGGGCGTGAGCAGCAGCACCTCCGTGAACATGTCCATGGGTGGCACTGATGGG
GACACCTTCAGCTGCCCACAGACCAGCTTATCCATGCAGATTTCGGGAATGTCCCCCCAGCTCCAGTATATCATG
CCATCACCCTCCAGCAATGCCTTCGCCACTAACCAGACCCATCAGGGTTCCTATAATACTTTTAGATTACACAGC
CCCTGTGCACTATATGGATATAACTTCTCCACATCCCCCAAACTGGCTGCCAGTCCTGAGAAAATTGTTTCTTCC
CAAGGAAGTTTCTTGGGGTCCTCACCGAGTGGGACCATGACGGATCGGCAGATGTTGCCCCCTGTGGAAGGAGTG
CACCTGCTTAGCAGTGGGGGTCAGCAGAGTTTCTTTGACTCTAGGACCCTAGGAAGCTTAACTCTGTCATCATCT
CAAGTATCTGCACATATGGTCTGATGAAGCCTTTAAGTTAAATGACATTTGGATCTGTCTAACATATTTTCTTTT
TCTTTTTAAAAGCTATGTGGAAAGAAACTCTCTGTGGTTTATAAAATGTACATATAATAGAAAATGAAGGCTCA
CTGGGTTTTTTGACTTTATCATGGTGAGATTGTAATTATCTATGGTATATATGTATGCTGTATATACATAGCACA
TGGAGTATCACGGCCCCTATTGTTCCCCTGTTTCATCCAGTTGCACGGAGTATTGGCATGCGTGTAGTATGTTTA
AGCAAAGTTCTCAGACTCTTTTAAAAACAAGATGGTAAACTTAAAACTTGGCAATTATACTATCCAGAAGAACAC
TTATAACTTAATTTATCAGAAAAATGCTCTAAACGGTTTCATACTTGATGTATTGATAACCAGCAGTAACCAGCA
TGTAGAGTCTTGTGATTTCTGTTATTCTTGGACACAGTGTGAGAATCTAAAATACAAAAGCCAGTTGAAGTCTTA
GTGTTAGTCCTGAGGTATTTGTAATCATGAAGGATCAGCTTTTTCATTCCTGCTTATTATTTACCACACATACTA
TATGACCTTGGGTCTATAAAAAAATCATAACCCATAATAATTGTTATTTTCTTAAGGAAGGTAAAGGAGAGGCTT
```

-continued

GTGATTTTTTTTTTACACTTTCCATTGGGCACATAAGAGGTTCTTATTCATCTGTAGAGAACAAATTTCCAGTA

TTTTCGATTTTTTGCTTATTTTATATATCAAATAGACCATTAAAGAATGTTCTATAAACATTTTTAAATTCCAAT

TTTCACCAGGGGAGGAATATGTGATATGAGTGGAATGGCAAAAGGAAAATAAATCCACCTCAAATTCATTGATTC

CAATGAGAAATGTCTATCTTTTAAATCAAGAGTAATACTATTGTTAACTATACCTTATGTTTTTGTATAGTTTGT

TTTTAAATTTAGAATATTTTTTCCATCTTGCTCTGAGCTTCCTGACCGATAGTATATAAGTAAAAAAATGCATT

TATGCTACTTATTTATATCTTGTAATTCCTACACATTGAACCCTTTTCCCCTTCTTAACCTTGTCCGTCTGCCTG

AGTCTTTCCCAAAACAGATAGTTCCTAGGCCTGTATGGTGTTAAATAACACGGTGAGGAATTTCAGTAGGTTATC

TCCAGCAATCTGTCTTTTGGGAGCTATAGTGCAAAGGCCAAAGCCCATTACTATAAAGACCCTCTTGGAGGACTA

AGAAGGAAGATACTAATTATGATAAAGGAACTATAAAACTTTTAACCTCAACAGAATTTGTAATGTCAGAACTGG

AGAAATTAAAATCAGTATTAAATTTTTTAATTCCTAAAATAATATATGCATGGTTGAAGAGTTAAAAACAAGTAA

CTTTGAGAGCACAGTATGAGATAAATAAAAAAGGCTAAGAATACATGATGAGGCACATTCCCCTTCTGAGGAGAA

AGCGAAATAACATGTCTGTGCATTGACCCATTCATTACATTTCATGTATCTTAAGCAAAAGAGCATGATTTTCTC

TCATTGCTAAAAAGAGTTGCTTTAACTCATCCCTGGATTTGGTGGGGAAAGGGTACAACTCCTGATTTGCTGTTT

CACTTTGAAACAACACAATTTGTTAGATACTTAGGGAGATATACTGTTGAATTTGCACAGGATGTGACTCTGTTT

ATACATATTAACAAATTTCCTTTTGGATTCCTTAGCAGTTCATCAAATTAGTATTAAATTTTTAAATTTAAAACT

AGCATGAAGGGACATGAAATATTTGCAGTAGGTGGATCTATGTAAGATGTTTGGGTATGGCATTAATAGCTTGAC

AAAGATTTGGGGAAAGGTGTTAAGAATGAGTCCATCTCAGCCAATAGTGCTTGGTGTATAATTCAAGAACAGAGA

GTTTTCCATCTTGAAAAAACATGGAAAGTAATGCTCTATACCCATATGTATTAATAAGAGCATTTTCCTTCTTGC

CGTTGATCATTTCAGATGATACCACAATATGAGTATAATTTTTATTAATCTTTTTTCTGGTAAAATTTTAGCAA

TATTGTACAAATGCTTTTTTTAGGTTTTACTGTAAATATTAATCACCACGTCACTTCAGAGACTAGCCTTTTATT

GCTGAATTAAATGACATGCATACATTGATAATTATATATCTGTATTTTATTAAAAAGTACTTAAAATTATATTAA

AATATGTTATTAAACCCTTT

Homo sapiens short stature homeobox 2 (SHOX2), transcript variant 1,
mRNA
Accession Number - NM_003030.4

SEQ ID No. 8

CCTCCTCCCTCTCCTCCCCCACCTCCTGTCCCATTGATGTGTTATTATTGGGGGGGCTGGAGCAGTAAAAAAGA

AGAAGGAAAAAAAGAGCGGGGCTCTGCTGGCAGAGGTTGAGCGCCGGGCTGACGTGCGGCGGCGATGGAAGAACT

TACGGCGTTCGTCTCCAAGTCTTTTGACCAGAAAGTGAAGGAGAAGAAGGAGGCGATCACGTACCGGGAGGTGCT

GGAGAGCGGGCCGCTGCGCGGGGCCAAGGAGCCGACCGGCTGCACCGAGGCGGGCCGCGACGACCGCAGCAGCCC

GGCAGTCCGGGCGGCCGGCGGAGGCGGCGGCGGAGGAGGCGGAGGCGGCGGCGGAGGAGGCGGAGGAGGTGTAGG

AGGAGGAGGAGCAGGCGGAGGAGCTGGAGGAGGGCGCTCTCCCGTCCGGGAGCTGGACATGGGCGCCGCCGAGAG

AAGCAGGGAGCCGGGCAGCCCGCGACTGACGGAGGGTAGAAGGAAGCCAACGAAAGCTGAGGTCCAGGCTACGCT

GCTTCTCCCGGGCGAGGCGTTTCGGTTTCTTGTGTCCCCGGAGCTGAAAGATCGCAAAGAGGATGCGAAAGGGAT

GGAGGACGAAGGCCAGACCAAAATCAAGCAGAGGCGAAGTCGGACCAATTTCACCCTGGAACAACTCAATGAGCT

GGAGAGGCTTTTTGACGAGACCCACTATCCCGACGCCTTCATGCGAGAGGAACTGAGCCAGCGACTGGGCCTGTC

GGAGGCCCGAGTGCAGGTTTGGTTTCAAAATCGAAGAGCTAAATGTAGAAAACAAGAAAATCAACTCCATAAAGG

TGTTCTCATAGGGGCCGCCAGCCAGTTTGAAGCTTGTAGAGTCGCACCTTATGTCAACGTAGGTGCTTTAAGGAT

GCCATTTCAGCAGGATAGTCATTGCAACGTGACGCCCTTGTCCTTTCAGGTTCAGGCGCAGCTGCAGCTGGACAG

CGCTGTGGCGCACGCGCACCACCACCTGCATCCGCACCTGGCCGCGCACGCGCCCTACATGATGTTCCCAGCACC

GCCCTTCGGACTGCCGCTCGCCACGCTGGCCGCGGATTCGGCTTCCGCCGCCTCGGTAGTGGCGGCCGCAGCAGC

CGCCAAGACCACCAGCAAGAACTCCAGCATCGCCGATCTCAGACTGAAAGCCAAAAAGCACGCCGCAGCCCTGGG

TCTGTGACGCCAACGCCAGCACCAATGTCGCGCCTGTCCCGCGGCACTCAGCCTGCACGCCCTCCGCGCCCCGCT

-continued

```
GCTTCTCCGTTACCCCTTTGAGACCTCGGGAGCCGGCCCTCTTCCCGCCTCACTGACCATCCCTCGTCCCTATC

GCATCTTGGACTCGGAAAGCCAGACTCCACGCAGGACCAGGGATCTCACGAGGCACGCAGGCTCCGTGGCTCCTG

CCCGTTTTCCTACTCGAGGGCCTAGAATTGGGTTTTGTAGGAGCGGGTTTGGGGGAGTCTGGAGAGAGACTGGAC

AGGGGAGTGCTGGAACCGCGGAGTTTGGCTCACCGCAAAGCTGCAACGATGGACTCTTGCATAGAAAAAAAAATC

TTGTTAACAATGAAAAAATGAGCAAACAAAAAAATCGAAAGACAAACGGGAGAGAAAAGAGGAAGGGAACTTAT

TTCTTAACTGCTATTTGGCAGAAGCTGAAATTGGAGAACCAAGGAGCAAAAACAAATTTTAAAATTAAAGTATTT

TATACATTTAAAAATATGGAAAAACAACCCAGACGATTCTCGAGAGACTGGGGGAGTTACCAACTTAAATGTGT

GTTTTTAAAAATGCGCTAAGAAGGCAAAGCAGAAAGAAGAGGTATACTTATTTAAAAAACTAAGATGAAAAAGT

GCGCAGCTGGGAAGTTCACAGGTTTTGAAACTGACCTTTTTCTGCGAAGTTCACGTTAACACGAGAAATTTGATG

AGAGAGGCGGGCCTCCTTTTACGTTGAATCAGATGCTTTGAGTTTAAACCCACCATGTATGGAAGAGCAAGAAAA

GAGAAAATATTAAAACGAGGAGAGAGAAAAATAATATTAACACAAAAAAATGCCACAGACAATGATTTCTCTGAG

AAATTATTATGGCAAAACTGTCTGGACTGCTGACAGTAAATTCCGGTTTGCATGTTACTTGTATTCCATTGATGG

TGTGTCTCCTCCCACCCCCTTATCTCCCATGCACTCACTCCATTTTCATCTTCACTATGAAAACAATACCAAAA

GTATCTGGAAATTGATATATATATATCCATATATATATATCATATATTTGCCATATATATATATATATATATATA

TATATATATATATATATTTGCCCTGTCTTTGATCCTGGGGAACAAAAGAAAAAAGTCAGAAAGGGAAAAAATT

ACACTCATTGTCCTAAGAAGACAGAGGTGGGCAGAATATGTGGGGAAAGGAAAAAGAAAACAAGACCACCAAATG

AAATAATGAAGGTACAGCGCCTCGCTGTGCCAGACACAGTAGGCGCTCAATCAGTATTAGTTCCCACCATTCCCC

TTTTCTTGTGTTCCTTCTTGTTGGTTTCCTGAAGTCCTATTTGAAGACAGTGGTTTATTTCCCCCTCTCTATCCC

GTCAAATTCACCTTAAATAACACCCAGCTAGATACAGGCACTAGGTTTGTGTAAGATATGTTGATACACACGAAC

AAAGTTTATTTTGACTATAATGTGTGGACTGACTTTCAACATTTGCATTTTATCTCACAAAGGTGTATCTATTCA

AGTAACCTTTTTTTTTGTTTGTTTGTTTCTTTTTTGTTTTTTTTTCTTTTGGTTGTTTGTTTCAATTCATGT

AGCTATTTAAACTGGGATACCTTGGACTAAGCCAGTCTGTATCCCAATTCGCTAGCAAGCCTAAGTTTGTGGGGT

TTTGTTTTTGTTTTGTTTTACCTTCTAATTTACAAGAAAGAGGAAAAGCTCTTCTAACTGAACTTTGGTATGCG

GTTGAGCTTTGTAACTATTTGTTCTCCATGAAAACAAAATTATTTATATTTGACATATTTTTTCTAGTGTATTA

AGTTATTTTAAACAAAAGATGTTATCTCATGACGTGTTGTCAGTACAAAATGTGTCGCCTCCAATTCTGTTAAAC

CTTTTAAATAAGTGCCAAGTTATTAATTGAAGACACTTTGCGATCAATTGAATGAAAATATCGTTTCATTTGAAA

AAAAAAA
```

*Homo sapiens* short stature homeobox 2 (SHOX2), transcript variant 2, mRNA
Accession Number - NM_006884.3
SEQ ID No. 9

```
CCTCCTCCCTCTCCTCCCCCACCTCCTGTCCCATTGATGTGTTATTATTGGGGGGCTGGAGCAGTAAAAAAGA

AGAAGGAAAAAAGAGCGGGGCTCTGCTGGCAGAGGTTGAGCGCCGGGCTGACGTGCGGCGGCGATGGAAGAACT

TACGGCGTTCGTCTCCAAGTCTTTTGACCAGAAAGTGAAGGAGAAGAAGGAGGCGATCACGTACCGGGAGGTGCT

GGAGAGCGGGCCGCTGCGCGGGGCCAAGGAGCCGACCGGCTGCACCGAGGCGGGCCGCGACGACCGCAGCAGCCC

GGCAGTCCGGGCGGCCGGCGGAGGCGGCGGCGGAGGAGGCGGAGGCGGCGGCGGAGGAGGCGGAGGAGGTGTAGG

AGGAGGAGGAGCAGGCGGAGGAGCTGGAGGAGGGCGCTCTCCCGTCCGGGAGCTGGACATGGGCGCCGCCGAGAG

AAGCAGGGAGCCGGGCAGCCCGCGACTGACGGAGGTGTCCCCGGAGCTGAAAGATCGCAAAGAGGATGCGAAAGG

GATGGAGGACGAAGGCCAGACCAAAATCAAGCAGAGGCGAAGTCGGACCAATTTCACCCTGGAACAACTCAATGA

GCTGGAGAGGCTTTTTGACGAGACCCACTATCCCGACGCCTTCATGCGAGAGGAACTGAGCCAGCGACTGGGCCT

GTCGGAGGCCCGAGTGCAGGTTTGGTTTCAAAATCGAAGAGCTAAATGTAGAAAACAAGAAAATCAACTCCATAA

AGGTGTTCTCATAGGGGCCGCCAGCCAGTTTGAAGCTTGTAGAGTCGCACCTTATGTCAACGTAGGTGCTTTAAG

GATGCCATTTCAGCAGGATAGTCATTGCAACGTGACGCCCTTGTCCTTTCAGGTTCAGGCGCAGCTGCAGCTGGA
```

-continued

```
CAGCGCTGTGGCGCACGCGCACCACCACCTGCATCCGCACCTGGCCGCGCACGCGCCCTACATGATGTTCCCAGC

ACCGCCCTTCGGACTGCCGCTCGCCACGCTGGCCGCGGATTCGGCTTCCGCCGCCTCGGTAGTGGCGGCCGCAGC

AGCCGCCAAGACCACCAGCAAGAACTCCAGCATCGCCGATCTCAGACTGAAAGCCAAAAAGCACGCCGCAGCCCT

GGGTCTGTGACGCCAACGCCAGCACCAATGTCGCGCCTGTCCCGCGGCACTCAGCCTGCACGCCCTCCGCGCCCC

GCTGCTTCTCCGTTACCCCTTTGAGACCTCGGGAGCCGGCCCTCTTCCCGCCTCACTGACCATCCCTCGTCCCCT

ATCGCATCTTGGACTCGGAAAGCCAGACTCCACGCAGGACCAGGGATCTCACGAGGCACGCAGGCTCCGTGGCTC

CTGCCCGTTTTCCTACTCGAGGGCCTAGAATTGGGTTTTGTAGGAGCGGGTTTGGGGGAGTCTGGAGAGAGACTG

GACAGGGGAGTGCTGGAACCGCGGAGTTTGGCTCACCGCAAAGCTGCAACGATGGACTCTTGCATAGAAAAAAAA

ATCTTGTTAACAATGAAAAAATGAGCAAACAAAAAAATCGAAAGACAAACGGGAGAGAAAAGAGGAAGGGAACT

TATTTCTTAACTGCTATTTGGCAGAAGCTGAAATTGGAGAACCAAGGAGCAAAAACAAATTTTAAAATTAAAGTA

TTTTATACATTTAAAAATATGGAAAAACAACCCAGACGATTCTCGAGAGACTGGGGGGAGTTACCAACTTAAATG

TGTGTTTTTAAAAATGCGCTAAGAAGGCAAAGCAGAAAGAAGAGGTATACTTATTTAAAAAACTAAGATGAAAAA

AGTGCGCAGCTGGGAAGTTCACAGGTTTTGAAACTGACCTTTTTCTGCGAAGTTCACGTTAACACGAGAAATTTG

ATGAGAGAGGCGGGCCTCCTTTTACGTTGAATCAGATGCTTTGAGTTTAAACCCACCATGTATGGAAGAGCAAGA

AAAGAGAAAATATTAAAACGAGGAGAGAGAAAAATAATATTAACACAAAAAAATGCCACAGACAATGATTTCTCT

GAGAAATTATTATGGCAAAACTGTCTGGACTGCTGACAGTAAATTCCGGTTTGCATGTTACTTGTATTCCATTGA

TGGTGTGTCTCCTCCCACCCCCTTATCTCCCATGCACTCACTCCATTTTCATCTTCACTATGAAAACAATACCA

AAAGTATCTGGAAATTGATATATATATATCCATATATATATATCATATATTTGCCATATATATATATATATATAT

ATATATATATATATATATATTTGCCCTGTCTTTGATCCTGGGGAACAAAAGAAAAAAGTCAGAAAGGGAAAAA

ATTACACTCATTGTCCTAAGAAGACAGAGGTGGGCAGAATATGTGGGGAAAGGAAAAAGAAAACAAGACCACCAA

ATGAAATAATGAAGGTACAGCGCCTCGCTGTGCCAGACACAGTAGGCGCTCAATCAGTATTAGTTCCCACCATTC

CCCTTTTCTTGTGTTCCTTCTTGTTGGTTTCCTGAAGTCCTATTTGAAGACAGTGGTTTATTTCCCCCTCTCTAT

CCCGTCAAATTCACCTTAAATAACACCCAGCTAGATACAGGCACTAGGTTTGTGTAAGATATGTTGATACACACG

AACAAAGTTTATTTTGACTATAATGTGTGGACTGACTTTCAACATTTGCATTTTATCTCACAAAGGTGTATCTAT

TCAAGTAACCTTTTTTTTTGTTTGTTTGTTTCTTTTTTGTTTTTTTTTTCTTTTGGTTGTTTGTTTCAATTCA

TGTAGCTATTTAAACTGGGATACCTTGGACTAAGCCAGTCTGTATCCCAATTCGCTAGCAAGCCTAAGTTTGTGG

GGTTTTGTTTTTGTTTTTGTTTTACCTTCTAATTTACAAGAAAGAGGAAAAGCTCTTCTAACTGAACTTTGGTAT

GCGGTTGAGCTTTGTAACTATTTGTTCTCCATGAAAACAAAATTATTTATATTTGACATATTTTTTTCTAGTGTA

TTAAGTTATTTTAAACAAAAGATGTTATCTCATGACGTGTTGTCAGTACAAAATGTGTCGCCTCCAATTCTGTTA

AACCTTTTAAATAAGTGCCAAGTTATTAATTGAAGACACTTTGCGATCAATTGAATGAAAATATCGTTTCATTTG

AAAAAAAAAA
```

Homo sapiens short stature homeobox 2 (SHOX2), transcript variant 3,
mRNA
Accession Number - NM_001163678.1

SEQ ID No. 10

```
CCTCCTCCCTCTCCTCCCCCACCTCCTGTCCCATTGATGTGTTATTATTGGGGGGGCTGGAGCAGTAAAAAAAGA

AGAAGGAAAAAAGAGCGGGGCTCTGCTGGCAGAGGTTGAGCGCCGGGCTGACGTGCGGCGGCGATGGAAGAACT

TACGGCGTTCGTCTCCAAGTCTTTTGACCAGAAAGTGAAGGAGAAGAAGGAGGCGATCACGTACCGGGAGGTGCT

GGAGAGCGGGCCGCTGCGCGGGGCCAAGGAGCCGACCGGCTGCACCGAGGCGGGCCGCGACGACCGCAGCAGCCC
```

-continued

```
GGCAGTCCGGGCGGCCGGCGGAGGCGGCGGCGGAGGAGGCGGAGGCGGCGGCGGAGGAGGCGGAGGAGGTGTAGG
AGGAGGAGGAGCAGGCGGAGGAGCTGGAGGAGGGCGCTCTCCCGTCCGGGAGCTGGACATGGGCGCCGCCGAGAG
AAGCAGGGAGCCGGGCAGCCCGCGACTGACGGAGGTGTCCCCGGAGCTGAAAGATCGCAAAGAGGATGCGAAAGG
GATGGAGGACGAAGGCCAGACCAAAATCAAGCAGAGGCGAAGTCGGACCAATTTCACCCTGGAACAACTCAATGA
GCTGGAGAGGCTTTTTGACGAGACCCACTATCCCGACGCCTTCATGCGAGAGGAACTGAGCCAGCGACTGGGCCT
GTCGGAGGCCCGAGTGCAGGTTTGGTTTCAAAATCGAAGAGCTAAATGTAGAAAACAAGAAAATCAACTCCATAA
AGGTGTTCTCATAGGGGCCGCCAGCCAGTTTGAAGCTTGTAGAGTCGCACCTTATGTCAACGTAGGTGCTTTAAG
GATGCCATTTCAGCAGGTTCAGGCGCAGCTGCAGCTGGACAGCGCTGTGGCGCACGCGCACCACCACCTGCATCC
GCACCTGGCCGCGCACGCGCCCTACATGATGTTCCCAGCACCGCCCTTCGGACTGCCGCTCGCCACGCTGGCCGC
GGATTCGGCTTCCGCCGCCTCGGTAGTGGCGGCCGCAGCAGCCGCCAAGACCACCAGCAAGAACTCCAGCATCGC
CGATCTCAGACTGAAAGCCAAAAAGCACGCCGCAGCCCTGGGTCTGTGACGCCAACGCCAGCACCAATGTCGCGC
CTGTCCCGCGGCACTCAGCCTGCACGCCCTCCGCGCCCCGCTGCTTCTCCGTTACCCCTTTGAGACCTCGGGAGC
CGGCCCTCTTCCCGCCTCACTGACCATCCCTCGTCCCCTATCGCATCTTGGACTCGGAAAGCCAGACTCCACGCA
GGACCAGGGATCTCACGAGGCACGCAGGCTCCGTGGCTCCTGCCCGTTTTCCTACTCGAGGGCCTAGAATTGGGT
TTTGTAGGAGCGGGTTTGGGGGAGTCTGGAGAGAGACTGGACAGGGGAGTGCTGGAACCGCGGAGTTTGGCTCAC
CGCAAAGCTGCAACGATGGACTCTTGCATAGAAAAAAAAATCTTGTTAACAATGAAAAAATGAGCAAACAAAAAA
ATCGAAAGACAAACGGGAGAGAAAAAGAGGAAGGGAACTTATTTCTTAACTGCTATTTGGCAGAAGCTGAAATTG
GAGAACCAAGGAGCAAAAACAAATTTTAAAATTAAAGTATTTTATACATTTAAAAATATGGAAAAACAACCCAGA
CGATTCTCGAGAGACTGGGGGGAGTTACCAACTTAAATGTGTGTTTTTAAAAATGCGCTAAGAAGGCAAAGCAGA
AAGAAGAGGTATACTTATTTAAAAAACTAAGATGAAAAAAGTGCGCAGCTGGGAAGTTCACAGGTTTTGAAACTG
ACCTTTTTCTGCGAAGTTCACGTTAACACGAGAAATTTGATGAGAGAGGCGGGCCTCCTTTTACGTTGAATCAGA
TGCTTTGAGTTTAAACCCACCATGTATGGAAGAGCAAGAAAAGAGAAAATATTAAAACGAGGAGAGAAAAATA
ATATTAACACAAAAAAATGCCACAGACAATGATTTCTCTGAGAAATTATTATGGCAAACTGTCTGGACTGCTGA
CAGTAAATTCCGGTTTGCATGTTACTTGTATTCCATTGATGGTGTGTCTCCTCCCACCCCCTTATCTCCCATGCA
CTCACTCCATTTTCATCTTCACTATGAAAAACAATACCAAAAGTATCTGGAAATTGATATATATATATCCATATA
TATATATCATATATTTGCCATATATATATATATATATATATATATATATATATATATATATTTGCCCTGTCTTTG
ATCCTGGGGAACAAAAGAAAAAAGTCAGAAAGGGAAAAAATTACACTCATTGTCCTAAGAAGACAGAGGTGGGCA
GAATATGTGGGGAAAGGAAAAAGAAAACAAGACCACCAAATGAAATAATGAAGGTACAGCGCCTCGCTGTGCCAG
ACACAGTAGGCGCTCAATCAGTATTAGTTCCCACCATTCCCCTTTTCTTGTGTTCCTTCTTGTTGGTTTCCTGAA
GTCCTATTTGAAGACAGTGGTTTATTTCCCCCTCTCTATCCCGTCAAATTCACCTTAAATAACACCCAGCTAGAT
ACAGGCACTAGGTTTGTGTAAGATATGTTGATACACACGAACAAAGTTTATTTTGACTATAATGTGTGGACTGAC
TTTCAACATTTGCATTTTATCTCACAAAGGTGTATCTATTCAAGTAACCTTTTTTTTTGTTTGTTTGTTTCTTT
TTTGTTTTTTTTTTCTTTTGGTTGTTTGTTTCAATTCATGTAGCTATTTAAACTGGGATACCTTGGACTAAGCC
AGTCTGTATCCCAATTCGCTAGCAAGCCTAAGTTTGTGGGGTTTTGTTTTTGTTTTTGTTTTACCTTCTAATTTA
CAAGAAAGAGGAAAAGCTCTTCTAACTGAACTTTGGTATGCGGTTGAGCTTTGTAACTATTTGTTCTCCATGAAA
ACAAAATTATTTATATTTGACATATTTTTTCTAGTGTATTAAGTTATTTTAAACAAAAGATGTTATCTCATGAC
GTGTTGTCAGTACAAAATGTGTCGCCTCCAATTCTGTTAAACCTTTTAAATAAGTGCCAAGTTATTAATTGAAGA
CACTTTGCGATCAATTGAATGAAAATATCGTTTCATTTGAAAAAAAAAAA
```

This application includes SEQ ID NO:1-10 of the Sequence Listing contained in CSMC001WO_ST25.txt (created Nov. 8, 2012, 49 KB) filed in parent International Application No. PCT/US2012/064204 and presented on Pgs. 60-78 of the Specification of International Application No. PCT/US2012/064204, which are fully incorporated by reference herein.

What is claimed is:

1. A method of generating a biological pacemaker in vivo using transcription factors to modify the electrical activity of the cardiac tissue of a subject comprising:
identifying a subject having cardiac tissue exhibiting abnormal electrical activity,
wherein said subject has cardiac tissue comprising quiescent cells,
wherein the quiescent cells comprise cardiomyocytes,
wherein the quiescent cells do not exhibit spontaneous, repetitive electrical activity; and
administering one or more transcription factors to said quiescent cells to generate treated cells in vivo,
wherein the treated cells exhibit spontaneous, repetitive electrical activity, thereby modifying electrical activity of the cardiac tissue said subject, and the one or more transcription factors comprises Tbx18.

2. The method of claim 1, wherein said subject is afflicted with a condition selected from the group consisting of sick sinus syndrome, sinus bradycardia, tachycardia-bradycardia syndrome, atrial fibrillation, atrioventricular block, chronotropic incompetence, prolonged QT syndrome, and heart failure.

3. The method of claim 1, wherein said abnormal cardiac electrical activity is due to a cardiac arrhythmia.

4. The method of claim 1, wherein said administration occurs in vitro, and the method further comprises administering the cells to said subject.

5. The method of claim 1, wherein said administration occurs in vivo.

6. The method claim 1, wherein the one or more transcription factors is selected from the group consisting of: Shox-2, Tbx3, Tbx5, functional fragments thereof, and combinations thereof.

7. The method of claim 1, wherein the one or more transcription factors comprises Shox-2.

8. The method of claim 5, wherein said administration is to a site selected from the group consisting of the apex of the heart, right branch of the Bundle of His, the left branch of the Bundle of His, the Purkinje fibers, the inter-ventricular septum, the right ventricular free wall, the left ventricular free wall, the SA node, the AV node.

9. The method according to claim 8, wherein said administration site is accessed via the right ventricle.

10. The method according to claim 8, wherein said administration site is accessed via the right atrium.

11. The method according to claim 8, wherein said administration site is accessed by accessing the heart directly.

12. The method of claim 11, wherein said accessing is achieved by a map guided catheter injection system.

13. The method of claim 11, wherein said accessing is achieved by fluoroscopy guidance.

14. The method of claim 11, wherein said accessing is achieved by X-ray guidance.

15. The method of claim 11, wherein said accessing is achieved by echocardiography guidance.

16. The method of claim 11, wherein said accessing is achieved by guidance via magnetic resonance imaging.

17. The method of claim 1, wherein said administration comprises delivering a DNA delivery system comprising a polynucleotide encoding said one or more transcription factors.

18. The method of claim 17, wherein the DNA delivery system comprises a viral vector.

19. The method of claim 18, wherein the viral vector is selected from the group consisting of adenovirus, adeno-associated virus, lentivirus, retrovirus, HJV, HIV, and HSV.

20. The method of claim 17, wherein the DNA delivery system comprises a non-viral vector.

21. The method of claim 20, wherein the non-viral vector is one or more of the following: liposomal vectors, a cationic polymers, and/or DNA binding polymers.

22. The method of claim 17, wherein the DNA delivery system comprises naked DNA.

23. The method of claim 1, wherein the treated cells exhibit a length-to-width morphology substantially similar to a length-to-width morphology of native SAN cells.

24. The method of claim 23, wherein the treated cells have a length-to-width ratio of at least about 10.

25. The method of claim 1, wherein the treated cells exhibit an increase in spontaneous intracellular $Ca^{2+}$ oscillations.

26. The method of claim 1, wherein said spontaneous, repetitive electrical activity increases in response to β-adrenergic stimulation, or decreases in response to cholinergic suppression.

27. The method of claim 1, wherein the converted cells do not express atrial natriuretic peptide (ANP) or skeletal α-actin (αSkA).

28. The method of claim 1, wherein the subject has an electronic pacemaker to modify the electrical activity of the cardiac tissue.

29. The method of claim 28, wherein the generation of the biological pacemaker supplements the function of the electronic pacemaker.

30. The method of claim 28, wherein the generation of the biological pacemaker functionally replaces the electronic pacemaker.

31. A method of generating a biological pacemaker using transcription factors to treat a cardiac arrhythmia comprising:
identifying a subject suffering from cardiac arrhythmia,
wherein said subject has cardiac tissue comprising quiescent cells,
wherein the quiescent cells comprise cardiomyocytes,
wherein the quiescent cells do not exhibit spontaneous, repetitive electrical activity; and
administering one or more transcription factors to said quiescent cells to generate treated cells,
wherein the treated cells exhibit spontaneous, repetitive electrical activity; thereby treating said cardiac arrhythmia, and the one or more transcription factors comprises Tbx18.

32. A method of converting a population of quiescent cells, comprising:
  obtaining a population of quiescent cells comprising cardiomyocytes;
  culturing said quiescent cells in vitro; and
  delivering one or more transcription factors to said quiescent cells to generate converted cells,
  wherein said cultured quiescent cells do not exhibit spontaneous, repetitive electrical activity, the converted cells exhibit spontaneous, repetitive electrical activity, and the one or more transcription factors comprises Tbx 18.

33. A method of treating a cardiac arrhythmia using transcription factors comprising:
  identifying a subject suffering from cardiac arrhythmia,
  wherein said subject has cardiac tissue comprising quiescent cells,
  wherein the quiescent cells comprise cardiomyocytes,
  wherein the quiescent cells do not exhibit spontaneous, repetitive electrical activity; and
  administering one or more transcription factors to said quiescent cells to generate treated cells,
  wherein the treated cells exhibit spontaneous, repetitive electrical activity; thereby treating said cardiac arrhythmia, and the one or more transcription factors comprises Tbx18.

34. The method of claim 32, wherein delivering one or more transcription factors to said quiescent cells comprises contacting the quiescent cells with a viral vector encoding the one or more transcription factors, wherein the viral vector comprises a eukaryotic promoter.

35. The method of claim 34, wherein the viral vector is an adenoviral vector.

36. The composition of claim 35, wherein the adenoviral vector further comprises the following operably linked components in sequence:
  a first inverted terminal repeat sequence (ITR);
  a first lox P site;
  a packaging site ($\psi$, psi);
  a cytomegalovirus promoter;
  an internal ribosome entry site (IRES);
  a polyadenylation signal (poly A);
  a second lox P site;
  a sequence encoding the adenovirus early region 2 and early region 4 genes; and
  a second inverted repeat sequence (ITR).

* * * * *